(12) United States Patent
Laby et al.

(10) Patent No.: US 10,512,757 B2
(45) Date of Patent: Dec. 24, 2019

(54) FLUID-ACTUATED SHEATH DISPLACEMENT AND ARTICULATION BEHAVIOR IMPROVING SYSTEMS, DEVICES, AND METHODS FOR CATHETERS, CONTINUUM MANIPULATORS, AND OTHER USES

(71) Applicant: Project Moray, Inc., Belmont, CA (US)

(72) Inventors: Keith Phillip Laby, Oakland, CA (US); Mark D. Barrish, Belmont, CA (US)

(73) Assignee: Project Moray, Inc., Belmont, CA (US)

( * ) Notice: Subject to any disclaimer, the term of this patent is extended or adjusted under 35 U.S.C. 154(b) by 162 days.

(21) Appl. No.: 15/469,085

(22) Filed: Mar. 24, 2017

(65) Prior Publication Data

US 2018/0071492 A1    Mar. 15, 2018

Related U.S. Application Data

(60) Provisional application No. 62/313,390, filed on Mar. 25, 2016.

(51) Int. Cl.
*A61M 25/01* (2006.01)
*A61F 2/958* (2013.01)
(Continued)

(52) U.S. Cl.
CPC ....... *A61M 25/0155* (2013.01); *A61F 2/2433* (2013.01); *A61F 2/958* (2013.01);
(Continued)

(58) Field of Classification Search
CPC . A61F 2/2427–2439; A61F 2/958–2002/9586; A61F 2/962–2002/9665
See application file for complete search history.

(56) References Cited

U.S. PATENT DOCUMENTS

| | | | |
|---|---|---|---|
| 3,284,964 A | 11/1966 | Saito | |
| 3,459,221 A | 8/1969 | Axelrod | |

(Continued)

FOREIGN PATENT DOCUMENTS

| | | |
|---|---|---|
| CN | 107835703 | 3/2018 |
| CN | 107835704 | 3/2018 |

(Continued)

OTHER PUBLICATIONS approppedia.org, "3-D Printing of Electrically Conductive Materials Literature Review", Appropedia: The sustainability Wiki, By Michigan Tech's Open Sustainability Technology Lab, Jul. 13, 2016, 9 pages.

(Continued)

*Primary Examiner* — Shaun L David
*Assistant Examiner* — Brigid K Byrd
(74) *Attorney, Agent, or Firm* — Kilpatrick Townsend & Stockton LLP

(57) ABSTRACT

Catheter-supported therapeutic and diagnostic tools can be introduced into a patient body with a sheath slidably disposed over the tool. Once the tool is aligned with a target tissue, a fluid-driven actuator can move the sheath axially from over the tool, for example, to allow a stent, stent-graft, prosthetic valve, or the like to expand radially within the cardiovascular system, without having to transmit large deployment forces along the catheter shaft and sheath from outside the patient. Well-behaved articulation structures will often include simple balloon arrays, with inflation of the balloons interacting with elongate skeletal support structures so as to improve articulation behavior of the skeleton. The array can be used to improve uniformity of bending along a segment of a flexible body such as a catheter. The articulation improvement structures can be employed in minimally invasive medical catheter systems, and also for industrial (Continued)

continuum robotics, for supporting imaging systems, for entertainment and consumer products, and the like.

14 Claims, 48 Drawing Sheets

(51) Int. Cl.
*A61F 2/966* (2013.01)
*A61M 25/00* (2006.01)
*A61F 2/24* (2006.01)
*A61B 17/00* (2006.01)

(52) U.S. Cl.
CPC ............ *A61F 2/966* (2013.01); *A61M 25/00* (2013.01); *A61B 17/00234* (2013.01); *A61B 2017/00309* (2013.01); *A61F 2/2436* (2013.01); *A61M 25/0136* (2013.01); *A61M 2205/0266* (2013.01)

(56) References Cited

U.S. PATENT DOCUMENTS

| | | | |
|---|---|---|---|
| 3,523,547 A | 8/1970 | Hatch, Jr. et al. | |
| 3,915,194 A | 10/1975 | Friedrich | |
| 3,934,605 A | 1/1976 | Legris | |
| 4,082,324 A | 4/1978 | Obrecht | |
| 4,230,143 A | 10/1980 | Dettmann et al. | |
| 4,494,417 A | 1/1985 | Larson et al. | |
| 4,762,130 A | 8/1988 | Fogarty et al. | |
| 4,784,042 A | 11/1988 | Paynter | |
| 4,794,912 A | 1/1989 | Lia | |
| 4,838,859 A | 6/1989 | Strassmann | |
| 4,890,611 A | 1/1990 | Monfort et al. | |
| 4,893,613 A | 1/1990 | Hake | |
| 4,900,218 A | 2/1990 | Sutherland | |
| 4,983,165 A * | 1/1991 | Loiterman | A61M 25/01 604/95.03 |
| 5,018,506 A | 5/1991 | Danna et al. | |
| 5,304,132 A | 4/1994 | Jang | |
| 5,308,356 A | 5/1994 | Blackshear, Jr. et al. | |
| 5,337,733 A | 8/1994 | Bauerfeind et al. | |
| 5,413,107 A | 5/1995 | Oakley et al. | |
| 5,469,756 A | 11/1995 | Feiten | |
| 5,489,270 A | 2/1996 | Van Erp | |
| 5,501,667 A | 3/1996 | Verduin, Jr. | |
| 5,529,088 A | 6/1996 | Asou | |
| 5,534,007 A * | 7/1996 | St Germain | A61F 2/95 606/191 |
| 5,619,993 A | 4/1997 | Lee | |
| 5,817,101 A * | 10/1998 | Fiedler | A61F 2/95 623/1.11 |
| 5,820,595 A | 10/1998 | Parodi | |
| 5,823,955 A | 10/1998 | Kuck et al. | |
| 5,865,801 A | 2/1999 | Houser | |
| 6,066,125 A | 5/2000 | Webster, Jr. | |
| 6,113,608 A * | 9/2000 | Monroe | A61F 2/966 604/264 |
| 6,146,339 A | 11/2000 | Biagtan et al. | |
| 6,178,872 B1 | 1/2001 | Schulz | |
| 6,503,194 B2 | 1/2003 | Pauker | |
| 6,527,739 B1 | 3/2003 | Bigus et al. | |
| 6,648,879 B2 | 11/2003 | Joye et al. | |
| 6,811,550 B2 | 11/2004 | Holland et al. | |
| 6,875,170 B2 | 4/2005 | Francois et al. | |
| 6,928,313 B2 | 8/2005 | Peterson | |
| 6,951,226 B2 | 10/2005 | Eriksson et al. | |
| 7,060,062 B2 | 6/2006 | Joye et al. | |
| 7,373,955 B2 | 5/2008 | Steinberg | |
| 7,422,579 B2 | 9/2008 | Wahr et al. | |
| 7,570,981 B2 | 8/2009 | Peterson | |
| 7,578,787 B2 | 8/2009 | Boese et al. | |

| | | | |
|---|---|---|---|
| 7,780,723 B2 | 8/2010 | Taylor | |
| 7,824,391 B2 | 11/2010 | Gesswein | |
| 7,850,683 B2 | 12/2010 | Elkins et al. | |
| 7,879,004 B2 | 2/2011 | Seibel et al. | |
| 7,957,790 B2 | 6/2011 | Kleen | |
| 7,963,911 B2 | 6/2011 | Turliuc | |
| 8,125,755 B2 | 2/2012 | Garcia et al. | |
| 8,201,473 B2 | 6/2012 | Knoll | |
| 8,372,055 B2 | 2/2013 | Thornton et al. | |
| 8,388,520 B2 | 3/2013 | Stefanchik et al. | |
| 8,398,540 B2 | 3/2013 | Hassidov et al. | |
| 8,423,115 B2 | 4/2013 | Koblish | |
| 8,469,059 B1 | 6/2013 | Forst | |
| 8,764,725 B2 | 7/2014 | Averbuch | |
| 8,845,523 B2 | 9/2014 | Lawrence et al. | |
| 8,863,608 B2 | 10/2014 | Fischer et al. | |
| 2001/0007070 A1 | 7/2001 | Stewart et al. | |
| 2002/0045929 A1 | 4/2002 | Diaz | |
| 2002/0049408 A1 | 4/2002 | Van Moorlegem et al. | |
| 2002/0058951 A1 | 5/2002 | Fiedler | |
| 2003/0069475 A1 | 4/2003 | Banik et al. | |
| 2006/0058598 A1 | 3/2006 | Esposito | |
| 2006/0084964 A1 | 4/2006 | Knudson et al. | |
| 2006/0235368 A1 | 10/2006 | Oz | |
| 2007/0060997 A1 | 3/2007 | de Boer | |
| 2007/0100235 A1 | 5/2007 | Kennedy, II | |
| 2007/0123925 A1 | 5/2007 | Benjamin et al. | |
| 2007/0169761 A1 | 7/2007 | Price | |
| 2007/0270686 A1 | 11/2007 | Ritter et al. | |
| 2007/0288095 A1 | 12/2007 | Wirtel et al. | |
| 2008/0091073 A1 | 4/2008 | Park et al. | |
| 2008/0215008 A1 | 9/2008 | Nance et al. | |
| 2009/0076584 A1 | 3/2009 | Mao et al. | |
| 2009/0105816 A1 | 4/2009 | Olsen et al. | |
| 2009/0281523 A1 | 11/2009 | Sacco et al. | |
| 2010/0168665 A1 * | 7/2010 | Skerven | A61M 25/0155 604/95.03 |
| 2011/0112632 A1 | 5/2011 | Chau et al. | |
| 2011/0270126 A1 | 11/2011 | Gunday et al. | |
| 2011/0295247 A1 | 12/2011 | Schlesinger et al. | |
| 2011/0295248 A1 | 12/2011 | Wallace et al. | |
| 2012/0271319 A1 | 10/2012 | Bromander et al. | |
| 2012/0310227 A1 | 12/2012 | Katou | |
| 2013/0091974 A1 | 4/2013 | Riwan et al. | |
| 2013/0096377 A1 | 4/2013 | Duindam et al. | |
| 2013/0103019 A1 | 4/2013 | Joye et al. | |
| 2013/0178838 A1 | 7/2013 | Malkowski et al. | |
| 2013/0296983 A1 | 11/2013 | Keller et al. | |
| 2013/0304181 A1 * | 11/2013 | Green | A61F 2/966 623/1.11 |
| 2014/0062405 A1 | 3/2014 | Videbaek | |
| 2014/0142666 A1 | 5/2014 | Phelan et al. | |
| 2014/0200649 A1 * | 7/2014 | Essinger | A61F 2/2436 623/1.12 |
| 2014/0243688 A1 | 8/2014 | Caron et al. | |
| 2014/0276933 A1 | 9/2014 | Hart et al. | |
| 2014/0276934 A1 | 9/2014 | Balaji et al. | |
| 2015/0057738 A1 * | 2/2015 | Hepke | A61F 2/2436 623/1.11 |
| 2015/0209558 A1 | 7/2015 | Charlebois et al. | |
| 2015/0265807 A1 | 9/2015 | Park et al. | |
| 2016/0128767 A1 | 5/2016 | Azamian et al. | |
| 2016/0279388 A1 | 9/2016 | Barrish et al. | |
| 2017/0021132 A1 | 1/2017 | Laby et al. | |
| 2017/0021143 A1 | 1/2017 | Barrish et al. | |
| 2017/0157361 A1 | 6/2017 | Barrish et al. | |
| 2017/0157363 A1 | 6/2017 | Barrish et al. | |
| 2018/0085559 A1 | 3/2018 | Laby et al. | |
| 2018/0200483 A1 | 7/2018 | Laby et al. | |

FOREIGN PATENT DOCUMENTS

| | | |
|---|---|---|
| CN | 107921236 | 4/2018 |
| EP | 3274038 | 1/2018 |
| EP | 3274039 | 1/2018 |
| EP | 3274040 | 1/2018 |

(56) References Cited

FOREIGN PATENT DOCUMENTS

| WO | 2007053625 | 5/2007 |
|---|---|---|
| WO | 2014128507 | 8/2014 |

OTHER PUBLICATIONS

Arsalan et al., "Comparison of Current Costs and Reimbursement for Transcatheter and Surgical Aortic Valve Replacement", J. Am. Coll. Cardiol., vol. 67, No. 13, ACC.i2 Interventional Cardiology, Available online at http://content.onlinejacc.org/article.aspxarticleid=2508037, Apr. 5, 2016, 2 pages.

Atzori et al., "Indoor Navigation System Using Image and Sensor Data Processing on a Smartphone", Optimization of Electrical and Electronic Equipment (OPTIM), 2012 13th International Conference, Available online at https://www.researchgate.net/publication/261267019_Indoor_navigation_system_using_image_and_sensor data_processing_on_a_smartphone, May 24-26, 2012, pp. 1158-1163.

Au et al., "Microvalves and Micropumps for BioMEMS", Micromachines, vol. 2, ISSN 2072-666X, Available online at www.mdpi.com/journal/micromachines, 2011, pp. 179-220.

Backer et al., "Percutaneous Transcatheter Mitral Valve Replacement", Circulation: Cardiovascular Interventions, Available online at http://circinterventions.ahajournals.org/content/7/3/400.full, 2014, pp. 400-409.

Bar-Cohen , "Worldwide ElectroActive Polymers", EAP (Artificial Muscles) Newsletter, vol. 16, No. 1, (The 31th issue), Available online at http://eap.jpl.nasa.gov, Jun. 2014, pp. 1-18.

BBC News Science & Environment , "Nanotube Yarns Twist Like Muscles", BBC News, Available online at http://www.bbc.co.uk/news/science-environment-15287185, Oct. 14, 2011, 8 pages.

Beahm et al., "Catheter Bonding Technology Overview", Avaialble online at www.beahmdesigns.com, Apr. 2012, 4 pages.

Biswal et al., "Development of an Active Catheter Mechanism Using IPMC for in Vivo Inspection", Journal of Mechatronics and Automation vol. 1, No. 1, Available online at: http://www.academia.edu/10757534/Development_of_an_Active_Catheter_Mechanism_using_IPMC_for_in_vivo_Inspection, 2014, 10 pages.

Bolling , "Can We Predict Mitral Valve Repair Rates by Individual Surgeons' Mitral Volume", Tex Heart Inst J., vol. 38, No. 6, 8th Current Trends in Aortic and Cardiothoracic Surgery, Available online at http://www.ncbi.nlm.nih.gov/pmc/articles/PMC3233323/, 2011, pp. 703-704.

Buntz , "Forget IoT: The Internet of Moving Things Is Where It Is At", Qmed, Available online at http://www.qmed.com/mpmn/medtechpulse/forget-iot-internet-moving-things-where-it, Dec. 10, 2014, 3 pages.

Buntz , "Graphene Breakthrough Could Be a Boon to Flexible Electronics", Electronic Components, Qmed, Available online at http://www.qmed.com/mpmn/medtechpulse/graphene-breakthrough-could-be-boon-flexible-electronicscid=nl.qmed02, Nov. 14, 2013, 1 page.

Buntz , "How Tiny Artificial Muscles Could Be Huge Energy Savers", Motion Control, Qmed, Available online at http://www.qmed.com/mpmn/medtechpulse/how-tiny-artificial-muscles-could-be-huge-energy-saverscid=nl.qmed02.20150223, Feb. 20, 2015, 3 pages.

Buntz , "Using a T-Shirt Printer to Make Medical Circuits", Qmed, Electronic Components, Available online at http://www.qmed.com/mpmn/medtechpulse/using-t-shirt-printer-make-medical-circuits, Nov. 17, 2014, 3 pages.

Catherine et al., "Comparative Review of Endoscopic Devices Articulations Technologies Developed for Minimally Invasive Medical Procedures", Applied Bionics and Biomechanics, vol. 8, 2011, pp. 151-171.

Chakraborty et al., "Mems Micro-Valve for Space Applications", Sensors and Actuators A: Physical, vol. 83, No. 1-3, 2000, pp. 188-193.

Chandgadkar , "An Indoor Navigation System for Smartphones", Available online at http://www.doc.ic.ac.uk/teaching/distinguished-projects/2013/a.chandgadkar.pdf, Jun. 18, 2013, 80 pages.

Chang et al., "Electrostatically-Actuated Reconfigurable Elastomer Microfluidics", Available online at http://people.eecs.berkeley.edu/~maharbiz/HH_paper_mpchang_0008.pdf, 4 pages.

Chen et al., "High-Pressure On-Chip Mechanical Valves for Thermoplastic Microfluidic Devices", The Royal Society of Chemistry, Lab Chip, vol. 9, 2009, pp. 3511-3516.

Clippard New! , "New 7 mm Electronic Valves", Available online at http://www.clippard.com/products/electronic-valve-7mm, 2 pages.

Conrad et al., "Closed Loop Task Space Control of an Interleaved Continuum-Rigid Manipulator", IEEE International Conference on Robotics and Automation, Available online at http://robotics.engr.wisc.edu/cgi-bin/wikiwp/category/continuum-robotics/, 2015, 8 pages.

Corma Inc. , "Corrugators and Pulsating Corrugators", Available online at http://corma.com/products/corrugators-pulsating-corrugators/, 2011, 3 pages.

Coyne , "Comprehensive Manufacturing of Microfluidic Diagnostic Devices", IVD, MDDI Medical Device and Diagnostic Industry, Jun. 17, 2014, 4 pages.

Creganna TACTX Medical , "Deflectable and Steerable Catheter Handbook", Terminology Guide & Design Options, Available online at http://www.creganna.com/wp-content/uploads/Steeringand-DeflectionTerminologyrev3.pdf, 7 pages.

Dabove et al., "Inertial Sensors for Smartphones Navigation", SpringerPlus, vol. 4, No. 834, Available online at http://www.ncbi.nlm.gov/pmc/articles/PMC4695469/, 2015, 18 pages.

D'Arcy et al., "Valvular Heart Disease: The Next Cardiac Epidemic", vol. 97, No. 2, Available online at http://heart.bmj.com/content/97/2/91.extract, 2011, pp.91-93.

De Sars et al., "A Practical Approach to the Design and Control of Active Endoscopes", Mechatronics, vol. 20, Available online at http://www.elsevierscitech.com/pdfs/Mechatronics_DeSars.pdf, 2010, pp. 251-264.

DMQ Inc. , "Product Datasheet: silQflo™ Silicon Servo Valve", Available online at http://www.dmq-us.com/wp-content/uploads/2015/02/SSV-Datasheet-Rev-1.001.pdf, 2 pages.

Don et al., "Novel Velocity Model to Improve Indoor Localization Using Inertial Navigation With Sensors on a Smart Phone", Available online at http://arxiv.org/pdf/1601.03004.pdf, Jan. 12, 2016, 5 pages.

Dupont et al., "Snakes, Worms and Catheters: Continuum and Serpentine Robots for Minimally Invasive Surgery", IEEE ICRA Full Day Workshop, May 3, 2010, 60 pages.

Eitel , "The Rise of Soft Robots and the Actuators that Drive Them", Available online at http://machinedesign.com/robotics/rise-soft-robots-and-actuators-drive-them, Sep. 12, 2013, 7 pages.

Elveflow Plug & Play , "Microfluidics and Microfluidic Devices: A Review", Available online at http://www.elveflow.com/microfluidic-tutorials/microfluidic-reviews-and-tutorials/microfluidics-and-microfluidic-device-a-review/, 2015, 10 pages.

EP Vantage Ltd. , "Edwards Tightens Transcatheter Valve Stranglehold", Available online at http://www.epvantage.com/Universal/View.aspxtype=Story&id=580885&isEPVantage=yes, Jun. 18, 2015, 2 pages.

EUCOG Wiki , "Compliant Robots", Available online at http://www.eucognition.org/eucog-wiki/Compliant_robots, 2012, 5 pages.

Fedak et al., "Evolving Concepts and Technologies in Mitral Valve Repair", American Heart Association, Inc., Contemporary Reviews in Cardiovascular Medicine, vol. 117, No. 7, Available online at http://circ.ahajournals.org/content/117/7/963.full, Feb. 19, 2008, pp. 963-974.

Festo AG & Co. KG , "Systematic Expertise Through Continuous Further Development", Bionic Handling Assistant, Available online at https://www.festo.com/net/supportportal/files/42050/brosch_fc_bha_3_0_en_lo.pdf, Apr. 2012, 6 pages.

Fite et al., "A Gas-Actuated Anthropomorphic Prosthesis for Transhumeral Amputees", IEEE Transactions on Robotics, vol. 24, No. 1, Feb. 2008, pp. 159-169.

Flexpoint Sensor Systems, Inc. , "The Benefits of Using Bend Sensors", Sensor Products, Inc., Available online at www.sensorprod.com, 2 pages.

(56) References Cited

OTHER PUBLICATIONS

Fornell, "Transcatheter Mitral Valve Replacement Devices in Development", Diagnostic and Interventional Cardiology, Available online at http://www.dicardiology.com/article/transcatheter-mitral-valve-replacement-devices-development, Dec. 30, 2014, 5 pages.

Fu et al., "Research on the Axis Shape of an Active Catheter", Int. J. Med. Robot.; vol. 4, No. 1, Mar. 2008, pp. 69-76.

Fu et al., "Steerable Catheters in Minimally Invasive Vascular Surgery", Int. J. Med. Robot., vol. 5, No. 4, Dec. 2009, pp. 381-391.

Gionata et al., "An Inertial and Qr Code Landmarks-Based Navigation System for Impaired Wheelchair Users", Available online at https://www.researchgate.net/publication/261551014_An_inertial_and_QR_code_landmarks-based_navigation_system_for_impaired_wheelchair_users, May 29, 2014, pp. 205-214.

Grube, "Development of a TMVR Device Challenge to Innovators", ICI meeting, Dec. 13-15, 2015, 30 pages.

Haga et al., "Active Bending Catheter and Endoscope Using Shape Memory Alloy Actuators", Available online at www.intechopen.com, Shape Memory Alloys, 2010, 21 pages.

Haga et al., "Multi-Functional Active Catheter", Available online at http://bdml.stanford.edu/twiki/pub/Haptics/DesignReferencesSummer2009/MultifunctionalActiveCatheter.pdf, pp. 147-186.

Herrmann et al., "Novel Transcatheter Approaches", Heart Valve Summit, American association of Thoracic surgery, Available online at http://aats.org/multimedia/files/valve/2015/Presentations/Thursday/600-Herrmann.pdf, 2015, 26 pages.

Ikeuchi et al., "Development of Pressure-Driven Micro Active Catheter using Membrane Micro Emboss Following Excimer Laser Ablation (MeME-X) Process", IEEE International Conference on Robotics and Automation, Available online at http://ir.nul.nagoya-u.ac.jp/jspui/bitstream/2237/13924/1/ICRA09_MeMEX.pdf, May 12-17, 2009, pp. 4469-4472.

Jagadeesan, "Design and Control of an Active Catheter", Available online at http://scholar.harvard.edu/jayender/activecatheter, Jul. 14, 2016, 2 pages.

Jia et al., "Online Camera-Gyroscope Auto-Calibration for Cellphones", IEEE Transactions on Image Processing, Available online at http://users.ece.utexas.edu/~bevans/papers/2015/autocalibration/autocalibrationIEEETransImageProcPaperDraft.pdf, 2013, 11 pages.

John Muir Health, "U.S. Aortic Stenosis Disease Prevalence and Treatment Statistics", Facts and Figures, Available Online at https://www.johnmuirhealth.com/services/cardiovascular-services/intervention/transcatheter-aortic-valve-replacement/facts-and-figures.html, 2016, 3 pages.

Johnson, "Modeling of Frictional Gas Flow in a Piezoelectrically Actuated High-pressure Microvalve for Flowrate Control", Dec. 16, 2005, 197 pages.

Jung et al., "A Modeling Approach for Continuum Robotic Manipulators: Effects of Nonlinear Internal Device Friction", IEEE/RSJ International Conference on Intelligent Robots and Systems, Sep. 25-30, 2011, pp. 5139-5146.

Kasahara et al., "Surface Modification of Polyethylene Terephthalate (PET) by 172-nm Excimer lamp", Technical paper, 2012, pp. 47-54.

Kato et al., "An Inchworm Type In-Pipe Mobile Microrobot Driven by Three Gas-liquid Phase-change Actuators", Proceedings of the Annual Meeting—American Society for Precision Engineering, 2003, pp. 295-298.

Kim et al., "Materials for Multifunctional Balloon Catheters with Capabilities in Cardiac Electrophysiological Mapping and Ablation Therapy", Nat Mater., vol. 10, No. 4, Available online at http://www.ncbi.nlm.nih.gov/pmc/articles/PMC3132573/, Apr. 2011, pp. 316-323.

Kirby et al., "Microfluidic Routing of Aqueous and Organic Flows at High Pressures: Fabrication and Characterization of Integrated Polymer Microvalve Elements", The Royal Society of Chemistry, Lab Chip, vol. 5, 2005, pp. 184-190.

Korane, "Robot Imitates an Elephant's Trunk", Available online at http://machinedesign.com/robotics/robot-imitates-elephant-s-trunk, Sep. 13, 2010, 5 pages.

Labsmith, Inc., "LabSmith uProcess™ System", LabSmith, Inc., Microfluidic Automation, Available online at http://www.labsmith.com/products/LabSmith_uProcess_Brochure.pdf_ga=1.142274551.472763250.1458083262., 2015, 6 pages.

Langelaar et al., "Modeling of a Shape Memory Alloy Active Catheter", 45th AIAA/ASME/ASCE/AHS/ASC Structures, Structural Dynamics & Materials Conference, American Institute of Aeronautics and Astronautics, Available online at http://citeseerx.ist.psu.edu/viewdoc/downloaddoi=10.1.1.125.1080&rep=rep1&type=pdf, Apr. 19-22, 2004, 16 pages.

Lee et al., "Fabrication, Characterization, and Computational Modeling of a Piezoelectrically Actuated Microvalve for Liquid Flow Control", Journal of Microelectromechanical Systems, vol. 15, No. 3, IEEE, Jun. 2006, pp. 686-696.

Levy, "Tiny Ultrasound Camera Images Blood Vessel Interior in 3-D", Medical Imaging, Qmed, Available online at http://www.qmed.com/mpmn/medtechpulse/tiny-ultrasound-camera-images-blood-vessel-interior-3-dcid=nl.qmed02, Mar. 3, 2014, 5 pages.

Maglione et al., "Ultra-High-Pressure Balloon Angioplasty for Treatment of Resistant Stenoses Within or Adjacent to Previously Implanted Pulmonary Arterial Stents", Circulation: Cardiovascular Interventions, Available online at http://circinterventions.ahajournals.org/content/2/1/52.full, 2009, pp. 52-58.

Malek et al., "Femtosecond Laser Machining and Lamination for Large-Area Flexible Organic Microfluidic Chips", European Physical Journal: Applied Physics, EDP Sciences, Available online at https://hal.archives-ouvertes.fr/hal-00480155/document, Apr. 2009, 8 pages.

Mazzarese, "Low-Profile Balloon Catheters are Critical to TAVR's Success", Medical Tubing Types by MDDI Staff, Available online at http://www.mddionline.com/article/low-profile-balloon-catheters-are-critical-tavr-success-10-21-2014cid=nl.mddi01.20141023, Oct. 21, 2014, 3 pages.

MDDI, Medical Plastics, "The Effect of Extrusion and Blow Molding Parameters on Angioplasty Balloon Production", Available online at http://www.mddionline.com/article/effect-extrusion-and-blow-molding-parameters-angioplasty-balloon-production, May 1, 1998, 4 pages.

Medtronic, "CoreValve™ System", Transcatheter Aortic Valve Delivery Catheter System Compression Loading System, 2014, 61 pages.

Messenger, "A Comprehensive Guide to the U.S. TAVR Market: Surveying the Field", Available online at http://www.meddeviceonline.com/doc/a-comprehensive-guide-to-the-u-s-tavr-market-surveying-the-field-0001, Apr. 12, 2016, 7 pages.

Mohty et al., "Valvular Heart Disease in Elderly Adults", Available online at http://www.uptodate.com/contents/valvular-heart-disease-in-elderly-adults, 2016, 6 pages.

Mount Sinai Hospital, "Researchers Compare Two-Year Clinical Outcomes of Mitral Valve Replacement and Repair in Treating Severe Valve Regurgitation", Icahn School of Medicine at Mount Sinai, Available online at http://www.mountsinai.org/about-us/newsroom/press-releases/researchers-compare-twoyear-clinical-outcomes-of-mitral-valve-replacement-and-repair-, Nov. 9, 2015, 2 pages.

Mueller et al., "An Overview of Mems-based Micropropulsion Developments at JPL", Acta Astronautica, vol. 52, No. 9-12, Selected Proceedings of the 3rd IAA International Symposium on Small Satellites for Earth Observation, May-Jun. 2003, 15 pages.

Mueller et al., "Design and Fabrication of MEMS-Based Micropropulsion Devices at JPL", Proceedings of SPIE vol. 4558, 2001, pp. 57-71.

Muller et al., "Remote Control Catheter Navigation: Options for Guidance Under MRI", Journal of Cardiovascular Magnetic Resonance, vol. 14, No. 33, Available online at http://www.jcmr-online.com/content/14/1/33, 2012, pp. 1-9.

Newmarker, "How Lasers are Changing MedTech", Lasers, Qmed, Available online at http://www.qmed.com/mpmn/medtechpulse/how-lasers-are-changing-medtechcid=nl.qmed02, Jan. 14, 2014, 3 pages.

Newmarker, "How Scotch Tape is Driving Diagnostics Breakthroughs", Medical Plastics, Qmed, Available online at http://www.qmed.com/mpmn/medtechpulse/how-scotch-tape-driving-diagnostics-breakthroughscid=nl.qmed02.20141002, Oct. 1, 2014, 3 pages.

(56) References Cited

OTHER PUBLICATIONS

Nolker et al., "Differences in Tissue Injury and Ablation Outcomes in Atrial Fibrillation Patients—Manual versus Robotic Catheters", Journal of Atrial Fibrillation, Department of Cardiology, Heart and Diabetes Center, vol. 6, No. 2, Aug.-Sep. 2013, pp. 82-88.

Nucryovascular, LLC , "Peripheral Dilatation Catheter Peripheral Dilatation System", Vascular solutions, PolarCath™ over-the-wire, Available online at www.vasc.com, pp. 1-12.

Oh et al., "A Review of Microvalves", Topical Review, Journal of Micromechanics and Microengineering, vol. 16, 2006, pp. R13-R39.

OMED Qualified Suppliers , "A Tiny Spectrometer that Costs 10 Bucks", Qmed, Available online at http://www.qmed.com/mpmn/medtechpulse/tiny-spectrometer-costs-10-buckscid=nl.qmed02.20141216, Dec. 12, 2014, 3 pages.

OMED Qualified Suppliers , "How 3-D Printing Can Help Accelerate Fluidic Manifold Delivery", Qmed, Available online at http://www.qmed.com/mpmn/medtechpulse/how-3-d-printing-can-help-accelerate-fluidic-manifold-deliverycid=nl.qmed02.20150507, May 6, 2015, 3 pages.

OMED Qualified Suppliers , "Introducing 3-D Injection Molding", Qmed, Available online at http://www.qmed.com/mpmn/gallery/image/4-introducing-3-d-injection-molding, 2014, 2 pages.

OMED Qualified Suppliers , "Overcoming Engineering Challenges: Developing a Tiny Robotically Steerable Guidewire", Qmed, Medtech Pulse Blog, Available online at http://www.qmed.com/mpmn/medtechpulse/overcoming-engineering-challenges-developing-tiny-robotically-steerable-guidewirecid=nl_qmed_daily, Feb. 15, 2013, 2 pages.

Ono et al., "Development of a Cylinder Type Gas-liquid Phase-change Actuator", 2 pages.

Parmar , "FDA Approves St. Jude Medical's Force-Sensing Ablation Catheters for AF", Regulatory and Compliance, MDDI Medical Device and Diagnostic Industry, Available online at http://www.mddionline.com/article/fda-approves-st-jude-medicals-force-sensing-ablation-catheters-af-102714cid=nl.mddi01.20141028, Oct. 27, 2014, 3 pages.

Peelsil™ Tubing , "Scientific Tubing", SGE, Glass Lined Tubing (GLT™), Available online at www.sge.com, Fused Silica Tubing brochure PD-0230-Aw, 2001, 6 pages.

Penning et al., "A Combined Modal-Joint Space Control Approach for Minimally Invasive Surgical Continuum Manipulators", Advanced Robotics, vol. 28, No. 16, Jul. 2014, 41 pages.

Penning et al., "An Evaluation of Closed-Loop Control Options for Continuum Manipulators", IEEE, 2012, 6 pages.

Penning , "ICRA 2012 Recap", Available online at http://robotics.engr.wisc.edu/cgi-bin/wikiwp/2012/11/icra-2012-recap/, Nov. 11, 2012, 2 pages.

Penning et al., "Towards Closed Loop Control of a Continuum Robotic Manipulator for Medical Applications", IEEE, 2011, 6 pages.

Plastics , "Corrugator Technologies: Overview and New Developments", Corrugator technologies overview, Available at http://www.plastics.gl/extrusion-profile/corrugator-technologies-overview/, 2015, 8 pages.

Pollock , "Bionic Ants Could be Tomorrow's Factory Workers", Available online at http://www.reuters.com/article/2015/03/30/us-germany-bionic-ants-idUSKBN0MQ1WD20150330, Mar. 30, 2015, 3 pages.

Preston-Maher et al., "A Technical Review of Minimally Invasive Mitral Valve Replacements", Cardiovascular Engineering and Technology, vol. 6, No. 2, Jun. 2015, pp. 174-184.

Profilepipe Machinery Inc. , "Convoluted Tubing to an Outer Diameter of 65 mm", Available online at http://www.profilepipe.com/small_corrugators.html, 2015, 2 pages.

QMED Qualified Suppliers , "Tiny Artificial Muscles", Available online at http://www.qmed.com/mpmn/gallery/image/1-tiny-artificial-muscles, Jul. 14, 2016, 1 page.

QMED, Electronic Components , "How Micro-Location Could Boost Healthcare IoT", Available online at http://www.qmed.com/mpmn/medtechpulse/how-micro-location-could-boost-healthcare-iotcid=nl.x.qmed02.edt.aud.qmed.20160606, Jun. 3, 2016, 2 pages.

Quero et al., "A Novel Pressure Balanced Microfluidic Valve", Proc. ISCAS, IEEE, 2002, pp. 1-4.

Rich et al., "Costs for Mitral Valve Surgery According to STS Preoperative Risk: Implications for Transcatheter Mitral Therapies", American Association for Thoracic Surgery, Available Online at http://aats.org/mitral/abstracts/2015/P165.cgi, 2016, 2 pages.

Roriz et al., "Fiber Optic Intensity-Modulated Sensors: A Review in Biomechanics", Photonic Sensors, vol. 2, No. 4, 2012, pp. 315-330.

Rossiter et al., "Printing 3D Dielectric Elastomer Actuators for Soft Robotics", SPIE Proceedings, vol. 7287, Apr. 6, 2009, 2 pages.

Schut , "Corrugator Vacuum Forming", Plastics Technology, Available online at http://www.ptonline.com/articles/'corrugator-vacuum-forming', Jul. 2005, 4 pages.

SGE Analytical Science , "Tubing, Stainless Steel Tubing and Terry-Tool Tubing Cutter", 2011, 10 pages.

Shoa et al., "Conducting Polymer Based Active Catheter for Minimally Invasive Interventions inside Arteries", Conf Proc IEEE Eng Med Biol Soc, Available online at http://mm.ece.ubc.ca/mediawiki/images/b/b7/PID616280.pdf, 2008, pp. 2063-2066.

Sparkfun , "Accelerometer, Gyro and IMU Buying Guide", Available online at https://www.sparkfun.com/pages/accel_gyro_guide, accessed from the internet on Jul. 14, 2016, 10 pages.

Strickland , "Inside an MRI, a Non-Metallic Robot Performs Prostate Surgery", Available online at http://spectrum.ieee.org/automaton/robotics/medical-robots/inside-an-mri-a-nonmetallic-robot-performs-prostate-surgery, Jul. 8, 2015, 3 pages.

Takizawa et al., "Development of a Microfine Active Bending Catheter Equipped with MIF Tactile Sensors", Available online at http://www.ics.forth.gr/bioloch/internal/papers/Olympus.pdf, 1999, 7 pages.

Taramasso et al., "Current Challenges in Interventional Mitral Valve Treatment", J. Thorac. Dis., vol. 7, No. 9, Available online at http://www.ncbi.nlm.nih.gov/pmc/articles/PMC4598533/, 2015, pp. 1536-1542.

Teleflex Incorporated , "Balloons and Balloon Catheters", Available online at http://www.teleflexmedicaloem.com/diagnostic-and-interventional-catheters/balloon-catheters/, 2015, 3 pages.

Temiz et al., "Lab-on-a-Chip Devices: How to Close and Plug the Lab", Microelectronic Engineering, vol. 132, 2015, pp. 156-175.

Tokai Medical Products Inc. , "PTA Sphere-Curve", Available online at http://www.tokaimedpro.co.jp/en/products/2009/000056.html, Jul. 14, 2016, 2 pages.

Tung et al., "Laser-Machined Shape Memory Alloy Actuators for Active Catheters", Mechatronics, IEEE/ASME Transactions on, vol. 12, No. 4, Aug. 2007, pp. 439-446.

Van Oosten et al., "Printed Artificial Cilia from Liquid-crystal Network Actuators Modularly Driven by Light", Nature Materials, vol. 8, Available online at http://www.nature.com/nmat/journal/v8/n8/full/nmat2487.html, 2009, pp. 677-682.

Veeramani , "A Transformative Tool for Minimally Invasive Procedures: Design, Modeling and Real-time Control of a Polycrystalline Shape Memory Alloy Actuated Robotic Catheter", 2009, 198 pages.

Walters , "Gas-Flow Calculations: Don't Choke", Applied Flow Technology, Chemical Engineering, Available online at http://www.aft.com/documents/AFT-CE-Gasflow-Reprint.pdf, Jan. 2000, 8 pages.

Wasserman , "Edwards and Medtronic Turn up TAVR Competition with Positive Study Data", Available online at http://www.fiercemedicaldevices.com/story/edwards-and-medtronic-turn-tavr-competition-positive-study-data/2015-03-16, Mar 16, 2015, 3 pages.

Webb et al., "Transcatheter Aortic Valve Implantation: The Evolution of Prostheses, Delivery Systems and Approaches", Archives of Cardiovascular Disease, vol. 105, 2012, pp. 153-159.

Weber et al., "Side-Selective Atrial Transseptal Laser Puncture", The Journal of Innovations in Cardiac Rhythm Management, vol. 4, Avaiable online at http://www.innovationsincrm.com/cardiac-rhythm-management/2013/december/524-side-selective-atrial-transseptal-laser-puncture, Dec. 2013, pp. 1481-1485.

Wirtl et al., "White Paper Piezo Technology in Pneumatic Valves", Festo AG & Co. KG, 2014, pp. 1-9.

(56) References Cited

OTHER PUBLICATIONS

Wood, "Early Results for Transcatheter Mitral Valve Replacement Reveal Complications and Challenges for the Long Road Ahead", Available online at http://www.tctmd.com/show.aspxid=133937, Feb. 22, 2016, 1 pages.

Wutzler et al., "Robotic Ablation of Atrial Fibrillation", Department of Cardiology, . Vis. Exp. (99), e52560, Available online at http://www.jove.com/video/52560/robotic-ablation-of-atrial-fibrillation, 2015, 14 pages.

Yang et al., "Leak-Tight Piezoelectric Microvalve for High-Pressure Gas Micropropulsion", Journal of Microelectromechanical Systems, vol. 13, No. 5, IEEE, Available Online at http://web.stevens.edu/ses/documents/fileadmin/documents/pdf/JMEMS_hp_valve.pdf, Oct. 2004, pp. 799-807.

Yarbasi et al., "On the Design of a Continuum Robot with Extendable Balloons", Department of Mechanical Engineering, 2015, 1 page.

You et al., "A Doubly Cross-Linked Nano-Adhesive for the Reliable Sealing of Flexible Microfluidic Devices", Lab Chip., vol. 13, No. 7, Available online at http://www.ncbi.nlm.nih.gov/pubmed/23381132, Apr. 2013, pp. 1266-1272.

\* cited by examiner

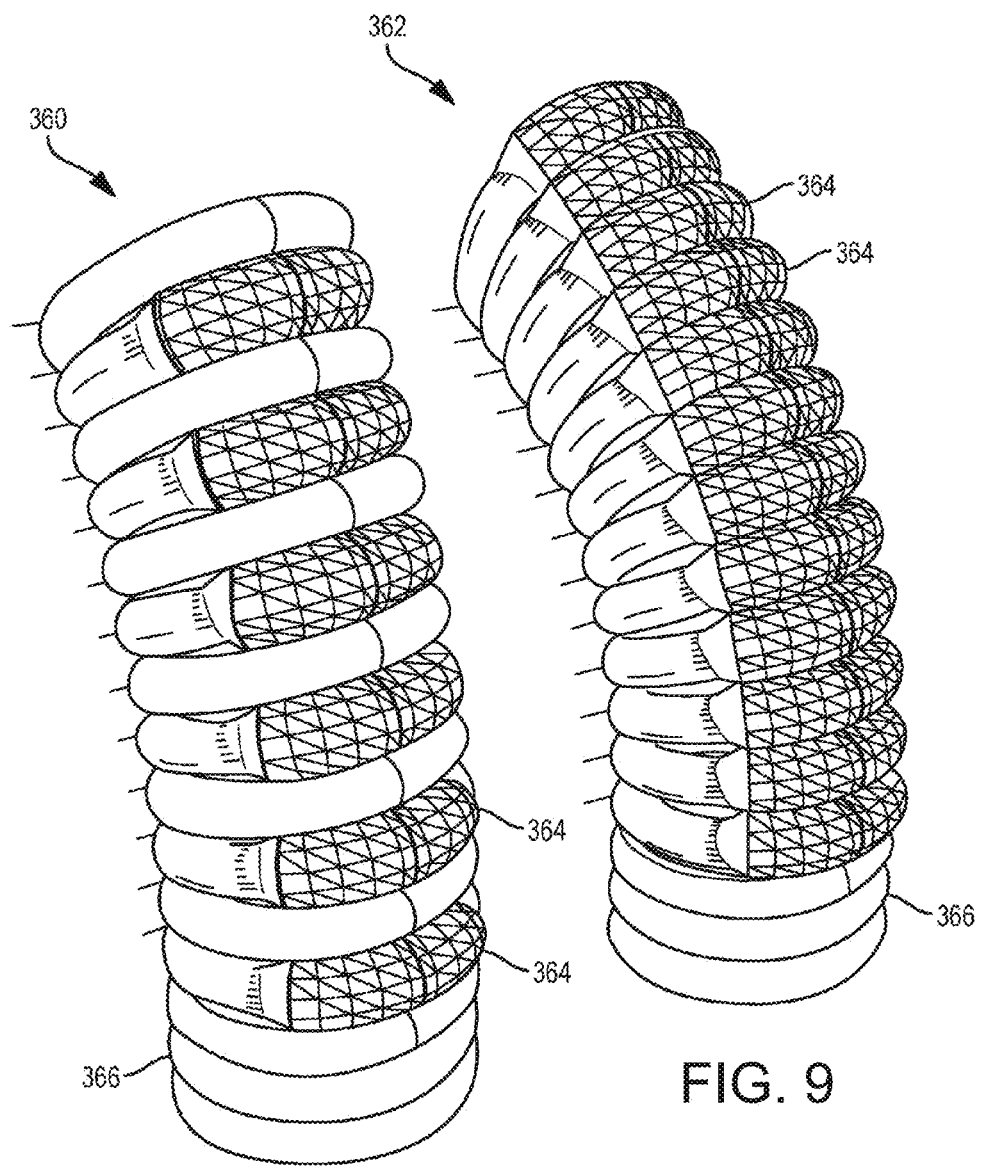

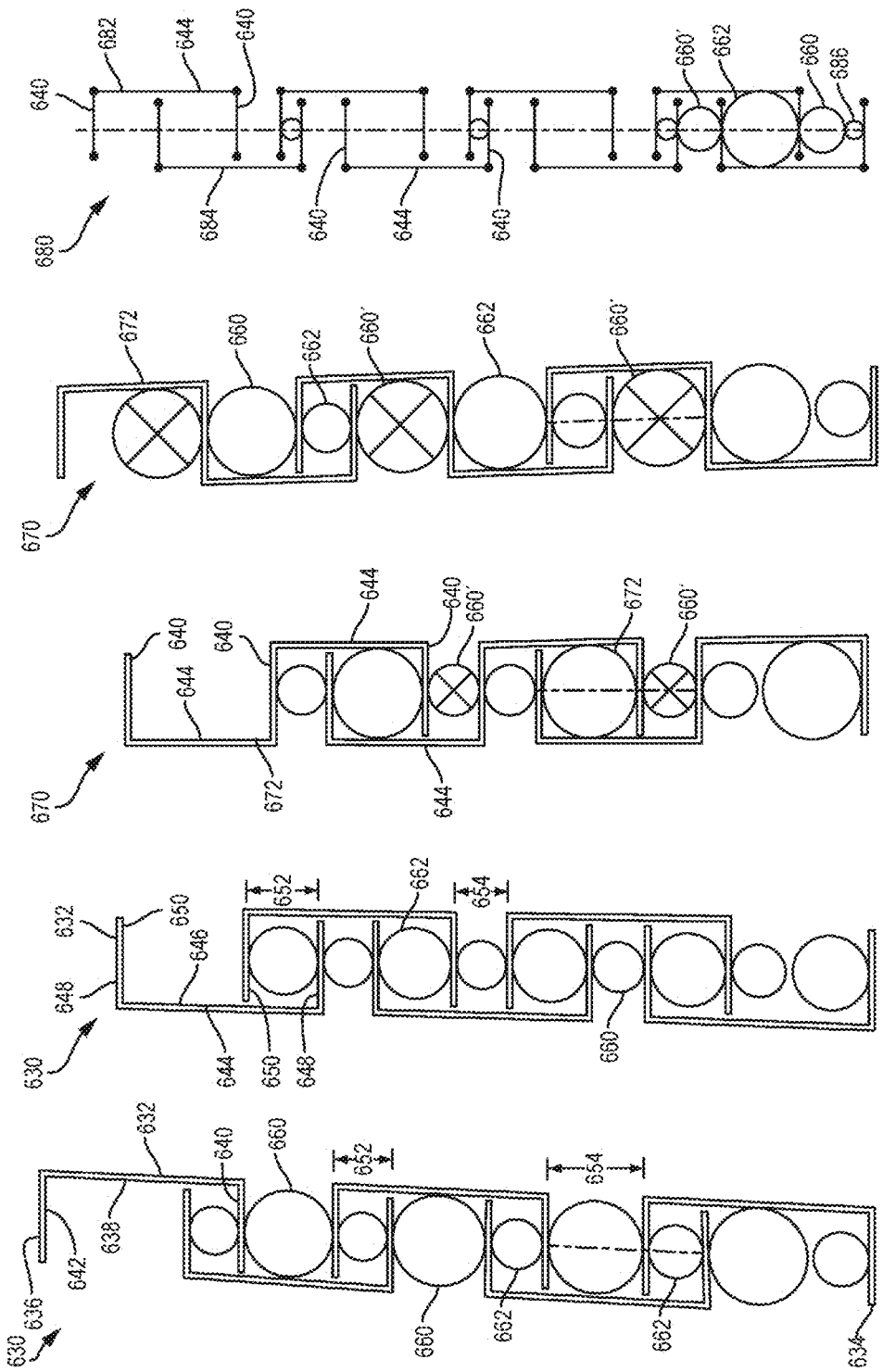

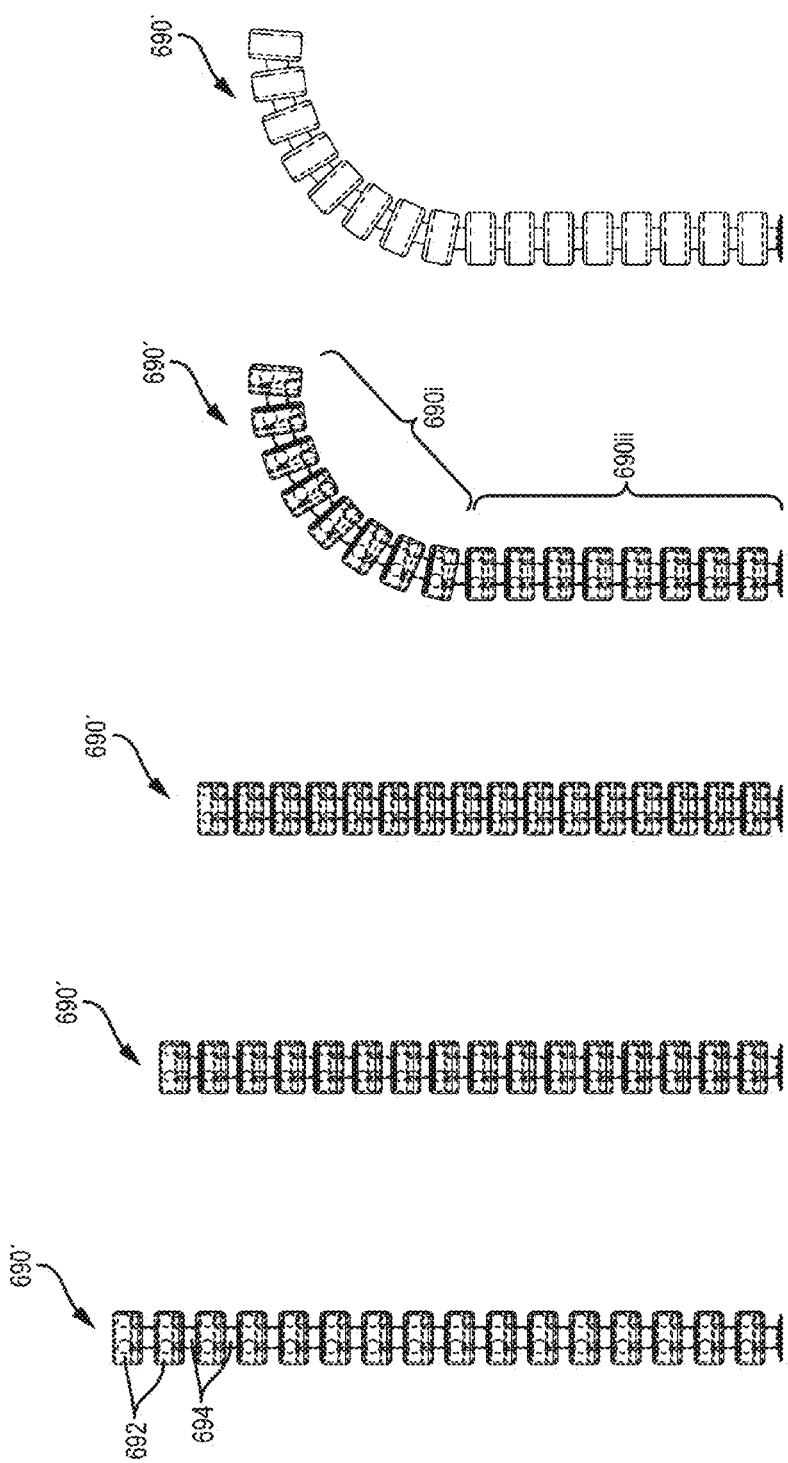

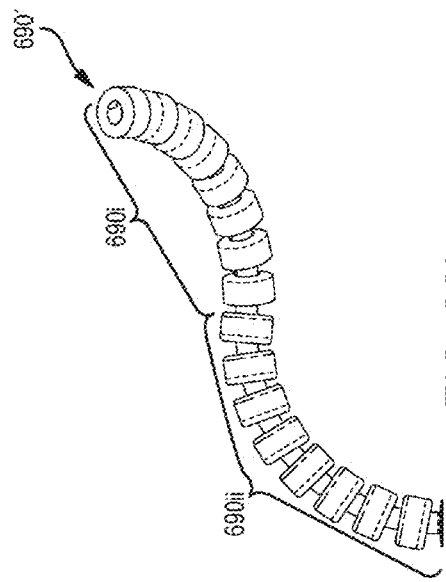
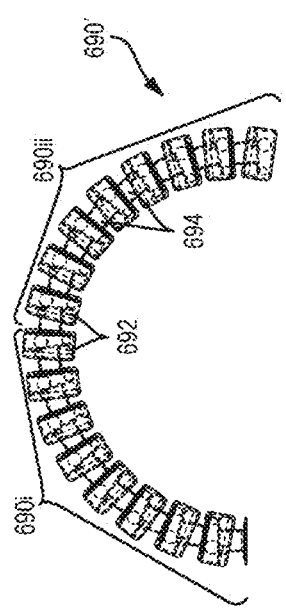
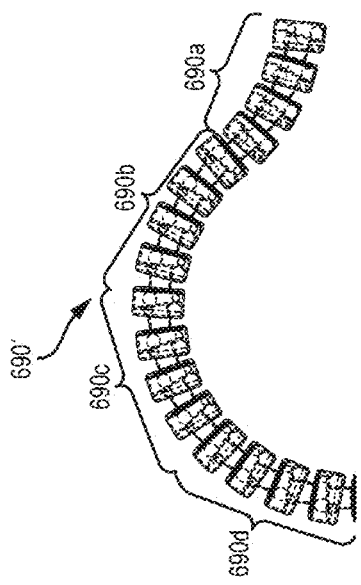
FIG. 23H
FIG. 23I
FIG. 23J

FIG. 24A
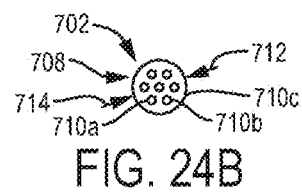
FIG. 24B
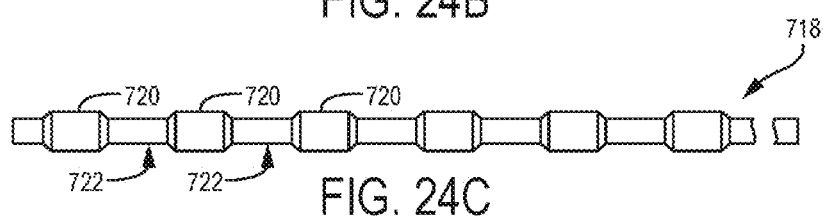
FIG. 24C
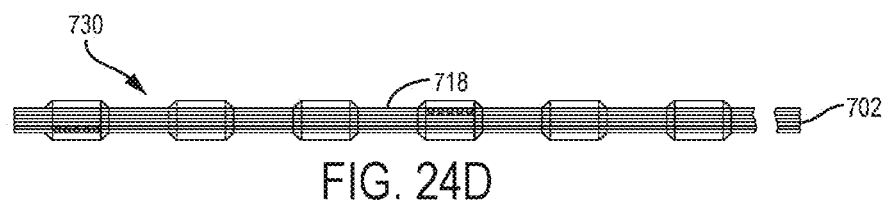
FIG. 24D
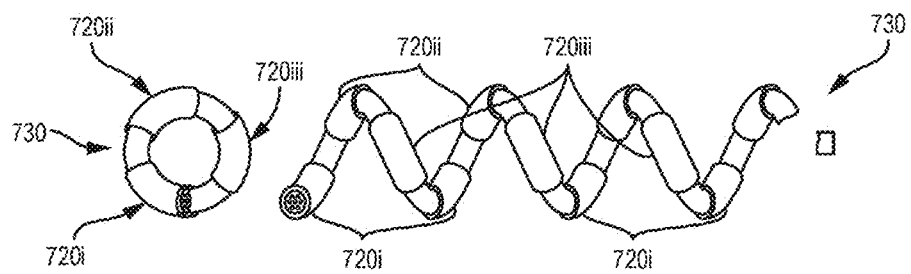
FIG. 24E1    FIG. 24E
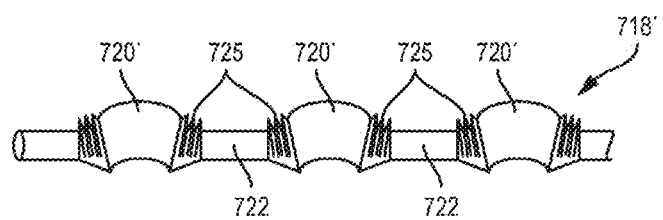
FIG. 24E-2

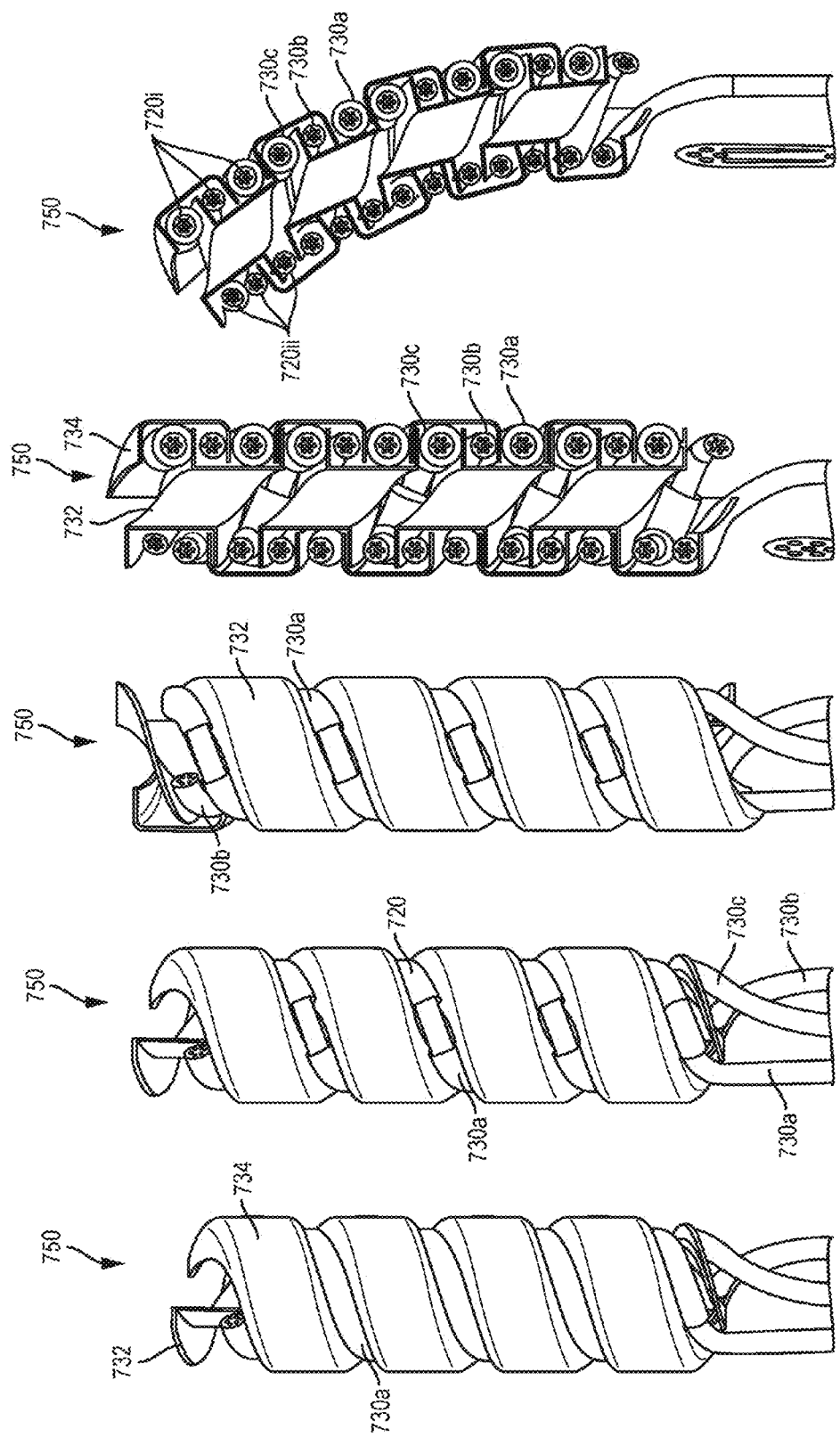

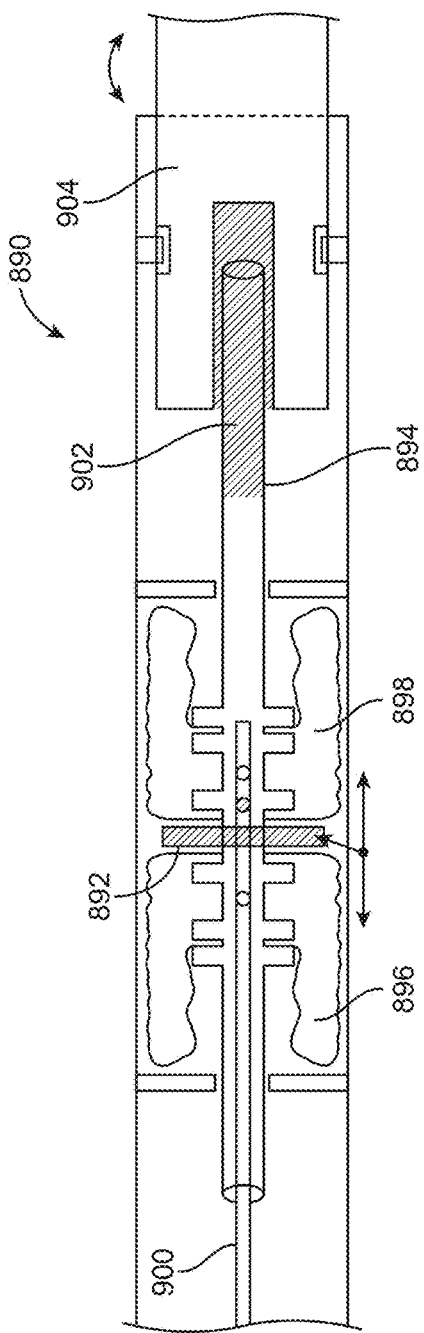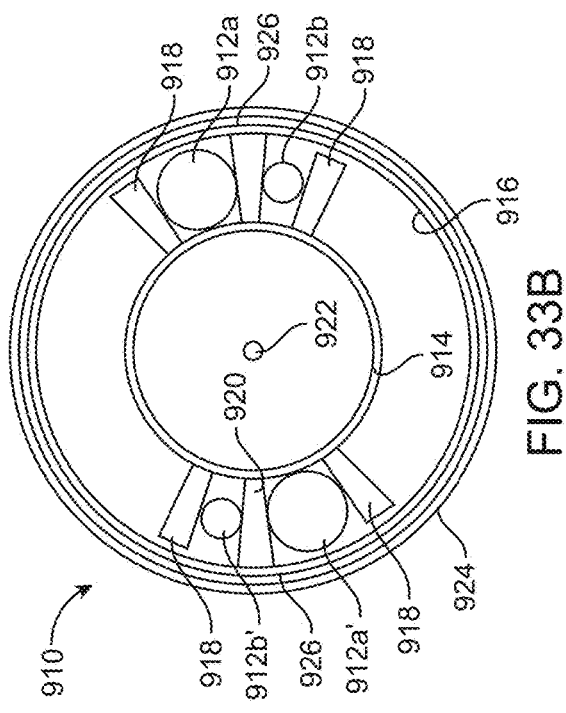

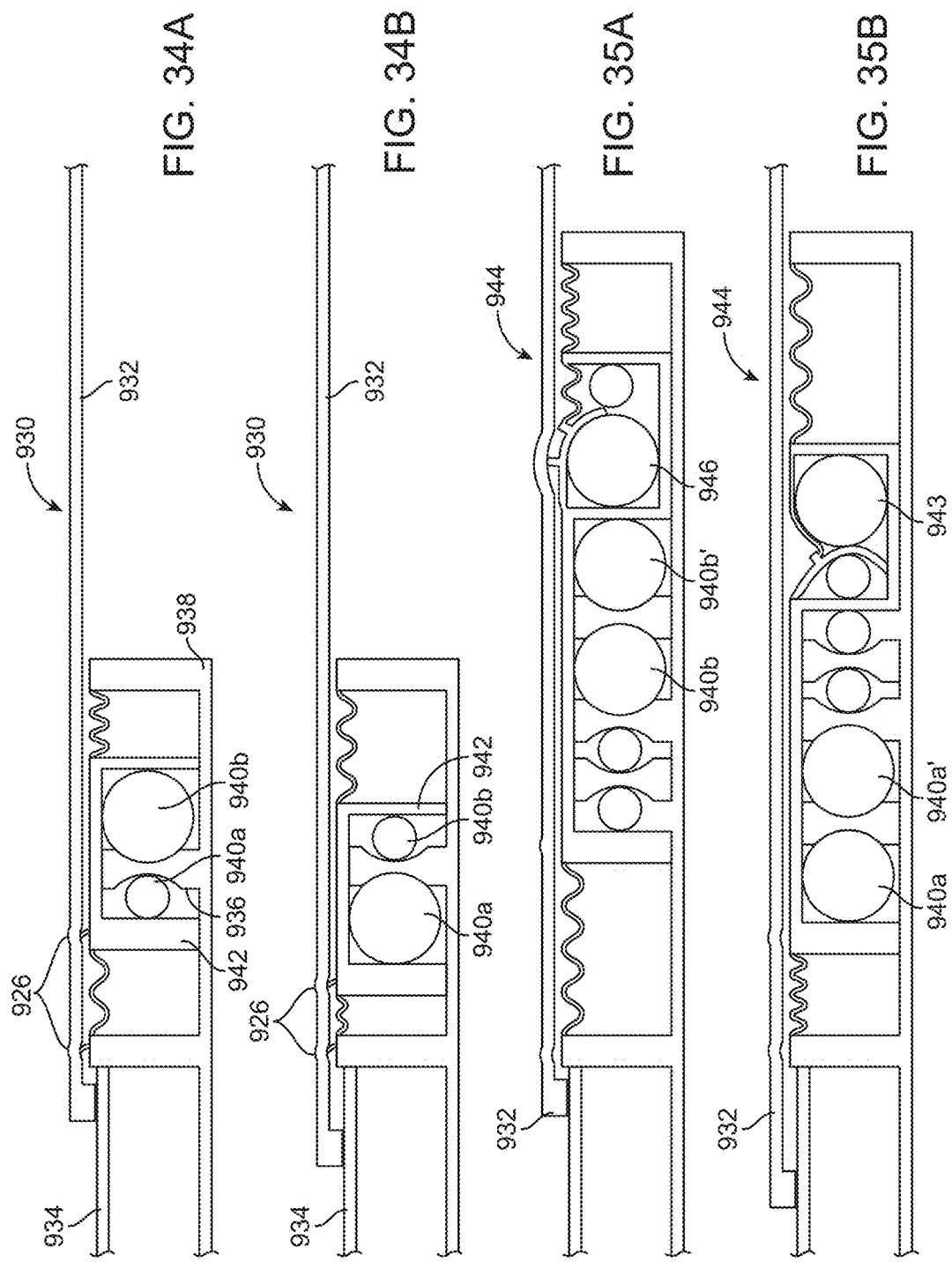

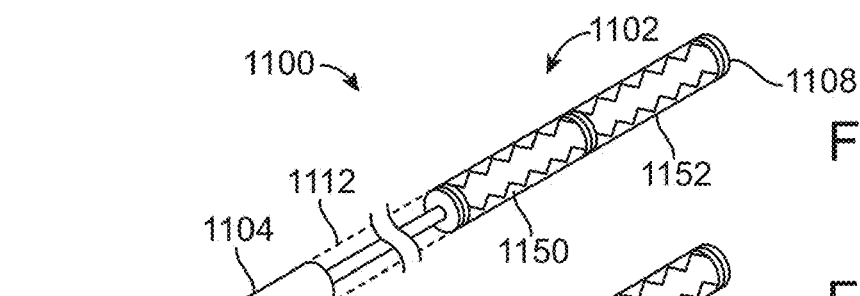
FIG. 38A
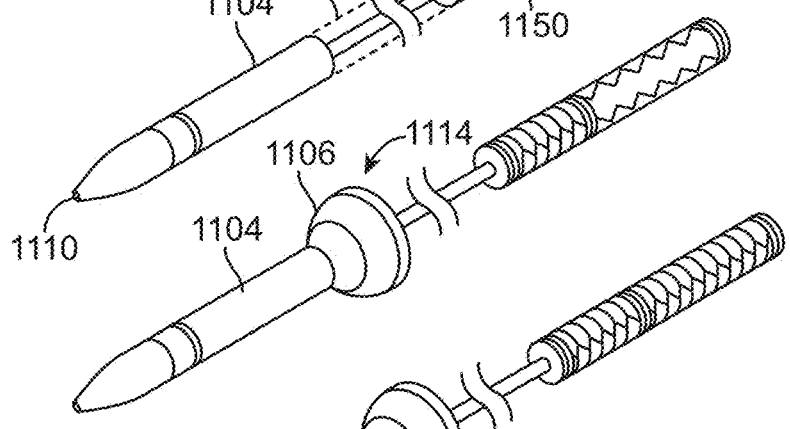
FIG. 38B
FIG. 38C
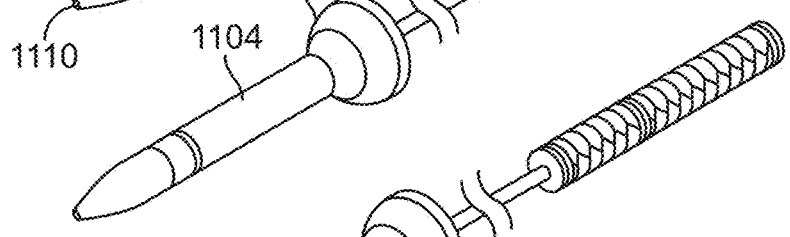
FIG. 38D
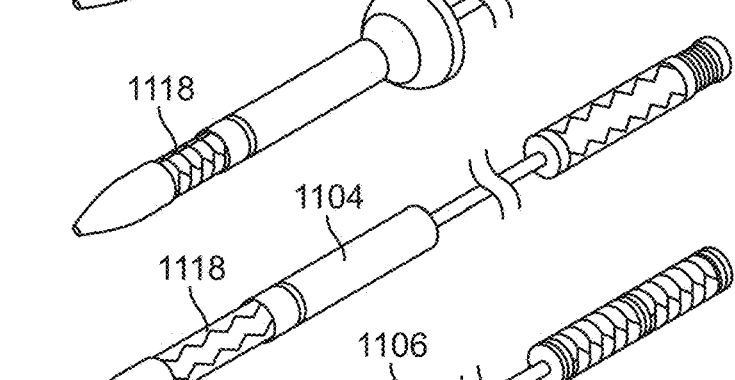
FIG. 38E
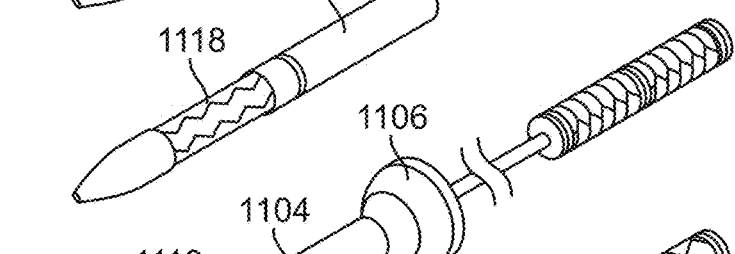
FIG. 38F
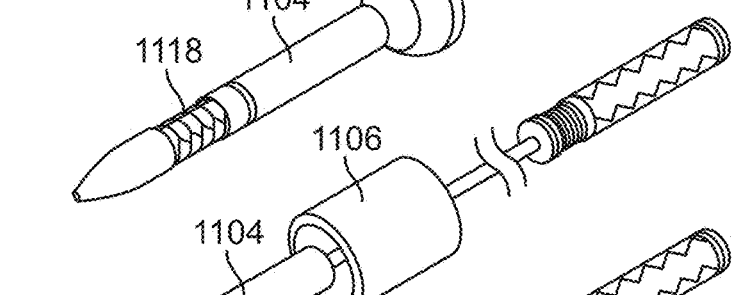
FIG. 38G
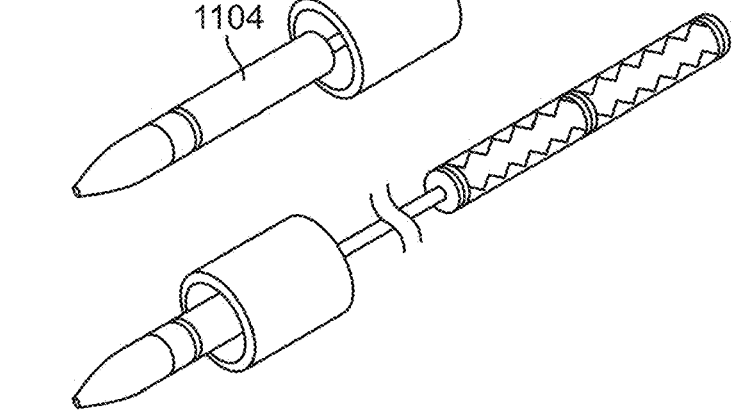

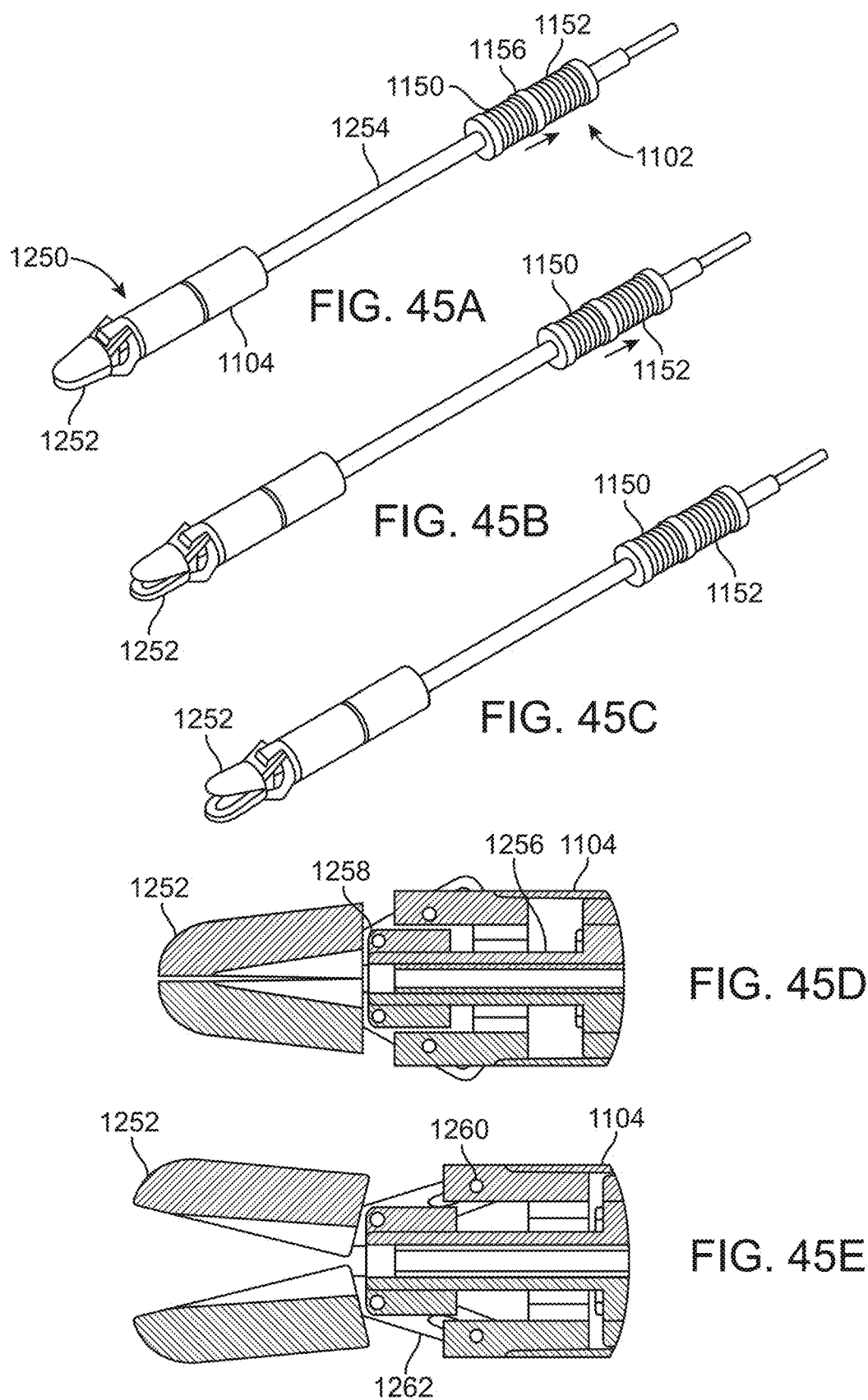

FLUID-ACTUATED SHEATH DISPLACEMENT AND ARTICULATION BEHAVIOR IMPROVING SYSTEMS, DEVICES, AND METHODS FOR CATHETERS, CONTINUUM MANIPULATORS, AND OTHER USES

CROSS REFERENCE TO RELATED APPLICATIONS

The present application claims the benefit of priority from co-assigned U.S. Provisional Patent Appln. No. 62/313,390, filed on Mar. 25, 2016, entitled "BEHAVIOR IMPROVING SYSTEMS, DEVICES, AND METHODS FOR CATHETERS, CONTINUUM MANIPULATORS, AND OTHER USES"; the full disclosure of which is incorporated herein by reference in its entirety for all purposes.

The subject matter of the present application is related to that of co-assigned U.S. patent application Ser. No. 15/081,026 entitled "Articulation Systems, Devices, and Methods for Catheters and Other Uses"; and Ser. No. 15/080,979 entitled "Fluid Drive System for Catheter Articulation and Other Uses"; and Ser. No. 15/080,949, entitled "Fluid-Expandable Body Articulation of Catheters and Other Flexible Structures"; all filed on Mar. 25, 2016; the full disclosures which are also incorporated herein by reference in their entirety for all purposes.

FIELD OF THE INVENTION

In exemplary embodiments, the present invention provides structures, systems, and methods for selectively actuating, bending, or otherwise altering the bend characteristics of catheters and other elongate flexible bodies, the lengths of such bodies, and the like. Particularly advantageous embodiments described herein can use fluid-driven actuators (optionally in the form of balloons) to (among other uses) axially displace a sheath from over a tool mounted on the end of a catheter or other elongate flexible body, for example, so as to release a self-expanding endoluminal prosthesis within the cardiovascular system of a patient. The invention also provides improved medical devices, systems, and method, with more specific embodiments providing improved articulated medical systems having a fluid-driven balloon array that can help shape, steer and/or advance a catheter, guidewire, or other elongate flexible structure along a body lumen. Advantageously, balloon arrays or other fluid-driven actuators coupled together by multi-lumen shafts can improve the behavior of a wide range of elongate flexible bodies by, for example, urging a plurality of joints or flexible regions along a segment to bend evenly, thereby making the control of continuum robotic manipulators, pull-wire driven catheters, and the like, more robust, predictable, and repeatable. Alternative embodiments make use of balloon arrays distributed along single or multi-lumen shafts for improving the articulation behavior of a wide range of continuum robotic structures, flexible manipulators and/or end effectors, industrial robots, borescopes, prosthetic fingers, robotic arms, positioning supports or legs, consumer products, or the like.

BACKGROUND OF THE INVENTION

Diagnosing and treating disease often involve accessing internal tissues of the human body. Once the tissues have been accessed, medical technology offers a wide range of diagnostic tools to evaluate tissues and identify lesions or disease states. Similarly, a number of therapeutic tools have been developed that can help surgeons interact with, remodel, deliver drugs to, or remove tissues associated with a disease state so as to improve the health and quality of life of the patient. Unfortunately, gaining access to and aligning tools with the appropriate internal tissues for evaluation or treatment can represent a significant challenge to the physician, can cause serious pain to the patient, and may (at least in the near term) be seriously detrimental to the patient's health.

Open surgery is often the most straightforward approach for gaining access to internal tissues. Open surgery can provide such access by incising and displacing overlying tissues so as to allow the surgeon to manually interact with the target internal tissue structures of the body. This standard approach often makes use of simple, hand-held tools such as scalpels, clamps, sutures, and the like. Open surgery remains, for many conditions, a preferred approach. Although open surgical techniques have been highly successful, they can impose significant trauma to collateral tissues, with much of that trauma being associated with gaining access to the tissues to be treated.

To help avoid the trauma associated with open surgery, a number of minimally invasive surgical access and treatment technologies have been developed. Many minimally invasive techniques involve accessing the vasculature, often through the skin of the thigh, neck, or arm. One or more elongate flexible catheter structures can then be advanced along the network of blood vessel lumens extending throughout the body and its organs. While generally limiting trauma to the patient, catheter-based endoluminal therapies are often reliant on a number of specialized catheter manipulation techniques to safely and accurately gain access to a target region, to position a particular catheter-based tool in alignment with a particular target tissue, and/or to activate or use the tool. In fact, some endoluminal techniques that are relatively simple in concept can be very challenging (or even impossible) in practice (depending on the anatomy of a particular patient and the skill of a particular physician). More specifically, advancing a flexible guidewire and/or catheter through a tortuously branched network of body lumens might be compared to pushing a rope. As the flexible elongate body advances around first one curve and then another, and through a series of branch intersections, the catheter/tissue forces, resilient energy storage (by the tissue and the elongate body), and movement interactions may become more complex and unpredictable, and control over the rotational and axial position of the distal end of a catheter can become more challenging and less precise. Hence, accurately aligning these elongate flexible devices with the desired luminal pathway and target tissues can be a significant challenge.

A variety of mechanisms can be employed to steer or variably alter deflection of a tip of a guidewire or catheter in one or more lateral directions to facilitate endoluminal and other minimally invasive techniques. Pull wires may be the most common catheter tip deflection structures and work well for many catheter systems by, for example, controllably decreasing separation between loops along one side of a helical coil, braid, or cut hypotube near the end of a catheter or wire. It is often desirable to provide positive deflection in opposed directions (generally by including opposed pull wires), and in many cases along two orthogonal lateral axes (so that three or four pull wires are included in some devices). Where additional steering capabilities are desired in a single device, still more pull wires may be included. Complex and specialized catheter systems having dozens of pull wires have been proposed and built, in some cases with each pull wire being articulated by a dedicated motor attached to the proximal end. Alternative articulation systems have also been proposed, including electrically actuated shape memory alloy structures, piezoelectric actuation, phase change actuation, and the like. As the capabilities of steerable systems increase, the range of therapies that can use these technologies should continue to expand.

Unfortunately, as articulation systems for catheters get more complex, it can be more and more challenging to maintain accurate control over these flexible bodies. For example, pull wires that pass through bent flexible catheters often slide around the bends over surfaces within the catheter, with the sliding interaction extending around not only bends intentionally commanded by the user, but also around bends that are imposed by the tissues surrounding the catheter. Hysteresis and friction of a pull-wire system may vary significantly with that sliding interaction and with different overall configurations of the bends, so that the articulation system response may be difficult to predict and control. The location of the bend that is imposed by a pull-wire can also be inconsistent. For example, while the stiffness of an articulated catheter segment may to some extent promote distribution of a bend throughout that segment, tissue forces or internal friction may concentrate bending along a short portion of the segment, making the overall behavior of the catheter erratic. Furthermore, more complex pull wire systems may add additional challenges. While opposed pull-wires can each be used to bend a catheter in opposite directions from a generally straight configuration, attempts to use both together—while tissues along the segment are applying unknown forces in unknown directions—may lead to widely inconsistent results. Even after a diagnostic or therapeutic tool is positioned in alignment with a target tissue, it can be difficult to maintain that alignment while deploying or using the tool. For example, withdrawing a sheath proximally from over a self-expanding endoluminal prosthesis (such as a stent, valve, stent-graft, or the like) using standard techniques can involve applying many pounds of force to the portion of the deployment system that extends outside the patient. The combination of pulling the sheath proximally while pushing distally against a tool-supporting catheter shaft can make it difficult to maintain tool positioning inside the patient. Hence, there could be benefits to providing improved flexible body articulation behavior, and particularly to providing more accurate small and precise motions, to improving the lag time, and/or to providing improved transmission of motion over known catheter pull-wire systems so as to avoid compromising the positioning and coordination, as experienced by the surgeon, between the input and output of catheters and other elongate flexible tools.

Along with catheter-based therapies, a number of additional minimally invasive surgical technologies have been developed to help treat internal tissues while avoiding at least some of the trauma associated with open surgery. Among the most impressive of these technologies is robotic surgery. Robotic surgeries often involve inserting one end of an elongate rigid shaft into a patient, and moving the other end with a computer-controlled robotic linkage so that the shaft pivots about a minimally invasive aperture. Surgical tools can be mounted on the distal ends of the shafts so that they move within the body, and the surgeon can remotely position and manipulate these tools by moving input devices with reference to an image captured by a camera from within the same workspace, thereby allowing precisely scaled micro-surgery. Alternative robotic systems have also been proposed for manipulation of the proximal end of flexible catheter bodies from outside the patient so as to position distal treatment tools. These attempts to provide automated catheter control have met with challenges, which may be in-part because of the difficulties in providing accurate control at the distal end of a flexible elongate body using pull-wires extending along bending body lumens. Still further alternative catheter control systems apply large magnetic fields using coils outside the patient's body to direct catheters inside the heart of the patient, and more recent proposals seek to combine magnetic and robotic catheter control techniques. While the potential improvements to surgical accuracy make all of these efforts alluring, the capital equipment costs and overall burden to the healthcare system of these large, specialized systems is a concern.

In light of the above, it would be beneficial to provide improved articulation systems and devices, methods of articulation, and methods for making articulation structures. Improved techniques for controlling the bending of elongate structures (articulated or non-articulated) would also be beneficial. It would be particularly beneficial if these new technologies were suitable to provide therapeutically effective control over movement of a distal end of a flexible guidewire, catheter, or other elongate body extending into a patient body. It would also be beneficial if the movement provided by these new techniques would allow enhanced ease of use. It would also be helpful if these techniques could provide improved motion and control capabilities for a wide range of distinct medical and industrial devices.

BRIEF SUMMARY OF THE INVENTION

The present invention generally provides improved medical devices, systems, and methods, and also provides structures and techniques for improving the behavior of flexible and/or articulated structures such as continuum robotic manipulators, pull-wire catheters, and the like. Catheter-supported therapeutic and diagnostic tools can be introduced into a patient body with a sheath slidably disposed over the tool. Once the tool is aligned with a target tissue, a fluid-driven actuator can move the sheath axially from over the tool, for example, to allow a stent, stent-graft, prosthetic valve, or the like to expand radially within the cardiovascular system, without having to transmit large deployment forces along the catheter shaft and sheath from outside the patient. The devices, systems, methods herein can also improve articulation, and methods for fabricating well-behaved articulation structures are also provided. The systems will often include simple balloon arrays, with inflation of the balloons interacting with elongate skeletal support structures so as to improve articulation behavior of the skeleton. The balloons can be mounted to a substrate of an array, with the substrate having channels that can direct inflation fluid between balloons and/or subsets of the balloons. The skeleton may comprise a simple helical coil, interlocking helical channels, or even a monolithic polymer body with a helical channel, and the array can be used to improve uniformity of bending along a segment of a flexible body such as a catheter. The articulation improvement structures can be employed in minimally invasive medical catheter systems, and also for industrial continuum robotics, for supporting imaging systems, for entertainment and consumer products, and the like.

In a first aspect, the invention provides a catheter-based tool deployment system comprising an elongate flexible catheter body having a proximal end and a distal portion with an axis therebetween. A receptacle for a therapeutic or diagnostic tool is included along the distal portion of the catheter body. A tubular sheath has a lumen that can slide over the distal portion of the catheter. A first fluid channel extends axially along the catheter body, and a first actuator is disposed along the distal portion in fluid communication with the first channel. The first actuator couples the distal portion with the sheath so that, in response to fluid transmitted along the first channel, the first actuator drives the sheath axially between a first position (extending over the receptacle) and a second position (axially offset from the first position such that the tool is uncovered for use).

The systems, devices, and methods described herein may further include one or more of a number of different general features. For example, the tool may comprise an endoluminal implant biased to expand from a small profile configuration to a large profile configuration. The sheath can be configured to radially constrain the implant when the sheath is in the first position, and to slide axially over the implant from the first position toward the second position so as to radially release the implant, optionally within a cardiovascular system of a patient. The tool may optionally comprise a prosthetic valve, often a prosthetic mitral valve. A wide variety of alternative tools may be supportable by the catheter body, with the tool typically being releasably held in the receptacle, although some sheathed tools may be fixed in place. The distal portion of the catheter body may comprise an articulated segment disposed proximally of the receptacle. The distal portion of the catheter body, can, for example, have a plurality of articulated segments configured to position and orient the valve (or other tool) with at least 3 degrees of freedom, with the articulated segment ideally including an articulation balloon array (though other articulation actuators could be used, including pull-wires). Counterintuitively, the second position of the sheath may be distal of the first position so that the sheath moves distally and away from bends of the catheter body disposed between the receptacle and the proximal end when uncovering the tool for use. Regardless, a fluid-driven balloon, bellows, piston, or other actuator can generate significant sheath actuation forces locally (often 3 lb or more, often being 5 or even 10 lb or more, and in some cases being 15 lb or more) sufficiently near where the sheath is to be moved from over the tool so that as to avoid any need for transmitting these forces around bends of the elongate catheter system associated with tortuosity of the vasculature or other body lumen access pathway.

The sheath actuation devices, systems, and methods described herein may benefit from any of a number of additional technologies and features. Optionally, the first actuator comprises a first balloon. The transmission of the fluid can inflate the first balloon from an uninflated configuration to an inflated configuration. The first balloon in the uninflated configuration can have an uninflated axial length, and the first balloon in the inflated configuration can have an inflated axial length that is greater than the uninflated axial length. Somewhat surprisingly, the first balloon can be distal of the tool and the inflation state of the balloon may help define an overall length of the catheter system. Hence, expansion of the first balloon from the first axial length to the second axial length may extend a distal end of the catheter system distally relative to the receptacle. Where, for example, both deployment and retrieval are desired a second actuator may be in fluid communication with a second channel extending along the catheter body, and the second actuator can axially couple the distal portion of the catheter with the sheath so that transmission of inflation fluid along the second channel drives the sheath axially away from the second position and toward the first position. The second actuator may comprise a second balloon, and the transmission of the fluid along the second channel can inflate the second balloon from an uninflated configuration to an elongate inflated configuration. Optionally, the second balloon is distal of the first balloon, and a tension member extends axially along the first and second balloons to limit a total combined length of the two balloons and distal advancement of the end of the catheter during inflation of the second balloon so that axial elongation of the second balloon drives the first balloon and the sheath proximally toward the first position.

The first channel is optionally disposed between an outer tubular shaft and an intermediate tubular shaft. The outer shaft can be axially affixed to the tool receptacle so as to form a structure of the catheter body, and the second channel can be disposed between an inner shaft and the intermediate shaft. The tension member can axially couple the inner shaft to the outer shaft. The intermediate shaft and inner shaft may optionally extend proximally beyond the proximal end of the catheter body, and a third balloon that is in fluid communication with the first channel can also be included. A fourth balloon in fluid communication with the second channel may similarly be included, and the third balloon may axially couple the intermediate shaft with the outer shaft, with the fourth balloon axially coupling the intermediate shaft with the inner shaft. The balloons can have axially oriented ends coupled to the shafts so that distally driving a proximal portion of the inner shaft relative to the intermediate shaft shortens the first balloon and drives inflation fluid along the first channel so as to inflate the first balloon. Similarly, distally driving a proximal portion of the intermediate shaft relative to the outer shaft shortens the fourth balloon and drives inflation fluid along the second channel so as to inflate the second balloon. One, some, or all of the sheath actuation balloons can have a first plurality of laterally opposed folds extending transverse to the axis and a second plurality of laterally opposed folds circumferentially offset from the first folds. Alternative balloon fold arrangements can also be employed, including having a series of bellows-like folds, a helical folding pattern, or the like.

Optionally, the distal portion of the catheter body has a lumen slidably receiving a shaft, and a distal end of the shaft is affixed to a distal end of the sheath. A proximal end of the first balloon can be affixed to the catheter body, and a distal end of the first balloon can be affixed to the shaft. A seal is maintained between the shaft and the catheter body when the sheath moves between the first position and the second position, for example, using an axially elongateable balloon wall to function as the seal. Alternative seal structures can also be used, including an o-ring or other annular body sliding against the shaft or catheter body, an evertable sleeve extending axially in an annular space between the shaft and catheter body, or the like. In still further alternative arrangements described herein, the sleeve actuator comprises a first balloon, and an opposed balloon is also provided. Alternating inflation of the first balloon and the opposed balloon can incrementally drive the sheath axially. In some embodiments, alternating balloon systems can selectably uncover or recover a tool, such as by including a balloon-actuated clutch to selectably drive a sheath proximally or distally.

In another aspect the invention provides a catheter-based prosthetic heart valve deployment system comprising an elongate flexible catheter body having a proximal end and a distal portion with an axis therebetween. The distal portion is configured for supporting a prosthetic heart valve. A tubular sheath has a lumen slidably receiving the distal portion therein. A first fluid channel extends axially along the catheter body. A first balloon is in fluid communication with the first channel and axially couples the distal portion of the catheter body with the sheath so that when inflation fluid is transmitted along the first channel the first balloon drives the sheath axially or rotationally between a first position and a second position.

In another aspect, the invention provides a method for deploying a catheter-based tool. The method comprises introducing an elongate flexible catheter body distally into a patient body, the distal portion supporting a tool. Fluid is transmitted distally from outside the patient into a first channel extending along the catheter body, and a tubular sheath is driven over the distal portion, between a first position over the tool and a second position, by the transmitted fluid.

In another aspect, the invention provides an elongate flexible structure comprising an elongate body having a proximal end and a distal end with an axis therebetween. An axial segment of the elongate body has a first axial lumen and is flexible to accommodate a lateral bend. First and second balloons are separated axially along the segment, and the lumen provides fluid communication between the balloons. The first and second balloons are coupled with the elongate body so as to apply differing first and second balloon/body forces to the elongate body, respectively, so that the first and second balloons distribute curvature of the bend along the segment.

The differentiated forces applied by the balloons of the devices and systems described herein can urge an axis of the segment toward a shape having a more even and uniform curvature than would be generated by a series of balloons or other fluid-driven actuators that are pressurized by a common fluid supply channel and that applied force vectors of similar magnitude and direction at separated actuator locations. Note that the forces applied by the first and second balloons may differ despite open fluid communication between the balloons through the first lumen (and hence, despite the balloons having a common pressure). This control over curvature distribution may provide significant advantages over other fluid-driven actuators, as well as over pull-wire articulated continuum robots and other prior systems that seek to control the shape of elongate flexible bodies such as catheters, industrial "snake" robots, and the like, and some embodiments may be used to passively distribute or even-out the curvature along bends of un-articulated elongate flexible catheters or other bodies. While compatible with more sophisticated systems, these advantages can also be provided without having to resort to complex feedback system or complicated mechanical architectures. Instead, relatively simple arrangement of the balloons, a fluid channel system, and/or balloon/support structure interface surfaces can be configured so that: a) different balloons impose lateral bending forces in different (typically opposed) lateral bending orientations, and at axially separated balloon locations along the segment, with magnitudes of those opposed forces increasing with increasing local axial curvature differences at the balloon locations so as to urge the segment toward a more uniform curvature; and/or b) an effective pressure transmission area of the balloon/flexible body interface varies with local axial curvature, so that (for example) the pressurized inflation fluid inside the first balloon can apply a different load to a first balloon location along the segment than is being applied by the second balloon inflated to the same pressure, with the load magnitudes varying with local curvature so as to help more evenly distribute bending applied by a group of axially aligned balloons of an articulation array.

In devices and systems that apply opposed loads, the first balloon can optionally be offset from the axis so that inflation of the first balloon urges the axis to bend along a +X bending orientation, for example. The second balloon can be offset from the axis so that inflation of the second balloon urges the axis to bend along a −X bending orientation opposite the +X orientation, with the axis being disposed between the +X and −X orientations. An intermediate location (ideally an axial mid-point of the segment) can be disposed along the segment between the first and second balloons. The first and second balloons will often be included in a first subset of balloons of a balloon array, which may include 2 to 50 balloons, often 2 to 20 balloons coupled to a common lumen. The first portion of the subset (including the first balloon) can be axially aligned proximal of the intermediate location and a second portion of the subset (including the second balloon) being axially aligned (opposite the first portion) and being distal of the intermediate location), with the numbers of balloons in each portion being the same. The array may include a plurality of subsets of balloons, each subset having an associated lumen providing fluid communication between associated first and second balloons (or subset portions) with opposed lateral bending orientations and the intermediate location disposed therebetween. For example, a first balloon of a second subset can be offset from the axis so as to urge the axis to bend along the −X orientation adjacent the first balloon of the first subset, and first balloons of third and fourth subsets can be adjacent the first balloon of the first subset and offset from the axis so as to urge the axis to bend along +Y and −Y orientations, respectively, so that these four subsets have first balloons arranged in quadrature about the axis. Some or all of the subsets may optionally include a first plurality of balloons having a first common bending axis disposed proximal of the intermediate location and a second plurality of balloons having a second common bending axis opposite the first common bending axis and disposed distal of the intermediate location. The proximal end of the structure can optionally be configured to couple with a liquid fluid supply so that the lumen can maintain a desired common pressure of incompressible fluid in the first and second balloons as a length of the segment varies. In other embodiments, a volume of incompressible liquid may be sealed in the lumen and balloons, and variations in segment length may be inhibited, or compressible fluids may be used in the lumen and balloons to resiliently urge the segment toward uniform curvature. An articulation system can be coupled to the segment so as to vary the bend from the proximal end of the elongate body, with the articulation system optionally comprising an articulation balloon array (preferably with balloons that are separate from the curvature distribution balloons), a pull-wire articulation system, or the like.

In many of the other devices and systems described herein, the first force from the first balloon will vary in response to a first local curvature of the axis adjacent the first balloon. The second force varies with a second local curvature of the axis adjacent the second balloon, and these variations may result in changes in the relative magnitudes of these forces such that when the first curvature differs from the second curvature the first force urges the first curvature toward the second curvature. More specifically, the first force often has a different magnitude than the second force, with ratios between the magnitude varying with local curvature so as to urge the first curvature toward the second curvature. Optionally, the first balloon may here be offset from the axis so that inflation of the first balloon urges the axis to bend along a +X bending orientation, and the second balloon can be offset from the axis so that inflation of the second balloon also urges the axis to bend along the +X bending orientation, the first and second balloons being circumferentially aligned.

The elongate body will often have a lateral bending stiffness. Advantageously, the variable forces applied by the balloons may help supplement the total lateral bending stiffness of the system to external loads that would otherwise induce localized buckling, so that the elongate body alone need not be so stiff as to accommodate the expected loads without the balloon reinforcement. To provide differentiated force magnitudes that are responsive to local curvature using balloons along a common lumen, the first balloon can engage a first surface of the elongate body with a first effective engagement area, while the second balloon engages a second surface of the elongate body with a second effective engagement area. The first engagement area may vary with the first curvature, and the second engagement area may vary with the second curvature such that the first force urges the first curvature toward the second curvature. Variation of the first force with the first curvature at a constant first lumen inflation state may define a first effective stiffness of the balloon system. The segment will often also have a more standard structural segment bending stiffness, and the first stiffness can be at least a major portion of the segment bending stiffness, often being at least as large as the segment bending stiffness, and ideally being larger than the segment bending stiffness. In some embodiments, the first stiffness has a first linear spring constant throughout at least a portion of an operating range of the segment, the first linear spring constant being higher than a spring constant of the segment. Other embodiments may have non-linear stiffness characteristics. The forces between the first balloon and the elongate body, together with a pressure of the lumen, can define a first effective engagement area, and the first effective area may correlate with the first curvature (and may be largely independent of the first force) within at least a portion of an operating range of the segment. Advantageously, the first and second balloons can be included in a first subset of balloons of an articulation balloon array, so that these balloons are used to both articulate the segment and to distribute bending along the segment. In a relatively simple example of a structure that can provide beneficial balloon/structure interface area characteristics, the first balloon can be disposed between a first surface of the elongate body and a third surface of the elongate body, a first axial offset separating the first and third surfaces (which can be relatively flat, such as having a minimum radius of curvature that is larger than the balloon diameter). The second balloon can similarly be disposed between a second surface of the elongate body and a fourth surface of the elongate body, with a second axial offset separating the third and fourth (optionally again largely flat) surfaces of the elongate body. The first and second offsets can vary with the first second curvatures, respectively, and the first and second engagement areas vary inversely with the first and second offsets, respectively. Note that offset-defining surfaces which are more highly curved may result in very different (and in many cases less beneficial) system responses.

In yet another aspect, the invention provides a method comprising flexing an elongate body to form a lateral bend along an axial segment of the elongate body. Differing first and second balloon/body forces are applied between a first balloon and the elongate body, and between a second balloon and the elongate body, respectively, so that the first and second balloons distribute curvature of the bend.

In yet another aspect, the invention provides an articulated catheter comprising an elongate flexible catheter body having a proximal end and a distal end with an axis therebetween. The distal end is configured for insertion into a patient and the catheter body has a fluid channel extending along the axis. An articulatable tool is supported near the distal end of the catheter, and a fluid-driven actuator couples the fluid channel with the tool so that fluid transmitted along the channel articulates the tool.

The actuator of the tool will preferably comprise a balloon, with many systems having opposed first and second balloons mechanically coupled to jaws so as to drive open or drive closed the jaws of a grasper, scissors, vessel sealer, stapler, or any of a large number of alternative surgical tools.

In another aspect, the invention provides a system comprising an elongate flexible body having a proximal end and a distal end with an axis therebetween. The body has an axial segment adjacent the distal end, and an input is coupled to the proximal end of the body. An interface surface is coupled to the segment of the body. A sender couples the input to the interface surface so as controllable impose an articulation force to the segment from the input. First, second, third, and fourth groups of balloons are disposed along the segment, the first and second groups being proximal of the third and fourth groups, the first and third groups of balloons being disposed along a first lateral bending orientation, the second and third groups of balloons being disposed along a second lateral bending orientation. The axis is disposed between the first and second orientations. First and second lumens extend along the segment, the balloons of the first and fourth groups being in fluid communication with the first lumen, the balloons of the second and third groups being in fluid communication with the second lumen.

In another aspect, the invention provides a system for use with an articulated catheter having an elongate flexible body having a proximal end and a distal end with an axis therebetween. The body has an axial segment adjacent the distal end, the segment being articulatable from adjacent the proximal end. The system comprises first, second, third, and fourth groups of balloons disposed along the segment. The first and second groups are proximal of the third and fourth groups, the first and third groups of balloons being disposed along a first lateral bending orientation. The second and third groups of balloons are disposed along a second lateral bending orientation, the axis being disposed between the first and second orientations. First and second lumens extend along the segment, the balloons of the first and fourth groups being in fluid communication with the first lumen, the balloons of the second and third groups being in fluid communication with the second lumen.

Optionally, fifth, sixth, seventh, and eighth groups of balloons may also be provided. The fifth and sixth groups will often be proximal of the seventh and eighth groups, the fifth and sixth groups of balloons being disposed along a third lateral bending orientation. The seventh and eighth groups of balloons can be disposed along a fourth lateral bending orientation, the axis being disposed between the third and fourth orientations. The first orientation can be transverse to the third orientation. Third and fourth lumens may extend along the segment. The balloons of the fifth and eighth groups can be in fluid communication with the third lumen, the balloons of the sixth and seventh groups being in fluid communication with the fourth lumen.

In another aspect, the invention provides a system comprising an elongate flexible body having a proximal end and a distal end and defining an axis therebetween. A channel is bordered by proximal and distal surfaces, the proximal and distal surfaces separated by offsets that change with flexing of the skeleton. A helical multi-lumen shaft can be disposed in the helical channel, the shaft having first and second lumens. First, second, third, and fourth balloons can be disposed in the channel, the axis being disposed between the first and second balloons, and also between the third and fourth balloons. The first and third balloons can be aligned along a first lateral bending orientation, the first balloon being proximal of the third balloon, and the second balloon being proximal of the fourth balloon. The first and fourth balloon may be in fluid communication with the first lumen, the second and third balloons being in fluid communication with the second lumen.

In another aspect, the invention provides a system for use with an articulated catheter having an elongate flexible body having a proximal end and a distal end with an axis therebetween. The body has an axial segment adjacent the distal end, the segment being articulatable from adjacent the proximal end. The system comprises first, second, third, and fourth balloons disposed along the segment. The first and second balloons can be proximal of the third and fourth balloons, the first and third balloons being disposed along a first lateral bending orientation. The second and third balloons being disposed along a second lateral bending orientation, the axis being disposed between the first and second orientations. Fifth, sixth, seventh, and eighth balloons, may also be provided, the fifth and sixth balloons being proximal of the first and second balloons, the fifth and sixth balloons being distal of the third and fourth balloons. The fifth and seventh balloons may be disposed along the first orientation, the sixth and eighth groups of balloons being disposed along the second lateral bending orientation. First, second, third, and fourth lumens may extend along the segment, the balloons of the first and fourth groups being in fluid communication with the first lumen, the balloons of the second and third groups being in fluid communication with the second lumen, the balloons of the fifth and eighth groups being in fluid communication with the third lumen, the balloons of the sixth and seventh groups being in fluid communication with the fourth lumen.

In another aspect, the invention provides a system comprising an elongate flexible body having a proximal end and a distal end and defining an axis therebetween, a segment of the elongate body having a first length and a second length different than the first length. First and second lumens extend along the segment and to the proximal end, and first, second, third, and fourth balloons are disposed along the segment. The axis is disposed between the first and second balloons, and also between the third and fourth balloons. The first and third balloons are aligned along a first lateral bending orientation, the first balloon being proximal of the third balloon, and the second balloon being proximal of the fourth balloon, the first and fourth balloon being in fluid communication with the first lumen, the second and third balloons being in fluid communication with the second lumen. A fluid supply system can be in fluid communication with the first and second lumen so as to direct fluid distally as the segment elongates from the first length to the second length.

As optional general features of the systems described herein, an elongate flexible body may comprise articulatable bodies and/or may have an elongate flexible skeleton with a proximal a helical channel bordered by proximal and distal surfaces separated by offsets. Alternative skeletons have other offsets, with the offsets changing with flexing of the skeleton. A helical multi-lumen shaft can be disposed in the helical channel. The shaft can have first and second lumens. First, second, third, and fourth balloons can also be disposed in the channel. The axis is disposed between the first and second balloons, and is also between the third and fourth balloons. The first balloon is aligned along a lateral orientation, as is the third balloon. The first balloon is proximal of the third balloon, and the second balloon is proximal of the fourth balloon. The first and fourth balloon are in fluid communication with the first lumen, and the second and third balloons are in fluid communication with the second lumen.

Advantageously, coupling of balloons that are on opposed lateral sides, and that are axially offset (optionally at opposed axial locations relative to, for example, an axial mid-point of a segment), may improve the behavior, predictability, and/or repeatability of articulation under varying environmental loads. Exemplary embodiments of extension-retraction articulatable structures described herein have skeletons that include helical frame members, and these members may include helical channels that can are particularly well suited to receive helical shaft/balloon assemblies for articulation purposes. Some of these helical frame structures include additional helical channels beyond those needed for articulation; other frame structures may be extruded or machined so as to have an available helical channel. Regardless, the helical multi-lumen shafts or cores described herein can be used to couple laterally and axially opposed balloons (and optionally groups of two or more axially and laterally opposed balloons. The balloons may be aligned in quadrature (with four sets of balloons distributed about the axis and 90 degrees between centerlines of the balloon sets), and the opposed coupled balloon(s) also optionally being in quadrature, the multi-lumen shaft here optionally having 4, 8, 12 . . . or (4×I, I being an integer) lumens. Optionally, the lumens and balloons of such behavior-improving assemblies may be filled with a liquid (typically comprising water in medical embodiments or another suitable hydraulic fluid), and the lumens may be sealed at the proximal and distal ends of the segment, so that each segment may optionally have an associated, separately sealed multi-lumen system to help evenly distribute flexing within that segment. Note that while such a behavior-improving assembly may be particularly well suited for use with the fluid articulation described herein, they may also be used with standard pull-wire or other continuum manipulator technologies.

Alternative embodiments may have inflation fluids that comprise gas, and/or which have associated lumens extending to the proximal end of the articulated structure to facilitate controlling pressures and/or elongation. As an example of a preferred arrangement, the first, second, third, and fourth balloons may be on the same lateral plane (as opposed to being off 90 or 120 degrees around the circumference, for example). More specifically, if the first balloon can be at an orientation that can be designated as being at 0 degrees from the axis, the second may be at 180, the third at 0, and the fourth at 180 degrees. A similar set of four additional balloons can be at 90 and 270 degrees for the transverse bend directions.

BRIEF DESCRIPTION OF THE DRAWINGS

FIG. 1-1 schematically illustrates a catheter articulation system having a hand-held proximal housing and a catheter with a distal articulatable portion in a relaxed state.

FIGS. 8 and 9 schematically illustrate balloon arrays in which the balloons are disposed over multi-lumen helical coil cores, shafts, or conduits, and also show the effects of varying balloon inflation density on a radius of curvature of a catheter or other flexible body.

FIGS. 13A-3C schematically illustrate an exemplary multi-lumen cable structure having an integrated stiffening balloon, a multi-lumen helical core structure, and a transition between a helical core and thin multi-channel fluid transmission cable, respectively.

FIGS. 20A-22A schematically illustrate skeletons structures having frames or members with balloons mounted in opposition so as to axially extend with inflation of one subset of the balloons, and to axially contract with inflation of another subset of balloons.

FIGS. 23A-23J are illustrations of alternative elongate articulated flexible structures having annular skeletons and two sets of opposed balloons, and show how a plurality of independently controllable axial segments can be combined to allow control of the overall elongate structure with 6 or more degrees of freedom.

FIGS. 24A-24G illustrate components of another alternative elongate articulated flexible structure having axial expansion balloons and opposed axial contraction balloons, the structures here having helical skeleton members and helical balloon assemblies.

FIGS. 25A-25F illustrate exemplary elongate articulated flexible structures having helical skeleton members and three helical balloon assemblies supported in opposition along the skeleton, and also show how selective inflation of subsets of the balloons can locally axially elongate and/or contract the skeleton to bend the structure laterally and/or alter the overall length of the structure.

FIGS. 32A and 32B illustrate a still further alternative articulatable structure having a frame that may be formed using laterally cuts in a polymer tube, by 3D printing, or the like.

FIGS. 33A and 33B schematically illustrate alternative inflatable balloon actuators and associated mechanisms that can rotate a distal sheath or other structure about an axis of a catheter or another articulatable structure.

FIGS. 34A and 34B schematically illustrate a reciprocating balloon and frame assembly for incrementally moving a sheath or other structure adjacent the distal end of an articulated structure proximally or distally.

FIGS. 35A and 35B schematically illustrate an alternative balloon and frame arrangement for incrementally moving a sheath or other structure adjacent the distal end of an articulated structure proximally and/or distally.

FIGS. 38A-38G are perspective illustrations of a prosthetic heart valve delivery system having a fluid-driven sheath actuation system, showing how inflation of balloon actuators can generate forces within a patient body so as to move a sheath over a self-expanding heart valve to partially deploy the valve, recapture the valve, and fully deploy the valve, and also showing how actuation can be driven using a proximal balloon system to generate controlled fluid flows and help move fluid transmission shafts from outside the patient.

FIGS. 45A-45E illustrate an alternative catheter system having fluid-driven jaw actuation system with first and second distal balloons to generate articulation forces along the distal portion of the catheter, as well as first and second drive balloons near the proximal end, with the balloons being similar to those of FIGS. 38A-39G.

DETAILED DESCRIPTION OF THE INVENTION

Figure 1:
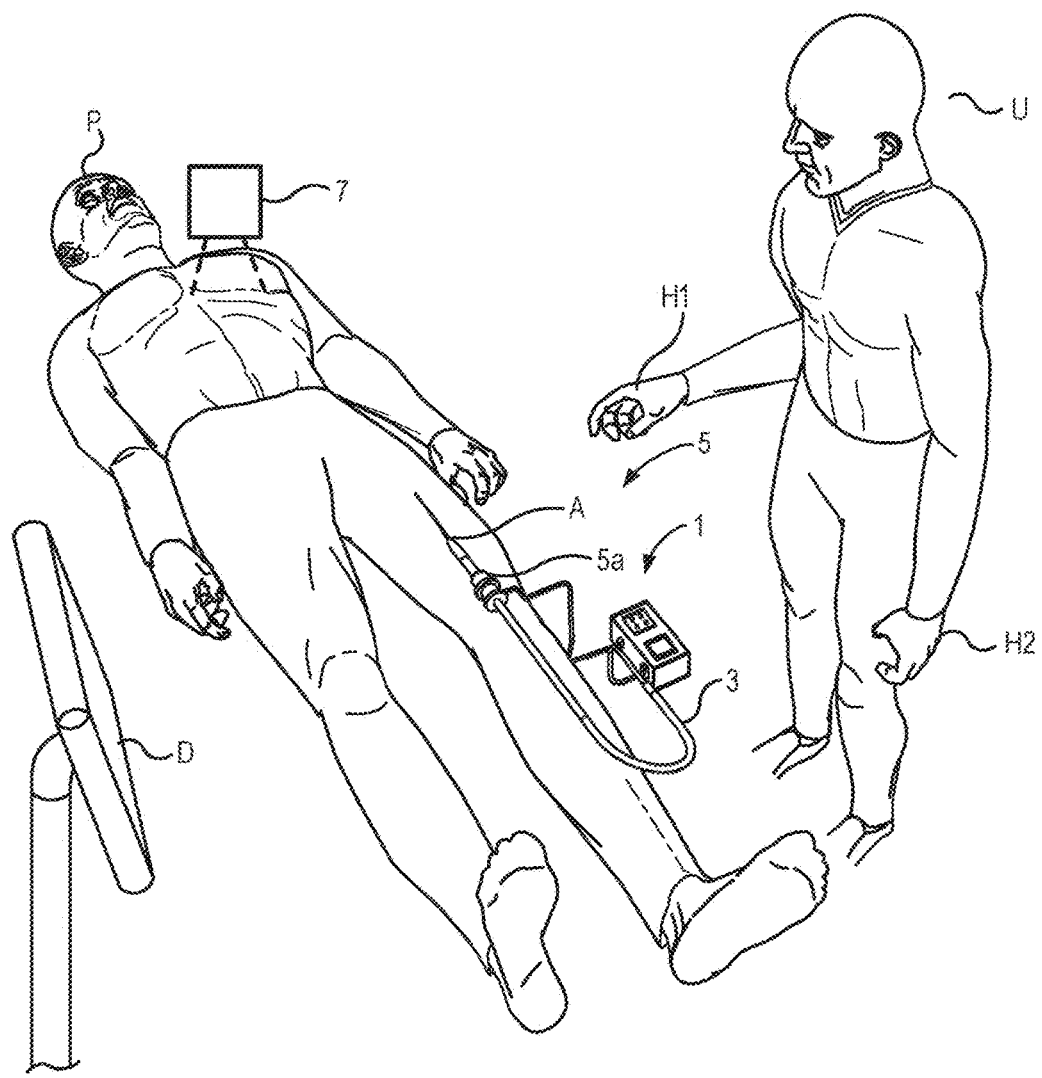
FIG. 1 is a simplified perspective view of a medical procedure in which a physician can input commands into a catheter system so that a catheter is articulated using systems and devices described herein.
Figure 1:
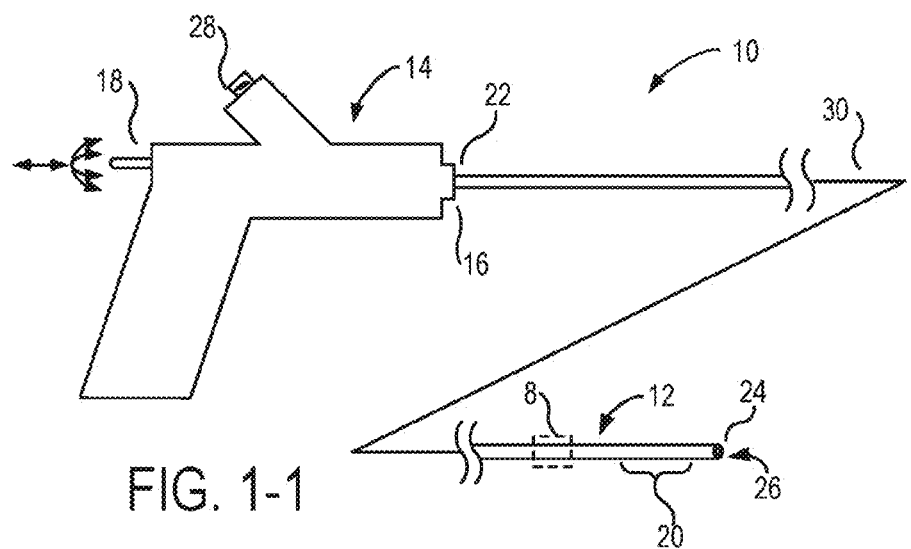

The present invention generally provides fluid control devices, systems, and methods that are particularly useful for articulating catheters and other elongate flexible structures. In exemplary embodiments the invention provides a modular manifold architecture that includes plate-mounted valves to facilitate fluid communication along a plurality of fluid channels included in one or more multi-lumen shafts, often for articulating actuators of a catheter. Preferred actuators include balloons or other fluid-expandable bodies, and the modular manifold assemblies are particularly well suited for independently controlling a relatively large number of fluid pressures and/or flows. The individual plate modules may include valves that control fluid supplied to a catheter or other device, and/or fluid exhausted from the catheter or other device. A receptacle extending across a stack of such modules can receive a fluid flow interface having a large number of individual fluid coupling ports, with the total volume of the modular valve assembly, including the paired receptacle and fluid flow interface of the device often being quite small. In fact, the modular manifold will preferably be small enough to hold in a single hand, even when a controller (such as a digital processor), a pressurized fluid source (such as a canister of cryogenic fluid), and an electrical power source (such as a battery) are included. When used to transmit liquids that will vaporize to a gas that inflates a selected subset of microballoons within a microballoon array, control over the small quantities of inflation liquids may direct microfluidic quantities of inflation fluids. Microelectromechanical system (MEMS) valves and sensors may find advantageous use in these systems; fortunately, suitable microfluidic and MEMS structures are now commercially available and/or known valve structures may be tailored for the applications described herein by a number of commercial service providers and suppliers.

The catheter bodies (and many of the other elongate flexible bodies that benefit from the inventions described herein) will often be described herein as having or defining an axis, such that the axis extends along the elongate length of the body. As the bodies are flexible, the local orientation of this axis may vary along the length of the body, and while the axis will often be a central axis defined at or near a center of a cross-section of the body, eccentric axes near an outer surface of the body might also be used. It should be understood, for example, that an elongate structure that extends "along an axis" may have its longest dimension extending in an orientation that has a significant axial component, but the length of that structure need not be precisely parallel to the axis. Similarly, an elongate structure that extends "primarily along the axis" and the like will generally have a length that extends along an orientation that has a greater axial component than components in other orientations orthogonal to the axis. Other orientations may be defined relative to the axis of the body, including orientations that are transvers to the axis (which will encompass orientation that generally extend across the axis, but need not be orthogonal to the axis), orientations that are lateral to the axis (which will encompass orientations that have a significant radial component relative to the axis), orientations that are circumferential relative to the axis (which will encompass orientations that extend around the axis), and the like. The orientations of surfaces may be described herein by reference to the normal of the surface extending away from the structure underlying the surface. As an example, in a simple, solid cylindrical body that has an axis that extends from a proximal end of the body to the distal end of the body, the distal-most end of the body may be described as being distally oriented, the proximal end may be described as being proximally oriented, and the surface between the proximal and distal ends may be described as being radially oriented. As another example, an elongate helical structure extending axially around the above cylindrical body, with the helical structure comprising a wire with a square cross section wrapped around the cylinder at a 20 degree angle, might be described herein as having two opposed axial surfaces (with one being primarily proximally oriented, one being primarily distally oriented). The outermost surface of that wire might be described as being oriented exactly radially outwardly, while the opposed inner surface of the wire might be described as being oriented radially inwardly, and so forth.

Referring first to FIG. 1, a first exemplary catheter system 1 and method for its use are shown. A physician or other system user U interacts with catheter system 1 so as to perform a therapeutic and/or diagnostic procedure on a patient P, with at least a portion of the procedure being performed by advancing a catheter 3 into a body lumen and aligning an end portion of the catheter with a target tissue of the patient. More specifically, a distal end of catheter 3 is inserted into the patient through an access site A, and is advanced through one of the lumen systems of the body (typically the vasculature network) while user U guides the catheter with reference to images of the catheter and the tissues of the body obtained by a remote imaging system.

Exemplary catheter system 1 will often be introduced into patient P through one of the major blood vessels of the leg, arm, neck, or the like. A variety of known vascular access techniques may also be used, or the system may alternatively be inserted through a body orifice or otherwise enter into any of a number of alternative body lumens. The imaging system will generally include an image capture system 7 for acquiring the remote image data and a display D for presenting images of the internal tissues and adjacent catheter system components. Suitable imaging modalities may include fluoroscopy, computed tomography, magnetic resonance imaging, ultrasonography, combinations of two or more of these, or others.

Catheter 3 may be used by user U in different modes during a single procedure, including two or more of a manual manipulation mode, an automated and powered shape-changing mode, and a combination mode in which the user manually moves the proximal end while a computer articulates the distal portion. More specifically, at least a portion of the distal advancement of catheter 3 within the patient may be performed in a manual mode, with system user U manually manipulating the exposed proximal portion of the catheter relative to the patient using hands H1, H2. Catheter 3 may, for example, be manually advanced over a guidewire, using either over-the-wire or rapid exchange techniques. Catheter 3 may also be self-guiding during manual advancement (so that for at least a portion of the advancement of catheter 3, a distal tip of the catheter may guide manual distal advancement). Automated lateral deflection of a distal portion of the catheter may impose a desired distal steering bend prior to a manual movement, such as near a vessel bifurcation, followed by manual movement through the bifurcation. In addition to such manual movement modes, catheter system 1 may also have a 3-D automated movement mode using computer controlled articulation of at least a portion of the length of catheter 3 disposed within the body of the patient to change the shape of the catheter portion, often to advance or position the distal end of the catheter. Movement of the distal end of the catheter within the body will often be provided per real-time or near real-time movement commands input by user U, with the portion of the catheter that changes shape optionally being entirely within the patient so that the movement of the distal portion of the catheter is provided without movement of a shaft or cable extending through the access site. Still further modes of operation of system 1 may also be implemented, including concurrent manual manipulation with automated articulation, for example, with user U manually advancing the proximal shaft through access site A while computer-controlled lateral deflections and/or changes in stiffness over a distal portion of the catheter help the distal end follow a desired path or reduce resistance to the axial movement.

Referring next to FIG. 1-1 components which may be included in or used with catheter system 1 or catheter 3 (described above) can be more fully understood with reference to an alternative catheter system 10 and its catheter 12. Catheter 12 generally includes an elongate flexible catheter body and is detachably coupled to a handle 14, preferably by a quick-disconnect coupler 16. Catheter body 12 has an axis 30, and an input 18 of handle 14 can be moved by a user so as to locally alter the axial bending characteristics along catheter body 12, often for variably articulating an actuated portion 20 of the catheter body. Catheter body 12 will often have a working lumen 26 into or through which a therapeutic and/or diagnostic tool may be advanced from a proximal port 28 of handle 14. Alternative embodiments may lack a working lumen, may have one or more therapeutic or diagnostic tools incorporated into the catheter body near or along actuated portion 20, may have a sufficiently small outer profile to facilitate use of the body as a guidewire, may carry a tool or implant near actuated portion 20 or near distal end 26, or the like. In particular embodiments, catheter body 12 may support a therapeutic or diagnostic tool 8 proximal of, along the length of, and/or distal of actuated portion 20. Alternatively, a separate elongate flexible catheter body may be guided distally to a target site once catheter body 20 has been advanced (with the elongate body for such uses often taking the form and use of a guidewire or guide catheter).

The particular tool or tools included in, advanceable over, and/or introducible through the working lumen of catheter body 20 may include any of a wide range of therapeutic and/or treatment structures. Examples include cardiovascular therapy and diagnosis tools (such as angioplasty balloons, stent deployment balloons or other devices, atherectomy devices, tools for detecting, measuring, and/or characterizing plaque or other occlusions, tools for imaging or other evaluation of, and/or treatment of, the coronary or peripheral arteries, structural heart tools (including prostheses or other tools for valve procedures, for altering the morphology of the heart tissues, chambers, and appendages, and the like), tools for electrophysiology mapping or ablation tools, and the like); stimulation electrodes or electrode implantation tools (such as leads, lead implant devices, and lead deployment systems, leadless pacemakers and associated deployments systems, and the like); neurovascular therapy tools (including for accessing, diagnosis and/or treatment of hemorrhagic or ischemic strokes and other conditions, and the like); gastrointestinal and/or reproductive procedure tools (such as colonoscopic diagnoses and intervention tools, transurethral procedure tools, transesophageal procedure tools, endoscopic bariatric procedure tools, etc.); hysteroscopic and/or falloposcopic procedure tools, and the like; pulmonary procedure tools for therapies involving the airways and/or vasculature of the lungs; tools for diagnosis and/or treatment of the sinus, throat, mouth, or other cavities, and a wide variety of other endoluminal therapies and diagnoses structures. Such tools may make use of known surface or tissue volume imaging technologies (including imaging technologies such as 2-D or 3-D cameras or other imaging technologies; optical coherence tomography technologies; ultrasound technologies such as intravascular ultrasound, transesophogeal ultrasound, intracardiac ultrasound, Doppler ultrasound, or the like; magnetic resonance imaging technologies; and the like), tissue or other material removal, incising, and/or penetrating technologies (such a rotational or axial atherectomy technologies; morcellation technologies; biopsy technologies; deployable needle or microneedle technologies; thrombus capture technologies; snares; and the like), tissue dilation technologies (such as compliant or non-compliant balloons, plastically or resiliently expandable stents, reversibly expandable coils, braids or other scaffolds, and the like), tissue remodeling and/or energy delivery technologies (such as electrosurgical ablation technologies, RF electrodes, microwave antennae, cautery surfaces, cryosurgical technologies, laser energy transmitting surfaces, and the like), local agent delivery technologies (such as drug eluting stents, balloons, implants, or other bodies; contrast agent or drug injection ports; endoluminal repaving structures; and the like), implant and prosthesis deploying technologies, anastomosis technologies and technologies for applying clips or sutures, tissue grasping and manipulation technologies; and/or the like. In some embodiments, the outer surface of the articulation structure may be used to manipulate tissues directly. Other examples of surgical interventions which can impose significant collateral damage, and for which less-invasive endoluminal approaches may be beneficial, include treatments of the brain (including nerve stimulation electrode implantation, neurovascular therapies including for diagnosis and/or treatment of hemorrhagic or ischemic strokes and other conditions, and the like); cardiovascular therapies and diagnoses (including evaluation and/or treatments of the coronary or peripheral arteries, structural heart therapies such as valve procedures or closure of atrial appendages, electrophysiology procedures such as mapping and arrhythmia treatments, and the like); gastrointestinal and/or reproductive procedures (such as colonoscopic diagnoses and interventions, transurethral procedures, transesophageal procedures, endoscopic bariatric procedures, etc.); hysteroscopic and/or falloposcopic procedures, and the like; pulmonary procedures involving the airways and/or vasculature of the lungs; diagnosis and/or treatment of the sinus, throat, mouth, or other cavities, and a wide variety of other endoluminal therapies and diagnoses. Unfortunately, known structures used for different therapies and/or insertion into different body lumens are quite specialized, so that it will often be inappropriate (and possibly ineffective or even dangerous) to try to use a device developed for a particular treatment for another organ system. Non-medical embodiments may similarly have a wide range of tools or surfaces for industrial, assembly, imaging, manipulation, and other uses.

Addressing catheter body 12 of system 10 (and particularly articulation capabilities of actuated portion 20) in more detail, the catheter body generally has a proximal end 22 and a distal end 24 with axis 30 extending between the two. As can be understood with reference to FIG. 2, catheter body 12 may have a short actuated portion 20 of about 3 diameters or less, but will often have an elongate actuated portion 20 extending intermittently or continuously over several diameters of the catheter body (generally over more than 3 diameters, often over more than 10 diameters, in many cases over more than 20 diameters, and in some embodiments over more than 40 diameters). A total length of catheter body 12 (or other flexible articulated bodies employing the actuation components described herein) may be from 5 to 500 cm, more typically being from 15 to 260 cm, with the actuated portion optionally having a length of from 1 to 150 cm (more typically being 2 to 20 cm) and an outer diameter of from 0.65 mm to 5 cm (more typically being from 1 mm to 2 cm). Outer diameters of guidewire embodiments of the flexible bodies may be as small as 0.012" though many embodiments may be more than 2 Fr, with catheter and other medical embodiments optionally having outer diameters as large as 34 French or more, and with industrial robotic embodiments optionally having diameters of up to 1" or more. Exemplary catheter embodiments for structural heart therapies (such as trans-catheter aortic or mitral valve repair or implantation, left atrial appendage closure, and the like) may have actuated portions with lengths of from 3 to 30 cm, more typically being from 5 to 25 cm, and may have outer profiles of from 10 to 30 Fr, typically being from 12 to 18 Fr, and ideally being from 13 to 16 Fr. Electrophysilogy therapy catheters (including those having electrodes for sensing heart cycles and/or electrodes for ablating selected tissues of the heart) may have sizes of from about 5 to about 12 Fr, and articulated lengths of from about 3 to about 30 cm. A range of other sizes might also be implemented for these or other applications.

Figure 1A:
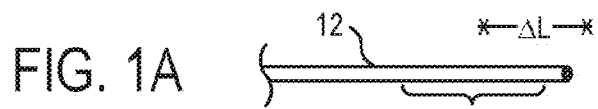
FIGS. 1A-1C schematically illustrate a plurality of alternative articulation states of the distal portion of the catheter in the system of FIG. 1.
Figure 1B:
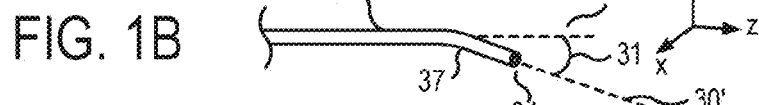
Figure 1C:
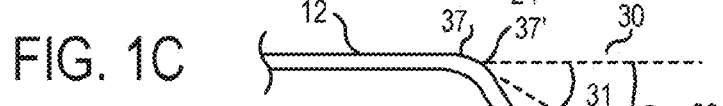

Referring now to FIGS. 1A, 1B, and 1C, system 10 may be configured to articulate actuated portion 20. Articulation will often allow movement continuously throughout a range of motion, though some embodiments may provide articulation in-part or in-full by selecting from among a plurality of discrete articulation states. Catheters having opposed axial extension and contraction actuators are described herein that may be particularly beneficial for providing continuous controlled and reversible movement, and can also be used to modulate the stiffness of a flexible structure. These continuous and discrete systems share many components (and some systems might employ a combination of both approaches).

First addressing the use of a discrete state system, FIG. 1A, system 10 can, for example, increase an axial length of actuated portion 20 by one or more incremental changes in length $\Delta L$. An exemplary structure for implementation of a total selectable increase in length $\Delta L$ can combine a plurality of incremental increases in length $\Delta L = \Delta L_1 + \Delta L_2 + \ldots$ ), as can be understood with reference to FIG. 4D. As shown in FIGS. 1B and 1C, system 10 may also deflect distal end 24 to a first bent state having a first bend angle 31 between unarticulated axis 30 and an articulated axis 30' (as shown schematically in FIG. 1B), or to a second bent state having a total bend angle 33 (between articulated axis 30 and articulated axis 30"), with this second bend angle being greater than the first bend angle (as shown schematically in FIG. 1C). An exemplary structure that could optionally be used by combining multiple discrete bend angle increments to form a total bend angle 33 (and/or which could also provide continuous movement) can be understood with reference to FIG. 4C. Regardless, the additional total cumulative bend angle 33 may optionally be implemented by imposing the first bend 31 (of FIG. 1B) as a first increment along with one or more additional bend angle increments 35. The incremental changes to actuated portion 20 may be provided by fully inflating and/or deflating actuation balloons of the catheter system. In fact, some embodiments could even be capable of only a single bend and/or elongation increment, but would more often have significantly more incremental articulation state options beyond those shown in FIGS. 1A-1C (and still more often would provide bending throughout a continuous range), so that a number of bend angles, bend orientations, axial lengths, and the like can and will often be available. For example, system 10 may be configured to provide any of a plurality of discrete alternative total bend angles (often being 3 or more, 5 or more, 10 or more, 20 or more, or even 40-100 angles, with embodiments providing between 3 and 20 alternative bend angles in a given lateral orientation), with one of the alternative bend angles typically comprising a resting or unarticulated angle (optionally being straight or having a zero degree bend angle; alternatively having some preset or physician-imposed bend). Incremental or continuous bend capabilities may be limited to a single lateral orientation, but will more typically be available in different lateral orientations, most typically in any of 3 or 4 orientations (for example, using balloons positioned along two pairs of opposed lateral axes, sometimes referred to as the +X, −X, +Y and −Y orientations), and by combining different bend orientations, in intermediate orientations as well. Continuous positioning may be implemented using similar articulation structures by partially inflating or deflating balloons or groups of balloons.

System 10 may also be configured to provide catheter 12 with any of a plurality of discrete alternative total axial lengths. As with the bend capabilities, such length actuation may also be implemented by inflating balloons of a balloon array structure. To provide articulation with the simple balloon array structures described herein, each actuation may be implemented as a combination of discrete, predetermined actuation increments (optionally together with one or more partial or modulated actuation) but may more often be provided using modulated or partial inflation of some, most, or all of the balloons. Hence, regardless of whether or not a particular catheter includes such bend-articulation capabilities, system 10 may be configured to provide catheter 12 with at least any of a plurality of discrete alternative total axial lengths (often being 3 or more, 5 or more, 10 or more, 20 or more, or even 40-100 lengths, with most embodiments providing between 3 and 20 alternative total lengths), more typically providing lengths throughout an elongation range. Nonetheless, embodiments of system 10 can be configured to implement each total actuation, in-part or in-full, as a combination of discrete, predetermined actuation increments. Some or all of the discrete actuation increments (and the associated balloon(s)) may have an associated location 37 or length segment along axis 30 within actuated portion 20, optionally an associated lateral X-Y orientation, and/or an associated predetermined incremental actuation amount. The lateral X-Y orientation of at least some of the actuation increments may be transverse to the local axis of catheter body 12 (shown as the Z axis in FIG. 1B) and the relationship between the positions of the various actuation balloons 36 and the lateral deflection axes X-Y can be understood with reference to FIG. 4. Regarding the incremental actuation amount, inflation and/or deflation of a particular balloon may be characterized using an incremental bend angle, an axial offset change, axial elongation displacement, and/or the like. Each actuation increment (including inflation or deflation of one or more balloon) may also have an associated increment actuation time (for full inflation or deflation of the balloon, with these often being different). While these times may be variably controlled in some embodiments, optionally with controlled variations in fluid flow (such as ramp-up or ramp downs) during a single actuation increment, many embodiments may instead use relatively uniform incremental actuation pressures and flow characteristics (optionally via fixed throttled or damped fluid flows into and/or out of the balloons). Nonetheless, controllable (and relatively high) overall distal velocities may be provided from coordinated timing of the discrete actuation increments along the length of the catheter body, for example, by controlled initiating of inflation of multiple balloons so that at least a portion of their associated inflation times overlap. An actuation increment implementation structure (generally one or more associated actuation balloons) can be associated with each actuation increment, with the actuation structure optionally being commanded to be in either an actuated configuration or an unactuated configuration (such as with the actuation balloon being fully inflated or fully deflated, respectively). Varying of the bend angles may, for example, be implemented by changing the number of balloons along one side of the catheter body 12 that are commanded to be fully inflated at a given time, with each additional balloon inflation incrementally increasing the overall bend angle. The balloons will often have differing associated axial locations 37, 37' along actuated portion 20. This can allow the axial location of a commanded bend increment to be selected from among a plurality of discrete axial locations 37, 37' by selection of the associated balloon axial locations to be included in the inflated group, which will typically be less than all of the balloons in an array. Desired total actuations can be implemented by identifying and combining a sub-set of bend increments (and/or other actuation increments) from among the available incremental actuations and inflating the associated sub-set of actuation balloons from among the overall balloon array or arrays). Hence, along with allowing control over the total bend angle, appropriate selection of the sub-set from among the pre-determined bend increments along actuated portion 20 may allow control over an average radius of the bend, for example, by axially distributing or separating the subset of discrete bend increments over an overall length of the bend. Control over an axial location of the overall bend can be provided by selecting the axial locations of the inflated balloon subset; and control over the lateral X-Y orientation of the total bend can be provided by selecting the subset from among the differing available incremental lateral orientations so as to combine together to approximate a desired orientation; and the like.

As suggested above, actuated portion 20 can often be articulated into any of a plurality of different overall bend profiles with a plurality of differing bend angles. Additionally, and often substantially independently of the bend angle, actuated portion 20 can be reconfigured so as to bend in any of a plurality of differing lateral bend directions (in the cross-sectional or X-Y plane, often through a combination of discrete incremental bend orientations), can bend at any of a plurality of axial locations, and/or can be actuated to bend with any of a plurality of differing overall bend radii. Furthermore, the bend orientation and/or bend radius may controllably differ along the axial length of actuated portion 20. Interestingly, and contrary to most catheter steering systems, some embodiments of the present invention may not be capable of driving axis 30 of catheter body 20 to intermediate bend angles between sums of the discrete bend increments 31, 35, as total articulation may be somewhat digital in nature. Note, however, that while some or all of the actuation increments may be uniform, the individual bend angles and the like may alternatively be non-uniform (such as by including balloons of different sizes within the array), so that a subset of the pre-determined bend increments can be configured to allow fine-tuning of bend angle and the like. Alternatively, as total actuation will often be a sum of a series of incremental actuations, one or more balloons can be configured to provide analog (rather than digital) articulation, with the analog movement often being sufficient to bridge between discrete digital articulations and thereby providing a continuous position range. This can be implemented, for example, by configuring the system to variably partially inflate one or more of the balloons of the array (rather than relying on full inflation or deflation) such as by using an associated positive displacement pump. Still more commonly, balloons or groups of balloons may be inflated to variable pressures throughout a range, providing effectively analog movement throughout the range of motion of the system.

Conveniently, the overall actuation configuration or state of catheter body 12 may be described using a plurality of scalar quantities that are each indicative of the states of associated actuation increments and balloons, with those incremental states optionally being combined to define an actuation state vector or matrix. Where the actuation increments are digital in nature (such as being associated with full inflation or full deflation of a balloon), some or all of the actuation state of catheter 12 may be described by a digital actuation state vector or matrix. Such digital embodiments (particularly those without analog components) may take advantage of these simple digital state vectors or digital state matrices to significantly facilitate data manipulations and enhance control signal processing speeds, helping to lessen minimum desired processing capabilities and overall system costs. Note also that many of the resolution, flexibility, and accuracy advantages of the balloon array systems described above are also available when all of the balloons of the array are inflatable to variable inflation states. Hence, some embodiments of the systems described herein may include fluid control systems that direct modulated quantities and/or pressures of fluids to multiple balloons along one or more fluid transmission channels. Control systems for such embodiments may employ similar processing approaches, but with the balloon inflation scalar values having variable values in a range from minimal or no effective inflation to fully inflated.

Figure 2:
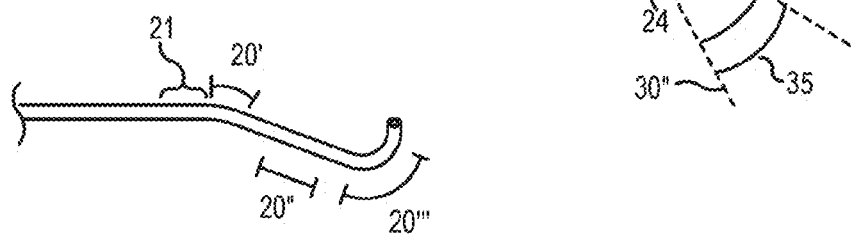
FIG. 2 schematically illustrates an alternative distal structure having a plurality of articulatable sub-regions or segments so as to provide a desired total number of degrees of freedom and range of movement.

Referring now to FIGS. 1-1 and 2, embodiments of articulation system 10 will move the distal end 24 of catheter 12 toward a desired position and/or orientation in a workspace relative to a base portion 21, with the base portion often being adjacent to and proximal of actuated portion 20. Note that such articulation may be relatively (or even completely) independent of any bending of catheter body 12 proximal of base portion 21. The location and orientation of proximal base 21 (relative to handle 14 or to another convenient fixed or movable reference frame) may be identified, for example, by including known catheter position and/or orientation identification systems in system 10, by including radiopaque or other high-contrast markers and associated imaging and position and/or orientation identifying image processing software in system 10, by including a flexible body state sensor system along the proximal portion of catheter body 12, by foregoing any flexible length of catheter body 12 between proximal handle 14 and actuated portion 20, or the like. A variety of different degrees of freedom may be provided by actuated portion 20. Exemplary embodiments of articulation system 10 may allow, for example, distal end 24 to be moved with 2 degrees of freedom, 3 degrees of freedom, 4 degrees of freedom, 5 degrees of freedom, or 6 degrees of freedom relative to base portion 21. The number of kinematic degrees of freedom of articulated portion 20 may be much higher in some embodiments, particularly when a number of different alternative subsets of the balloon array could potentially be in different inflation states to give the same resulting catheter tip and/or tool position and orientation.

Note that the elongate catheter body 12 along and beyond actuated portion 20 may (and often should) remain flexible before, during, and after articulation, so as to avoid inadvertently applying lateral and/or axial forces to surrounding tissues that are beyond a safe threshold. Nonetheless, embodiments of the systems described herein may locally and controllably increase a stiffness of one or more axial portions of catheter body 12, along actuated portion 20, proximal of actuated portion 20, and/or distal of actuated portion 20. Such selective stiffening of the catheter body may be implemented with or without active articulation capabilities, may extend along one or more axial portion of catheter body 12, and may alter which portions are stiffened and which are more flexible in response to commands from the user, sensor input (optionally indicating axial movement of the catheter), or the like.

As shown in FIG. 2, actuated portion 20 may comprise an axial series of 2 or more (and preferably at least 3) actuatable sub-portions or segments 20', 20", 20''', with the segments optionally being adjacent to each other, or alternatively separated by relatively short (less than 10 diameters) and/or relatively stiff intermediate portions of catheter 12. Each sub-portion or segment may have an associated actuation array, with the arrays working together to provide the desired overall catheter shape and degrees of freedom to the tip or tool. At least 2 of the sub-portions may employ similar articulation components (such as similar balloon arrays, similar structural backbone portions, similar valve systems, and/or similar software). Commonality may include the use of corresponding actuation balloon arrays, but optionally with the characteristics of the individual actuation balloons of the different arrays and the spacing between the locations of the arrays varying for any distal tapering of the catheter body. There may be advantages to the use of differentiated articulation components, for example, with proximal and distal sub portions, 20', 20''' having similar structures that are configured to allow selective lateral bending with at least two degrees of freedom, and intermediate portion 20" being configured to allow variable axial elongation. In many embodiments, however, at least two (and preferably all) segments are substantially continuous and share common components and geometries, with the different segments having separate fluid channels and being separately articulatable but each optionally providing similar movement capabilities.

For those elongate flexible articulated structures described herein that include a plurality of axial segments, the systems will often determine and implement each commanded articulation of a particular segment as a single consistent articulation toward a desired segment shape state that is distributed along that segment. In some exemplary embodiments, the nominal or resting segment shape state may be constrained to a 3 DOF space (such as by continuous combinations of two transverse lateral bending orientations and an axial (elongation) orientation in an X-Y-Z work space). In some of the exemplary embodiments described herein (including at least some of the helical extension/contraction embodiments), lateral bends along a segment may be at least approximately planar when the segment is in or near a design axial length configuration (such as at or near the middle of the axial or Z range of motion), but may exhibit a slight but increasing off-plane twisting curvature as the segment moves away from that design configuration (such as near the proximal and/or distal ends of the axial range of motion). The off-plane bending may be repeatably accounted for kinematically by determining the changes in lateral orientation of eccentric balloons resulting from winding and unwinding of helical structures supporting those balloons when the helical structures increase and decrease in axial length. For example, a segment may be commanded (as part of an overall desired pose or movement) to bend in a −Y orientation with a 20 degree bend angle. If the bend is to occur at a design axial length (such as at the middle of the axial range of motion), and assuming balloons (or opposed balloon pairs) at 4 axial bend locations can be used to provide the commanded bend, the balloons (or balloon pairs) may each be inflated or deflated to bend the segment by about 5 degrees (thereby providing a total bend of 5*4 or 20 degrees) in the −Y orientation. If the same bend is to be combined with axial lengthening of the segment to the end of its axial range of motion, the processor may determine that the segment may would exhibit some twist (say 2 degrees) so that there would be a slight +X component to the commanded bend, so that the processor may compensate for the twist by commanding a corresponding −X bend component, or by otherwise compensating in the command for another segment of the flexible body.

Figure 3:
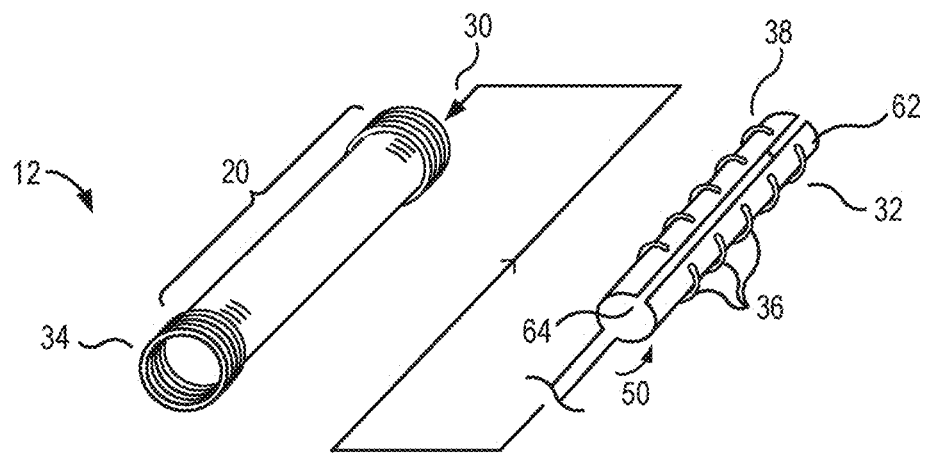
FIG. 3 is a simplified exploded perspective view showing a balloon array that can be formed in a substantially planar configuration and rolled into a cylindrical configuration, and which can be mounted coaxially to a helical coil or other skeleton framework for use in the catheter of the system of FIGS. 1 and 2.
Figure 5:
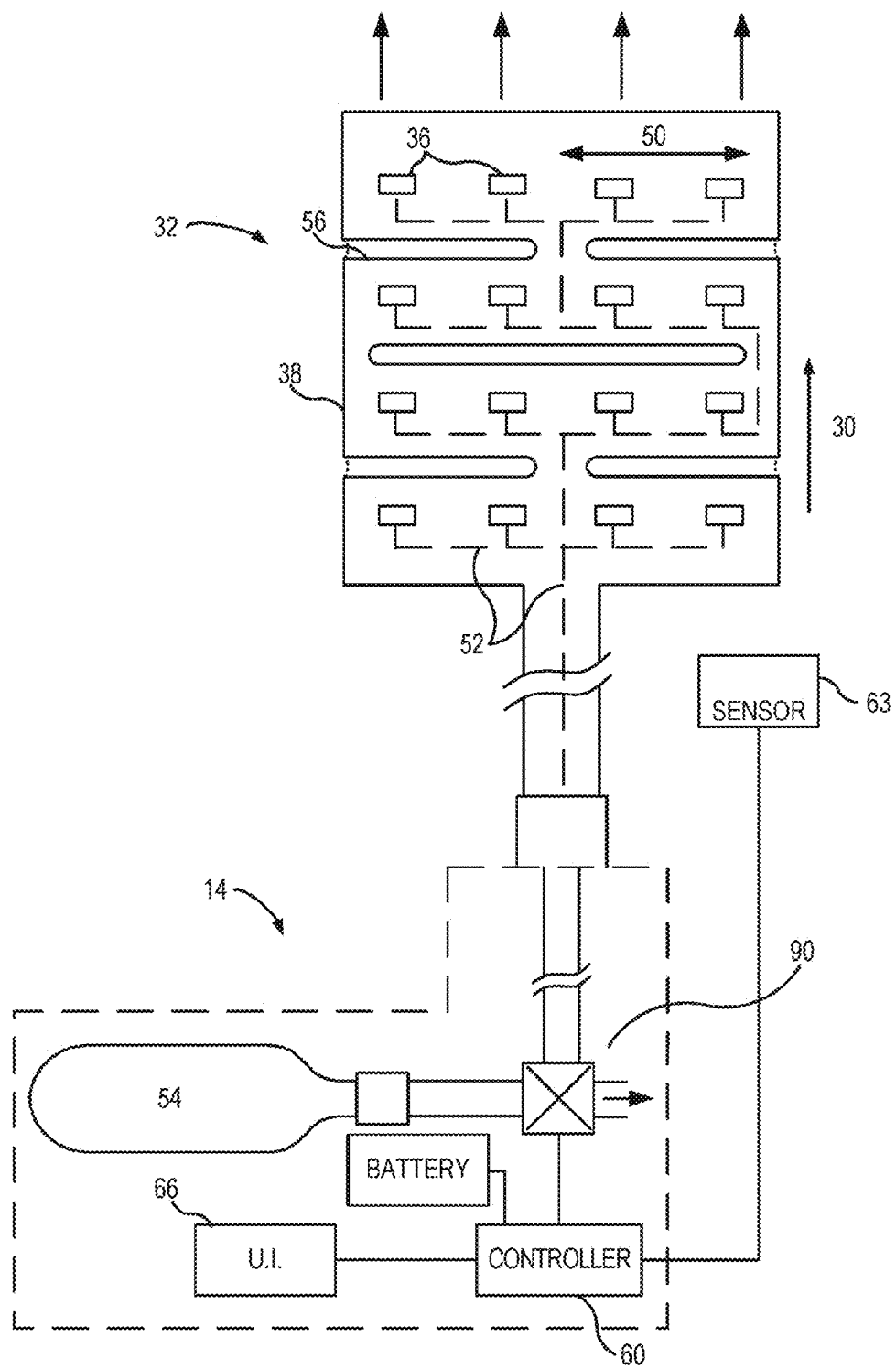
FIG. 5 schematically illustrates components for use in the catheter system of FIG. 1, including the balloon array, inflation fluid source, fluid control system, and processor.

Referring to FIGS. 3 and 5, catheter body 12 of system 10 includes an actuation array structure 32 mounted to a structural skeleton (here in the form of a helical coil 34). Exemplary balloon array 32 includes fluid expandable structures or balloons 36 distributed at balloon locations along a flexible substrate 38 so as to define an M×N array, in which M is an integer number of balloons distributed about a circumference 50 of catheter 12 at a given location along axis 30, and N represents an integer number of axial locations along catheter 12 having actuation balloons. Circumferential and axial spacing of the array element locations will generally be known, and will preferably be regular. This first exemplary actuation array includes a 4×4 array for a total of 16 balloons; alternative arrays may be from 1×2 arrays for a total of 2 balloons to 8×200 arrays for a total of 1600 balloons (or beyond), more typically having from 3×3 to 6×20 arrays. While balloon arrays of 1×N may be provided (particularly on systems that rely on rotation of the catheter body to orient a bend), M will more typically be 2 or more, more often being from 3 to 8, and preferably being 3 or 4. Similarly, while balloon arrays of M×1 may be provided to allow imposition of a single bend increment at a particular location in any of a number of different desired lateral orientations, array 32 will more typically have an N of from 2 to 200, often being from 3 to 20 or 3 to 100. In contraction/expansion embodiments described below, multiple arrays may be provided with similar M×N arrays mounted in opposition. Not all array locations need have inflatable balloons, and the balloons may be arranged in more complex arrangements, such as with alternating circumferential numbers of balloons along the axis, or with varying or alternating separation between balloons along the axial length of the array.

The balloons of a particular segment or that are mounted to a common substrate may be described as forming an array, with the actuation balloon array structure optionally being used as a sub-array in a multi-segment or opposed articulation system. The combined sub-arrays together may form an array of the overall device, which may also be described simply as an array or optionally an overall or combined array. Exemplary balloon arrays along a segment or sub-portion of articulated portion 20 include 1×8, 1×12, and 1×16 arrays for bending in a single direction (optionally with 2, 3, 4, or even all of the balloons of the segment in fluid communication with a single common inflation lumen so as to be inflated together) and 4×4, 4×8, and 4×12 arrays for X-Y bending (with axially aligned groups of 2-12 balloons coupled with 4 or more common lumens for articulation in the +X, −X, +Y, and −Y orientations). Exemplary arrays for each segment having the opposed extension/retraction continuous articulation structures described herein may be in the form of a 3×2N, 3×3N, 4×2N, or 4×3N balloons arrays, for example, 3×2, 3×4, 3×6, 3×8, 3×10, 3×12, 3×14, and 3×16 arrays with 6 to 48 balloons, with the 3 lateral balloon orientations separated by 120 degrees about the catheter axis. Extension balloons will often be axially interspersed with contraction balloons along each lateral orientation, with separate 3×N arrays being combined together in a 3×2N extension/contraction array for the segment, while two extension balloons may be positioned axially between each contraction balloon for 3×3N arrangements. The contraction balloons may align axially and/or be in plane with the extension balloons they oppose, though it may be advantageous in some embodiments to arrange opposed balloons offset from a planer arrangement, so that (for example) two balloons of one type balance one balloon of the other, or vice versa. The extension balloons along each orientation of the segment may share a common inflation fluid supply lumen while the contraction balloons of the segment for each orientation similarly share a common lumen (using 6 fluid supply lumens per segment for both 3×2N and 3×3N arrays). An extension/contraction catheter may have from 1 to 8 such segments along the articulated portion, more typically from 1 to 5 segments, and preferably being 2 to 4 segments. Other medical and non-medical elongate flexible articulated structures may have similar or more complex balloon articulation arrays.

As can be seen in FIGS. 3, 4A, 4B, and 4C, the skeleton will often (though not always) include an axial series of loops 42. When the loops are included in a helical coil 34, the coil may optionally be biased so as to urge adjacent loops 42 of the coil 34 toward each other. Such axially compressive biasing may help urge fluid out and deflate the balloons, and may by applied by other structures (inner and/or outer sheath(s), pull wires, etc.) with or without helical compression. Axial engagement between adjacent loops (directly, or with balloon walls or other material of the array between loops) can also allow compressive axial forces to be transmitted relatively rigidly when the balloons are not inflated. When a particular balloon is fully inflated, axial compression may be transmitted between adjacent loops by the fully inflated balloon wall material and by the fluid within the balloons. Where the balloon walls are non-compliant, the inflated balloons may transfer these forces relatively rigidly, though with some flexing of the balloon wall material adjacent the balloon/skeleton interface. Rigid or semi-rigid interface structures which distribute axial loads across a broader balloon interface region may limit such flexing. Axial tension forces (including those associated with axial bending) may be resisted by the biasing of the skeleton (and/or by other axial compressive structures). Alternative looped skeleton structures may be formed, for example, by cutting hypotube with an axial series of lateral incisions across a portion of the cross-section from one or more lateral orientations, braided metal or polymer elements, or the like. Non-looped skeletons may be formed using a number of alternative known rigid or flexible robotic linkage architectures, including with structures based on known soft robot structures. Suitable materials for coil 34 or other skeleton structures may comprise metals such as stainless steel, spring steel, superelastic or shape-memory alloys such as Nitinol™ alloys, polymers, fiber-reinforced polymers, high-density or ultrahigh-density polymers, or the like.

When loops are included in the skeleton, actuation array 32 can be mounted to the skeleton with at least some of the balloons 36 positioned between two adjacent associated loops 42, such as between the loops of coil 34. Referring now to FIG. 4C, an exemplary deflated balloon 36i is located between a proximally adjacent loop 42i and a distally adjacent loop 42ii, with a first surface region of the balloon engaging a distally oriented surface of proximal loop 34i, and a second surface region of the balloon engaging a proximally oriented surface of distal loop 42ii. The walls of deflated balloon 36i have some thickness, and the proximal and distal surfaces of adjacent loops 42i and 42ii maintain a non-zero axial deflated offset 41 between the loops. Axial compression forces can be transferred from the loops through the solid balloon walls. Alternative skeletal structures may allow the loops to engage directly against each other so as to have a deflated offset of zero and directly transmit axial compressive force, for example by including balloon receptacles or one or more axial protrusions extending from one or both loops circumferentially or radially beyond the balloon and any adjacent substrate structure. Regardless, full inflation of the balloon will typically increase the separation between the adjacent loops to a larger full inflation offset 41'. The simplified lateral cross-sections of FIGS. 4B, 4C, and 4D schematically show a direct interface engagement between a uniform thickness thin-walled balloon and a round helical coil loop. Such an interface may result in relatively limited area of the balloon wall engaging the coil and associated deformation under axial loading. Alternative balloon-engaging surface shapes along the coils (often including locally increased convex radii, locally flattened surfaces, and/or local concave balloon receptacles) and/or along the coil-engaging surfaces of the balloon (such as by locally thickening the balloon wall to spread the engagement area), and/or providing load-spreading bodies between the balloons and the coils may add axial stiffness. A variety of other modifications to the balloons and balloon/coil interfaces may also be beneficial, including adhesive bonding of the balloons to the adjacent coils, including folds or material so as to inhibit balloon migration, and the like.

Inflation of a balloon can alter the geometry along catheter body 12, for example, by increasing separation between loops of a helical coil so as to bend axis 30 of catheter 12. As can be understood with reference to FIGS. 1B, 1C and 4-4C, selectively inflating an eccentric subset of the balloons can variably alter lateral deflection of the catheter axis. As can be understood with reference to FIGS. 1A, 4, and 4D, inflation of all (or an axisymmetric subset) of the balloons may increase an axial length of the catheter structure. Inflating subsets of the balloons that have a combination of differing lateral orientations and axial positions can provide a broad range of potential locations and orientations of the catheter distal tip 26, and/or of one or more other locations along the catheter body (such as where a tool is mounted).

Some or all of the material of substrate 38 included in actuation array 32 will often be relatively inelastic. It may, however, be desirable to allow the skeleton and overall catheter to flex and/or elongate axially with inflation of the balloons or under environmental forces. Hence, array 32 may have cutouts 56 so as to allow the balloon array to move axially with the skeleton during bending and elongation. The array structure could alternatively (or in addition) be configured for such articulation by having a serpentine configuration or a helical coiled configuration. Balloons 36 of array 32 may include non-compliant balloon wall materials, with the balloon wall materials optionally being formed integrally from material of the substrate or separately. Note that elastic layers or other structures may be included in the substrate for use in valves and the like, and that some alternative balloons may include elastic and/or semi-compliant materials.

Figure 4A:
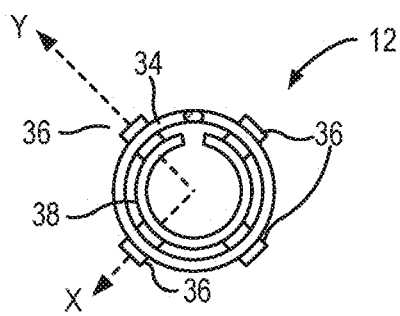
FIGS. 4A and 4B are a simplified cross-section and a simplified transverse cross-section, respectively, of an articulatable catheter for use in the system of FIG. 1, shown here with the balloons of the array in an uninflated, small axial profile configuration and between loops of the coil.
Figure 4B:
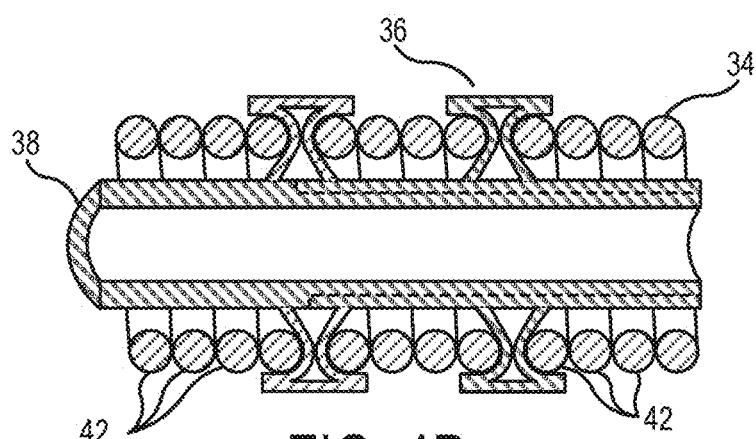
Figure 4C:
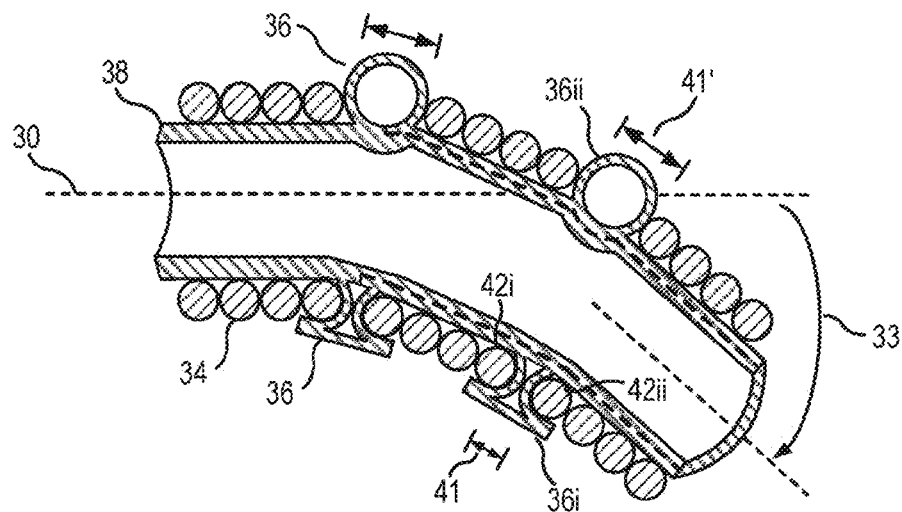
FIG. 4C is a simplified transverse cross-section of the articulatable catheter of FIGS. 4A and 4B, with a plurality of axially aligned balloons along one side of the articulatable region of the catheter inflated so that the catheter is in a laterally deflected state.
Figure 4D:
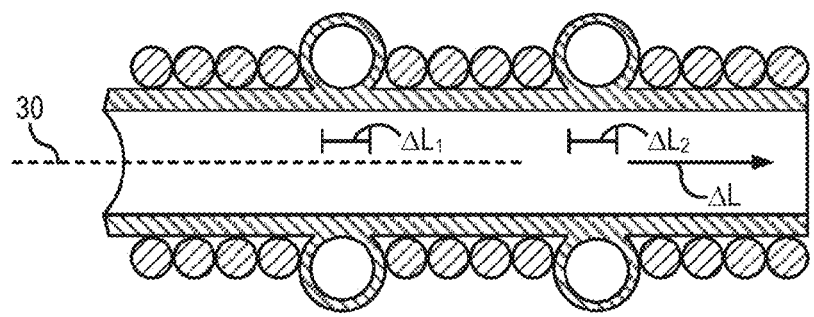
FIG. 4D is a simplified transverse cross-section of the articulatable catheter of FIG. 4, with a plurality of laterally opposed balloons inflated so that the catheter is in an axially elongated state.

Referring to FIGS. 3, 4A, and 5, substrate 38 of array 32 is laterally flexible so that the array can be rolled or otherwise assume a cylindrical configuration when in use. The cylindrical array may be coaxially mounted to (such as being inserted into or radially outwardly surrounding) the helical coil 34 or other structural backbone of the catheter. The cylindrical configuration of the array will generally have a diameter that is equal to or less than an outer diameter of the catheter. The opposed lateral edges of substrate 38 may be separated by a gap as shown, may contact each other, or may overlap. Contacting or overlapping edges may be affixed together (optionally so as to help seal the catheter against radial fluid flow) or may accommodate relative motion (so as to facilitate axial flexing). In some embodiments, lateral rolling or flexing of the substrate to form the cylindrical configuration may be uniform (so as to provide a continuous lateral curve along the major surfaces), while in other embodiments intermittent axial bend regions of the substrate may be separated by axially elongate relatively flat regions of the substrate so that a cylindrical shape is approximated by a prism-like arrangement (optionally so as to limit bending of the substrate along balloons, valves, or other array components).

It will often (though not always) be advantageous to form and/or assemble one or more components of the array structure in a flat, substantially planar configuration (and optionally in a linear configuration as described below). This may facilitate, for example, partial or final formation of balloons 36 on substrate 38, or alternatively, attachment of pre-formed balloons to the substrate. The flat configuration of the substrate may also facilitate the use of known extrusion or microfluidic channel fabrication techniques to provide fluid communication channels 52 so as to selectively couple the balloons with a fluid inflation fluid source or reservoir 54, and the like. Still further advantages of the flat configuration of the substrate may include the use of electrical circuit printing techniques to fabricate electrical traces and other circuit components, automated 3-D printing techniques (including additive and/or removal techniques) for forming valves, balloons, channels, or other fluid components that will be supported by substrate 38, and the like. When the substrate is in a rolled, tubular, or flat planar configuration, the substrate will typically have a first major surface 62 adjacent balloons 36, and a second major surface 64 opposite the first major surface (with first major surface 62 optionally being a radially inner or outer surface and second major surface 64 being a radially outer or inner surface, respectively, in the cylindrical configuration). To facilitate flexing substrate 38 and array 32 into the rolled configuration, relief cuts or channels may be formed extending into the substrate from the first and/or second major surfaces, or living hinge regions may otherwise be provided between relatively more rigid portions of the substrate. To further avoid deformation of the substrate adjacent any valves or other sensitive structures, local stiffening reinforcement material may be added, and/or relief cuts or apertures may be formed partially surrounding the valves. In some embodiments, at least a portion of the array components may be formed or assembled with the substrate at least partially in a cylindrical configuration, such as by bonding layers of the substrate together while the substrate is at least locally curved, forming at least one layer of the substrate as a tube, selectively forming cuts in the substrate (optionally with a femtosecond, picosecond, or other laser) to form fluid, circuit, or other components or allow for axial flexing and elongation (analogous to cutting a stent to allow for axial flexing and radial expansion) and/or to form at least some of the channels, and bonding the layers together after cutting.

As can be understood with reference to FIGS. 5-5C, substrate 38 of array 32 may include one or more layers 70, 72, 74 . . . of flexible substrate material. The substrate layers may comprise known flexible and/or rigid microfluidic substrate materials, such as polydimethylsiloxane (PDMS), polyimide (PI), polyethylene (PE) and other polyolefins, polystyrene (PS), polyethylene terephthalate (PET), polypropylene (PP), polycarbonate (PC), nanocomposite polymer materials, glass, silicon, cyclic olefin copolymer (COC), polymethyl methacrylate (PMMA), polyetheretherketone (PEEK), polyester, polyurethane (PU), and/or the like. These and still further known materials may be included in other components of actuation array 32, including known polymers for use in balloons (which will often include PET, PI, PE, polyether block amide (PEBA) polymers such as PEBAX™ polymers, nylons, urethanes, polyvinyl chloride (PVC), thermoplastics, and/or the like for non-compliant balloons; or silicone, polyurethane, semi-elastic nylons or other polymers, latex, and/or the like for compliant or semi-compliant balloons). Additional polymers than may be included in the substrate assembly may include valve actuation elements (optionally including shape memory alloy structures or foils; phase-change actuator materials such as paraffin or other wax, electrical field sensitive hydrogels, bimetallic actuators, piezoelectric structures, dielectric elastomer actuator (DEA) materials, or the like). Hence, while some embodiments may employ homogenous materials for actuation array 32, many arrays and substrate may instead be heterogeneous.

Fortunately, techniques for forming and assembling the components for actuation array 32 may be derived from a number of recent (and relatively widely-reported) technologies. Suitable techniques for fabricating channels in substrate layer materials may include laser micromachining (optionally using femtosecond or picosecond lasers), photolithography techniques such as dry resist technologies, embossing (including hot roller embossing), casting or molding, xerographic technologies, microthermoforming, stereolithography, 3-D printing, and/or the like. Suitable 3-D printing technologies that may be used to form circuitry, valves, sensors, and the like may include stereolithography, digital light processing, laser sintering or melting, fused deposition modeling, inkjet printing, selective deposition lamination, electron beam melting, or the like. Assembly of the components of actuation array 32 may make use of laser, thermal, and/or adhesive bonding between layers and other components, though laser, ultrasound, or other welding techniques; microfasteners, or the like may also be used. Electrical element fabrication of conductive traces, actuation, signal processor, and/or sensor components carried by substrate 38 may, for example, use ink-jet or photolithography techniques, 3-D printing, chemical vapor deposition (CVD) and/or more specific variants such as initiated chemical vapor deposition (iCVD), robotic microassembly techniques, or the like, with the electrical traces and other components often comprising inks and other materials containing metals (such as silver, copper, or gold) carbon, or other conductors. Many suitable fabrication and assembly techniques have been developed during development of microfluidic lab-on-a-chip or lab-on-a-foil applications. Techniques for fabricating medical balloons are well developed, and may optionally be modified to take advantage of known high-volume production techniques (optionally including those developed for fabricating bubble wrap, for corrugating extruded tubing, and the like). Note that while some embodiments of the actuation array structures described herein may employ fluid channels sufficiently small for accurately handling of picoliter or nanoliter fluid quantities, other embodiments will include channels and balloons or other fluid-expandable bodies that utilize much larger flows so as to provide desirable actuation response times. Balloons having at least partially flexible balloon walls may provide particular advantages for the systems described herein, but alternative rigid fluid expandable bodies such as those employing pistons or other positive displacement expansion structures may also find use in some embodiments.

The structures of balloons 36 as included in actuation array 32 may be formed of material integral with other components of the array, or may be formed separately and attached to the array. For example, as shown in FIGS. 5B and 5C, balloons 36 may be formed from or attached to a first sheet 74 of substrate material that can be bonded or otherwise affixed to another substrate layer 72 or layers. The material of the balloon layer 74 may optionally cover portions of the channels directly, or may be aligned with apertures 78 that open through an intermediate substrate layer surface between the channels and the balloons. Apertures 78 may allow fluid communication between each balloon and at least one associated channel 52. Alternative methods for fabricating individual balloons are well known, and the formed balloons may be affixed to the substrate 38 by adhesive bonding. Balloon shapes may comprise relatively simple cylinders or may be somewhat tailored to taper to follow an expanded offset between loops of a coil, to curve with the cylindrical substrate and/or to engage interface surfaces of the skeleton over a broader surface area and thereby distribute actuation and environmental loads. Effective diameters of the balloons in the array may range from about 0.003 mm to as much as about 2 cm (or more), more typically being in a range from about 0.3 mm to about 2 mm or 5 mm, with the balloon lengths often being from about 2 to about 15 times the diameter. Typical balloon wall thicknesses may range from about 0.0002 mm to about 0.004 mm (with some balloon wall thicknesses being between 0.0002 mm and 0.020 mm), and full inflation pressures in the balloons may be from about 0.2 to about 40 atm, more typically being in a range from about 0.4 to about 30 atm, and in some embodiments being in a range from about 10 to about 30 atm, with high-pressure embodiments operating at pressures in a range as high as 20-45 atm and optionally having burst pressures of over 50 atm.

Referring now to FIG. 5, balloons 36 will generally be inflated using a fluid supply system that includes a fluid source 54 (shown here as a pressurized single-use cartridge) and one or more valves 90. At least some of the valves 90 may be incorporated into the balloon array substrate, with the valves optionally being actuated using circuitry printed on one or more layers of substrate 38. With or without substrate-mounted valves that can be used within a patient body, at least some of the valves may be mounted to housing 14, or otherwise coupled to the proximal end of catheter 12. Valves 90 will preferably be coupled to channels 52 so as to allow the fluid system to selectively inflate any of a plurality of alternative individual balloons or subsets of balloons 36 included in actuation array 32, under the direction of a processor 60. Hence, processor 60 will often be coupled to valves 90 via conductors, the conductors here optionally including flex circuit traces on substrate 38.

Referring still to FIG. 5, fluid source 54 may optionally comprise a separate fluid reservoir and a pump for pressurizing fluid from the reservoir, but will often include a simple tank or cartridge containing a pressurized fluid, the fluid optionally being a gas or a gas-liquid mixture. The cartridge will often maintain the fluid at a supply pressure at or above a full inflation pressure range of balloons 36, with the cartridge optionally being gently heated by a resistive heater or the like (not shown) in housing 14 so as to maintain the supply pressure within a desired range in the cartridge during use. Supply pressures will typically exceed balloon inflation pressures sufficiently to provide balloon inflation times within a target threshold given the pressure loss through channels 52 and valves 90, with typical supply pressures being between 10 and 210 atm, and more typically being between 20 and 60 atm. Suitable fluids may include known medical pressurized gases such as carbon dioxide, nitrogen, oxygen, nitrous oxide, air, known industrial and cryogenic gasses such as helium and/or other inert or noble gasses, refrigerant gases including fluorocarbons, and the like. Note that the pressurized fluid in the canister can be directed via channels 52 into balloons 36 for inflation, or the fluid from the canister (often at least partially a gas) may alternatively be used to pressurize a fluid reservoir (often containing or comprising a benign biocompatible liquid such as water or saline) so that the balloon inflation fluid is different than that contained in the cartridge. Where a pressurized liquid or gas/liquid mixture flows distally along the catheter body, enthalpy of vaporization of the liquid in or adjacent to channels 52, balloons 36, or other tissue treatment tools carried on the catheter body (such as a tissue dilation balloon, cryogenic treatment surface, or tissue electrode) may be used to therapeutically cool tissue. In other embodiments, despite the use of fluids which are used as refrigerants within the body, no therapeutic cooling may be provided. The cartridge may optionally be refillable, but will often instead have a frangible seal so as to inhibit or limit re-use.

As the individual balloons may have inflated volumes that are quite small, cartridges that are suitable for including in a hand-held housing can allow more than a hundred, optionally being more than a thousand, and in many cases more than ten thousand or even a hundred thousand individual balloon inflations, despite the cartridge containing less than 10 ounces of fluid, often less than 5 ounces, in most cases less than 3 ounces, and ideally less than 1 ounce. Note also that a number of alternative fluid sources may be used instead of or with a cartridge, including one or more positive displacement pumps (optionally such as simple syringe pumps), a peristaltic or rotary pump, any of a variety of microfluidic pressure sources (such as wax or other phase-change devices actuated by electrical or light energy and/or integrated into substrate 38), or the like. Some embodiments may employ a series of dedicated syringe or other positive displacement pumps coupled with at least some of the balloons by channels of the substrate, and/or by flexible tubing.

Referring still to FIG. 5, processor 60 can facilitate inflation of an appropriate subset of balloons 36 of actuation array 32 so as to produce a desired articulation. Such processor-derived articulation can significantly enhance effective operative coupling of the input 18 to the actuated portion 20 of catheter body 12, making it much easier for the user to generate a desired movement in a desired direction or to assume a desired shape. Suitable correlations between input commands and output movements have been well developed for teleoperated systems with rigid driven linkages. For the elongate flexible catheters and other bodies used in the systems described herein, it will often be advantageous for the processor to select a subset of balloons for inflation based on a movement command entered into a user interface 66 (and particularly input 18 of user interface 66), and on a spatial relationship between actuated portion 20 of catheter 12 and one or more component of the user interface. A number of differing correlations may be helpful, including orientational correlation, displacement correlation, and the like. Along with an input, user interface 66 may include a display showing actuated portion 20 of catheter body 12, and sensor 63 may provide signals to processor 60 regarding the orientation and/or location of proximal base 21. Where the relationship between the input, display, and sensor are known (such as when they are all mounted to proximal housing 14 or some other common base), these signals may allow derivation of a transformation between a user interface coordinate system and a base coordinate system of actuated portion 20. Alternative systems may sense or otherwise identify the relationships between the sensor coordinate system, the display coordinate system, and/or the input coordinate system so that movements of the input result in catheter movement, as shown in the display. Where the sensor comprises an image processor coupled to a remote imaging system (such as a fluoroscopy, MRI, or ultrasound system), high-contrast marker systems can be included in proximal base 21 to facilitate unambiguous determination of the base position and orientation. A battery or other power source (such as a fuel cell or the like) may be included in housing 14 and coupled to processor 60, with the housing and catheter optionally being used as a handheld unit free of any mechanical tether during at least a portion of the procedure. Nonetheless, it should be noted that processor 60 and/or sensor 63 may be wirelessly coupled or even tethered together (and/or to other components such as a separate display of user interface 66, an external power supply or fluid source, or the like).

Regarding processor 60, sensor 63, user interface 66, and the other data processing components of system 10, it should be understood that the specific data processing architectures described herein are merely examples, and that a variety of alternatives, adaptations, and embodiments may be employed. The processor, sensor, and user interface will, taken together, typically include both data processing hardware and software, with the hardware including an input (such as a joystick or the like that is movable relative to housing 14 or some other input base in at least 2 dimensions), an output (such as a medical image display screen), an image-acquisition device or other sensor, and one or more processor. These components are included in a processor system capable of performing the image processing, rigid-body transformations, kinematic analysis, and matrix processing functionality described herein, along with the appropriate connectors, conductors, wireless telemetry, and the like. The processing capabilities may be centralized in a single processor board, or may be distributed among the various components so that smaller volumes of higher-level data can be transmitted. The processor(s) will often include one or more memory or storage media, and the functionality used to perform the methods described herein will often include software or firmware embodied therein. The software will typically comprise machine-readable programming code or instructions embodied in non-volatile media, and may be arranged in a wide variety of alternative code architectures, varying from a single monolithic code running on a single processor to a large number of specialized subroutines being run in parallel on a number of separate processor sub-units.

Figure 6:
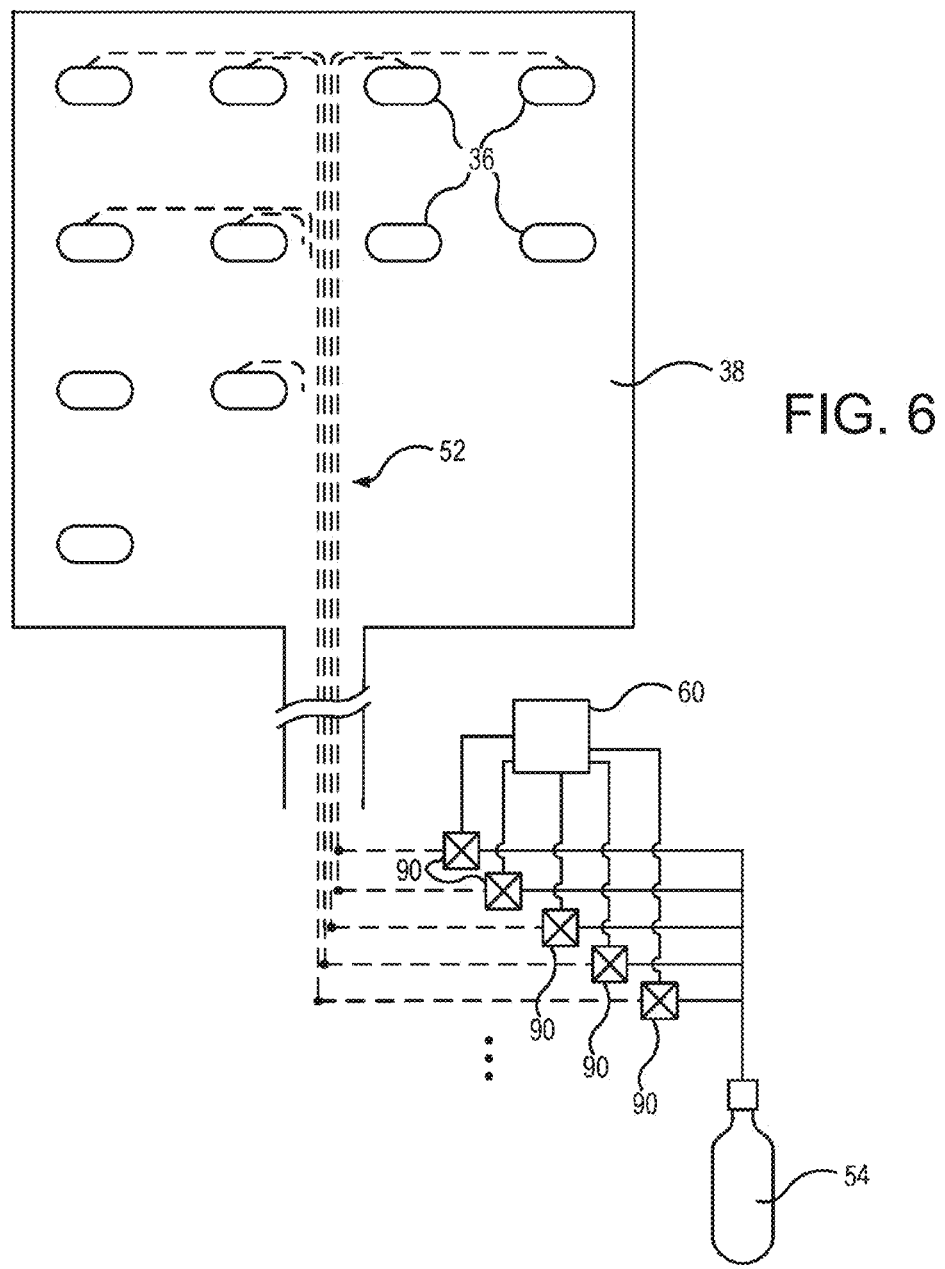
FIG. 6 is a simplified schematic of an alternative balloon array and fluid control system, in which a plurality of valves coupled with the proximal end of the catheter can be used to direct fluid to any of a plurality of channels of the array and thereby selectably determine a subset of balloons to be expanded.

Referring now to FIG. 6, an alternative actuation array and fluid supply system are shown schematically. As in the above embodiment, balloons 36 are affixed along a major surface of substrate 38, optionally prior to rolling the substrate and mounting of the actuation array to the skeleton of the catheter body. In this embodiment, each balloon has an associated dedicated channel 52 of substrate 38, and also an associated valve 90. Processor 60 is coupled with valves 90, and by actuating a desired subset of the valves the associated subset of balloons can be inflated or deflated. In some embodiments, each valve can be associated with more than one balloon 36, so that (for example), opening of a single valve might inflate a plurality (optionally 2, 3, 4, 8, 12, or some other desired number) of balloons, such as laterally opposed balloons so as to elongate the distal portion of the catheter. In these or other embodiments, a plurality of balloons (2, 3, 4, 5, 8, 12, or another desired number) on one lateral side of the catheter could be in fluid communication with a single associated valve 90 via a common channel or multiple channels so that opening of the valve inflates the balloons and causes a multi-balloon and multi-increment bend in the axis of the catheter. Still further variations are possible. For example, in some embodiments, channels 52 may be formed at least in-part by flexible tubes affixed within an open or closed channel of substrate 38, or glued along a surface of the substrate. The tubes may comprise polymers (such as polyimide, PET, nylon, or the like), fused silica, metal, or other materials, and suitable tubing materials may be commercially available from Polymicro Technologies of Arizona, or from a variety of alternative suppliers. The channels coupled to the proximal end of the actuatable body may be assembled using stacked fluidic plates, with valves coupled to some or all of the plates. Suitable electrically actuated microvalues are commercially available from a number of suppliers. Optional embodiments of fluid supply systems for all balloon arrays described herein may have all values mounted to housing 14 or some other structure coupled to and/or proximal of) the proximal end of the elongate flexible body. Advantageously, accurately formed channels 52 (having sufficiently tight tolerance channel widths, depths, lengths, and/or bends or other features) may be fabricated using microfluidic techniques, and may be assembled with the substrate structure, so as to meter flow of the inflation fluid into and out of the balloons of all of the actuation arrays described herein.

Figure 7:
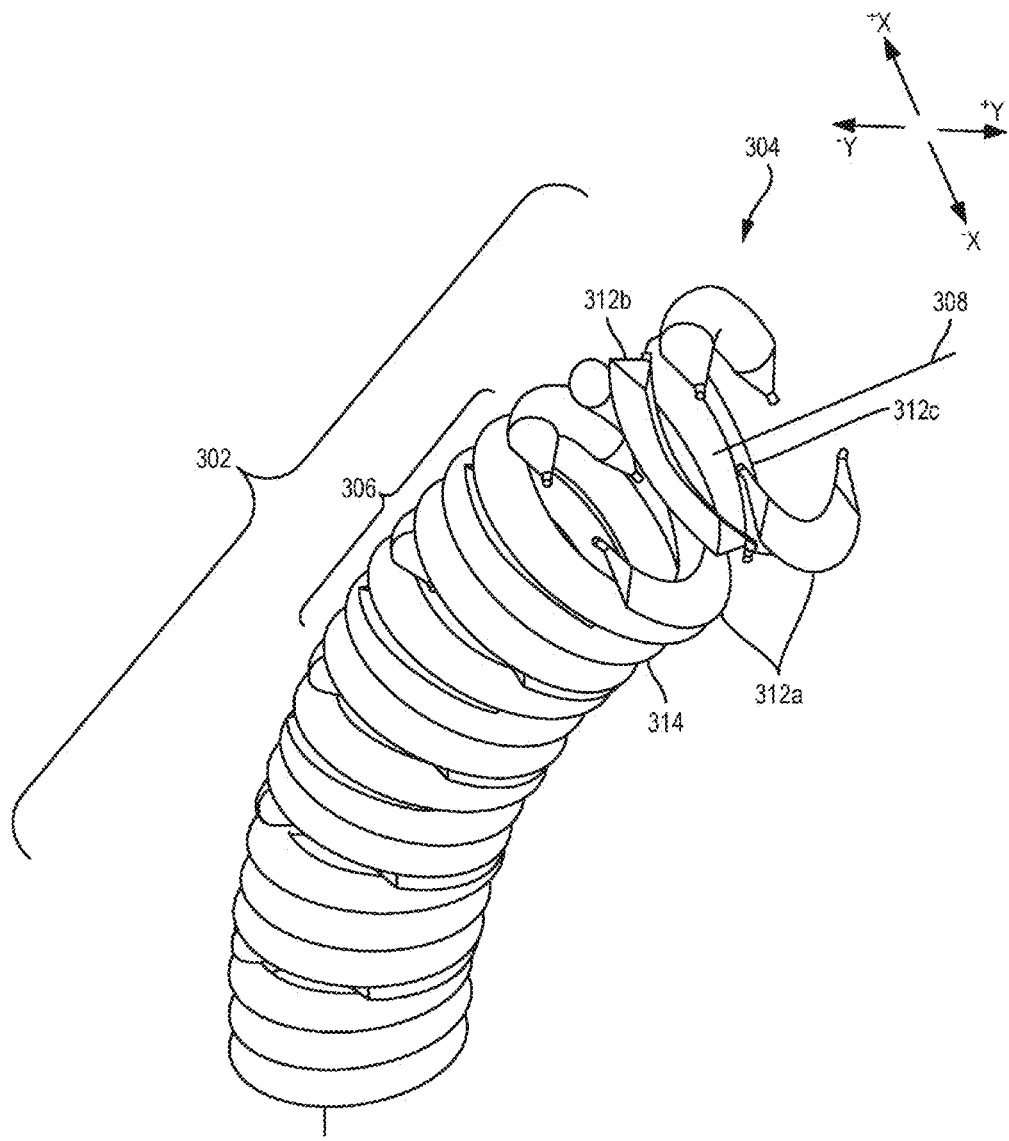
FIG. 7 shows a helical coil with inflated and uninflated balloons of a balloon array, with a distal portion of the coil removed to show the differing lateral orientations of the balloons relative to the axis of the coil.

Referring now to FIG. 7, selected components of an articulated portion 302 of an articulated catheter 304 can be seen in more detail. A plurality of inflated balloons 306 are offset from an axis 308 of catheter 304 along a first lateral orientation +X, so that the balloons urge corresponding pairs of axial (proximal and distal) surfaces on the loops of coil 310 apart. This urges the coil to bend away from inflated balloons 306 away from the +X orientation and toward the −X lateral orientation. Uninflated balloons 312a, 312b, and 312c are offset in the lateral −X, −Y, and +Y orientations, respectively, allowing selective inflations of differing subsets of these balloons to bend axis 308 in differing directions. Inflation of opposed balloons (such as −X and +X, or −Y and +Y, or both) may elongate coil 314 along axis 308. Note that a distal portion of coil 314 has been omitted from the drawing so that the arrangement of the balloons can be more clearly seen. This embodiment shows relatively standard offset balloon shapes, with the axes of the balloons bent to follow the coil. In this and other embodiments, a single balloon between coils may impose a bend in axis 308 in a range from 1 to 20 degrees, more typically being in a range from 2½ to 15 degrees, and often being from 6 to 13 degrees. To allow a single inflation lumen to achieve greater bend angles, 2, 3, 4, or more balloon inflation lumens or ports adjacent the balloons may be in fluid communication with a single common fluid inflation lumen.

Referring now to FIGS. 8 and 9, an alternative coaxial balloon/coil arrangement can be understood. In these embodiments, balloons 364 are mounted over a coil 366, with a plurality of the balloons typically being formed from a continuous tube of material that extends along the helical axis of the coil. The balloon material will generally have a diameter that varies locally, with the balloons being formed from locally larger diameter regions of the tube, and the balloons being separated by sealing engagement between the tube material and coil therein at locally smaller diameters of the tube. The variation in diameter may be formed by locally blowing the balloons outward from an initial tube diameter, by locally heat-shrinking and/or axially stretching the tube down from an initial tube diameter, or both, and adhesive or heat-bonding between the tube and coil core therein may enhance sealing. In alternative embodiments, metal rings may be crimped around the tubular balloon material to affix (and optionally seal) the tube to the underlying helical coil, with the rings and crimping optionally employing marker band structures and associated techniques. Some or even all of the variation in diameter of the balloon material along the coil may be imposed by the crimped rings, though selective heat shrinking and/or blowing of the balloons and/or laser thermal bonding of the balloon to the coil may be combined with the crimps to provide the desired balloon shape and sealing. Regardless, fluid communication between the inner volume of the balloon (between the balloon wall and the coil core) may be provided through a radial port to an associated lumen within the coil core. As can be understood with reference to coil assembly 360 of FIG. 8, the balloons may have outer surface shapes similar to those described above, and may similarly be aligned along one or more lateral bending orientations. As can be understood with reference to assemblies 360 and 362 of FIGS. 8 and 9, bend angles and radii of curvature of the catheter adjacent the balloon arrays may be determined by an axial spacing (and/or number of loops) between balloons, and/or by selective inflation of a subset of balloons (such as by inflating every other balloon aligned along a particular lateral axis, every third aligned balloon, every fourth aligned balloon, and so on).

Figure 10:
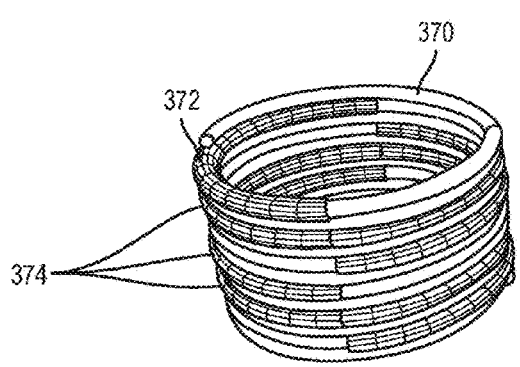
FIGS. 10 and 11 schematically illustrate structures having a plurality of interleaved coaxial helical coils.
Figure 11:
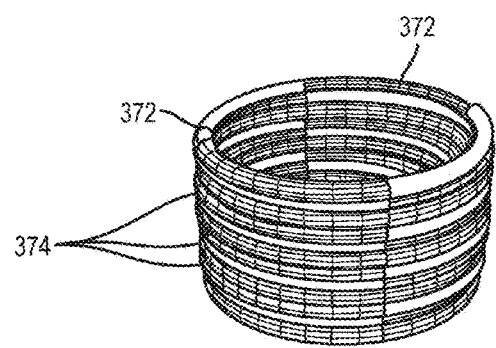
Figure 11A:
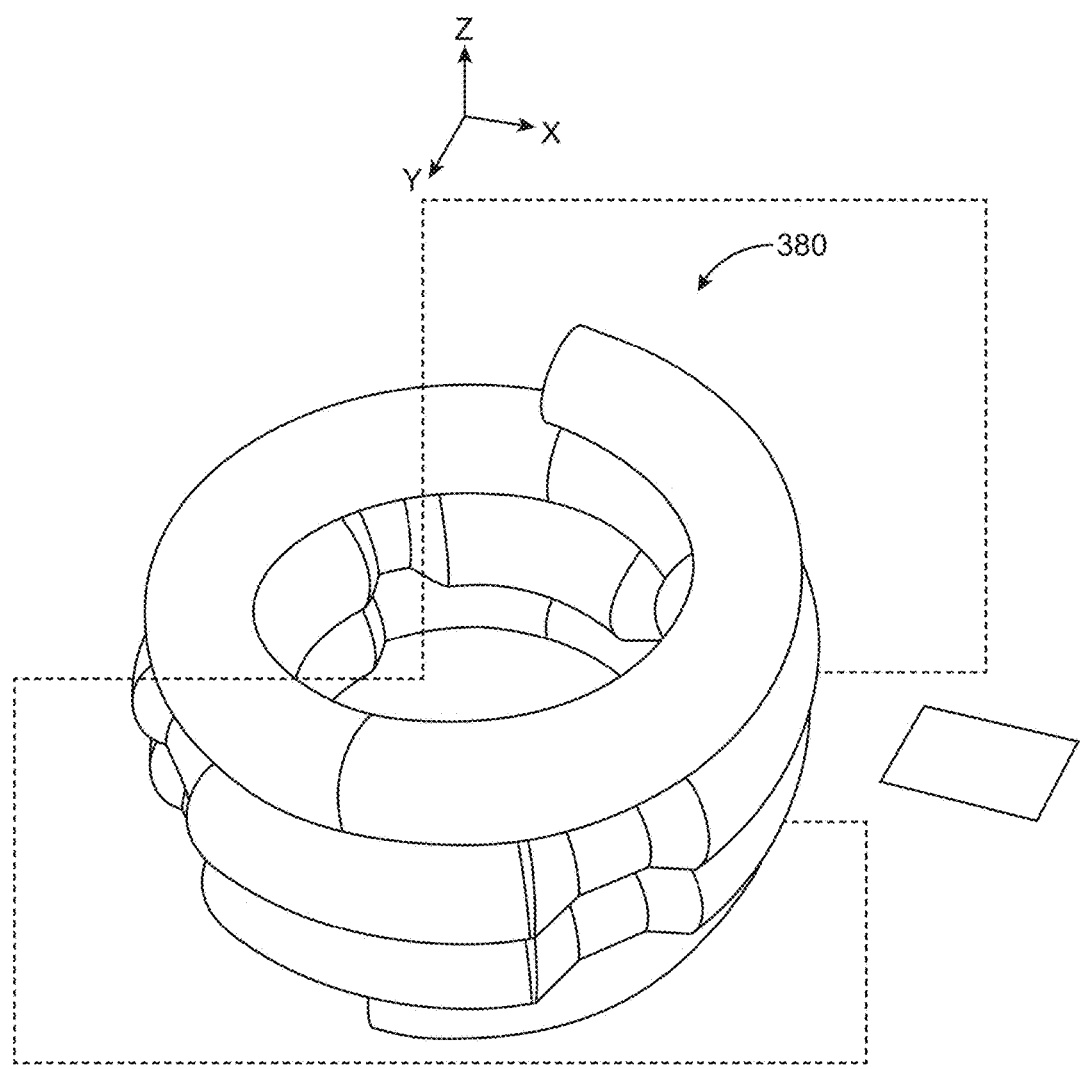
FIGS. 11A-11C schematically illustrate balloons disposed over a helical core at differing lateral orientations, and also show how extruded and/or micromachined multi-lumen helical cores can be used to provide fluid communication between and/or inflate one or more associated balloons at desired lateral orientations on a common core.

Referring now to FIGS. 10, 11, and 11A, alternative coaxial balloon/coil systems may take a variety of differing forms. In FIG. 10, a plurality of helical structures 370, 372 are interleaved together. One helical structure 370 here takes the form of a simple helical coil and functions as an element of the structural backbone of a catheter, compressing balloons between loops of the coil and the like. The other helical structure includes balloons 374 over a helical core, with one or more lumens extending within the helical core.

Note that the helical core supporting the balloons may or may not include a structural coil wire or the like, so that the components that provide fluid transmission functionality may be separated from or integrated with the structural components. In the embodiment of FIG. 11, a plurality of helical structures each have associated balloons, which may be inflated separately or together. In some embodiments, balloons aligned along one or more lateral orientations may be on a first helical structure, and balloons along one or more different orientations may be on a second interleaved helical structure, so that fluid transmission through a helical core may be simplified. In other embodiments (as can be understood with reference to 4-direction coaxial balloon/coil 380 of FIG. 11A), balloons subsets aligned along the differing lateral orientations may be mounted to a single helical core.

Figure 11B:
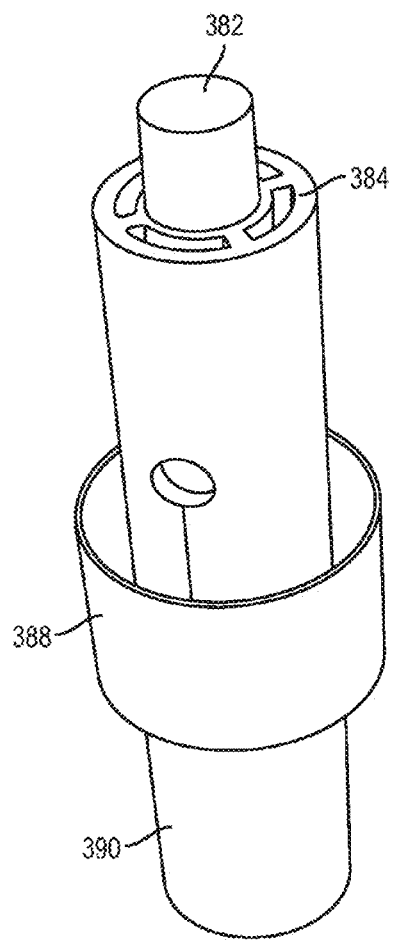
Figure 11C:
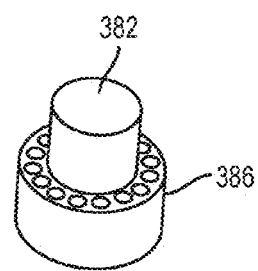

Referring now to FIGS. 11B and 11C, exemplary multi-lumen helical core structures can be understood. In these embodiments, an extruded polymer sheath is disposed over a structural coil wire 382, with the sheath having multiple peripheral lumens, such as 4 or 6 lumen sheath 384 or 16 lumen sheath 386. A tube of balloon material may be positioned over the sheath, with larger diameter portions of the tube forming balloons 388, and smaller diameter portions 390 engaging the sheath therein so as to seal between the balloons. A port 392 can be formed through the wall of the sheath into one of the lumens (typically prior to completion of the balloon structure) so that the interior of the balloon is in fluid communication with that associate lumen. The lumen may be dedicated to that one balloon, or will often be coupled to (and used to inflate) one or more balloons as a group or sub-set, with the group often being aligned along a lateral orientation of the coil so as to bend the coil in a common direction, opposed so as to axially elongate the coil, or the like. As can be understood by comparison of FIGS. 11B and 11C, the number of lumens in a helical core may impact the inflation lumen size (and response time), so that there may be benefits to using separate actuation sub-portions and running fluid flow channels outside the helical core. Where large numbers of lumens or complex lumen networks and geometries are desired, the core may include a first sheath layer having an outer surface which is processed (typically laser micromachined) to form some or all of the channels. A second sheath layer can be extruded or bonded radially over the first layer to laterally seal the channels. Similar processing of the outer surface of the second layer (and optionally subsequent layers) and extrusion or bonding of a third layer (and optionally subsequent layers) radially over the second layer may also be performed to provide multi-layered lumen systems.

Figure 12:
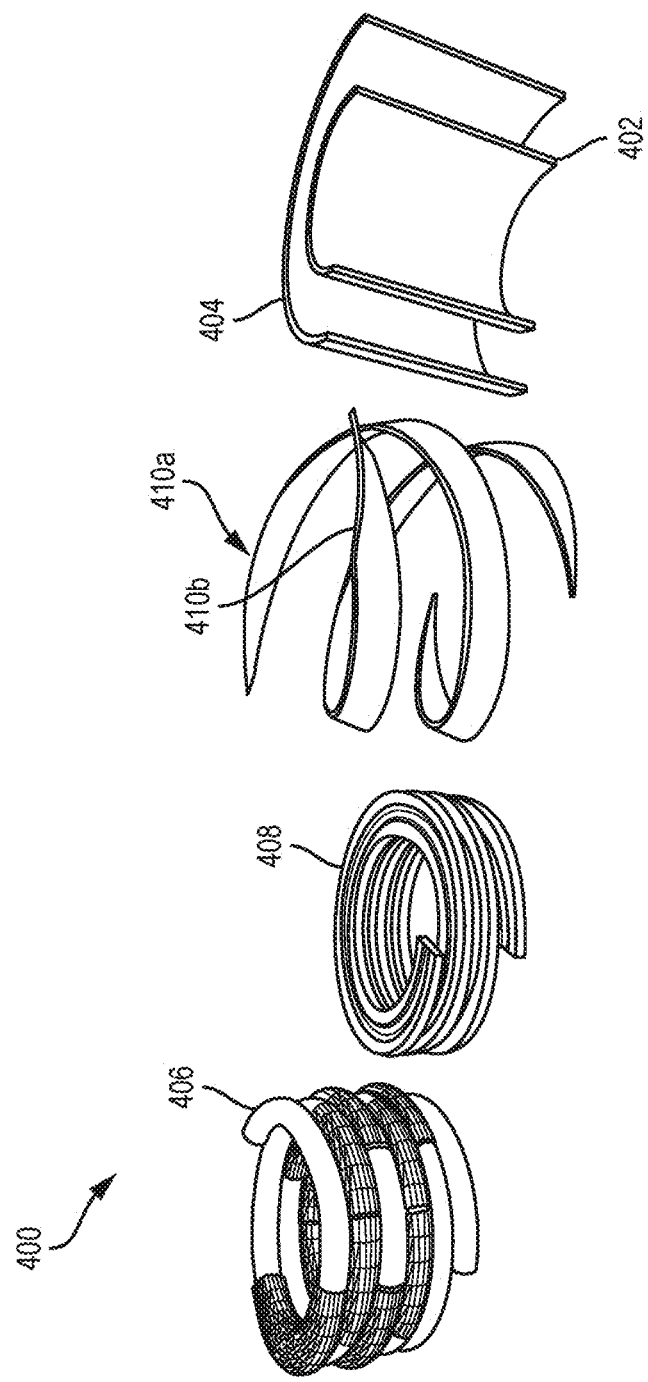
FIG. 12 is an exploded view of components that may be included in an articulated segment of an elongate articulated body, with the components laterally offset from their assembled position.

Referring now to FIG. 12, further separation of functionality among exemplary catheter components can be understood with reference to an exploded assembly 400, which shows an axial portion of an articulated catheter, the components here being laterally displaced from each other (and from their assembled coaxial positioning). The fluid-containing components of this portion are preferably contained between an inner sheath 402 and an outer sheath 404, with these sheaths being sealed to each other proximally and distally of the balloon array (or of some portion of the array). By drawing a vacuum between the sealed inner and outer sheaths (optionally using a simple positive syringe pump or the like) and by monitoring of the vacuum with a pressure sensing circuit coupled to a fluid supply shut off-valve, integrity of the fluid transmission and drive components within the patient body can be ensured, and inadvertent release of drive fluid within the patient can be inhibited.

Still referring to FIG. 12, a coaxial helical coil/balloon assembly 406 is disposed radially between the inner and outer sheaths 402, 404. The inner and/or outer sheaths may be configured so as to enhance radial strength and axial flexibility, such as by including circumferential fibers (optionally in the form of a polymer or metallic braid, loops, or windings), axial corrugations, or the like. As described above, balloons of assembly 406 are mounted to a helical core along a helical axis. At least one lumen extends along the helical core and allows the balloons on the core to be inflated and deflated. To help maintain axial alignment of the loops of assembly 406 an alignment spacer coil 408 is interleaved between the assembly loops. Spacer coil 408 has opposed surfaces with indented features so that axial compressive forces (from the environment or inflation of the balloons) squeezes the alignment spacer and keeps the assembly balloons and adjacent loops from being pushed radially out of axial alignment, as can be further understood with reference to FIGS. 6K and 6L and the associated text. Note that any of the structural skeleton or frame elements described herein (including the push-pull frames described below) may include balloon/frame engagement features (such as indentations along balloon-engaging surfaces), and/or separate balloon/frame interface bodies may be provided between the frames and the balloons to help maintain alignment balloon/frame alignment or to efficiently transmit and distribute loads or both. Note that compression between loops of assembly 406 may be imposed by the coil, by the spacer, by the inner and/or outer sheath, by a pullwire, or by a combination of two or more of these. Note also that alternative embodiments may replace the balloons mounted on the coil with balloons between loops of the coil coupled with a layered array substrate such as those shown in FIGS. 10C and 10D, optionally with a pair of alignment spacer coils on either axial surface of the balloons (and hence between the balloons and the coil). Still further alternatives include multiple interleaved coil/balloon assemblies, and/or other components and arrangements described herein.

As there may be a large total number of balloons in the overall balloon array of some embodiments, and as those arrays may be separated axially into articulated sub-portions of an overall catheter (or other articulated elongate body), and as the available space within the coil core of coil/balloon assembly 406 may be limited, it may be advantageous to have one or more separate structures extending axially within the annular space between inner and outer sheaths 402, 404. Those separate structures can have additional fluid inflation channels that are separate from the fluid inflation channels of the coil/balloon assembly or assemblies, and that can be used for inflating balloon articulation arrays that are mounted distally of the coil/balloon assembly 406. Toward that end, thin flat multi-lumen helical cable structures 410a, 410b may be disposed in the space radially between the coil/balloon assembly 406 and outer sheath 404, and/or between the coil/balloon assembly and inner sheath 402. Cables 410 may comprise a series of small diameter tubular structures (optionally comprising PET or fused silica with appropriate cladding) which may or may not be affixed together and are in a side-by-side alignment, a multichannel structure formed by micromachining and bonding layers (as described above), a multi-lumen extrusion having an elongate cross-section, or the like. Each cable 410a, 410b of a particular axial segment may be coupled to a core of a coil/balloon assembly for a more distal articulated axial segment. A helical or serpentine configuration of the cables may facilitate axial bending and/or elongation without stressing the cables, and the number of cables along an articulation segment may range from 0 (particularly along a distal articulation segment) to 10. Note that a number of alternative arrangements are also possible, including separating the cables from the coil/balloon assembly with an intermediate sheath, enhancing flexibility by using a number of separate fused silica tubes without bundling subsets of the tubes into cables, and the like.

Figure 13A:
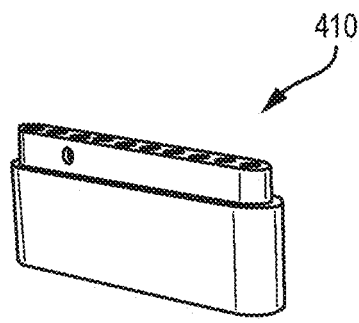

As can be understood with reference to FIG. 13A, one or more stiffening balloons may be incorporated into the cable structure, with the stiffening balloons of each segment optionally being in fluid communication with a common supply lumen, and optionally with a common supply lumen for one, some, or all other segments. In the exemplary cable structure shown, the stiffening balloon may comprises a tubular material disposed around a multi-lumen cable extrusion, and may be inflated using a port within the tube into a selected lumen of the extrusion. The stiffening balloon tube may be sealed to the cable extrusion or the like proximally and distally of the port, and may have an expandable length sufficient to extend along some or all of an axial articulation segment or sub-portion. The cables and any stiffening balloons thereon may extend axially between the coil and an inner or outer sheath, inflation of such stiffening balloons can induce radially engagement between the stiffening balloons and the coil, inhibiting changes in the offsets between loops and thereby stiffening the catheter against axial bending. The stiffening balloon may be inflated at pressures significantly lower than the bending or elongation actuation balloons, and may be used along segments or even catheters lacking bending or elongation balloons altogether. Alternatively, the cable may often be omitted, particularly where the core along a single segment can encompass sufficient channels for the desired degrees of freedom of the catheter.

Figure 13:
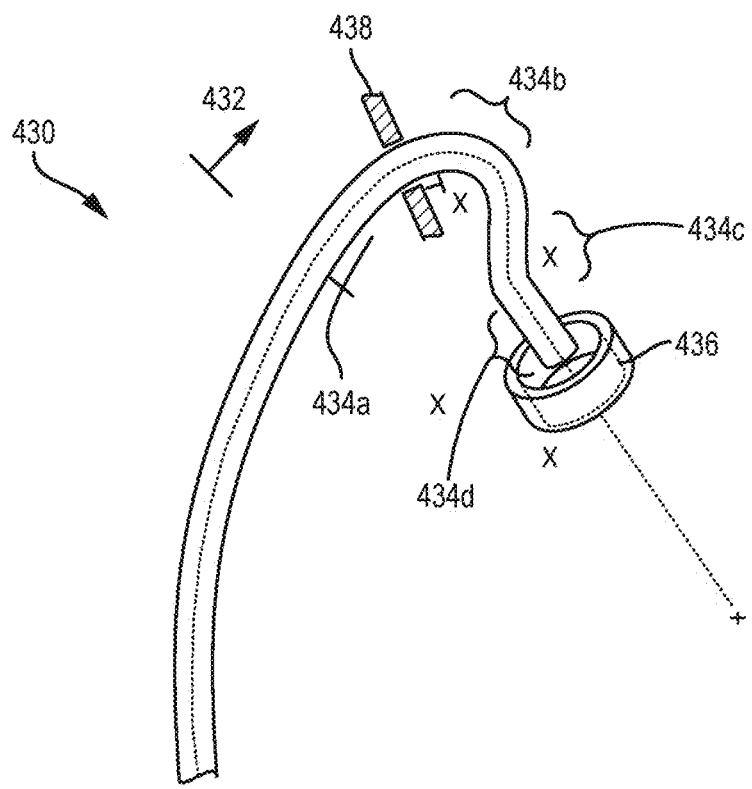
FIG. 13 schematically illustrates bending of a diagnosis or treatment delivery catheter into alignment with a target tissue by actuating a plurality of articulation sub-portions or segments of the catheter.
Figure 13C:
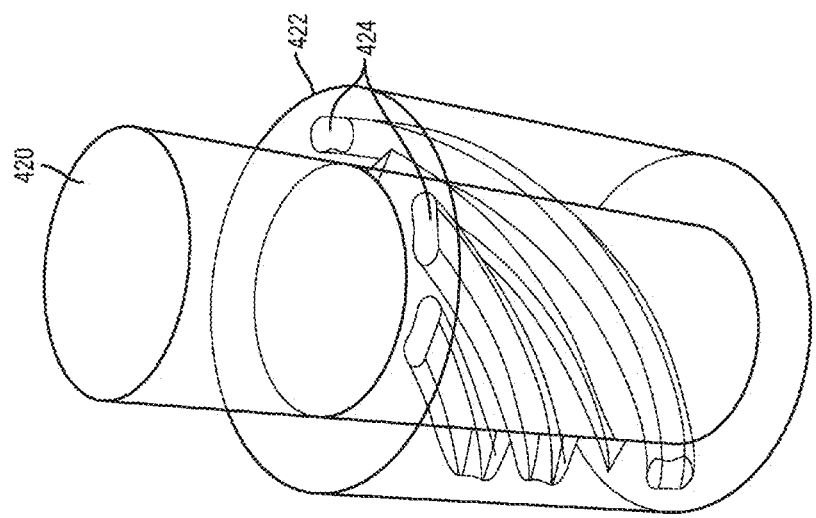
Figure 13B:
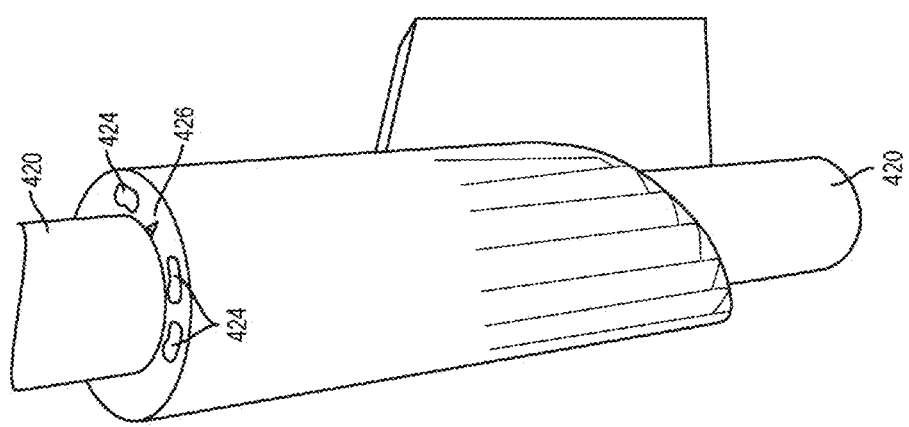

Referring now to FIGS. 13B and 13C, one exemplary transition from a multi-lumen helical core to a cable can be understood. The helical core here again includes a coil wire 420 surrounded by an extruded multi-lumen polymer body 422, with the body here having lumens 424 that twist around the coil wire. While only 3 lumens are shown, the spacing here would allow for 9 twisting lumens (the other lumens being omitted for simplicity). Radial ports from 8 of these lumens would allow, for example, independent inflation control over 8 balloons (or groups of balloons), and the ninth lumen may be used to draw and monitor a vacuum in a sealed axial segment around these balloons and between inner and outer sheaths (both as described above). Additionally, in the space between two adjacent lumens a notch 426 extends radially part way through body 422, with the notch winding around the core axis. Proximally of the most proximal balloon mounted on body 422, body 422 is separated at notch 426 and the body material and the lumens 424 therein are unwound from the coil wire 420. This unwound material can be flattened to form a multi-lumen cable as explained above regarding cables 410, 410a, and 410b of FIGS. 12 and 13, with the cable extending proximally from a helical multi-lumen core without having to rely on sealed tubular joints or the like. Alternative bonded joints or connectors between an extrusion, a single or multi-lumen tubular structure, and/or a layered channel system may also be employed.

Referring now to FIG. 13, an exemplary catheter 430 has an articulated portion 432 that includes a plurality of axially separate articulated segments or sub-portions 434a, 434b, 434c, and 434d. Generally, the plurality of articulation segments may be configured to facilitate aligning a distal end of the catheter with a target tissue 436. Suitable articulation segments may depend on the target tissue and planned procedure. For example, in this embodiment the articulation segments are configured to accurately align a distal end of the catheter with the angle and axial location of the native valve tissue, preferably for any patient among a selected population of patients. More specifically, the catheter is configured for aligning the catheter axis at the distal end of the catheter with (and particularly parallel to) an axis of the target tissue, and (as measured along the axis of the catheter) for axially aligning the end of the catheter with the target tissue. Such alignment may be particularly beneficial, for example, for positioning a prosthetic cardiac valve (optionally an aortic valve, pulmonary valve, or the like, and particularly a mitral valve) with tissues of or adjacent a diseased native valve. Suitable catheter articulation capabilities may also, in part, depend on the access path to the target tissue. For alignment with the mitral valve, the catheter may, for example, be advanced distally into the right atrium via the superior or inferior vena cava, and may penetrate from the right atrium through the septum 438 into the left atrium. Suitable transseptal access may be accomplished using known catheter systems and techniques (though alternative septal traversing tools using the articulated structures described herein might alternatively be used). Regardless, to achieve the desired alignment with the native valve tissue, the catheter may be configured to, for example: 1) from distally of (or near) the septum, form a very roughly 90 degree bend (+/−a sufficient angle so as to accommodate varying physiologies of the patients in the population); 2) extend a distance in desired range in three dimensions, including a) apically from the septal penetration site and b) away from the plane of the septal wall at the penetration; and 3) orient the axis of the catheter at the distal end in three dimensions and into alignment with the native valve tissue.

To achieve the desired alignment, catheter 430 may optionally provide consistent multi-axis bend capabilities as well as axial elongation capabilities, either continuously along the majority of articulatable portion 432 of catheter 430, or in articulated segments at regular intervals extending therealong. Alternative approaches may employ more functionally distinguished articulation segments. When present, each segment may optionally have between 4 and 32 balloons, subsets of the balloons within that segment optionally being oriented along from 1 to 4 lateral orientations. In some embodiments, the axis bending balloons within at least one segment may all be aligned along a single bend orientation, and may be served by a single inflation lumen, often served by a modulated fluid supply that directs a controlled inflation fluid volume or pressure to the balloons of the segment to control the amount of bending in the associated orientation. Alternative single lateral bending direction segments may have multiple sets of balloons served by different lumens, as described above. For example, segments 434a and 434b may both comprise single direction bending segments, each capable of imposing up to 60 degrees of bend angle and with the former having a first, relatively large bend radius in the illustrated configuration due to every-other axial balloon being inflated (as can be understood with reference to FIG. 7) or due to inflation with a limited quantity of inflation fluid. In segment 434b, all but the distal-most four balloons may be inflated, resulting in a smaller bend radius positioned adjacent segment 434a, with a relatively straight section of the catheter distal of the bend. Segment 434c may have balloons with four different bend orientations at a relatively high axial density, here having selected transverse balloons (such as 6 +X balloons and 2 −Y balloons) inflated so as to urge the catheter to assume a shape with a first bend component away from the septal plane and a second bend component laterally away from the plane of the bends of segments 434*a* and 434*b*. Segment 434*d* may comprise an axial elongation segment, with opposed balloons in fluid communication with the one or more inflation fluid supply lumen of this segment. Axial positioning of the end of the catheter may thus be accurately controlled (within the range of motion of the segment) by appropriate transmission of inflation fluid. Advantageously, such specialized segments may limit the number of fluid channels (and the cost, complexity and/or size of the catheter) needed to achieve a desired number of degrees of freedom and a desired spatial resolution. It should be understood that alternative segment arrangements might be employed for delivery of a prosthetic heart valve or the like, including the use of three segments. The valve might be positioned using a three-segment system by, for example, inserting the catheter so that the septum is positioned along the middle of the three segments, ideally with the catheter traversing the septum at or near the middle of the middle segment.

Figure 14:
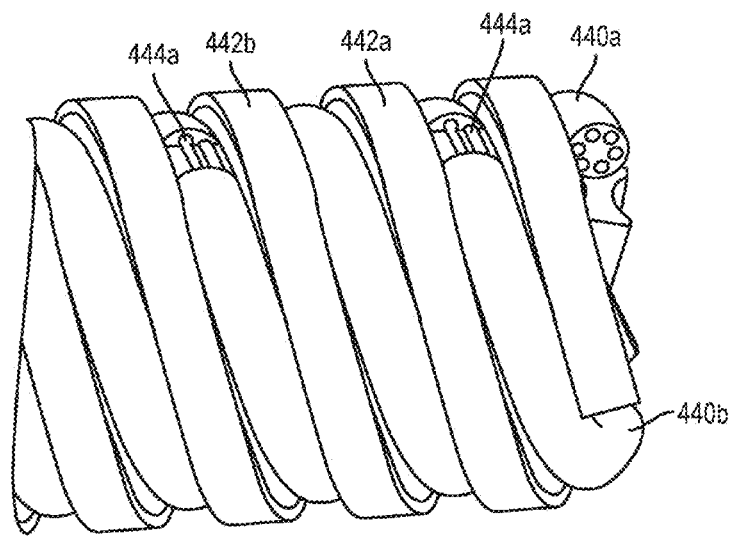
FIGS. 14-16 illustrate components of an alternative embodiment having a plurality of interleaved multi-lumen polymer helical cores interleaved with a plurality of resilient coil structures having axially oriented surfaces configured to radially restrain the balloons.
Figure 15:
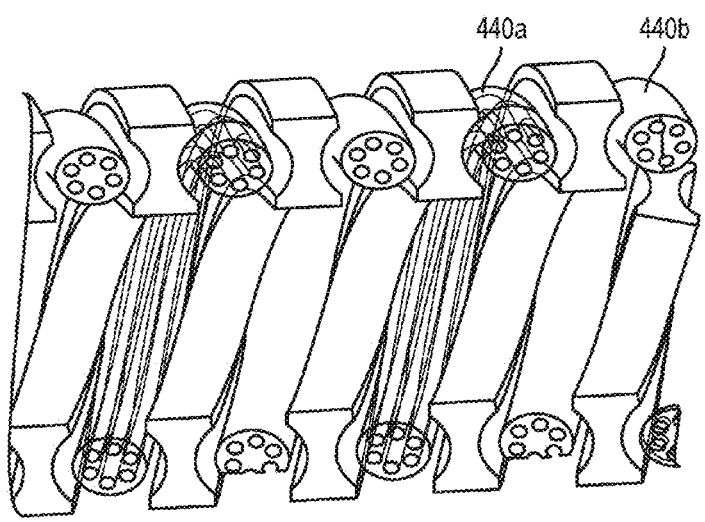
Figure 16:
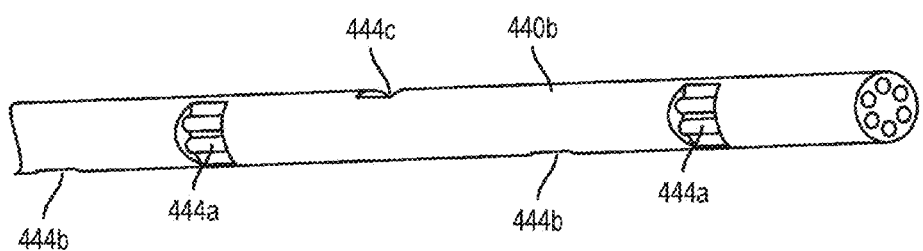

Referring now to FIGS. 14-16, a still further embodiment of an articulated catheter includes first and second interleaved helical multi-lumen balloon fluid supply/support structures 440*a*, 440*b*, along with first and second resilient helical coils 442*a*, 442*b*. In this embodiment, a series of balloons (not shown) are mounted around each of the multi-lumen structures, with the balloons spaced so as to be aligned along three lateral bending orientations that are offset from each other around the axis of the catheter by 120 degrees. Six lumens are provided in each multi-lumen structure, 440*a*, 440*b*, with one dedicated inflation lumen and one dedicated deflation lumen for each of the three lateral bending orientations. Radial fluid communication ports between the lumens and associated balloons may be provided by through cuts through pairs of the lumens.

By spacing the cuts 444*a*, 444*b*, 444*c*, as shown, and by mounting balloons over the cuts, the inflation and deflation lumens can be used to inflate and deflate a subset of balloons aligned along each of the three bending orientations. Advantageously, a first articulated segment having such a structure can allow bending of the catheter axis in any combination of the three bend orientations by inflating a desired subset of the balloons along that segment. Optionally, the bend angle for that subset may be controlled by the quantity and/or pressure of fluid transmitted to the balloons using the 6 lumens of just one multi-lumen structure (for example, 440*a*), allowing the segment to function in a manner analogous to a robotic wrist. Another segment of the catheter axially offset from the first segment can have a similar arrangement of balloons that are supplied by the 6 lumens of the other multi-lumen structure (in our example, 440*b*), allowing the catheter to position and orient the end of the catheter with flexibility analogous to that of a serial wrist robotic manipulators. In other embodiments, at least some of the balloons supplied by the two multi-lumen structures may axially overlap, for example, to allow increasing bend angles and/or decreasing bend radii by combining inflation of overlapping subsets of the balloons. Note also that a single lumen may be used for both inflation and deflation of the balloons, and that multi-lumen structures of more than 6 lumens may be provided, so that still further combinations these degrees of freedom may be employed.

In the embodiment illustrated in the side view of FIG. 14 and in the cross-section of FIG. 15, the outer diameter of the helical coils is about 0.130 inches. Multi-lumen structures 440*a*, 440*b* have outer diameters in a range from about 0.020 inches to about 0.030 inches (optionally being about 0.027 inches), with the lumens having inner diameters of about 0.004 inches and the walls around each lumen having a minimum thickness of 0.004 inches. Despite the use of inflation pressures of 20 atm or more, the small diameters of the lumens help limit the strain on the helical core structures, which typically comprise polymer, ideally being extruded. Rather than including a resilient wire or the like in the multi-lumen structure, axial compression of the balloons (and straightening of the catheter axis after deflation) is provided primarily by use of a metal in coils 442*a*, 442*b*. Opposed concave axial surfaces of coils 442 help maintain radial positioning of the balloons and multi-lumen structures between the coils. Affixing the ends of resilient coils 442 and balloon supply/support structures 440 together to the inner and outer sheaths at the ends of the coils, and optionally between segments may help maintain the helical shapes as well. Increasing the axial thickness of coils 442 and the depth of the concave surfaces may also be beneficial to help maintain alignment, with the coils then optionally comprising polymer structures. Still other helical-maintaining structures may be included in most or all of the helical embodiments described herein, including periodic structures that are affixed to coils 442 or other helical skeleton members, the periodic structures having protrusions that extend between balloons and can engage the ends of the inflated balloon walls to maintain or index lateral balloon orientations.

Many of the embodiments described herein provide fluid-driven articulation of catheters, guidewires, and other elongate flexible bodies. Advantageously, such fluid driven articulation can rely on very simple (and small cross-section) fluid transmission along the elongate body, with most of the forces being applied to the working end of the elongate body reacting locally against the surrounding environment rather than being transmitted back to a proximal handle or the like. This may provide a significant increase in accuracy of articulation, decrease in hysteresis, as well as a simpler and lower cost articulation system, particularly when a large number of degrees of freedom are to be included. Note that the presence of relatively high pressure fluid, and/or low temperature fluid, and/or electrical circuitry adjacent the distal end of an elongate flexible body may also be used to enhance the functionality of tools carried by the body, particularly by improving or adding diagnostic tools, therapeutic tools, imaging or navigations tools, or the like.

Figure 17:
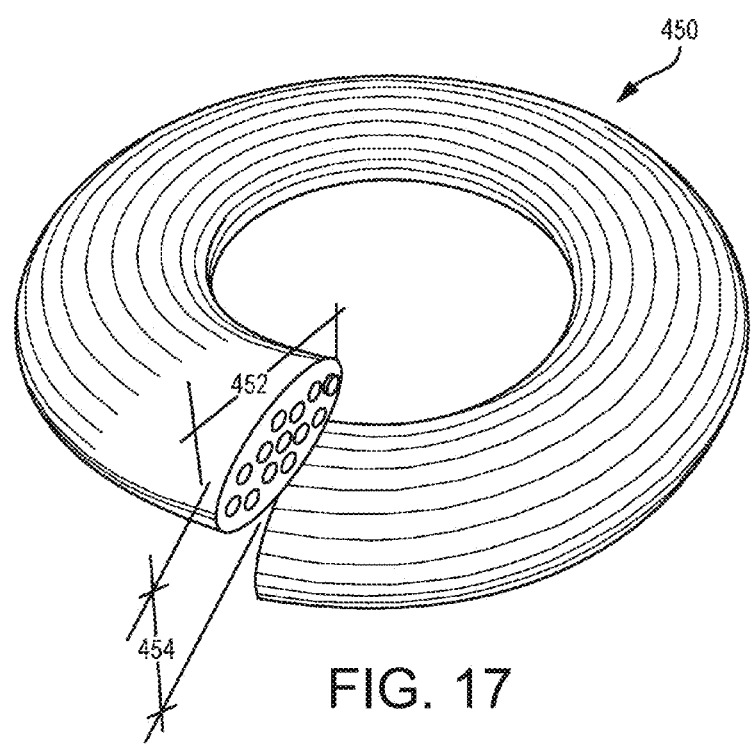
FIG. 17 is a perspective view of an alternative helical balloon core having a radially elongate cross-section to limit inflation fluid flows and provide additional fluid channels and/or channel sizes.

Referring now to FIG. 17, a radially elongate polymer helical balloon core structure 450 generally has a cross section with a radial thickness 452 that is significantly greater than its axial thickness 454. Radial thickness 452 may optionally be, for example 80% or more of the inflated diameter of the surrounding balloon, while axial thickness 454 may be between 20% and 75% of the inflated diameter. As compared to a circular core cross-section, such an elongate cross-section provides additional territory for balloon lumens extending within the coil core (allowing more lumens and separately inflatable balloons or groups of balloons, and/or allowing larger lumen sizes for faster actuation times) with the same the axial actuation stroke of the surrounding balloon. The exemplary cross-sectional shapes include elliptical or other continuously curved shapes to facilitate sealing engagement with the surrounding balloon wall material, with an alternative having proximal and distal regions with circular curvatures corresponding to those of the inflated balloon (so as to enhance axially compressive force transmission against an axially indented coil spring surface configured to evenly engage the inflated balloon).

Figure 18:
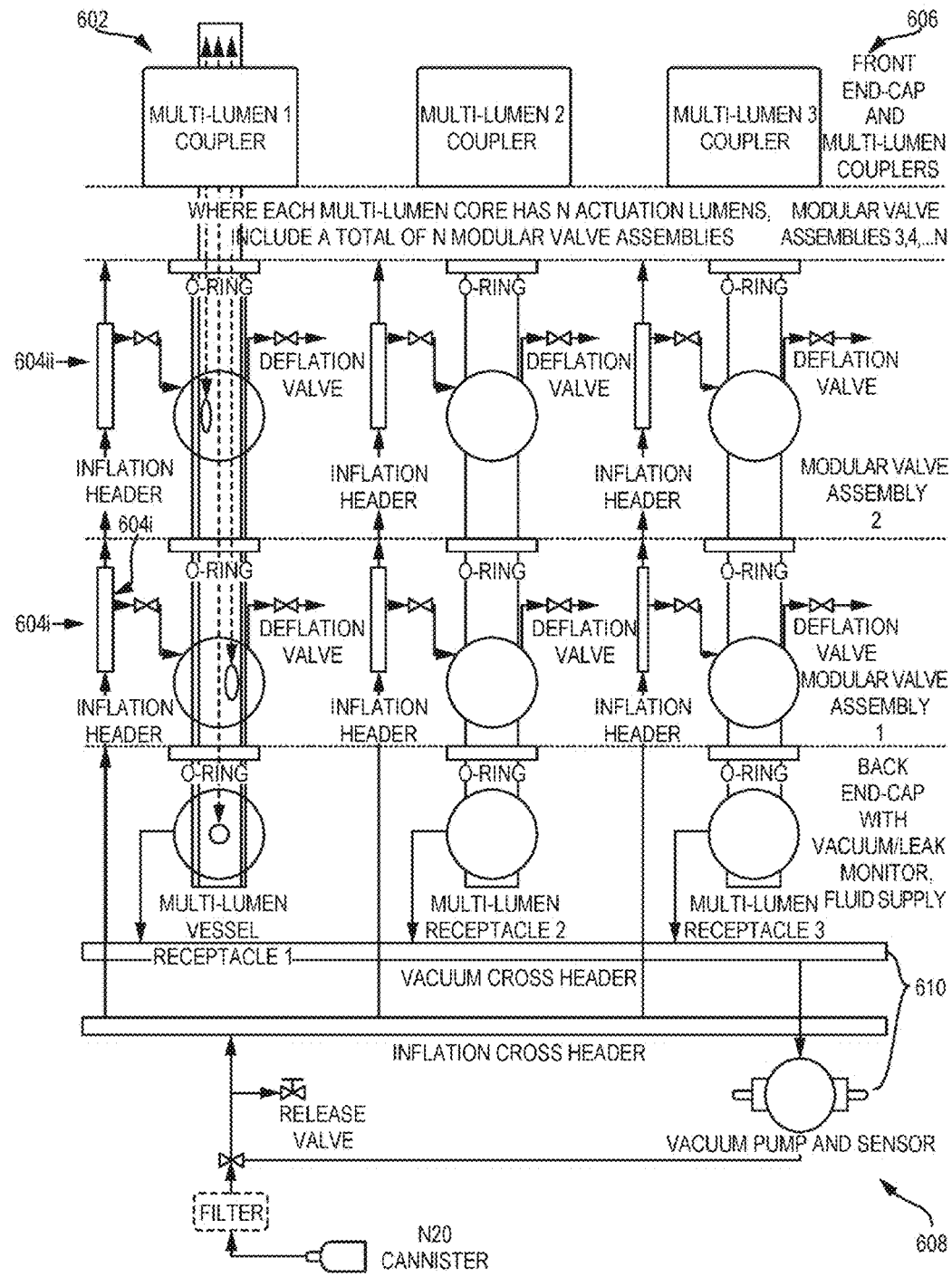
FIG. 18 is a simplified schematic of a modular manifold having a stack of valve plate assemblies through which a multi-lumen connector extends so as to provide controlled fluid flow to and from balloons of an array.

Referring now to FIG. 18, a simplified manifold schematic shows fluid supply and control components of an alternative manifold 602. As generally described above, manifold 602 has a plurality of modular manifold units or valve assembly plates 604i, 604ii, . . . stacked in an array. The stack of valve plates are sandwiched between a front end cap 606 and a back end-cap 608, and during use the proximal portion of the multi-lumen conduit core(s) extend through apertures in the front cap and valve plates so that the proximal end of the core is adjacent to or in the back cap, with the apertures defining a multi-lumen core receptacle. The number of manifold units or modules in the stack is sufficient to include a plate module for each lumen of each of the multi-lumen core(s). For example, where an articulatable structure has 3 multi-lumen core shafts and each shaft has 6 lumens, the manifold assembly may include a stack of 6 plates. Each plate optionally includes an inflation valve and a deflation valve to control pressure in one of the lumens (and the balloons that are in communication with that lumen) for each multi-lumen shaft. In our 3-multi-lumen shaft/6 lumen each example, each plate may include 3 inflation valves (one for a particular lumen of each shaft) and 3 deflation valves (one for that same lumen of each shaft). As can be understood with reference to the multi-lumen shaft shown in receptacle 1 of FIG. 18, the spacing between the ports along the shaft corresponds to the spacing between the fluid channels along the receptacle. By inserting the core shaft fully into the multi-lumen shaft receptacle, the plate channel locations can be registered axially with the core, and with the ports that were drilled radially from the outer surface of the multi-lumen core. The processor can map the axial locations of the valves along the receptacle with the axial locations of the ports along the core shafts, so that a port into a particular lumen of the core can be registered and associated with a fluid channel of specific inflation and deflation valves. One or more inflation headers can be defined by passages axially through the valve-unit plates; a similar deflation header (not shown) can also be provided to monitor pressure and quantity of fluid released from the lumen system of the articulated device. O-rings can be provided adjacent the interface between the plates surrounding the headers and receptacles. Pressure sensors (not shown) can monitor pressure at the interface between each plate and the multi-lumen receptacle.

Along with monitoring and controlling inflation and deflation of all the balloons, manifold 602 can also include a vacuum monitor system 610 to verify that no inflation fluid is leaking from the articulated system within the patient body. A simple vacuum pump (such as a syringe pump with a latch or the like) can apply a vacuum to an internal volume or chamber of the articulated body surrounding the balloon array. Alternative vacuum sources might include a standard operating room vacuum supply or more sophisticated powered vacuum pumps. Regardless, if the seal of the vacuum chamber degrades the pressure in the chamber of the articulated structure will increase. In response to a signal from a pressure sensor coupled to the chamber, a shut-off valve can automatically halt the flow of gas from the canister, close all balloon inflation valves, and/or open all balloon deflation valves. Such a vacuum system may provide worthwhile safety advantages when the articulated structure is to be used within a patient body and the balloons are to be inflated with a fluid that may initially take the form of a liquid but may vaporize to a gas. A lumen of a multi-lumen core shaft may be used to couple a pressure sensor of the manifold to a vacuum chamber of the articulated structure via a port of the proximal interface and an associated channel of the manifold assembly, with the vacuum lumen optionally comprising a central lumen of the multi-lumen shaft and the vacuum port being on or near the proximal end of the multi-lumen shaft.

Figure 19:
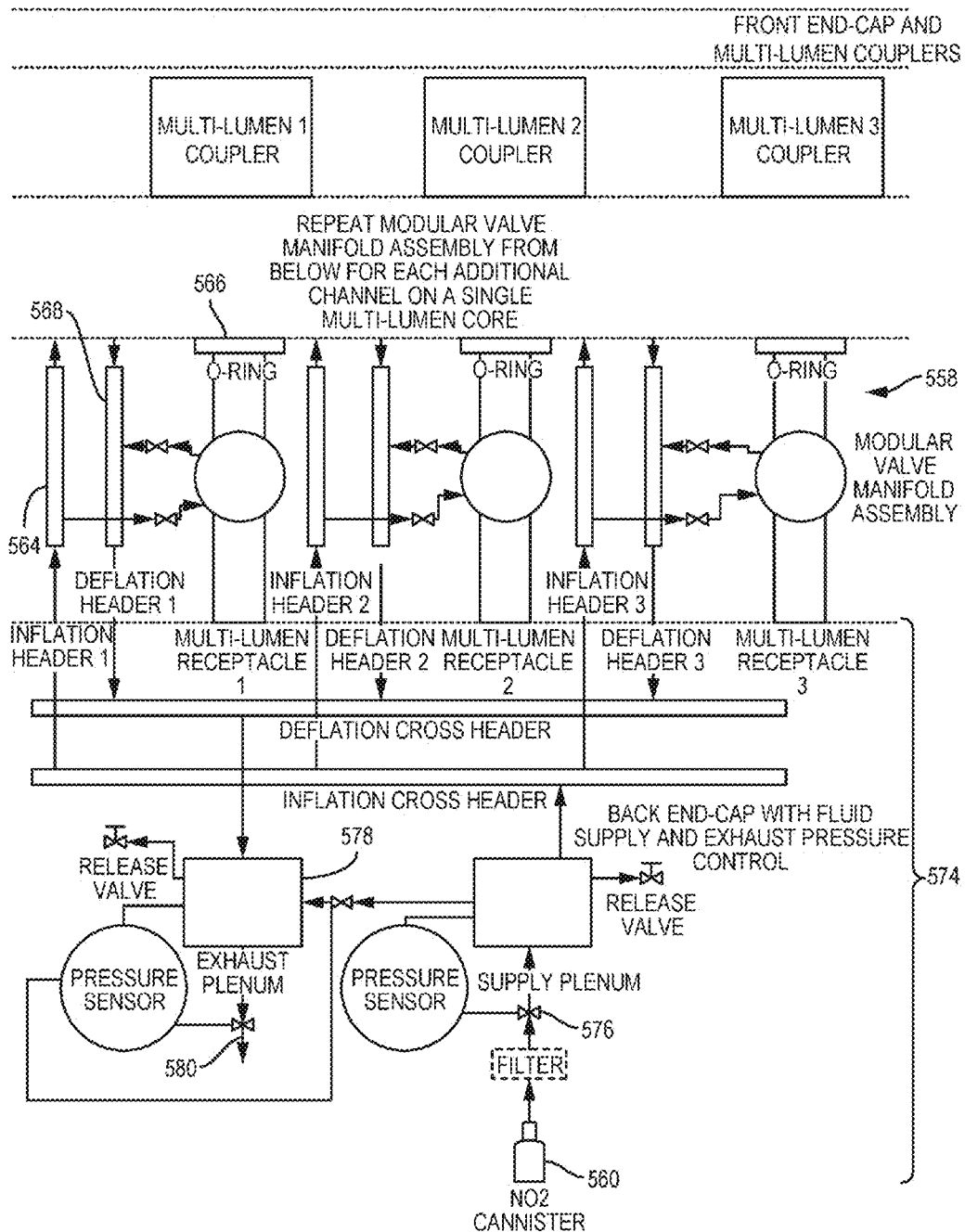
FIG. 19 is an alternative simplified schematic of a modular fluid manifold system showing additional components and systems that can be combined with those of FIG. 18.

Referring now to FIG. 19, additional optional components of the manifold assembly can be understood. The functionality of one, some, or all of these components may be included in any of the manifold assembly embodiments described herein. Back end cap 574 here includes a system fluid supply valve 576 disposed along channels coupling the inflation fluid canister 560 with the inflation header 564. Note that the end cap may include one or more cross headers to allow separate inflation or exhaust headers for the different multi-lumen core shafts. The system supply valve may halt or allow all of the fluid flow to the remaining components of the manifold and articulation structure. In some embodiments, fluid from canister 560 is used to pressurize a supply plenum, with a pressure sensor and the system supply valve being used to control the supply plenum pressure. This may be beneficial if it is desired to use a non-volatile balloon inflation liquid such as saline or the like, and/or if it is desired to preclude inflation of the balloons above a pressure that is below that of canister 560. However, transmitting inflation fluid directly from canister 560 to the inflation valves of the modular plates may present advantages, including enhanced inflation fluid flows through the small channels of the manifold and articulated structure when transmitting liquid or a liquid/gas mixture using the full canister pressure, as well as the relatively constant pressure that can be provided by vaporization of liquid within the canister. To keep the gas/liquid inflation fluid pressure within the canister even more constant, a resistive heater may be thermally coupled with the outer surface of the canister so as to compensate for the enthalpy of vaporization that occurs therein.

Referring still to FIG. 19, there may be more significant advantages to having an exhaust plenum 578 between one, some or all of the exhaust channels (often between the one or more exhaust header 568) and an exhaust port 580 to atmosphere. A pressure sensor or flow sensor coupled with exhaust plenum 578 can be used to monitor exhaust fluid flow. In some embodiments, a pressure sensor coupled to exhaust plenum 578 and an exhaust valve along a channel coupling the exhaust plenum to the exhaust port 580 can be used as a back-pressure control system to help control exhaust flows, to provide a uniform pressure to a number of balloons (via the deflation valves), or and/or to calibrate the individual pressure sensors of the plate modules. Manual release valves may optionally be included between the inflation and deflation headers and the surrounding environment to allow the system to be fully depressurized in case of failure of a valve or the like.

Many of the flexible articulated devices described above rely on inflation of one or more balloons to articulate a structure from a first resting state to a second state in which a skeleton of the flexible structure is resiliently stressed. By deflating the balloons, the skeleton can urge the flexible structure back toward the original resting state. This simple system may have advantages for many applications. Nonetheless, there may be advantages to alternative systems in which a first actuator or set of actuators urges a flexible structure from a first state (for example, a straight configuration) to a second state (for example, a bent or elongate configuration), and in which a second actuator or set of actuators are mounted in opposition to the first set such that the second can actively and controllably urge the flexible structure from the second state back to the first state. Toward that end, exemplary systems described below often use a first set of balloons to locally axially elongate a structural skeleton, and a second set of balloons mounted to the skeleton to locally axially contract the structural skeleton. Note that the skeletons of such opposed balloon systems may have very little lateral or axial stiffness (within their range of motion) when no balloons are inflated.

Referring now to FIGS. 20A and 20B, a simplified exemplary C-channel structural skeleton 630 (or portion or cross section of a skeleton) is shown in an axially extended configuration (in FIG. 19), and in an axially contracted configuration (in FIG. 20). C-frame skeleton 630 includes an axial series of C-channel members or frames 632 extending between a proximal end 634 and a distal end 636, with each rigid C-channel including an axial wall 638, a proximal flange 640, and a distal flange 642 (generically referenced as flanges 640). The opposed major surfaces of the walls 644, 646 are oriented laterally, and the opposed major surfaces of the flanges 648, 650 are oriented axially (and more specifically distally and proximally, respectively. The C-channels alternate in orientation so that the frames are interlocked by the flanges. Hence, axially adjacent frames overlap, with the proximal and distal surfaces 650, 648 of two adjacent frames defining an overlap offset 652. The flanges also define additional offsets 654, with these offsets being measured between flanges of adjacent similarly oriented frames.

In the schematics of FIGS. 19 and 20, three balloons are disposed in the channels of each C-frame 632. Although the balloons themselves may (or may not) be structurally similar, the balloons are of two different functional types: extension balloons 660 and contraction balloons 662. Both types of balloons are disposed axially between a proximally oriented surface of a flange that is just distal of the balloon, and a distally oriented surface of a flange that is just proximal of the balloon. However, contraction balloons 662 are also sandwiched laterally between a first wall 638 of a first adjacent C-channel 632 and a second wall of a second adjacent channel. In contrast, extension balloons 660 have only a single wall on one lateral side; the opposite sides of extension balloons 660 are not covered by the frame (though they will typically be disposed within a flexible sheath or other components of the overall catheter system).

A comparison of C-frame skeleton 630 in the elongate configuration of FIG. 19 to the skeleton in the short configuration of FIG. 20 illustrates how selective inflation and deflation of the balloons can be used to induce axial extension and contraction. Note that the C-frames 632 are shown laterally reversed from each other in these schematics. In FIG. 19, extension balloons 660 are being fully inflated, pushing the adjacent flange surfaces apart so as to increase the axial separation between the associated frames. As two contraction balloons 662 are disposed in each C-channel with a single extension balloon, and as the size of the channel will not significantly increase, the contraction balloons will often be allowed to deflate at least somewhat with expansion of the extension balloons. Hence, offsets 654 will be urged to expand, and contraction offsets 652 will be allowed to decrease. In contrast, when skeleton 630 is to be driven toward the axially contracted configuration of FIG. 20, the contraction balloons 662 are inflated, thereby pushing the flanges of the overlapping frames axially apart to force contraction overlap 652 to increase and axially pull the local skeleton structure into a shorter configuration. To allow the two contraction balloons 662 to expand within a particular C-channel, the expansion balloons 660 can be allowed to deflate.

While the overall difference between C-frame skeleton 630 in the contracted configuration and in the extended configuration is significant (and such skeletons may find advantageous uses), it is worthwhile noting that the presence of one extension balloon and two contraction balloons in a single C-channel may present disadvantages as compared to other extension/contraction frame arrangements described herein. In particular, the use of three balloons in one channel can limit the total stroke or axial change in the associated offset that some of the balloons may be able to impose. Even if similar balloon/core assemblies are used as extension and contraction balloons in a three-balloon wide C-channel, the two contraction balloons may only be used for about half of the stroke of the single extension balloon, as the single extension stroke in the channel may not accommodate two full contractions strokes. Moreover, there are advantages to limiting the number of balloon/core assemblies used in a single articulated segment.

Note that whichever extension/contraction skeleton configuration is selected, the axial change in length of the skeleton that is induced when a particular subset of balloons are inflated and deflated will often be local, optionally both axially local (for example, so as to change a length along a desired articulated segment without changing lengths of other axial segments) and—where the frames extend laterally and/or circumferentially—laterally local (for example, so as to impose a lateral bend by extending one lateral side of the skeleton without changing an axial length of the other lateral side of the skeleton). Note also that use of the balloons in opposition will often involve coordinated inflating and deflating of opposed balloons to provide a maximum change in length of the skeleton. There are significant advantages to this arrangement, however, in that the ability to independently control the pressure on the balloons positioned on either side of a flange (so as to constrain an axial position of that flange) allows the shape and the position or pose of the skeleton to be modulated. If both balloons are inflated evenly at with relatively low pressures (for example, at less than 10% of full inflation pressures), the flange may be urged to a middle position between the balloons, but can move resiliently with light environmental forces by compressing the gas in the balloons, mimicking a low-spring force system. If both balloons are evenly inflated but with higher pressures, the skeleton may have the same nominal or resting pose, but may then resist deformation from that nominal pose with a greater stiffness.

An alternative S-channel skeleton 670 is shown schematically in contracted and extended configurations in FIGS. 21A and 21B, respectively, which may have both an improved stroke efficiency (giving a greater percent change in axial skeleton length for an available balloon stroke) and have fewer components than skeleton 632. S-skeleton 670 has many of the components and interactions described above regarding C-frame skeleton 630, but is here formed of structural S-channel members or frames 672. Each S-channel frame 672 has two walls 644 and three flanges 640, the proximal wall of the frame having a distal flange that is integral with the proximal flange of the distal wall of that frame. Axially adjacent S-channels are again interlocked, and in this embodiment, each side of the S-channel frame has a channel that receives one extension balloon 660 and one contraction balloon 662. This allows all extension balloons and all contraction balloons to take full advantage of a common stroke. Moreover, while there are two extension balloons for each contraction balloon, every other extension balloon may optionally be omitted without altering the basic extension/contraction functionality (though the forces available for extension may be reduced). In other words, if the extension balloons 660' as marked with an X were omitted, the skeleton could remain fully constrained throughout the same nominal range of motion. Hence, S-channel frame 672 may optionally use three or just two sets of opposed balloons for a particular articulation segment.

Figure 22F:
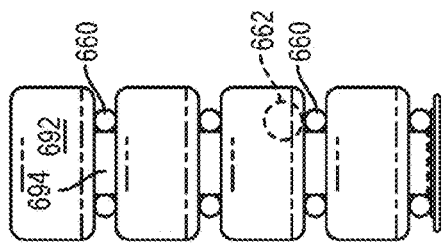
FIGS. 22D-22H are illustrations of elongate flexible articulated structures having annular skeletons with three opposed sets of balloons, and show how varying inflation of the balloons can be used to axially contract some portions of the frame and axially extend other portions to bend or elongate the frame and to control a pose or shape of the frame in three dimensions.
Figure 22E:
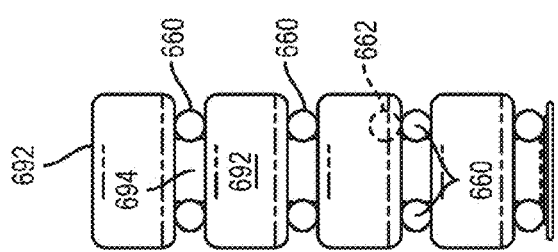
Figure 22D:
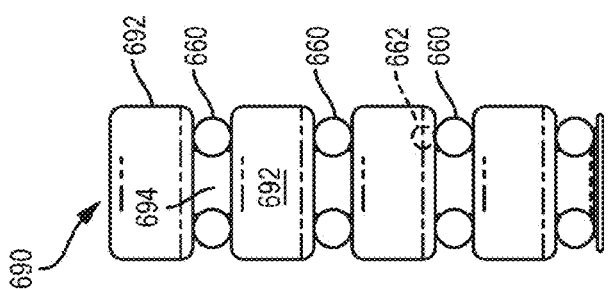

Referring now to FIG. 22A, a modified C-frame skeleton 680 has components that share aspects of both C-frame skeleton 630 and S-frame skeleton 670, and may offer advantages over both in at least some embodiments. Modified C skeleton 680 has two different generally C-frames or members: a C-frame 682, and a bumper C-frame 684. C-frame 682 and bumper frame 64 both have channels defined by walls 644 and flanges 648 with an axial width to accommodate two balloon assemblies, similar to the channels of the S-frames 672. Bumper frame 684 also has a protrusion or nub 686 that extends from one flange axially into the channel. The adjacent axial surfaces of these different frame shapes engage each other at the nub 686, allowing the frames to pivot relative to each other and facilitating axial bending of the overall skeleton, particularly when using helical frame members.

Figure 22C:
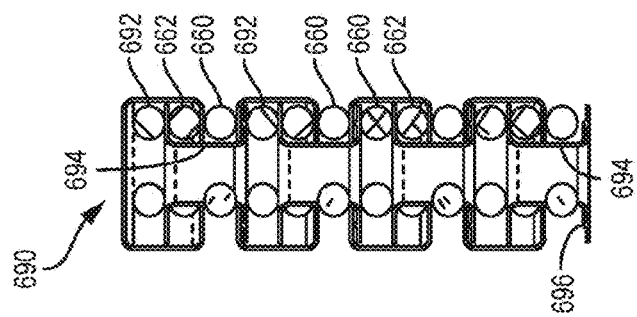
FIGS. 22B and 22C are a schematic illustration of an exemplary axial expansion/contraction skeleton with axial expansion and axial contraction balloons; and a corresponding cross-section of a skeleton having an axial series of annular members or rings articulated by the axial expansion and axial contraction balloons, respectively.
Figure 22B:
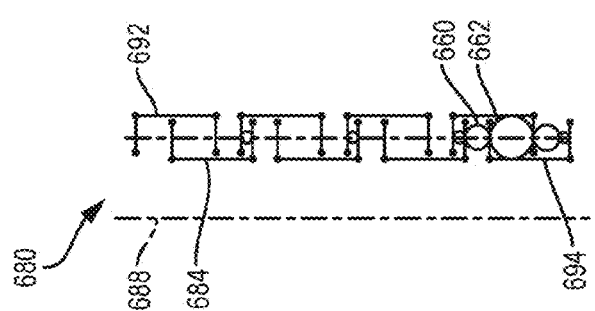

Referring now to FIGS. 22B and 22C, a relationship between the schematic extension/retraction frame illustration of FIGS. 20A-22A and a first exemplary three dimensional skeleton geometry can be understood. To form an axisymmetric ring-frame skeleton structure 690 from the schematic modified C-frame skeleton 680 of FIG. 22B, the geometry of frame members 682, 684 can be rotated about an axis 688, resulting in annular or ring frames 692, 694. These ring frames retain the wall and flange geometry described above, but now with annular wall and flanges being interlocked. The annular C-frames 682, 684 were facing different directions in schematic skeleton 680, so that outer C-frame ring 692 has an outer wall (sometimes being referred to as outer ring frame 692) and a channel that opens radially inwardly, while bumper C-frame ring 694 has a channel that is open radially outwardly and an inner wall (so that this frame is sometimes referred to as the inner ring frame 694). Ring nub 696 remains on inner ring frame 694, but could alternatively be formed on the adjacent surface of the outer ring frame (or using corresponding features on both). Note that nub 696 may add more value where the frame deforms with bending (for example, the frame deformation with articulation of the helical frame structures described below) as the deformation may involve twisting that causes differential angels of the adjacent flange faces. Hence, a non-deforming ring frame structure might optionally omit the nub in some implementations.

Referring now to FIGS. 22C-22F, uniform axial extension and contraction of a segment of ring-frame skeleton 690 is performed largely as described above. To push uniformly about the axis of the ring frames, three balloons are distributed evenly about the axis between the flanges (with centers separated by 120 degrees). The balloons are shown here as spheres for simplicity, and are again separated into extension balloons 660 and contraction balloons 662. In the straight extended configuration of FIG. 22D, the extension balloons 660 of the segment are all fully inflated, while the contraction balloons 662 are all fully deflated. In an intermediate length configuration shown in FIG. 22E, both sets of balloons 660, 662 are in an intermediate inflation configuration. In the short configuration of FIG. 22F, contraction balloons 662 are all fully inflated, while extension balloons 660 are deflated. Note that the state of the balloons remains axisymmetrical, so that the lengths on all lateral sides of the ring frame skeleton 690 remain consistent and the axis of the skeleton remains straight.

Figure 22G:
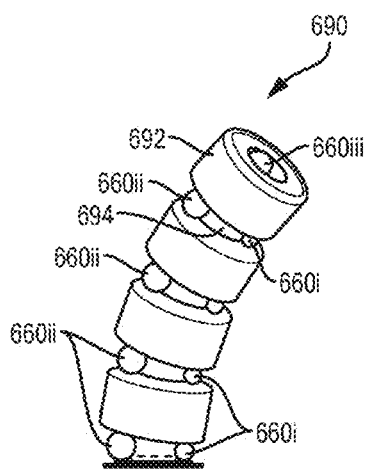
Figure 22H:
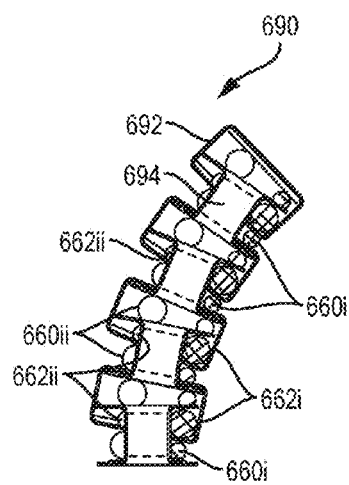

As can be understood with reference to FIGS. 22G and 22H, lateral bending or deflection of the axis of ring-frame skeleton 690 can be accomplished by differential lateral inflation of subsets of the extension and contraction balloons. There are three balloons distributed about the axis between each pair of articulated flanges, so that the extension balloons 660 are divided into three sets 660i, 660ii, and 660iii. Similarly, there are three sets of contraction balloons 662i, 662ii, and 662iii. The balloons of each set are aligned along the same lateral orientation from the axis. In some exemplary embodiments, each set of extension balloons (extension balloons 660i, extension balloons 660ii, and extension balloons 660iii) along a particular segment is coupled to an associated inflation fluid channel (for example, a channel i for extension balloons 660i, a channel ii for extension balloons 660ii, and a channel iii for extension balloons 660iii, the channels not shown here). Similarly, each set of contraction balloons 662i, 662ii, and 662iii is coupled to an associated inflation channel (for example, channels iv, v, and vi, respectively) so that there are a total of 6 lumens or channels per segment (providing three degrees of freedom and three orientation-related stiffnesses). Other segments may have separate fluid channels to provide separate degrees of freedom, and alternative segments may have fewer than 6 fluid channels. Regardless, by selectively deflating the extension balloons of a first lateral orientation 660i and inflating the opposed contraction balloons 662i, a first side of ring frame skeleton 690 can be shortened. By selectively inflating the extension balloons of the other orientations 660ii, 660iii, and by selectively deflating the contraction balloons of those other orientations 662ii, 662iii, the laterally opposed portion of ring frame skeleton 690 can be locally extended, causing the axis of the skeleton to bend. By modulating the amount of elongation and contraction distributed about the three opposed extension/contraction balloon orientations, the skeleton pose can be smoothly and continuously moved and controlled in three degrees of freedom.

Figure 23A:
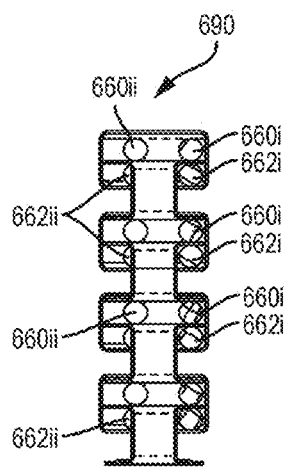
Figure 23B:
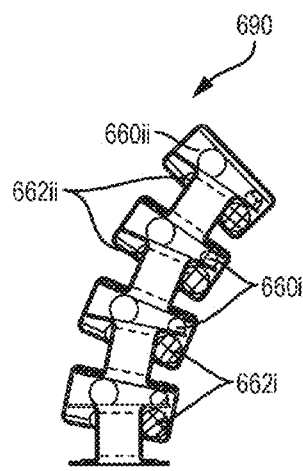

Referring now to FIGS. 23A and 23B, as described above with reference to FIGS. 21A and 21B, while it is possible to include balloons between all the separated flanges so as to maximize available extension forces and the like, there may be advantages to foregoing kinematically redundant balloons in the system for compactness, simplicity, and cost. Toward that end, ring frame skeletons having 1-for-1 opposed extension and contraction balloons (660i, 660ii, and 660iii; and 662i, 662ii, and 662iii) can provide the same degrees of freedom and range of motion as provided by the segments of FIGS. 22G and 22H (including two transverse X-Y lateral bending degrees of freedom and an axial Z degree of freedom), and can also control stiffness, optionally differentially modulating stiffness of the skeleton in different orientations in 3D space. The total degrees of freedom of such a segment may appropriately be referenced as being 4-D (X, Y, Z, & S for Stiffness), with the stiffness degree of freedom optionally having 3 orientational components (so as to provide as many as 5-D or 6-D. Regardless, the 6 fluid channels may be used to control 4 degrees of freedom of the segment.

As can be understood with reference to FIGS. 23C-23E and 23H, elongate flexible bodies having ring-frame skeletons 690' with larger numbers of inner and outer ring frames 692, 694 (along with associated larger numbers of extension and retraction balloons) will often provide a greater range of motion than those having fewer ring frames. The elongation or Z axis range of motion that can be provided by balloon articulation array may be expressed as a percentage of the overall length of the structure, with larger percentage elongations providing greater ranges of motion. The local changes in axial length that a balloon array may be able to produce along a segment having ring frames 690, 690' (or more generally having the extension contraction skeleton systems described herein) may be in a range of from about 1 percent to about 45 percent, typically being from about 2½ percent to about 25 percent, more typically being from about 5 percent to about 20 percent, and in many cases being from about 7½ percent to about 17½ percent of the overall length of the skeleton. Hence, the longer axial segment length of ring frame skeleton 690' will provide a greater axial range of motion between a contracted configuration (as shown in FIG. 23E) and an extended configuration (as shown in FIG. 23C), while still allowing control throughout a range of intermediate axial length states (as shown in FIG. 23D).

As can be understood with reference to FIGS. 23A, 23B, 23D and 23H, setting the balloon pressures so as to axially contract one side of a ring frame skeleton 690' (having a relatively larger number of ring frames) and axially extend the other side laterally bends or deflects the axis of the skeleton through a considerable angle (as compared to a ring frame skeleton having fewer ring frames), with each frame/frame interface typically between 1 and 15 degrees of axial bend angle, more typically being from about 2 to about 12 degrees, and often being from about 3 to about 8 degrees. A catheter or other articulated elongate flexible body having a ring frame skeleton may be bent with a radius of curvature (as measured at the axis of the body) of between 2 and 20 times an outer diameter of the skeleton, more typically being from about 2.25 to about 15 times, and most often being from about 2.4 to about 8 times. While more extension and contraction balloons 660, 662 are used to provide this range of motion, the extension and contraction balloon subsets (660i, 660ii, and 660iii; and 662i, 662ii, and 662iii) may still each be supplied by a single common fluid supply lumen. For example, 6 fluid supply channels may each be used to inflate and deflate 16 balloons in the embodiment shown, with the balloons on a single lumen being extension balloons 660i aligned along one lateral orientation.

As can be understood with reference to ring frame skeleton 690' in the straight configuration of FIG. 23D, in the continuously bent configuration of FIG. 23H, and in the combined straight and bent configuration of FIG. 23F, exemplary embodiments of the elongate skeleton 690' and actuation array balloon structures described herein may be functionally separated into a plurality of axial segments 690i, 690ii. Note that many or most of the skeleton components (including frame members or axial series of frame members, and the like) and actuation array components (including the substrate and/or core, some or all of the fluid channels, the balloon outer tube or sheath material, and the like), along with many of the other structures of the elongate flexible body (such as the inner and outer sheaths, electrical conductors and/or optical conduits for diagnostic, therapeutic, sensing, navigation, valve control, and other functions) may extend continuously along two or more axial segments with few or no differences between adjacent segments, and optionally without any separation in the functional capabilities between adjacent segments. For example, an articulated body having a two-segment ring frame skeleton 690' system as shown in FIG. 23H may have a continuous axial series of inner and outer ring frames 692, 694 that extends across the interface between the joints such that the two segments can be bent in coordination with a constant bend radius by directing similar inflation fluid quantities and pressures along the fluid supply channels associated with the two separate segments. As can be understood with reference to FIG. 23G, other than differing articulation states of the segments, there may optionally be few or no visible indications of where one segment ends and another begins.

Despite having many shared components (and a very simple and relatively continuous overall structure), functionally separating an elongate skeleton into segments provides tremendous flexibility and adaptability to the overall articulation system. Similar bend radii may optionally be provided with differing stiffnesses by applying appropriately differing pressures to the opposed balloons 660, 662 of two (or more) segments 690i, 690ii. Moreover, as can be understood with reference to FIG. 23F, two (or more) different desired bend radii, and/or two different lateral bend orientations and/or two different axial segments lengths can be provided by applying differing inflation fluid supply pressures to the opposed contraction/extension balloon sets 660i, 660ii, 660iii, 662i, 662ii, 662iii of the segments. Note that the work spaces of single-segment and two-segment systems may overlap so that both types of systems may be able to place an end effector or tool at a desired position in 3D space (or even throughout a desired range of locations), but multiple-segment systems will often be able to achieve additional degrees of freedom, such as allowing the end effector or tool to be oriented in one or more rotational degrees of freedom in 6D space. As shown in FIG. 23J, articulated systems having more than two segments offer still more flexibility, with this embodiment of ring frame skeleton 690' having 4 functional segments 690a, 690b, 690c, and 690d. Note that still further design alternatives may be used to increase functionality and cost/complexity of the system for a desired workspace, such as having segments of differing length (such as providing a relatively short distal segment 690a supported by a longer segment having the combined lengths of 690b, 690c, and 690d. While many of the multi-segment embodiments have been shown and described with reference to to planar configurations of the segments where all the segments lie in a single plane and are either straight or in a fully bent configuration, it should also be fully understood that the plurality of segments 690i, 690ii, etc., may bend along differing planes and with differing bend radii, differing axial elongation states, and/or differing stiffness states, as can be understood with reference to FIG. 23I.

Catheters and other elongate flexible articulated structures having ring frame skeletons as described above with reference to FIGS. 22C-23I provide tremendous advantages in flexibility and simplicity over known articulation systems, particularly for providing large numbers of degrees of freedom and when coupled with any of the fluid supply systems described herein. Suitable ring frames may be formed of polymers (such as nylons, urethanes, PEBAX, PEEK, HDPE, UHDPE, or the like) or metals (such as aluminum, stainless steel, brass, silver, alloys, or the like), optionally using 3D printing, injection molding, laser welding, adhesive bonding, or the like. Articulation balloon substrate structures may initially be fabricated and the balloon arrays assembled with the substrates in a planar configuration as described above, with the arrays then being assembled with and/or mounted on the skeletons, optionally with the substrates being adhesively bonded to the radially inner surfaces of the inner rings and/or to the radially outer surfaces of the outer rings, and with helical or serpentine axial sections of the substrate bridging between ring frames. While extension and retraction balloons 660, 662 associated with the ring frame embodiments are shown as spherical herein, using circumferentially elongate (and optionally bent) balloons may increase an area of the balloon/skeleton interface, and thereby enhance axial contraction and extension forces. A huge variety of modifications might also be made to the general ring-frame skeletal arrangement and the associated balloon arrays. For example, rather than circumferentially separating the balloons into three lateral orientations, alternative embodiments may have four lateral orientations (+X, −X, +Y, and −Y) so that four sets of contraction balloons are mounted to the frame in opposition to four sets of extension balloons. Regardless, while ring-frame skeletons have lots of capability and flexibility and are relatively geometrically simple so that their functionality is relatively easy to understand, alternative extension/contraction articulation systems having helical skeleton members (as described below) may be more easily fabricated and/or more easily assembled with articulation balloon array components, particularly when using the advantageous helical multi-lumen core substrates and continuous balloon tube structures described above.

First reviewing components of an exemplary helical frame contraction/expansion articulation system, FIGS. 24A-24E illustrate actuation balloon array components and their use in a helical balloon assembly. FIGS. 24F and 24G illustrate exemplary outer and inner helical frame members. After reviewing these components, the structure and use of exemplary helical contraction/expansion articulation systems (sometimes referred to herein as helical push/pull systems) can be understood with reference to FIGS. 25 and 26.

Referring now to FIGS. 24A and 24B, an exemplary multi-lumen conduit or balloon assembly core shaft has a structure similar to that of the core described above with reference to FIGS. 14-17. Core 702 has a proximal end 704 and a distal end 706 with a multi-lumen body 708 extending therebetween. A plurality of lumens 710a, 710b, 710c, . . . extend between the proximal and distal ends. The number of lumens included in a single core 702 may vary between 3 and 30, with exemplary embodiments have 3, 7 (of which one is a central lumen), 10 (including 1 central), 13 (including 1 central), 17 (one being central), or the like. The multi-lumen core will often be round but may alternatively have an elliptical or other elongate cross-section as described above. When round, core 702 may have a diameter 712 in a range from about 0.010" to about 1", more typically being in a range from about 0.020" to about 0.250", and ideally being in a range from about 0.025" to about 0.100" for use in catheters. Each lumen will typically have a diameter 714 in a range from about 0.0005" to about 0.05", more preferably having a diameter in a range from about 0.001" to about 0.020", and ideally having a diameter in a range from about 0.0015" to about 0.010". The core shafts will typically comprise extruded polymer such as a nylon, urethane, PEBAX, PEEK, PET, other polymers identified above, or the like, and the extrusion will often provide a wall thickness surrounding each lumen of more than about 0.0015", often being about 0.003" or more. The exemplary extruded core shown has an OD of about 0.0276"", and 7 lumens of about 0.004" each, with each lumen surrounded by at least 0.004" of the extruded nylon core material.

Referring still to FIGS. 24A and 24B, the lumens of core 702 may have radial balloon/lumen ports 716a, 716b, 716c, . . . , with each port comprising one or more holes formed through the wall of core 702 and into an associated lumen 710a, 710b, 710c, . . . respectively. The ports are here shown as a group of 5 holes, but may be formed using 1 or more holes, with the holes typically being round but optionally being axially elongate and/or shaped so as to reduce pressure drop of fluid flow therethrough. In other embodiments (and particularly those having a plurality of balloons supplied with inflation fluid by a single lumen), having a significant pressure drop between the lumen and the balloon may help even the inflation state of balloons, so that a total cross section of each port may optionally be smaller than a cross-section of the lumen (and/or by limiting the ports to one or two round lumens). Typical ports may be formed using 1 to 10 holes having diameters that are between 10% of a diameter of the associated lumen and 150% of the diameter of the lumen, often being from 25% to 100%, and in many cases having diameters of between 0.001" and 0.050". Where more than one hole is included in a port they will generally be grouped together within a span that is shorter than a length of the balloons, as each port will be contained within an associated balloon. Spacing between the ports will correspond to a spacing between balloons to facilitate sealing of each balloon from the axially adjacent balloons.

Regarding which lumens open to which ports, the ports along a distal portion of the core shaft will often be formed in sets, with each set being configured to provide fluid flow to and from an associated set of balloons that will be distributed along the loops of the core (once the core is bent to a helical configuration) for a particular articulated segment of the articulated flexible body. When the number of lumens in the core is sufficient, there will often be separate sets of ports for different segments of the articulated device. The ports of each set will often form a periodic pattern along the axis of the multi-lumen core 702, so that the ports provide fluid communication into M different lumens (M being the number of different balloon orientations that are to be distributed about the articulated device axis, often being 3 or 4, i.e., lumen 710a, lumen 710b, and lumen 710c) and the pattern repeating N times (N often being the number of contraction balloons along each orientation of a segment). Hence, the multi-lumen core conduit can function as a substrate that supports the balloons, and that defines the balloon array locations and associated fluid supply networks described above. Separate multi-lumen cores 702 and associated balloon arrays may be provided for contraction and expansion balloons.

As one example, a port pattern might be desired that includes a 3×5 contraction balloon array for a particular segment of a catheter. This set of ports might be suitable when the segment is to have three lateral balloon orientations (M=3) and 5 contraction balloons aligned along each lateral orientation (N=5). In this example, the distal-most port 716a of the set may be formed through the outer surface of the core into a first lumen 710a, the next proximal port 716b to lumen 710b, the next port 716c to lumen 710c, so that the first 3 (M) balloons define an "a, b, c" pattern that will open into the three balloons that will eventually be on the distal-most helical loop of the set. The same pattern may be repeated 5 times (for example: a, b, c, a, b, c, a, b, c, a, b, c, a, b, c) for the 5 loops of the helical coil that will support all 15 contraction balloons of a segment to the fluid supply system such that the 5 contraction balloons along each orientation of the segment are in fluid communication with a common supply lumen. Where the segment will include expansion balloons mounted 1-to-1 in opposition to the contraction balloons, a separate multi-lumen core and associated balloon may have a similar port set; where the segment will include 2 expansion balloons mounted in opposition for each contraction balloon, two separate multi-lumen cores and may be provided, each having a similar port set.

If the same multi-lumen core supplies fluid to (and supports balloons of) another independent segment, another set of ports may be provided axially adjacent to the first pattern, with the ports of the second set being formed into an M'×N' pattern that open into different lumens of the helical coil (for example, where M'=3 and N'=5: d, e, f, d, e, f, d, e, f, d, e, f, d, e, f), and so on for any additional segments. Note that the number of circumferential balloon orientations (M) will often be the same for different segments using a single core, but may be different in some cases. When M differs between different segments of the same core, the spacing between ports (and associated balloons mounted to the core) may also change. The number of axially aligned contraction balloons may also be different for different segments of the same helical core, but will often be the same. Note also that all the balloons (and associated fluid lumens) for a particular segment that are on a particular multi-lumen core will typically be either only extension or only contraction balloons (as the extension and contraction balloon arrays are disposed in helical spaces that may be at least partially separated by the preferred helical frame structures described below). A single, simple pattern of ports may be disposed near the proximal end of core shaft 702 to interface each lumen with an associated valve plate of the manifold, the ports here being sized to minimized pressure drop and the port-port spacing corresponding to the valve plate thickness. Regardless, the exemplary core shown has distal ports formed using groups of 5 holes (each having a diameter of 0.006", centerline spacing within the group being 0.012"), with the groups being separated axially by about 0.103".

Referring still to FIGS. 24A and 24B, an exemplary laser drilling pattern for forming ports appropriate for an articulated two distal segments, each having a 3×4 balloon array, may be summarized in table form as shown in Table 1:

TABLE 1

| Drill to Lumen #s | Theta 1 | Theta 2 | Theta 3 |
|---|---|---|---|
| Segment 1, N1 | 1 | 2 | 3 |
| N2 | 1 | 2 | 3 |
| N3 | 1 | 2 | 3 |
| N4 | 1 | 2 | 3 |
| Segment 2, N1 | 4 | 5 | 6 |
| N2 | 4 | 5 | 6 |
| N3 | 4 | 5 | 6 |
| N4 | 4 | 5 | 6 |

Theta 1, Theta 2, and Theta 3 here indicate the three lateral bending orientations, and as M=3, the balloons will typically have centerlines separated by about 120 degrees once the balloon/shaft assembly is coiled. Hence, the centerline spacing between the ports along the straight shaft (prior to coiling) will typically correspond to a helical segment length having about a 120 degree arc angle of the final articulated structure, both within a particular N subset and between adjacent N subsets of a segment. However, the alignment of each circumferential subset along a lateral bending axis does not necessarily mean that adjacent balloons are separated by precisely 120 degrees, or that the N balloons of a subset are aligned exactly parallel to the axis when the segment is in all configurations. For example, there may be some unwinding of the helical core associated with axial elongation, and there may be benefits to having the balloons along a particular bending orientation trending slightly circumferentially around the axis (when going from balloon to balloon of a lateral bending subset) so that lateral bends are closer to being planer in more segment states. The separation between balloons may remain consistent between segments, or may be somewhat longer to accommodate affixation of the balloon/shaft assembly to frames and inner and outer sheaths. Drill patterns for the proximal end may be somewhat simpler, as a single port may be drilled to provide fluid communication between each lumen and an associated valve plate module of the manifold assembly, as shown in Table 2:

TABLE 2

| | Drill to Lumen #s |
|---|---|
| Plate 1 | 1 |
| Plate 2 | 2 |
| Plate 3 | 3 |
| Plate 4 | 4 |
| Plate 5 | 5 |
| Plate 6 | 6 |
| Plate 7 | |
| Plate 8 | |

Note that this tabular data provides a correlation between valves of a plate and subsets of articulation balloons, and thus of the kinematics of the system. Hence, the system processor will often have access to this or related data when an articulated structure is coupled with the manifold, preferably on a plug-and-play basis. Similar (though possibly different) drill patterns may correlate the drill patterns of other multi-lumen cores with the valves and kinematics.

Referring now to FIGS. 24C and 24D, a continuous tube of flexible balloon wall material 718 may be formed by periodically varying a diameter of tube wall material to form a series of balloon shapes 720 separated by smaller profile sealing zones 722. Balloon tube 718 may include between about 9 and about 290 regularly spaced balloon shapes 720, with the sealing zones typically having an inner diameter that is about equal to the outer diameters of the multi-lumen helical core shafts 702 described above. In some embodiments, the inner diameters of the sealing zones may be significantly larger than the outer diameters of the associated cores when the balloon tube is formed, and the diameters of the sealing zones may be decreased (such as by heat shrinking or axially pull-forming) before or during assembly of the balloon tube and core shaft. The sealing zone may have a length of between about 0.025" and about 0.500", often being between about 0.050" and about 0.250". Decreasing the length of the sealing zone allows the length of the balloon to be increased for a given catheter size so as to provide larger balloon/frame engagement interfaces (and thus greater articulation forces), while longer sealing zones may facilitate assembly and sealing between balloons so as to avoid cross-talk between articulation channels.

Referring still to FIGS. 24C and 24D, the balloon shapes 720 of the balloon tube 718 may have diameters that are larger than the diameters of the sealing zones by between about 10% and about 200%, more typically being larger by an amount in a range from about 20% to about 120%, and often being from about 40% to about 75%. The thickness of balloon tube 718 will often vary axially with the varying local diameter of the tube, the locally large diameter portions forming the balloon shapes optionally being in a range from about 0.00008' (or about 2 microns) to about 0.005", typically being from about 0.001" and about 0.003". Balloon tube 718 may initially be formed with a constant diameter and thickness, and the diameter may be locally expanded (by blow forming, by vacuum forming, by a combination of both blow forming and vacuum forming, or by otherwise processing the tube material along the balloon shapes 720), and/or the diameter of the balloon tube may be locally decreased (by heat shrinking, by axial pull-forming, by a combination of both heat shrinking and pull forming, or by otherwise processing the tube material along the sealing zones), with the tube material often being processed so as to both locally expand the diameter along the desired balloon shapes and to locally contract the diameter along the sealing zones. Particularly advantageous techniques for forming balloon tubes may include the use of extruded polymer tubing corrugators, including the vertical small bore corrugators commercially available from Unicore, Corma, Fraenkische, and others. Suitable custom molds for such pipe corrugators may be commercially available from GlobalMed, Custom Pipe, Fraenkische, and others. Still more advanced fabrication techniques may allow blow or vacuum corrugation using a robotic shuttle corrugator and custom molds, particularly when it is desirable to change a size or spacing of balloons along a continuous tube. It should be noted that while a single continuous balloon tube is shown, a plurality of balloon tubes (each having a plurality (or in some cases, at least one) balloon shape) can be sealingly mounted onto a single core. Regardless, the sealing zones will often have a material thickness that is greater than that of the balloon shapes.

The balloon shapes 720 of the balloon tube 718 may each have a relatively simple cylindrical center section prior to assembly as shown. The tapers between the balloon center sections and the sealing zones can take any of a variety of shapes. The tapers may, for example, be roughly conical, rounded, or squared, and will preferably be relatively short so as to allow greater balloon/frame engagement for a given landing zone length. More complex embodiments may also be provided, including forming the balloon shapes with curved cylindrical center sections, optionally while corrugating or undulating the surfaces of the tapers so that the balloon tube overall remains relatively straight. The lengths of each center section is typically sufficient to define an arc-angle of from 5 to 180 degrees about the axis of the desired balloon assembly helix, more typically being from about 10 to about 50 degrees, the lengths of the center sections often being in a range from about 0.010" to about 0.400" for medical applications, more typically being from about 0.020" to about 0.150", and many times being in a range from about 0.025" to about 0.100". The exemplary balloon shapes may have an outer diameter of about 0.051" over a total balloon length (including the tapers) of about 0.059"

As can be understood with reference to FIGS. 24C, 24D, 24E, and 24E-1, balloon tube 718 may be sealingly affixed to core 702, and the core/balloon tube assembly may then be formed into a desired helical shape. The balloon tube may be sealed over the helical core using adhesive (such as any of those described above, often including UV-cured adhesives) thermal bonding, laser bonding, die bonding, and/or the like. Sealing of the balloons may also benefit from a compression structure disposed over the balloon material to help maintain tube/core engagement when the balloons are inflated. Suitable compression structures or techniques may include short sections of heat-shrink materials (such as PET) shrunk onto the sealing zones, high-strength filament windings wrapped circumferentially around the sealing zones and adhesively bonded, swaging of metallic ring structures similar to marker bands over the sealing zones, small bore crimp clamps over the sealing zones, heat-shrinking and/or pull forming the balloon tube onto the core, or the like. Any two or more of these may also be combined, for example, with the balloon tube being adhesively bonded to the core tube by injecting adhesive into the balloon tube around the sealing zone, heat shrinking the balloon tube and a surrounding PET sleeve over the sealing zone, and then swaging a metallic marker band over the sealing PET sleeve (so that the sleeve provides strain relief). Regardless, ports 716 will preferably be disposed within corresponding balloon shapes 720 and will remain open after the balloon/core assembly 730 is sealed together in the straight configuration shown in FIG. 24D. Shape setting of the balloon/core assembly from the straight configuration to the helically curved configuration of FIG. 24E can be performed by wrapping the assembly around and/or within a mandrel and heating the wrapped assembly. Helical channels may be included in the mandrel, which may also have discrete balloon receptacles or features to help ensure alignment of sets of balloons along the desired lateral balloon axes. Regardless, shape setting of the core/balloon assembly can help set the M different lateral orientations of the balloons, so that the balloons of each set 720*i*, 720*ii*, 720*iii* are aligned, as seen in 24E-1. As noted elsewhere, due to some slight changes in the geometry of the coiled assembly during axial elongation and the like, there may be some slight circumferential offset between balloons of the same lateral bending orientation when the articulated structure and/or its components are in some configurations, including when at rest.

Figures 3, 24E:
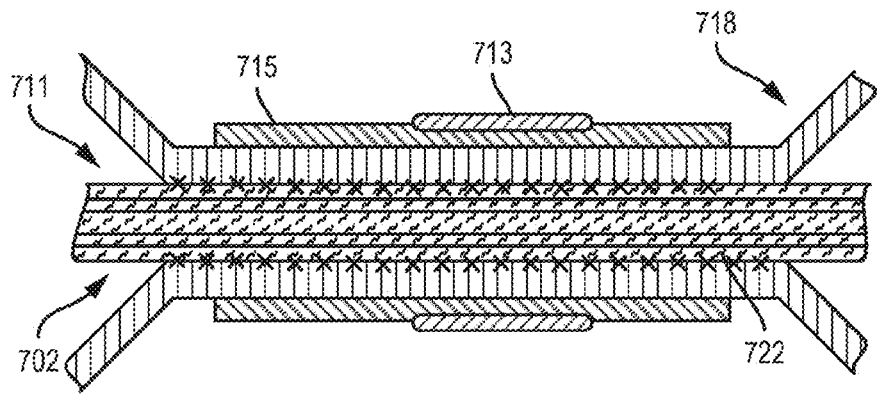
Figure 24F:
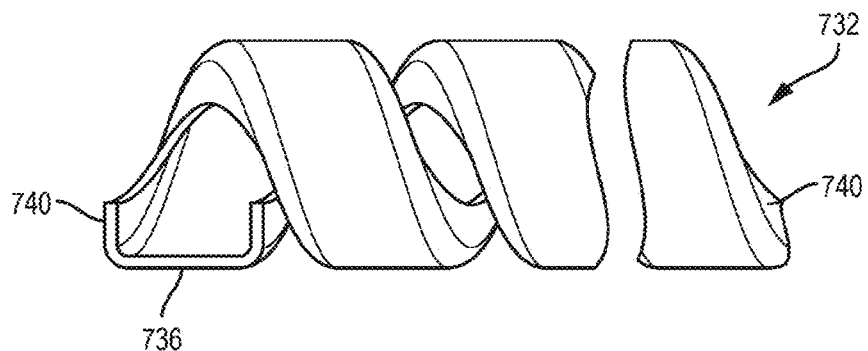
Figure 24G:
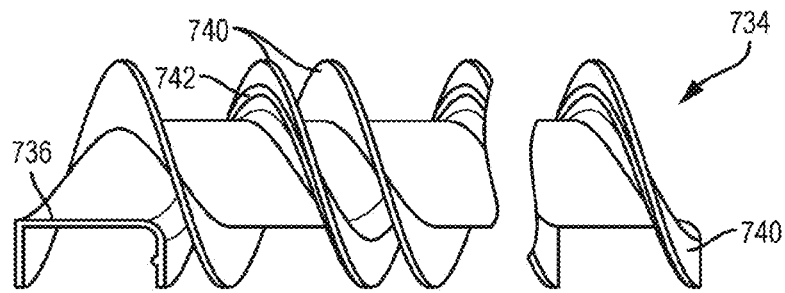

Referring to FIG. 24E-2, an alternative balloon tube 718' has a plurality of pre-curved balloon shapes 720' coupled together by sealing zones 722 to facilitate forming and/or keeping the balloon/core assembly in a helical configuration. The overall configuration of alternative balloon tube 718' is straight, and it may be beneficial to provide asymmetric corrugated transitions 725 between pre-curved balloon shapes 720' and sealing zones 722. Corrugated transitions 725 may have a form analogous to that of a corrugated straw along at least an outer radial portion of the helix, and the balloon shapes may optionally have corrugations along this outer portion instead of or in addition to the pre-curvature shown schematically here. The balloon shapes, transitions, and sealing zones may be formed by blow molding within machined or printed tooling using medical balloon blowing techniques, by blow molding with the moving tooling of a corrugation system, or the like.

Referring to FIG. 24E-3, a detail for an exemplary seal between sealing zone 722 of balloon tube 718 and an outer surface of multi-lumen core 702 is illustrated. In some embodiments, bonding 711 of balloon tube 718 to core 702 employs adhesives, thermal bonding, laser bonding, or the like, and is sufficient to inhibit fluid flow between adjacent balloons. Optionally, a band of radially compressive material 713 can be disposed over the balloon tube and core to help maintain sealing engagement when one or both of the adjacent balloons are inflated. Suitable bands may comprise metal and may be crimped or swaged onto the assembly, with the bands optionally comprise thin tubular marker bands-like structures (optionally comprising stainless steel, silver, gold, platinum, or the like) that are swaged on using standard marker band swaging tools and techniques. Alternative compressive bands may comprise a flexible filament of a polymer such as nylon, polyester, spectra, or the like, and may be wound over the balloon tube and core and adhesively bonded. Still further alternative compressive bands may comprise a micro-crimp clamp, or the like. A strain-relief tube 715 (optionally comprising PET or the like) may optionally be provided between band 713 and balloon tube 718 to inhibit damage along the edge of the band, and/or the band may be flared radially outwardly at the ends. Preferably, the band and any strain relief tube will be compressed onto the balloon so that some or all of the outer surface of the band and strain relief tube are recessed to near or even below the adjacent balloon tube, analogous to when a standard marker band is crimped onto a standard catheter tubing.

Referring now to FIGS. 24F and 24G, exemplary inner and outer helical C-channel frames, 732 and 734 respectively, can be seen. Inner helical frame 732 and outer helical frame 734 incorporate the modified C-channel frame 680 of FIG. 22a, but with the C-channels defined by axially continuous helical walls 736 with flanges 740 along their proximal and distal helical edges. The helical flanges are axially engaged by opposed balloons and allow inflation of the balloons to locally axially contract and/or extend the skeleton and catheter (or other articulatable body) in a manner that is analogous to the annular flanges of the ring frames described above. An optional helical nub 742 protrudes axially into the channel of inner ring frame 734 to allow the frames to pivot against each other along a flange/flange engagement, so that the nub could instead be included on the flange of the outer frame or on both (or may comprise a separate structure that is axially sandwiched between the flanges of the two frames). Alternative embodiments may forego such a pivotal structure altogether.

Referring now to FIGS. 25A-25D, a segment of an exemplary flexible extension/contraction helical frame articulation structure 750 (sometimes referred to herein as a push/pull helical structure) incorporates the components of FIGS. 24A-24G, and provides the functionality of the annular extension/contraction frame embodiments of FIGS. 22B-22I. Push/pull structure includes a skeleton defined by inner and outer helical frames 732, 734, and also includes three balloon/core assemblies 730a, 730b, and 730c, respectively. Each balloon/core assembly includes a set of balloons at three lateral orientations, 720i, 720ii, and 720iii. Balloon/core assembly 730b extends along a helical space that is axially between a flange of the inner frame and a flange of the outer frame, and that is radially between a wall of the inner frame and a wall of the outer frame, so that the frames overlap along this balloon/core assembly. Hence, when balloons 720 of balloon/core assembly 730 inflate, they push the adjacent flanges apart and increase the overlap of the frames, inducing axial contraction of the skeleton, such that the balloons of this assembly function as contraction balloons. In contrast, balloon/core assemblies 730a and 730c are radially adjacent to only inner frame 732 (in the case of assembly 730a) or outer frame 734 (in the case of assembly 730b). Expansion of the balloons 720 of assemblies 730a, 730c pushes axially against frames so as to decrease the overlap of the frames, and acts in opposition to the inflation of balloons 720 of assembly 730b. Hence, balloons 720 of assemblies 730a, 730c function as extension balloons.

Referring now to FIGS. 25A-25C, when all the contraction balloons 720 of assembly 730b are inflated and all the extension balloons of assemblies 730a, 730c are deflated, the push/pull structure 750 is in a straight short configuration as shown in FIG. 25A. Even partial inflation of the extension balloons and even partial deflation of the contraction balloons articulates push/pull structure 750 to a straight intermediate length configuration, and full inflation of all extension balloons of assemblies 730a, 730c (along with deflation of the contraction balloons) fully axially elongates the structure. As with the ring push/pull frames, inflating contraction balloons 720ii along one lateral orientation of assembly 730b (with corresponding deflation of the extension balloons 720ii of assemblies 730a, 730b) locally decreases the axial length of the skeleton along that side, while selective deflation of contraction balloons 720i of assembly 730b (with corresponding inflation of extension balloons 720i of assemblies 730a and 730c) locally increases the length of the skeleton, resulting in the fully laterally bent configuration of FIG. 25E. Note that extension and contraction balloons along the 720iii orientation may be inflated and deflated with the extension and contraction orientation balloons of orientation 720ii so as to keep the curvature in the plane of the drawing as shown. Stiffness of the structure may be modulated uniformly or locally (with axial and/or orientation variations) as described above regarding the ring frame embodiments. Similarly, the number of extension and contraction balloons along each orientation (which will often be associated with the number of loops of assemblies 730a, 730b, etc) may be determined to provide the desired range of motion, resolution, and response. As described with reference to the push/pull ring frame embodiments, the overall articulated portion of the structure will often be separated into a plurality of independently controllable segments.

Figure 25F:
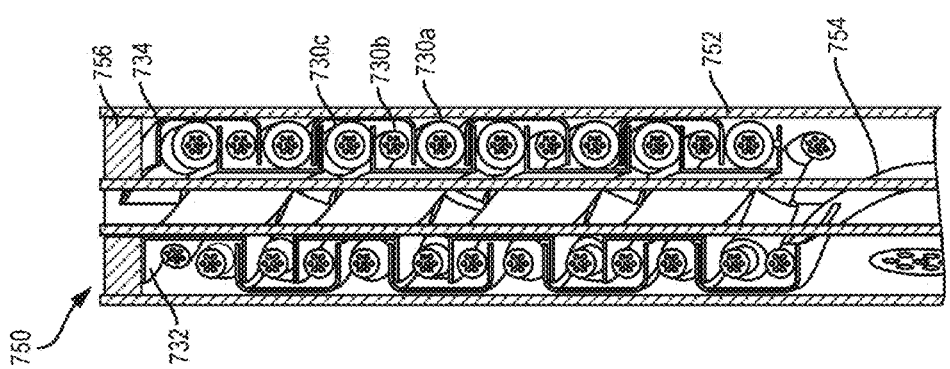

Referring now to FIG. 25F, push/pull structure 750 will often include an outer flexible sheath 752 and an inner flexible sheath 754. Sheaths 752, 754 may be sealed together at a distal seal 756 distal of the inflation lumens and balloons of assemblies 730, and one or more proximal seal (not shown) may be provided proximal of the balloons and/or near a proximal end of the catheter structure, so as to provide a sealed volume surrounding the articulation balloons. A vacuum can be applied to this sealed volume, and can be monitored to verify that no leaks are present in the balloons or inflation lumen system within a patient body.

Figure 26B:
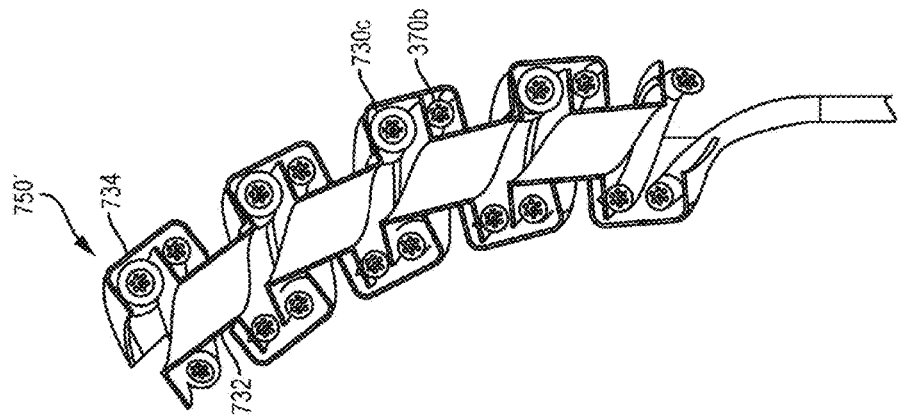
FIGS. 26A and 26B illustrate alternative articulated structures similar to those of FIG. 25, here with two balloon assemblies supported in opposition along the frames.
Figure 26A:
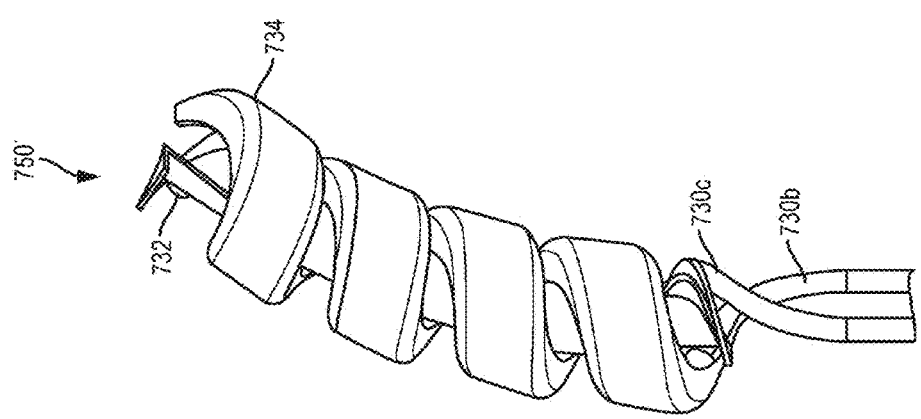

Referring now to FIGS. 26A and 26B, an alternative push/pull structure omits one of the two extension balloon assemblies 730a, 730c, and uses a 1-to-1 extension/contraction balloon opposition arrangement as described above with reference to FIGS. 23A and 23B. Note that this embodiment retains balloon assembly 730c that is radially adjacent to outer frame 734 (so that no balloons are visible even with the sheath removed). Alternative embodiments may retain assembly 730a and forego assembly 730c (so that balloons could be seen through a clear sheath, for example).

Figure 27:
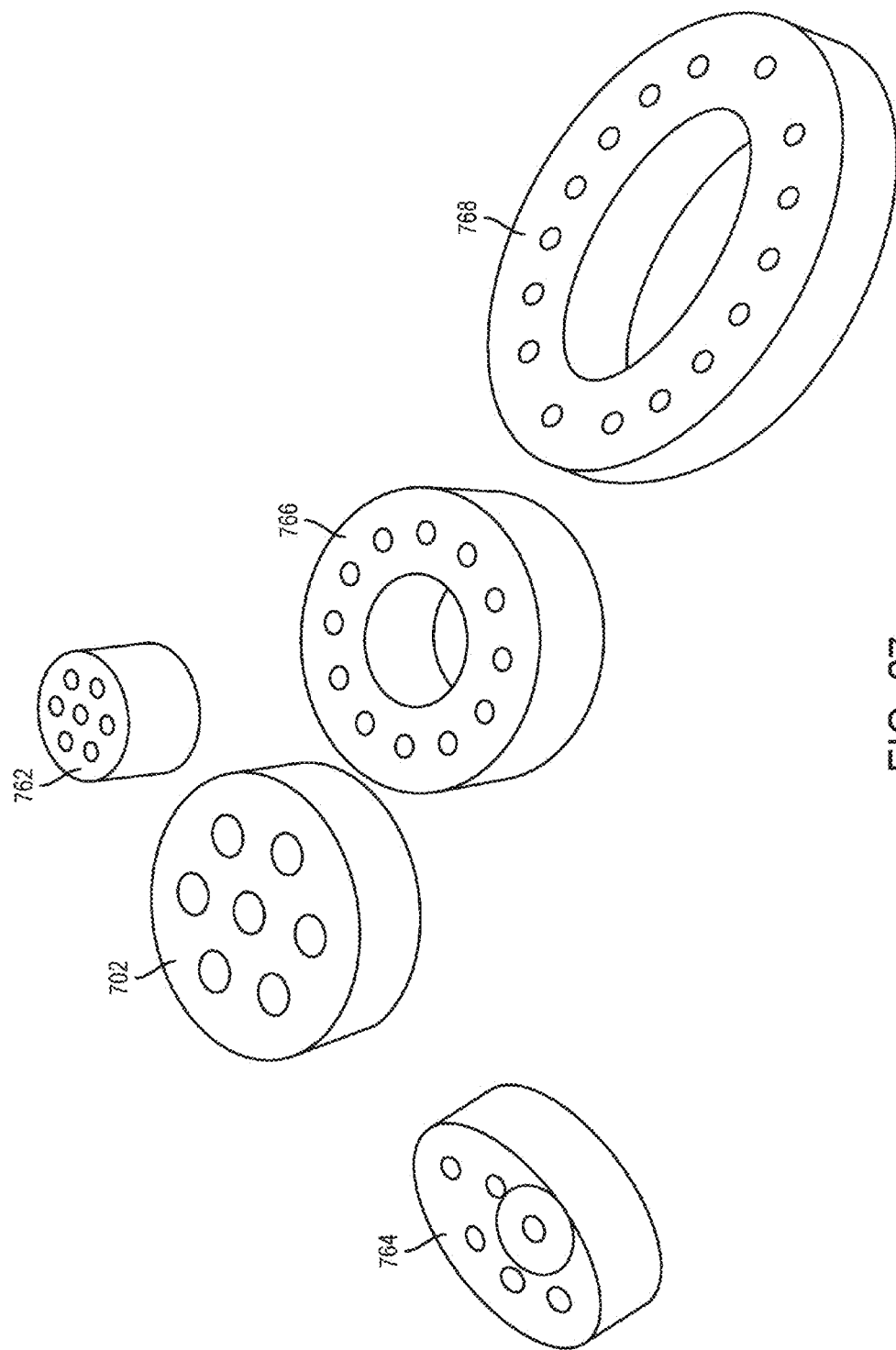
FIG. 27 illustrates alternative multi-lumen conduit or core structures for use in the balloon assemblies of FIGS. 24 and 25, showing a variety of different numbers of channels that can be used with different numbers of articulated segments.

Referring now to FIG. 27, short segments of alternative core structures are shown for comparison. Core shaft 702 has an outer diameter of about 0.028" and 7 lumens, with 6 peripheral lumens having an inner diameter of about 0.004" readily available for formation associated ports and use in transmitting inflation fluid to and from balloons. A central lumen might be used, for example, in monitoring of the vacuum system to verify integrity of the system. Core shaft 702 can be used, for example, in a 14-15 Fr catheter system having two segments that are each capable of providing up to 120 degrees of bending (or alternatively more or less depending on the number of balloons ganged together on each channel), with such a system optionally capable of providing a bend radius sufficient for to fit a 180 degree bend of the catheter within a space of 3 inches or less, ideally within 2½ inches or less, and in some cases within 2 inches or less. Such a system may be beneficial for structural heart therapies, for example, and particularly for mitral valve delivery, positioning, and/or implantation.

Referring still to FIG. 27, other therapies may benefit from smaller catheter profiles, and do not need the bending forces available from a 15 Fr catheter. Electrophysiology therapies such as AFib ablation from within an atrium of the heart may be good examples of therapies which would benefit from the degrees of freedom that can be provided in small structures using the systems described herein. Scaling the 15 Fr system down for a 7-8 Fr ablation catheter might make use of a directly scaled core 762 having half the overall outer diameter and half the lumen inner diameter of core 702, as the pressure-containing stresses in the material would scale with the lumen diameters. However, there may be cost benefits to maintaining minimum lumen wall thicknesses that are above 0.002", preferably at or above 0.0025", and ideally at or above about 0.003". Toward that end, and to provide 6 contraction or extension lumens for two 3D push/pull segments along a common helical core along with a desirably small bend radius, it may be beneficial to use radially elongate core 764 having a 6 lumens that are all surrounded by at least 0.003" of material. Core 764 has an axial height of half of core 702 and a radial width of that is less than half the balloon diameter of the 14-15 Fr system. There may be benefits to having the radial (elongate) dimension of the cross-section being less than the inflated inner diameter of the balloons mounted thereon, to inhibit trapping of inflation fluid on one axial side of the balloon (away from the inflation port).

Still further advantages may be provided by applying the smaller lumen and wall thickness dimensions of 7 Fr core 762 to a 15 Fr catheter core size, as it results in the 12 inflation lumen core 766. The large $13^{th}$ lumen of this embodiment may help enhance flexibility of the segments, and can again be used to monitor system integrity using a vacuum system. The 12 lumens may allow, for example, a continuous push/pull structure to have 4 independently controllable 3D shape (4D shape+stiffness) segments. A 16 inflation lumen core 768 combines the smaller lumen and wall thickness with a radially elongate cross-section, allowing 5 independently controllable 3D segments. It should be understood that still further numbers of lumens at smaller profiles are possible using known and relatively low cost multilumen extrusion techniques.

It should be understood that still further alternative embodiments may take advantage of the beneficial components and assemblies described herein. For example, as can be understood from the disclosure above regarding many of the flexible structures of FIGS. 3-12, inflation of a balloon may be resiliently opposed by a helical spring or other biasing structure so that the spring deflates the balloon and urges a flexible body back toward a pre-balloon-inflation state when the inflation fluid is released from the balloon. Rather than relying on 6 dedicated opposed expansion and contraction balloon channels for each segment (providing independent contraction and expansion along each lateral orientation) in the push/pull ring frame and push/pull helical frame embodiments described above, two or more of the channels (from the same segments or from different segments) may be grouped together to act as a common baising structure or fluid spring. As an example, all the contraction balloons along two adjacent segments might open to a single lumen that is inflated to less than full pressure. Modulating pressure to the different sets of extension balloons may still allow the extension balloons to articulate each segment with three independent degrees of freedom, as the grouped contraction balloons could selectively be overpowered by the extension balloons (like the coil springs) or may be allowed to deflate the extension balloons. In some embodiments, rather than relying on partial pressure of extension or contraction balloons, an elastomeric material may be mounted over the core of some or all of the extension or contraction balloons of a segment so as to passively oppose a set of the balloons.

Figure 28:
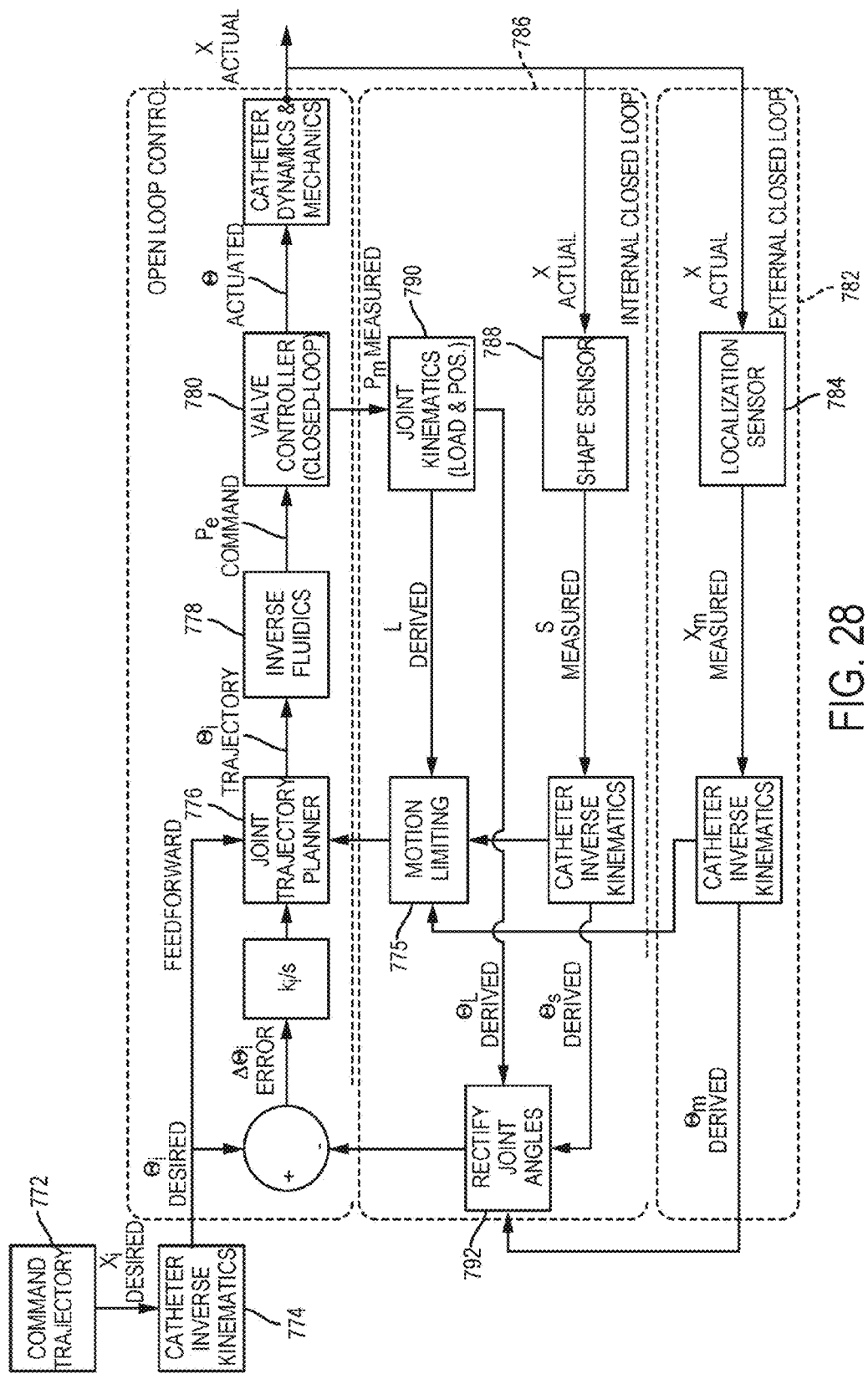
FIG. 28 schematically illustrates control system logic for using the fluid drive systems described herein to articulate catheters and other elongate flexible structures per input provided by a system user.

Referring now to FIG. 28, an articulation controller 770 for directing inflation fluid to and from the actuation balloons of the systems will typically have hardware and/or software configured and programmed to generally seek to cause the articulable structure to assume a new actual position or state $X_{actual}$ in response to a commanded trajectory 772 input by a system user. Many of the articulated flexible structures described herein may be included in robotic systems that can be analyzed and controlled using techniques associated with continuum robots, and the articulated structures will often be under-constrained with more joints then can be directly controlled using a standard controller. These excess or redundant degrees of freedom are often managed and made to cooperate by controller 770 using an internal compliance that directs the joints to be at a similar angle relative to the next joint within the segment. Controller 770 assumes equal joint angles within the segment for solving control equations. The segment bias (towards straight, for example) and strain associated with inducing a bend away from the preferred orientation causes a preference for internal joints to be at similar relative angles. The processor of the system will typically have software modules to determine the next desired position or state of the articulatable structure $X_{iDesired}$, and will apply inverse catheter kinematics 774 to determine the next desired joint state $\Theta_{iDesired}$. A difference between an actual joint state and the next desired joint state is determined to define a joint error, and the desired joint state can be fedforward to a joint trajectory planner 776 along with the joint error to define a joint error trajectory. This joint trajectory can be used in an inverse fluidic calculation 778 to determine command signals that can be fed into a closed-loop valve controller 780 so as to provide an actuated joint state. In some embodiments, closed loop control of the valves may depend on pressure sensing, and may be used to control to specific pressures as determined by valve inverse kinematics. The catheter dynamics and mechanics reaction to the actuated joint state (with the associated environment interactions with the catheter such as tissue forces and the like) result in a new actual position or state $X_{actual}$ of the articulated catheter system.

Feedback on the actual position or state of the articulated system to the controller may be omitted in some embodiments, but other embodiments may benefit from such feedback to provide more precise movements and better correlation (from the system user's perspective) between the command inputs and the actual changes in state. Toward that end, the controller may optionally use one or more closed loop feedback pathways. In some embodiments, a feedback system that is partially or fully external to the articulated structure 782 may sense the actual position or state of the catheter or other articulated structure using a localization sensor 784, such as an electromagnetic navigation system, an ultrasound navigation system, image processing coupled to 3D imaging (such as biplanor fluoroscopy, magnetic resonance imaging, computed tomography, ultrasonography, stereoscopic cameras, or the like; where the imaging modality may optionally also be used to produce images presented to the system user for image guided articulation). In many embodiments, the feedback will be provided using signals obtained from the articulated system itself under an internal closed loop feedback system 786. To obtain a measured shape or state of the articulated structure, a variety of known sensor technologies may be employed as an articulated structure shape sensor 788, including optical fiber shape sensors (such as those using fiber Bragg gratings), electrical shape sensors (such as those which use elastically deformable circuit components), or the like. The measured and/or sensed signals may be processed using inverse kinematics to derive associated measure and/or sensed joint states. Furthermore, balloon array pressure signals will often be available from the pressure sensors of the system, along with information correlating the pressures with the joint or shape state of the articulated system. The history of inflation fluid directed to and exhausted from the articulation balloons may also be used to help determine an estimated inflation fluid quantity present in each balloon (or set of balloons on a common inflation lumen). Where balloons are mounted in opposition or in parallel, the pressure and inflation fluid quantity of these related balloons on separate channels may also be available. Some or all of this pressure information may be processed using a joint kinematics processor 790 to determine a pressure-derived joint position or state (including a derived position of the pressure-articulated joints making up the flexible structure kinematic chain $\Theta_{LDevived}$). The pressure information, preferably along with internal localization information and/or external localization information, may also be used by the joint kinematic processor 790 to derive the loads on the joints, for determining of motion limits 775 as used by the joint trajectory planner 776, and the like. Where more than one is available, the external localization-based feedback joint state, the internal shape-sensor based joint state, and the pressure-derived joint state may be rectified 792 and the rectified (or otherwise any available) joint state compared to the desired joint state to determine the joint error signal.

Figure 29:
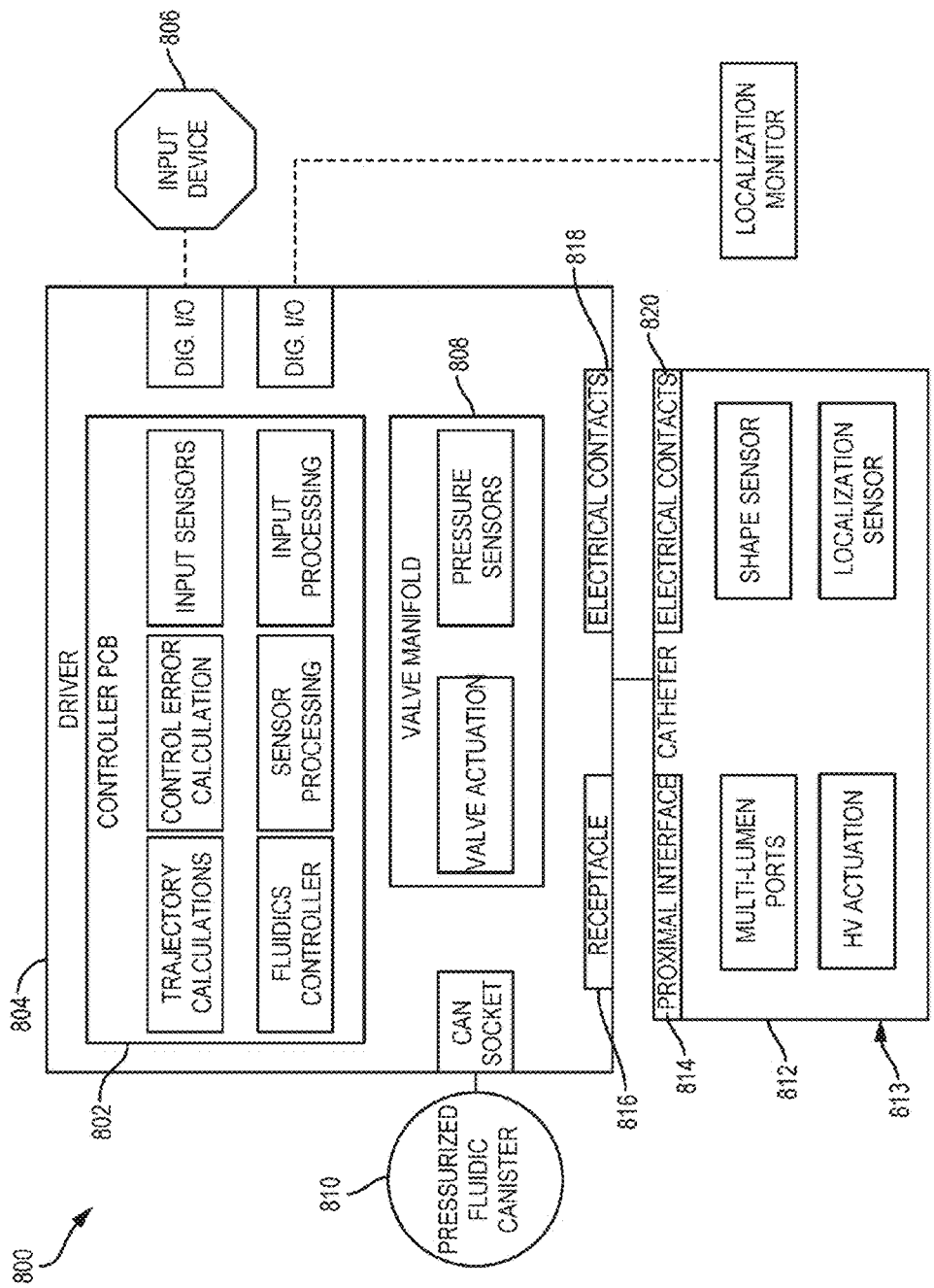
FIG. 29 schematically illustrates a data acquisition and processing system for use within the systems and methods described herein.

Referring now to FIG. 29, an exemplary data processing structure 800 for controlling the shape of a catheter or other articulated elongate flexible bodies described herein can be understood. Much of the data processing occurs on a controller board 802 of reusable driver 804, with the driver optionally comprising a hand-held capital equipment unit. The input device 806 may optionally include a separate workstation with wired or wireless data telemetry (so as to allow, for example, an interventional cardiologist or the like to perform a portion of the procedure while separated from the radiation field of a fluoroscopy system), or input device 806 may be a user interface integrated into the hand-held driver, or both. Preferably, the valve manifold 808 will comprise one of the modular plate manifold structures described herein, and will be contained within the hand-held driver unit 804. Canister 810 may be affixed to the driver (directly or by coupling of the catheter to the driver), and will often be included within a hand-held proximal assembly of deployment system that includes the driver, the proximal interface of the catheter, and other proximal components of the catheter (such as the heart valve actuation or deployment device 813, or the like) during use. Similarly, a battery of the system (not shown) may be integrated into the driver 804, may be mounted to the proximal interface of the catheter, or both.

A catheter 812 or other elongate flexible body for use with driver 804 will generally have a proximal interface 814 that mates with a receptacle 816 of the driver. As can be understood with reference to the descriptions above, the mating of the proximal interface with the receptacle will often provide sealed fluid communication between a balloon array of the catheter and the valves of the manifold assembly. Coupling of the proximal interface with the receptacle may also result in coupling of electrical contacts of the driver 818 with electrical contacts of the catheter 820, thereby facilitate access to internal shape sensor data, external localization data (which may employ a powered fiducial on the catheter and an external electromagnetic sensor system, or the like). Still further communications between the catheter and the driver may also be facilitated, including transmission of catheter identification data (which may include a catheter type for configuration of the controller, a unique catheter identifier so as to help inhibit undesirable and potentially deleterious re-use of the catheter, and the like). As an alternative to (or in addition to) electrical communication of this data, catheter 812 may have an RFID, bar code, or other machine-readable tag on or near proximal interface 814, and driver 804 may include a corresponding reader one or near receptacle 816.

Figure 30A:
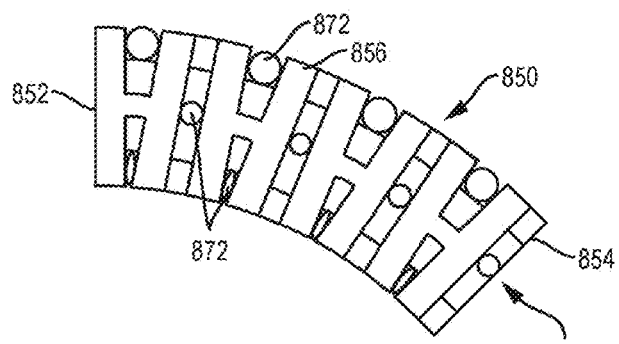
FIGS. 30A-30D and 31 illustrate an alternative articulatable structure having a single multi-lumen core with balloons extending eccentrically from the core, along with details of the structure's components and assembly.
Figure 30B:
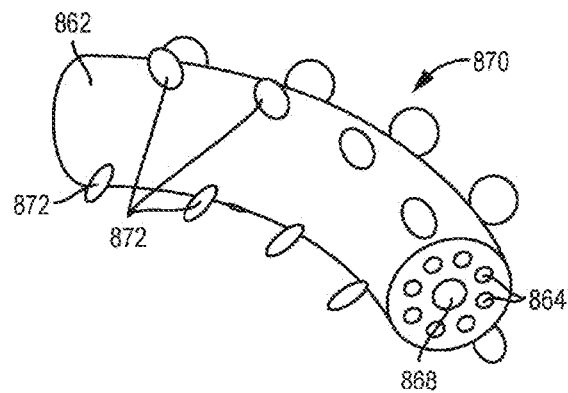
Figure 30C:
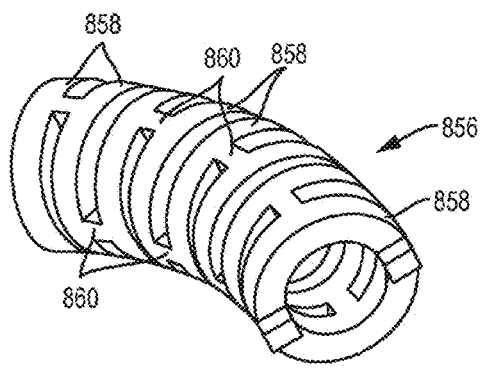
Figure 30D:
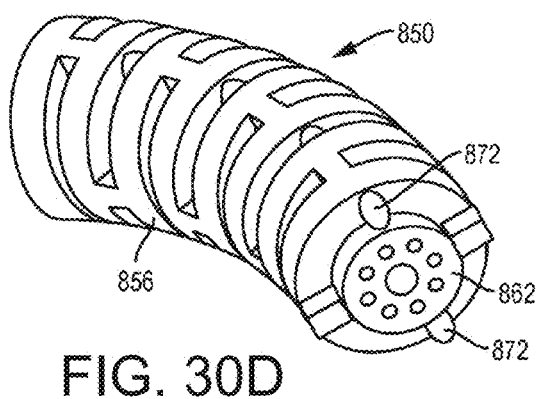
Figure 31:
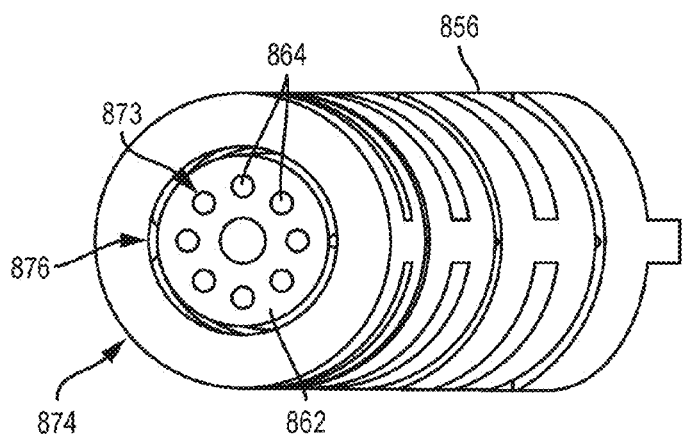

Referring now to FIGS. 30A-31, an alternative balloon-articulated structure 850 having a single multi-lumen core may be particularly well suited for smaller profile applications, such as for microcatheters having sizes down to 2 or 3 Fr, guidewires, or the like. Articulated structure 850 generally has a proximal end 852 and a distal end 854 and may define an axis therebetween. A frame 856 of the structure is shown by itself in FIG. 30C and is generally tubular, having a series of loops 858 interconnected by axial struts 860. Two struts may be provided between each pair of adjacent loops, with those two struts being circumferentially offset by about 180 degrees; axially adjacent struts between nearby loop pairs may be offset by about 90 degrees, facilitating lateral bending of the frame in orthogonal lateral bending orientations. As will be understood from many of the prior frame structures described herein, apposed surface region pairs between loops 858 will move closer together and/or farther apart with lateral bending of frame 850, so that a balloon can be used to control the offsets between these regions and thereby the bending state of the frame.

A multi-lumen core 862 is shown by itself in FIG. 30B, and extends axially within the lumen of frame 856 when used (as shown in FIG. 30D). Core 862 includes a plurality of peripheral lumens 864 surrounding a central lumen 868. Central lumen 868 may be left open as a working channel of articulated structure 850, to allow the articulated structure to be advanced over a guidewire, for advancing a guidewire or tool through the articulated structure, or the like. An array 870 of eccentric balloons 872 is distributed axially and circumferentially about the multi-lumen core, with the array again taking the form of an M×N array, with M subsets of balloons being distributed circumferentially, each of the M subsets being aligned along a lateral bending orientation (M here being 4, with alternative embodiments having 1, 2, 3, or other numbers of circumferential subsets as described above). Each of the M subsets includes N balloons, with N typically being from 1 to 20. The N balloons of each subset may be in fluid communication with an associated peripheral lumen 864 so that they can be inflated as a group. Eccentric balloons 872 may optionally be formed by drilling ports between selected peripheral lumens 864 to the outer surface of the body of the core, and by affixing a tube of balloon wall material affixed over the drilled body of multi-lumen core 862, with the inner surface of the balloon tube being sealingly affixed to an outer surface of the multi-lumen body of the core. Alternatively, eccentric balloons may be integral with the multi-lumen core structure, for example, with the balloons being formed by locally heating an appropriate region of the multi-lumen core and pressurizing an underlying lumen of the core to locally blow the material of the multi-lumen body of the core radially outwardly to form the balloons. Regardless, the balloons extend laterally from the body of the multi-lumen core, with the balloons optionally comprising compliant balloons, semi-compliant balloons, or non-compliant balloons. The shape of the inflated balloons may be roughly spherical, hemispherical, kidney shaped (curving circumferentially about the axis of the core), cylindrical (typically with a length:diameter aspect ratio of less than 3:1, with the length extending radially or circumferentially), or some combination of two or more of these.

When multi-lumen core 862 is assembled with frame 856 (as in FIGS. 30A, 30C, and 30D), the body of the multi-lumen core is received in the lumen of the frame and balloons 872 are disposed between the apposed surfaces of loops 858. By selectively inflating one subset of balloons 872 aligned along one of the lateral bending orientations, and by selectively deflating the opposed subset of balloons (offset from the inflated balloons by about 180 degrees), the axis of articulatable structure 850 can be curved. Controlling inflation pressures of the opposed balloon subsets may vary both a curvature and a stiffness of articulatable structure 850, with increasing opposed inflation pressures increasing stiffness and decreasing opposed inflation pressures decreasing stiffness. Varying inflation of the laterally offset balloon sets (at 90 and 270 degrees about the axis, for example) may similarly variably curve the structure in the orthogonal bending orientation and control stiffness in that direction.

As can be understood with reference to FIG. 31, the profile of the single-core assembly may be quite small, with an exemplary embodiment having an outer diameter 874 of frame 856 at about 1.4 mm, an outer diameter 876 of the body of multi-lumen core 862 of about 0.82 mm, and an inner diameter 878 of the peripheral lumens 864 of about 0.10 mm. The multi-lumen core body and balloons may comprise polymers, such as any of the extrusion or balloons materials described above, and the frame may comprise a polymer or metal structure, the frame optionally being formed by molding, cutting lateral incisions in a tube of material, 3D printing, or the like. Note that the exemplary multi-lumen core structure includes 8 peripheral lumens while the illustrated segment makes use of 4 lumens to articulate the segment in two degrees of freedom; a second segment may be axially coupled with the shown segment to provide additional degrees of freedom, and more lumens may be provided when still further segments are to be included.

Figure 32A:
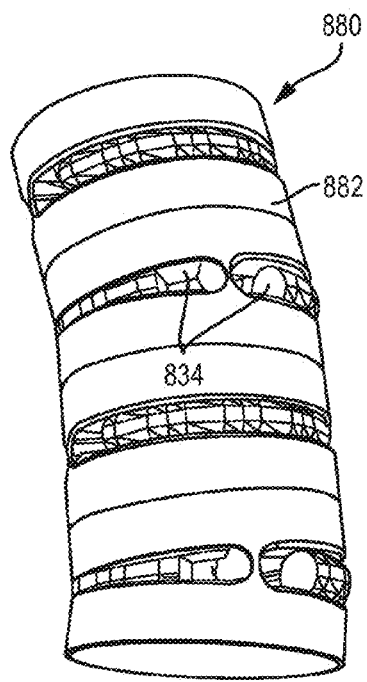
Figure 32B:
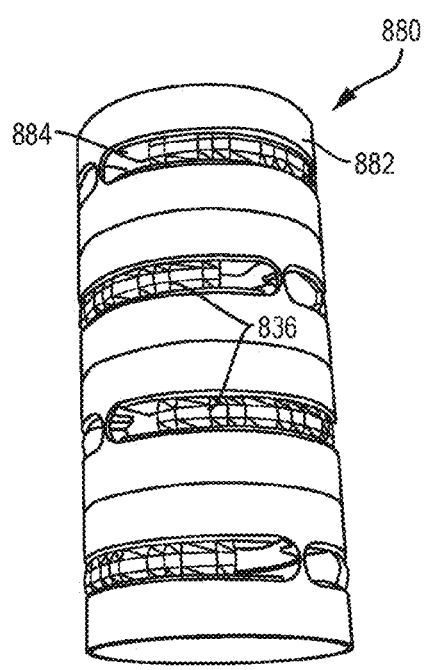

Referring now to FIGS. 32A and 32B, a still further alternative articulated structure 880 is shown in curved and straight configurations, respectively. Articulated structure 880 includes a frame 882 that is optionally formed by cutting lateral slits in tubular material and locally bending the tube wall near the slits inward to form shelves or tabs 884. The cut tubular material may comprise a polymer (optionally a polymer impregnated with a PTFE such as Teflon™), or a metal (such as hypotube or a superelastic alloy such as a Nitinol™ alloy). Similar structures may alternatively be formed by 3D printing or the like. Shelves 884 have surfaces that extend generally transverse to the tubular axis both proximally and distally of the slits. Balloons 886 can be disposed between apposed shelves 884 and can deflect an axis of articulated structure 880 laterally, with the balloons optionally extending eccentrically from a multi-lumen core body as described above regarding FIG. 31, having a helical balloon/core winding along the articulating structure as described above regarding FIG. 24, being formed by bonding balloon layers to a substrate material as described above regarding FIG. 10, and/or the like.

Referring now to FIG. 33A, a balloon piston system 890 may be used to provide axial articulation between distal components, and/or to provide rotation about a distal axis of any of the elongate articulated structures described herein. Balloon piston system 890 may employ inflation fluid for driving axial and/or rotational movement, with the fluid typically flowing distally along an elongate flexible structure within a substrate. Hence, balloon piston system 890 might be used, for example, with an endoluminal prosthetic delivery system to rotationally position an axially asymmetric mitral valve prosthesis in alignment with a mitral valve, to withdraw a sheath proximally from a valve prosthesis having a self-expanding frame, or the like.

System 890 generally includes a piston in the form of a plate 892 affixed to an axially slidable shaft 894 between first and second balloons 896, 898. Ports through slidable shaft 894 provide fluid communication between the balloons and first and second lumens of a multi-lumen supply shaft 900, with the first supply lumen being in fluid communication with first balloon 896 and the second lumen being in fluid communication with second balloon 898. Differential pressure between the two balloons acts on the piston and induces axial motion of slidable shaft 894, which may be used to axially actuate a movable component mounted to the articulated structure (such as to pull back a sheath from a self-expanding stent or valve prosthesis). Optionally, a lead screw or thread 902 at the distal end of slidable shaft 894 may engage threads of a corresponding rotatable component 904 (with the component being held at an axial location by rotational bearing surfaces or the like). Hence, piston system 890 can also be used to provide rotation of a component mounted to an articulated structure.

Referring now to FIG. 33B, an alternative incremental rotation system 910 provides incremental rotation about an axis of a catheter or other articulated structure, typically near a distal end of the catheter. Incremental rotation system 910 makes use of one or more pairs of opposed balloons 912a, 912b; 912a', 912b'; ..., with the balloons preferably being mounted on one or more multi-lumen core shaft that extends distally (and optionally that winds proximally and distally between some or all of the balloons). The core shaft(s) may take a number of different paths to rotation system 910, with the core shaft(s) optionally continuing distally from a core shaft of an adjacent articulated segment, or otherwise extending about the periphery of the catheter between an inner sheath 914 and an outer sheath 916; or the rotation system core shaft may alternatively be included in an inner catheter that extends distally through a working lumen of another articulated catheter (such as a lumen of the inner sheath shown in FIG. 25F); or the like. Balloons 912 are generally cylindrical in shape, with the axes of the balloons extending along the axis of the catheter, and the pairs of balloons are disposed within an axial channel bordered by axial ribs 918. Ribs 918 can be affixed to a distal portion of either the inner or outer sheath 914, 916 (here being affixed to the inner sheath) and a flange disposed between the balloons of each pair is affixed to the other (here to the outer sheath).

By alternatingly inflating a first of the opposed balloons of each pair 912a, 912a', ... while the second balloon of the pair 912b, 912b', ... is deflated; and then allowing the first to deflate while the second is inflated, the balloons can rotate the distal portion of outer sheath 916 relative to inner sheath 914 about the axis of the catheter 922, with the distal portion of outer sheath rotating back-and-forth. The back-and-forth rotation of the outer sheath can be used to incrementally rotate a rotatable sheath 924 by including one or more one-way clip(s) 926 that extend radially from the outer sheath to resiliently engage an inner surface of the rotatable sheath, with the clips angling circumferentially in the desired direction of rotation. Clips 926 typically have a sharpened outer edge, optionally comprising a metal or a high-strength polymer that allows the rotatable sheath to slide when rotated in the desired direction, but which inhibits movement in the opposed direction. Note that a low-torsional stiffness section or joint of the outer sheath just proximally of the incrementally rotated distal portion may facilitate incremental rotation in the desired direction. More specifically, one or more similar clips mounted to the outer sheath proximally of such as torsional joint (and which also engage the rotatable sheath) may be combined with clips 926 distal of the joint to help prevent the rotatable sheath from rotating counter to the desired direction when the distal clips slide along the inner surface of the rotatable sheath during the back-and-forth drive rotation (as can be understood with reference to the analogous use of clips 926 proximal and distal of an axially flexible section in the axial incremental movement system of FIG. 34). More pairs of opposed balloons and associated ribs and flanges may be provided about the axis (such as by having 3 sets at 120 degree centers, 4 sets at 90 degree increments, and so forth) to increase the rotational forces, and/or multiple balloons may be grouped together in series to increase the rotational increments (as may be understood with reference to the analogous use of balloons in series to increase axial movement increments sizes as described below and shown in FIG. 35).

Referring now to FIGS. 34A and 34B, an incremental axial actuation system 930 can axially articulate a component at or near the distal end of a flexible articulated structure. For example, axial incremental system 930 can incrementally move a slidable sheath 932 proximally over an outer sheath 934 at a distal end of an articulated catheter or other articulated structure so as deploy a self-expanding stent or valve. A cross-section through one side of axial incremental system 930 is shown in FIGS. 34A and 34B (the centerline of the catheter and actuation system being horizontal and below the figures). In this embodiment, a circumferential flange 936 is affixed to and extends radially outwardly from inner sheath 938 between opposed balloons 940a, 940b. The opposed balloons are disposed in a movable channel that is axially bordered by circumferential ribs 942, and those ribs extend radially inwardly from a distal portion of outer sheath 934. The distal portion of the outer sheath is coupled with the rest of the outer sheath by an axially flexible section or joint (shown here as a corrugated structure). Alternating inflation and deflation between opposed balloons 940a, 940b moves the channel and the distal portion of the outer sheath axially back-and-forth. Clips 926 disposed between the moving channel and the slidable sheath 932 (and similar clips disposed between the outer sheath proximal of the axial joint and the slidable sheath) help turn the axial back-and-forth motion of the channel to incremental axial movement of the slidable sheath in the proximal direction. Note that a similar system with clips 926 oriented in the axially opposed direction would instead result in axial movement of the sheath in the distal direction.

Where more axial actuation force is desired than is available from a single balloon pair, a plurality of opposed balloon pairs may be used in parallel to move the sheath proximally (or in some other desired actuation). To allow additional balloons, flange 936 and ribs 938 can comprise annular structures that extend circumferentially normal to the axis of the catheter (allowing 3 or 4 pairs of opposed balloons distributed about the axis at 120 or 90 degree centers, for example. Still larger forces may be provided, however, using advantageous helical flange and rib structures, each having one or more loops extending around the axis of the catheter to provide a desired number of opposed balloon pairs (and their associated axial articulation forces). Note that to provide additional load capability, flange 936 and ribs 938 may act as rigid bodies (such as by affixing flange 936 to either the inner or outer sheath throughout the helical length of the flange, and affixing ribs to the other throughout their lengths). Such opposed balloons may be mounted on first and second multi-lumen cores within the movable helical channel. Conveniently, a vacuum chamber may surround the balloons as described above, and the cores may extend distally from the distal-most lateral and/or axial articulation segment of any of the other articulation systems described herein, through a lumen of an inner sheath of one of the articulated structures described herein, or the like. The axial actuation balloons may optionally be the same size and shape as the articulation balloons, with one lumen of each core being used for the incremental axial actuation.

Referring now to FIGS. 35A and 35B, yet another incremental axial actuation system illustrates optional components which may add additional stroke and/or axially reversing capabilities. In this embodiment, much of the system operates as generally described above regarding FIG. 34, but a plurality of opposed balloons 940a, 940a'; 940b, 940b' . . . are used in series to provide a larger axial movement increment with each inflation/deflation cycle. Additionally, rather than relying on one-way clips to transform a back-and-forth motion to an incremental motion in a single desired direction, this system includes a simple clutch 944 that can be actuated by inflation of a clutch engagement balloon 946 so as to axially couple the drive channel to axially slidable sheath 932. A passive spring or a clutch disengagement balloon 948 disengages the drive channel from slidable sheath 932, with the clutch here comprising axially opposed edges or other features that that pivot or otherwise move into and out of engagement with the axially slidable sheath when the clutch is engaged. By appropriate sequencing of clutch engagement, disengagement, proximal motion of the drive channel, and distal motion of the drive channel, slidable sheath 932 may be moved, for example, first proximally by a desired total amount, and then distally by the same or a different amount, all in a single procedure. Such movement may help, for example, to recapture and reposition a partially deployed heart valve, and to redeploy the heart valve at an alternative position. When using one-way clips instead of a clutch, recapture of a partially deployed heart valve may alternatively be performed by advancing a recapture sheath distally over the catheter body, axially slidable sheath 932, and the partially deployed heart valve frame.

Some embodiments of extension/contraction systems may have an additional load-behaviour balloon array system extending along one, some, or all of the segments, with the array and fluid control system configured to improve the predictability of the associated segment(s) under various loads. Exemplary load-behavior balloon arrays may take the form of a 4×N array (N optionally being the same as the N extension array for the segment, and 4 (or another even number) lateral balloon orientations being even when the same segment has a 3×N actuation array).

Figure 36:
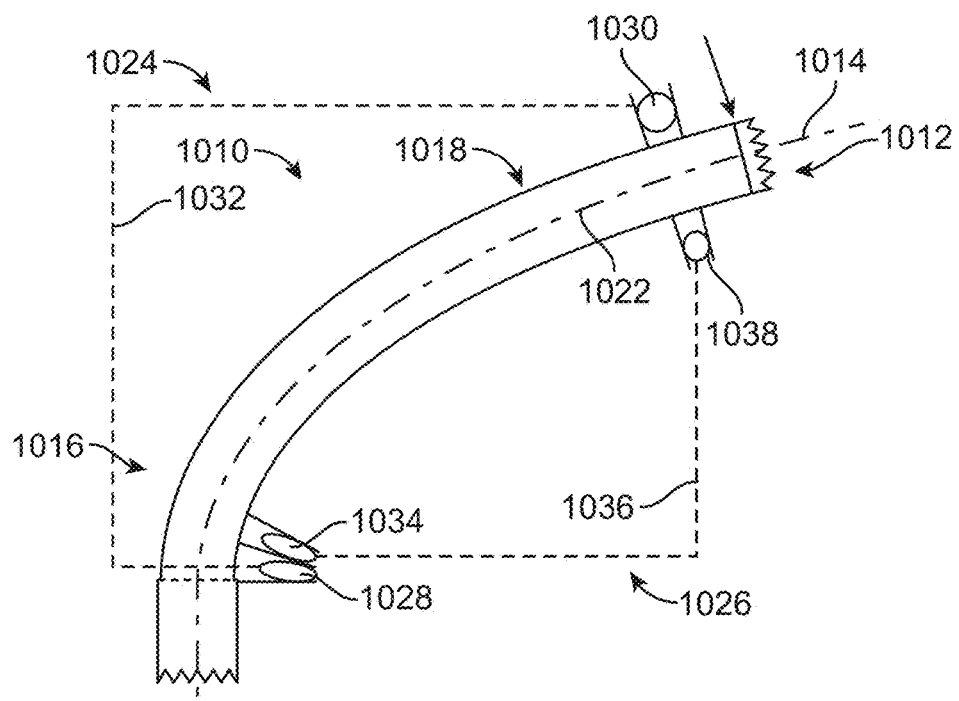
FIG. 36 schematically illustrates two different catheter behavior-improving balloon array systems and how they can help even the local curvature across a flexible catheter segment during bending.

Referring now to FIG. 36, a segment 1010 of a catheter (or other elongate body) is generally disposed along a flexible distal portion of the catheter near the distal end 1012, as is generally described above. A lateral bending force F' is applied to the catheter, resulting in a bend of catheter axis 1014 along segment 1012. The bending force has a greater bending arm and applies a greater bending torque along a proximal portion 1016 of segment 1010 than that of a distal portion 1018, with the difference in torque being sufficient (relative to a bending stiffness of the segment) that the curvature defined by bent axis 1014 has a significantly greater local curvature 1020 along the proximal portion 1016 than the local curvature 1022 along distal portion 1018. Changes in the orientation, location, and magnitude of bending force F' can result in different bend curvature distributions, and the changes in shape of some flexible segments with changes in the bending load may be larger than is desirable. To promote better (and specifically, more evenly distributed) bending behavior, segment 1010 is schematically shown here with two different simplified balloon array systems: an axially and laterally opposed bending behavior improvement balloon array system 1024, and variable balloon/frame effective area balloon array system 1026.

Regarding the axially and laterally opposed bending behavior improvement system 2024 of FIG. 36, a first bending behavior balloon 1028 along proximal portion 1016 is coupled to a second balloon 1030 along distal portion 1018 by a lumen 1032 (shown schematically here for simplicity, the lumen typically being included in a multilumen core of a balloon assembly as described above). As proximal portion 1016 bends with a relatively sharp local curvature, and as balloon 1028 is laterally offset from axis 1014 on the inside of the curve and disposed in an axial offset between surfaces of the balloon frame or skeleton as described above, balloon 1028 is significantly compressed. In contrast, balloon 1030 is disposed in an offset on the outside of the relatively limited local curvature along distal portion 1018, so that balloon 1030 has some room between the balloon-engaging surfaces of the frame to expand beyond what would be available if the local axis were in a straight configuration. However, the compression of balloon 1028 causes fluid and pressure to be transmitted along lumen 1024 from balloon 1028 to balloon 1030, and as balloon 1028 is compressed to relatively large extent, balloon 1030 seeks further expansion, which induces additional bending of distal portion 1018. This transfer of bending from highly curved proximal portion 1016 to less curved distal portion 1018 helps to even the amount of curvature along the segment. The balloon-induced additional bending of the distal portion is resisted by the distal catheter skeleton, which helps increase pressure in both balloons. The increased pressure in balloon 1028 limits the curvature along the proximal end, so that opposed balloon system 1024 also helps to limit the maximum local curvature. Note that inflation of balloons 1028, 1030 with incompressible liquids such as saline, water, or the like may enhance curvature distribution. Sealing of lumen 1024 proximally and distally adjacent segment 1010 may further enhance behavior modification, though axially elongatable catheter structures may benefit from a volume controlled fluid supply system coupled to lumen 1032 at the proximal end of the catheter. Inflation of balloons 1028, 1030 via such a fluid supply may imposed opposed bends for anchoring or the like, but most articulated bodies will benefit from a separate articulation system.

Regarding variable effective area balloon bending behavior improving system 1026, a balloon 1034 is again in a relatively highly-compressed state associated with the large curvature of proximal portion 1016. A lumen 1036 provides fluid communication between balloon 1034 and a balloon 1038 aligned along the same lateral bending orientation (inside the curvature of axis 1014 in this example), but along the smaller local curvature of distal portion 1018. Despite the equal pressures inside the balloons, and despite similar balloons and similar frame interface geometries, proximal balloon 1034 may impart more force to the frame (to resist further bending of the proximal portion) than is imposed by balloon 1038, because the effective area of the balloon/frame pressure transmitting interface increases with increasing compression. Note that this variable effective surface area is contrary to the constant effective areas of many pistons, bellows, and other hydraulic or pneumatic actuators, and can, with appropriate balloon geometry, frame/balloon interface surface geometry, frame stiffness, and fluid supply, help to apply more even curvature by an articulating balloon array. Variable effective area balloon systems will be described below with reference to FIGS. 43 and 44.

Figure 37A:
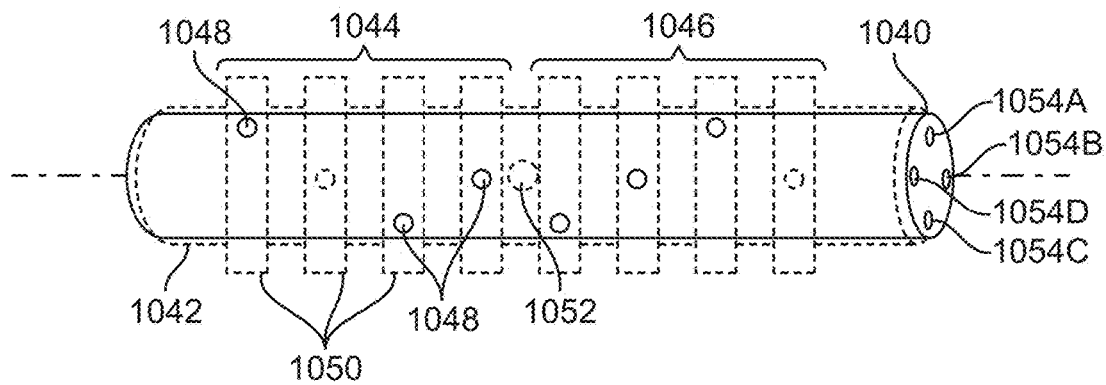
FIGS. 37A and 37B schematically illustrate a drill pattern for a two stage axially and laterally opposed behavior-improving balloon array, and a similar four stage balloon array assembly, respectively.
Figure 37B:
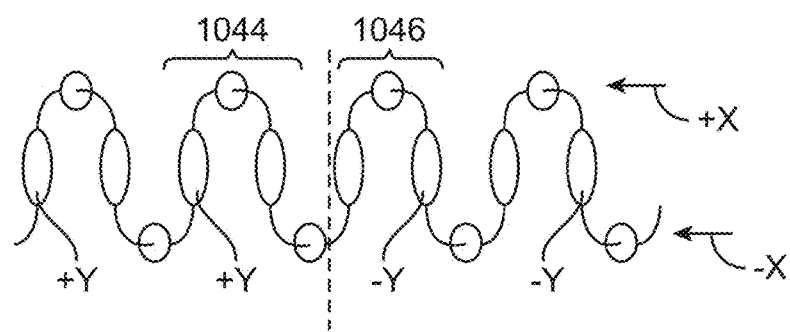
Figure 37C:
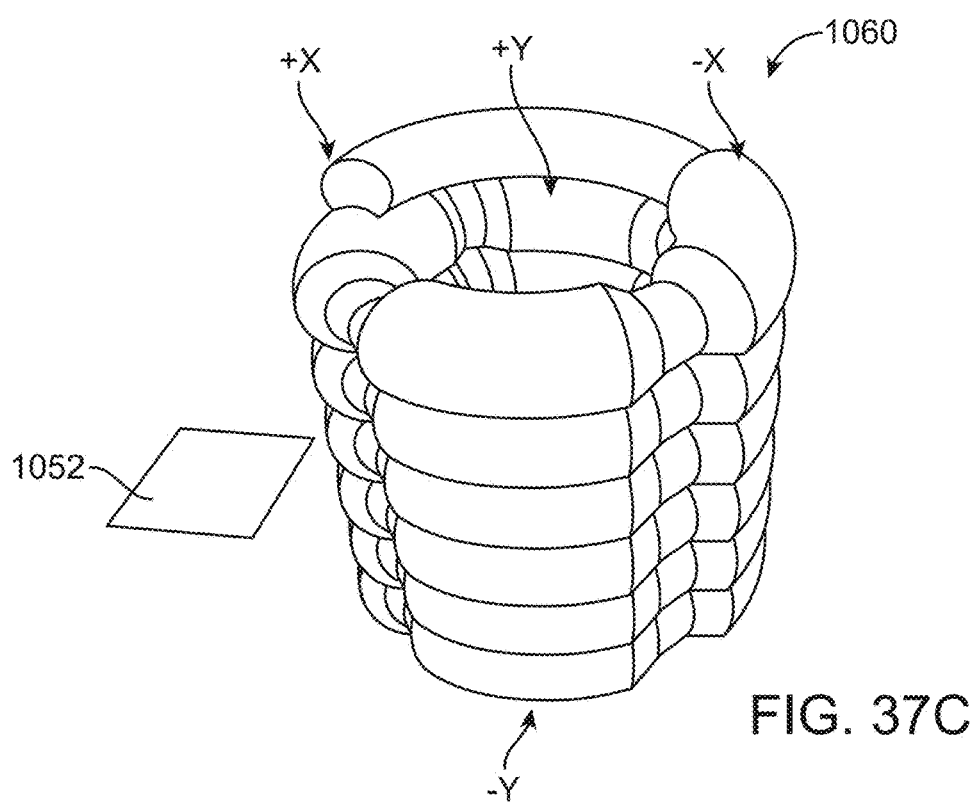
FIGS. 37C and 37D schematically illustrate axially and laterally opposed behavior-improving balloon arrays having 6 and 12 stages, respectively.

While some systems may benefit from balloon array systems that distribute curvature when bending only in one orientation (such as a +X orientation), two orientations (such as +X and +Y, or +X and −X), or three orientations, many systems may instead use axially and laterally opposed balloons in quadrature to distribute curvature in 4 orientations. Additionally, it will often be desirable to promote even bending at more than two locations along an axis in each orientation. Toward that end, the schematic illustration of FIG. 37A provides a simplified exemplary drill pattern for a 2 stage, 4 orientation (quadrature) behavior-improving balloon array, and FIG. 37B schematically illustrates a 4 stage behavior-improving balloon array for use in the elongate flexible bodies described herein. In FIG. 37A a multilumen core shaft 1040 has 4 lumens 1054A, 1054B, 1054C, 1054D. Core shaft 1040 is laser drilled to provide lateral ports 1048, and a balloon tube 1042 has been sealed over the core shaft so as to define an array of balloons 1050. Each sequential group of 4 balloons defines a +X, +Y, −X, −Y quadrature bending stage 1044, 1046, with the stages being on either side of an axial mid-point 1052 of the segment. The drill pattern, for example, couples both the +X balloon of stage 1044 and the −X balloon of stage 1046 to lumen 1054A. The +Y balloon of stage 1044 and −Y of stage 1046 are coupled to lumen 1054B, and the other laterally opposed balloons of these two stages are similarly coupled on opposed sides of mid-point 1052. When additional stages are included in the balloon array (such as a stage proximal of stage 1044 and another stage distal of stage 1066 as in FIG. 37B), with one or more +X balloons optionally on the same axial side of mid-point 1052 may be included on the lumen with the +X balloon of stage 1044, and a similar number of −X balloons being included on that lumen with the −X balloon of stage 1046. Alternatively, additional lumens may be provided, with the axially opposed balloons on each lumen optionally being equidistant from the mid-point.

Describing the axially and laterally opposed balloon array system in more detail, as can be understood with reference to FIGS. 11A, 20, 21, 23, 25, and 26, axially and laterally opposed behavior modification balloon array systems can be used with a wide variety of embodiments of the push-pull, ring frame, and coiled balloon systems described herein, and/or with any of a wide variety of alternative continuum robots and other elongate flexible structures. As exemplary ring-frame and push-pull helical frame systems may include only a 1-to-1 extension/contraction balloon opposition arrangement for driving articulation, but may also include one or more additional channel that can receive an additional helical balloon/core assembly. Use of the alternative helical balloon/core assembly described above, with the axially and laterally opposed balloons in fluid communication via a common lumen, can help promote desirable behavior of the overall segment and articulatable structure in response to drive commands, environmental forces, payload forces, and/or end effector/tissue interaction.

As may be understood with reference to FIG. 23, when 2 or more balloons are grouped together to be inflated by a common lumen (and particularly when the number of grouped balloons becomes relatively large for a particular task, such as with 6 or more, 8 or more, or even 16 or more grouped balloons on a common lumen), the shape and response of a segment may be difficult to predict and control. For example, differential bending loads on the various balloons may exceed the resilience of the segment, so that the bend adjacent one or more of the grouped balloons is markedly different than that along other balloons of the group. To make the behavior more predictable and controllable, it may be beneficial to fabricate a behavior improving balloon/core assembly having an array with an even number M of lateral offset orientations, so that each balloon has laterally opposed balloons (with the axis of the articulatable device directly between them).

Typically, the behavior improving assembly will have balloons arranged in quadrature as shown in FIG. 11A (even where the drive balloon/core assemblies may only have three balloon lateral orientations, as shown in FIG. 24). Additionally, the ports for the behavior improving assembly may be drilled so that 2, 4, 6, 8 or more opposed balloons—on opposite sides of the segment relative to the axis, and at opposed ends (proximal-distal) of the segment relative to the mid-point 1052 or middle plane of the segment—are coupled together by a lumen. As a result of this arrangement, a bend near the proximal end of the segment may be mirrored at the distal end (or at least the potential energy of the system increases as the proximal/distal "unevenness" of the bend increases). This should increase the ease with which the segment can be controlled.

Exemplary drill patterns for a six stage embodiment such as balloon coil 1060 shown may include that shown in Table 3:

TABLE 3

| Lumen #_\ | +X | +Y | −X | −Y |
|---|---|---|---|---|
| Stage 1 | 1 | 2 | 3 | 4 |
| Stage 2 | 5 | 6 | 7 | 8 |
| Stage 3 | 9 | 10 | 11 | 12 |
| Stage 4 | 11 | 12 | 9 | 10 |
| Stage 5 | 7 | 8 | 5 | 6 |
| Stage 6 | 3 | 4 | 1 | 2 |

Figure 37D:
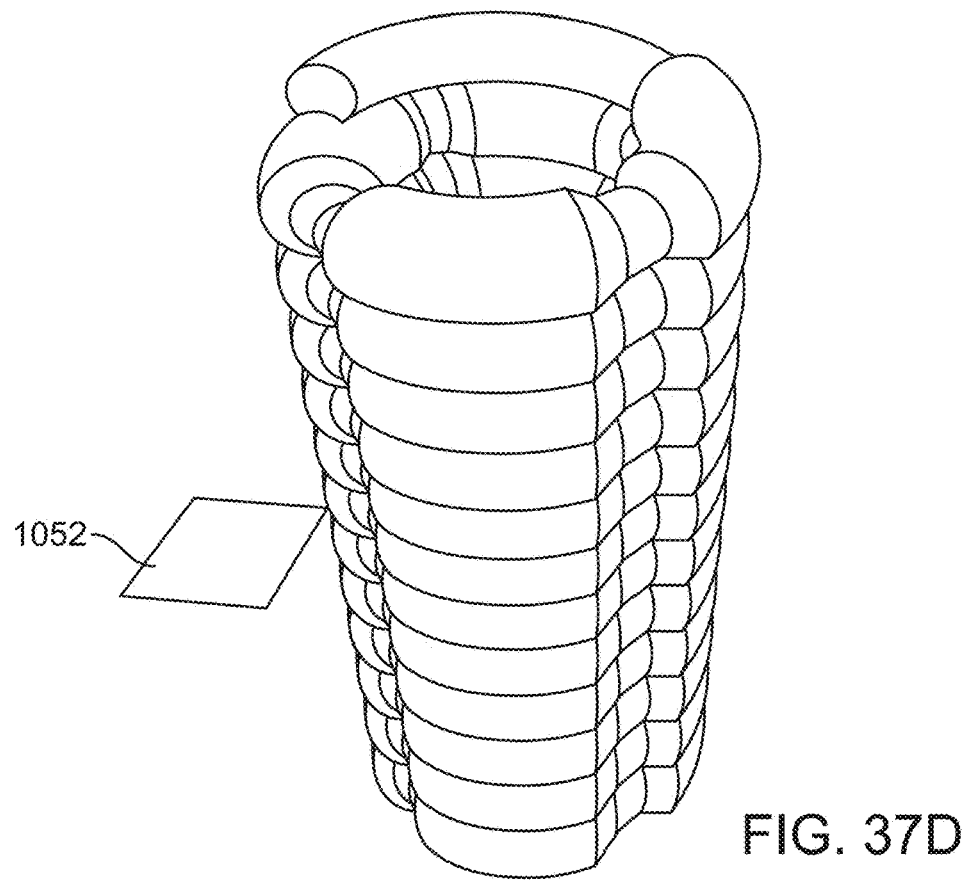

The arrangement of Table 3 assumes that the associated articulation balloon/core assemblies have 6 stages or balloons per orientation, but limits a behavior improving balloon/core assembly to 2 balloons per lumen and uses 12 lumens of the behavior improving balloon/core assembly for a single segment. Each 2 additional stages or balloons per lumen of the articulation system may use 4 additional lumens to maintain the 1-to-1 pairing of the balloons. Optionally, the channels of the behavior improving core are filled with a liquid (the liquid optionally comprising water, isotonic water, saline, or another suitable hydraulic fluid), even where the inflation fluid for the articulation balloons comprise gas or a gas/fluid mixture. In some embodiments, the lumens of the behavior improving core may be sealed at the ends of the segment (with the balloon/core assembly optionally terminating between each segment). Such embodiments may forego elongation capabilities, with the segment ends optionally affixing the balloon cores, the frames, and inner and outer sheaths together, and with the inner or outer sheath inhibiting elongation of the segment. Alternative behavior improving balloon/core assembly embodiments may group more than two balloons on each lumen, may include an inflation fluid that comprises gas, and/or may have lumens extending proximally to the proximal end (for coupling to an inflation fluid pressure or volume control system to facilitate elongation), or the like. In some embodiments, two behavior improving balloon/core assemblies may be included, with the balloons of one being extension balloons and the balloons of the other being contraction balloons, as described above regarding FIGS. 20A-25E. Helical or annular C-frame structures with the arrangement of FIGS. 20A and 20B may, for example, accommodate a combination of four balloon/core assemblies, with one having extension articulation balloons, one having extension behavior balloons, one having contraction articulation balloons, and one having contraction behavior balloons.

Where desired, such as when it is desired to limit the number of lumens in a behavior-improving assembly and/or when the behavior lumens will extend proximally to facilitate elongation of the segment, it may be desirable to group adjacent behavior balloons together, optionally with two, three, four, or more adjacent balloons along one lateral orientation in fluid communication with the same number on the opposite side and end of the segment. This may allow 4, 8, or 12 lumens to be used to improve the behavior of segments having large numbers of balloons, such as in the 12 stage segment of FIG. 37D. Exemplary drill patterns for such segments are provided in Tables 4 and 5:

TABLE 4

| Lumen #_\ | +X | +Y | −X | −Y |
|---|---|---|---|---|
| Stage 1 | 1 | 2 | 3 | 4 |
| Stage 2 | 5 | 6 | 7 | 8 |
| Stage 3 | 5 | 6 | 7 | 8 |
| Stage 4 | 7 | 8 | 5 | 6 |
| Stage 5 | 7 | 8 | 5 | 6 |
| Stage 6 | 3 | 4 | 1 | 2 |

TABLE 5

| Lumen #_\ | +X | +Y | −X | −Y |
|---|---|---|---|---|
| Stage 1 | 1 | 2 | 3 | 4 |
| Stage 2 | 1 | 2 | 3 | 4 |
| Stage 3 | 1 | 2 | 3 | 4 |
| Stage 4 | 3 | 4 | 1 | 2 |
| Stage 5 | 3 | 4 | 1 | 2 |
| Stage 6 | 3 | 4 | 1 | 2 |

Note that in many of these embodiments a behavior-improving flow of inflation fluid may occur within the segment. Optionally, the behavior-improving segments may be self-contained, so that no flows need to extend proximally through proximal segments or via the articulatable device/manifold interface, and no additional manifold or control complexity is needed to take advantage of the benefits of these structures, which may reside passively in the otherwise empty channel of the push-pull frame structure.

An alternative embodiment of an integrated articulation and behavior-improvement assembly can be understood with reference to FIGS. 30A-31. In this embodiment, pairs of circumferentially-adjacent balloons 872 are in fluid communication with associated adjacent peripheral lumens 864, with the balloons optionally being in contact when they are both fully inflated. Hence, there are 4 balloons at similar axial location along the body of core shaft 862, a first pair near each other (for example, with the pair centered at a 0 degree orientation) and another pair that are near each other and opposed to the first pair (for example, with the pair centered at 180 degrees). Axial balloon stations along core body 862 will have first and second pairs of balloons centered along opposed transverse bending orientations (for example, with one adjacent pair at 90 degrees and the opposed adjacent pair at 270 degrees). When assembled with the frame, each pair of balloons are disposed together in the same aperture between adjacent loops 853 and struts 860, so that the interface regions and offsets correspond for the balloons of the pair. One of the balloons of each pair can be inflated or deflated by a fluid supply system to articulate articulatable segment 850; the other balloon of each pair can be in fluid communication with one or more axially and circumferentially opposed balloon of the segment so as to urge the segment toward a uniform bend configuration. Coupling of the driven balloons aligned along a lateral bending orientation, and of the circumferentially opposed behavior balloons may be facilitated by a proximal manifold or other fluid channels system axially offset from the segment, by lumen paths that twist around an axis of the core body as shown in FIG. 13C, or the like.

Referring now to FIGS. 38A-39G, an exemplary valve deployment system 1100 includes a balloon drive system 1102 to move a sheath 1104 axially from over a self-expanding prosthetic heart valve 1106, and optionally to recapture the valve prior to complete deployment. Deployment system 1100 generally has a proximal end 1108 and a distal end 1110, with an elongate flexible catheter body 1112 extending much of the axial length of the catheter (not shown in some drawings).

Figure 39A:
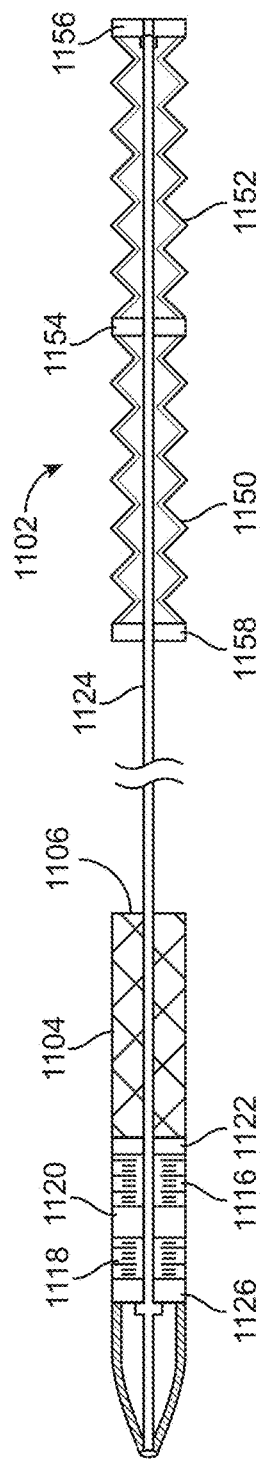
FIGS. 39A-39G are cross-sectional illustrations of the fluid-driven sheath actuation system of FIGS. 38A-38G showing how inflation of the balloon actuators can generate forces within a patient body so as to move the sheath over the self-expanding heart valve to partially deploy the valve, recapture the valve, and fully deploy the valve.
Figure 39B:
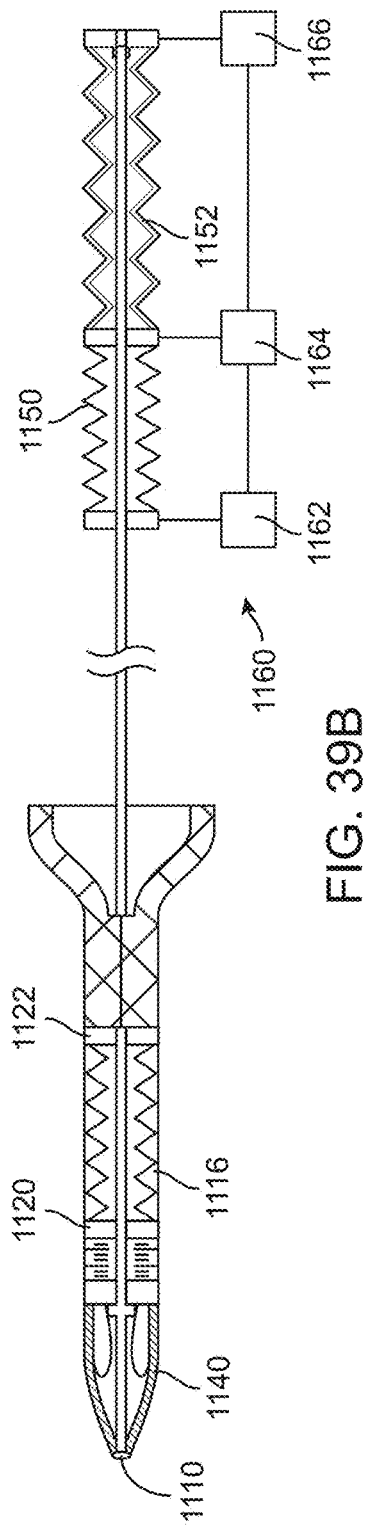
Figure 39C:
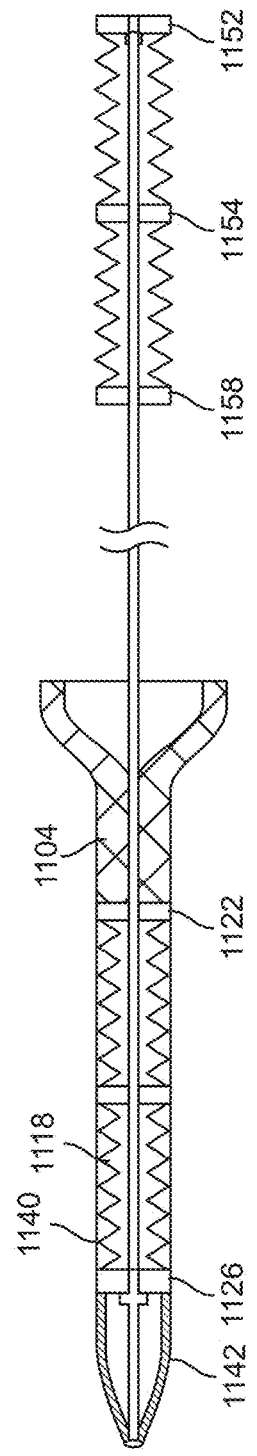
Figure 39D:
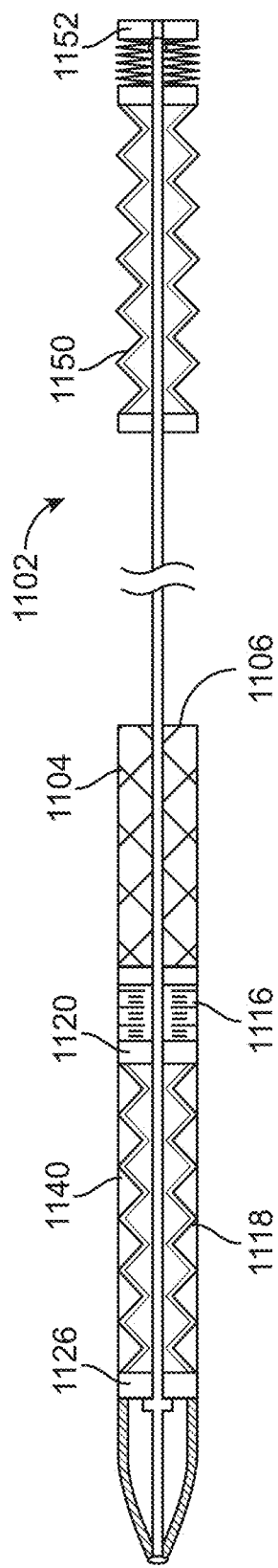
Figure 39E:
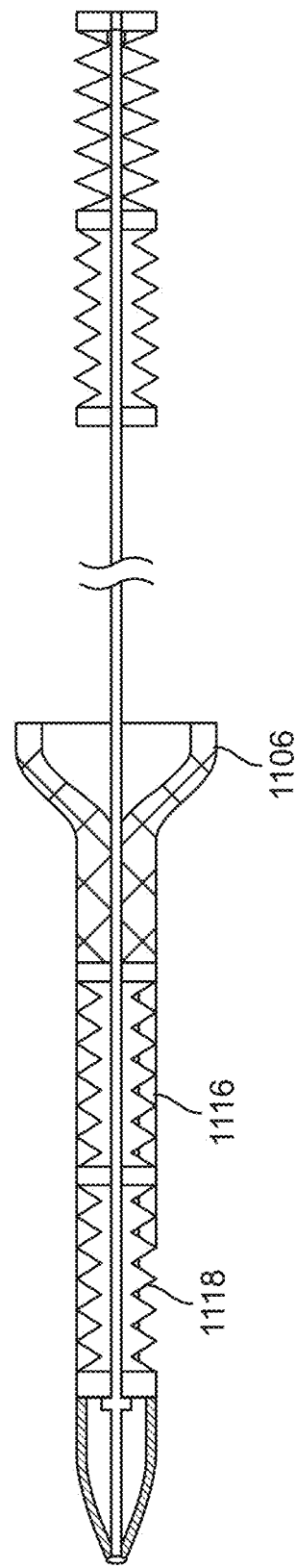
Figure 39F:
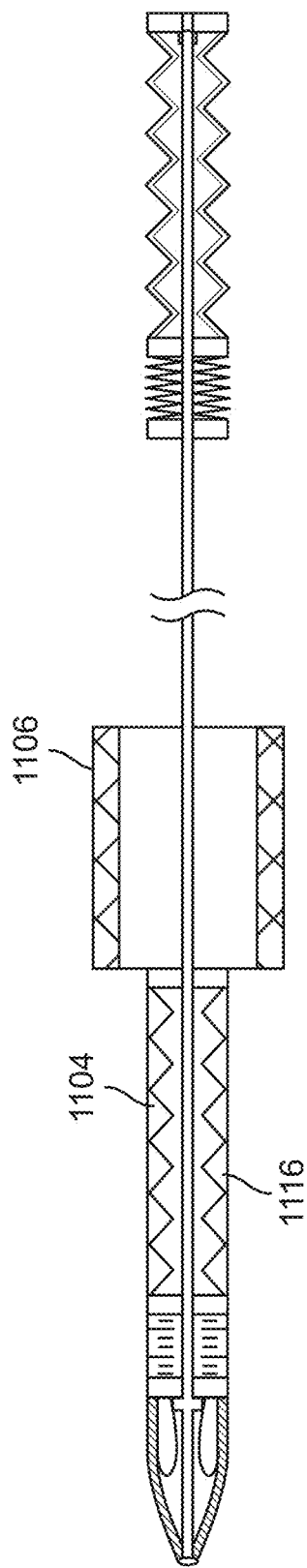
Figure 39G:
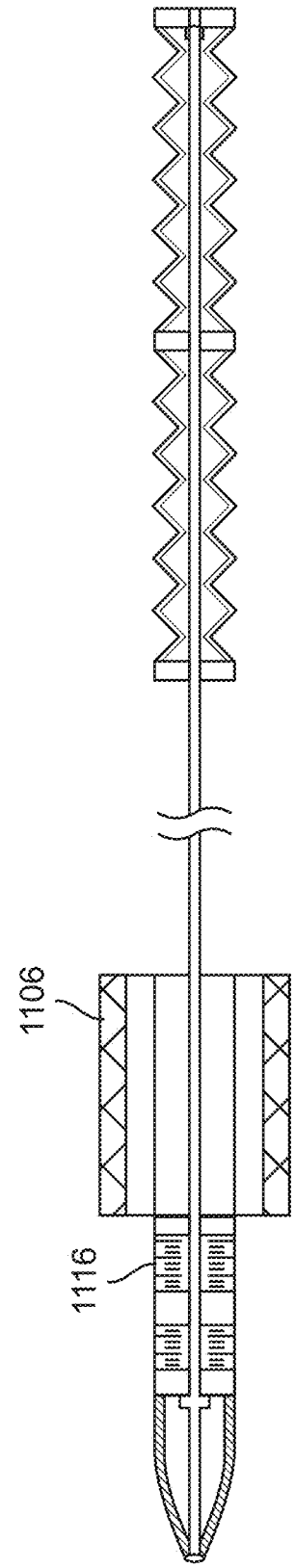
Figure 40A:
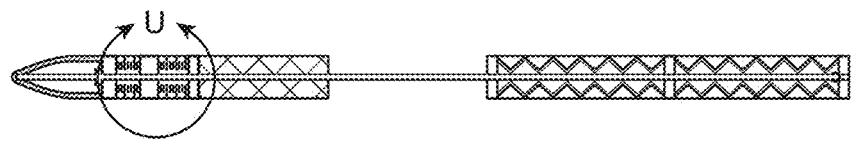
FIGS. 40A-40D are cross-sectional illustrations showing details of the structure and the fluid flow paths of the fluid-driven sheath actuation system of FIGS. 38A-38G.
Figure 40B:
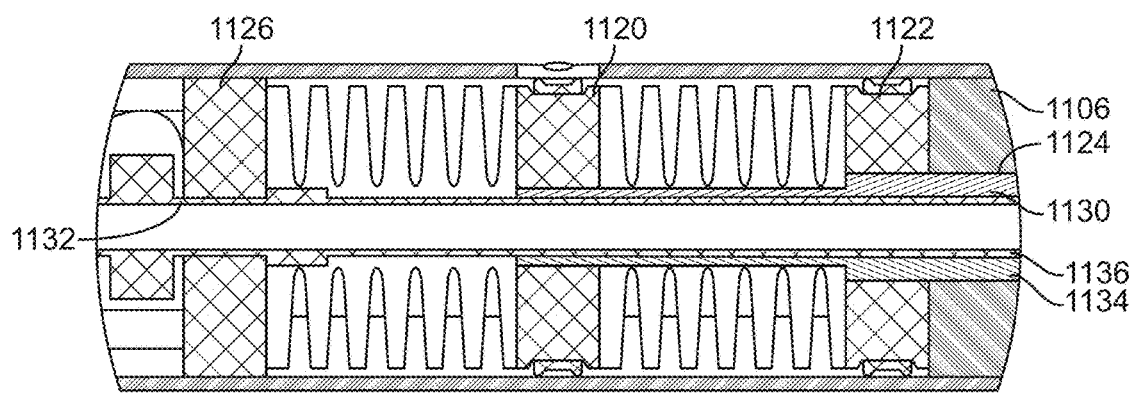
Figure 40C:
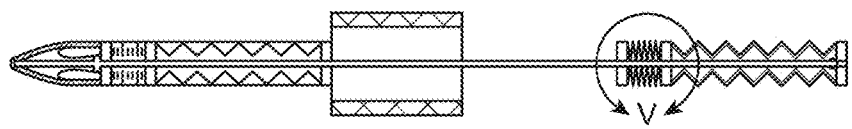
Figure 40D:
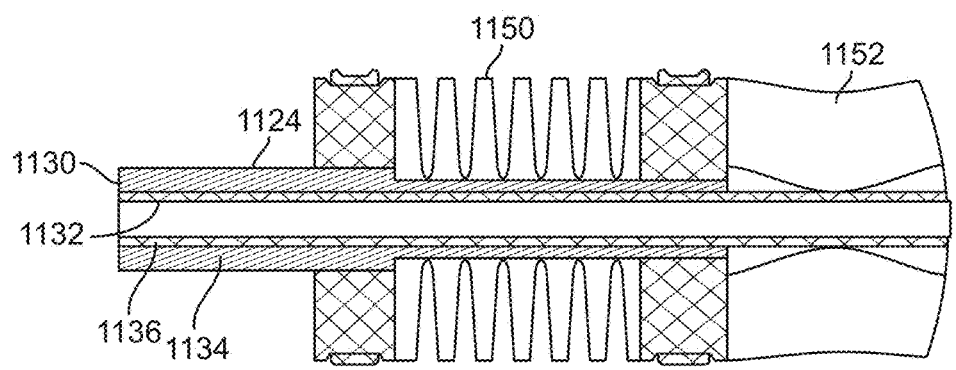
Figure 41A:
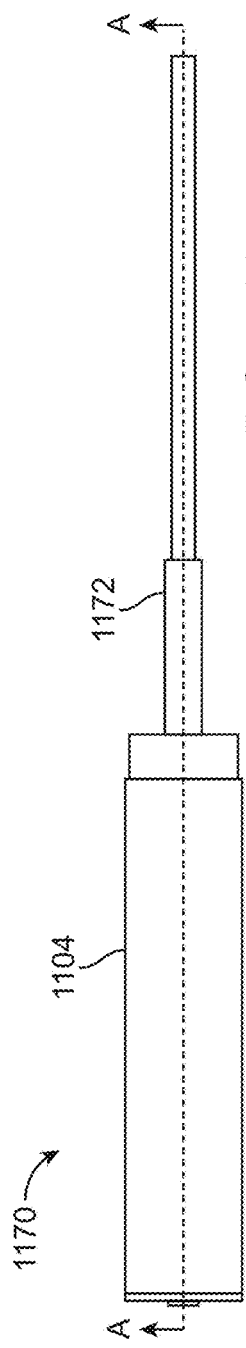
FIGS. 41A-41D are a side view, a cross-section, and two details views showing an alternative distal portion of a valve delivery system having a fluid-driven sheath driven by pressure contained between inner and outer balloons.
Figure 41B:
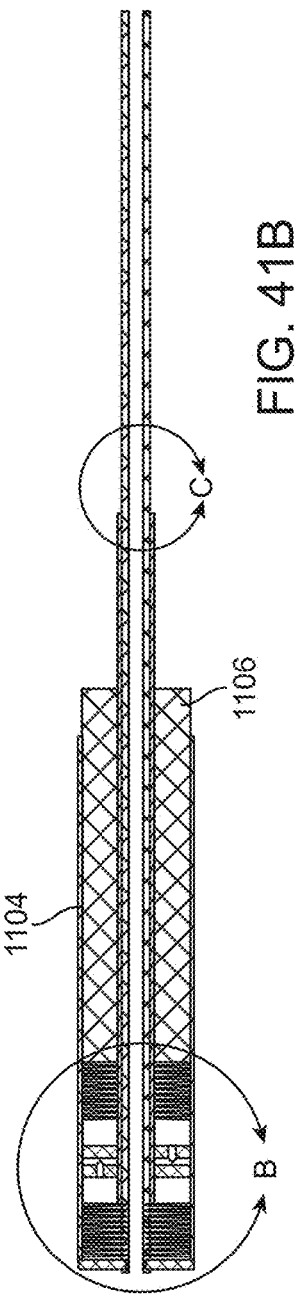
Figure 41D:
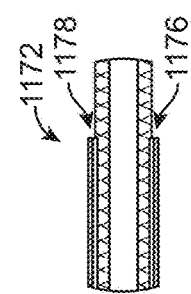
Figure 41C:
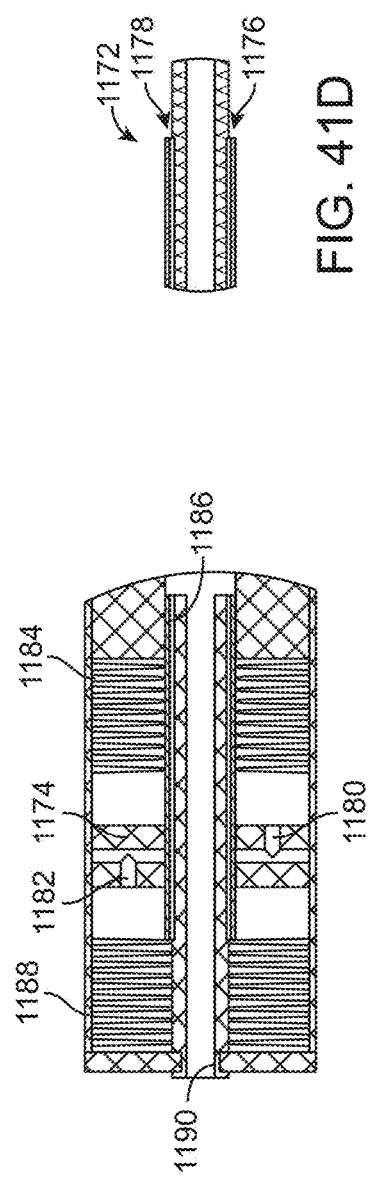

As shown in FIGS. 38A and 39A, when deployment system 1100 is configured to be inserted distally into the patient a receptacle 1114 of catheter body 1112 receives valve 1106. Sheath 1104 radially restrains valve 1106, and the valve can impose radial forces against the sheath that are sufficient to induce significant friction, so that many pounds of axial force will be applied to move the sheath axially from over the valve. Axially oriented surfaces of the catheter body can engage and maintain an axial position of the valve during articulation of the sheath. Sutures or other tension members, valve-engaging features radially protruding from the receptacle within the valve, or the like may be included to inhibit axial movement of the valve relative to the receptacle prior to complete release of the valve from the catheter system. As seen in FIGS. 38A, 39A, together with the detail view of FIG. 40B, distal of the receptacle, a proximal flange 1122 is affixed to a catheter shaft 1124 of the catheter body and forms the proximal end of a deployment balloon 1116, with a proximal surface of the proximal flange forming the distal border of the valve receptacle. Deployment balloon 1116 and a recapture balloon 1118 are separated by an intermediate flange 1120, which is affixed to an intermediate shaft 1130 that can slide axially in a lumen of the catheter shaft. A distal flange 1126 forms the distal end of recapture balloon 1118, and is affixed to an inner shaft 1132 that can slide axially in a lumen of the intermediate shaft. An annular deployment balloon inflation fluid flow path 1134 is bordered by the lumen of catheter shaft 1124 and the outer surface of the intermediate shaft, and an annular recapture balloon inflation fluid flow path 1136 is bordered by the lumen of the intermediate shaft and the outer surface of the inner shaft 1132.

Referring now to FIGS. 38A, 38B, 39A, 39B, and 40B, distal end 1110 may be advanced over a guidewire into a patient, often via femoral access to a right atrium of a heart. The deployment system may then be advanced transseptally through a left atrium so that valve 1106 is aligned with the native mitral valve tissue of the heart (ideally using an articulation balloon array system as described above, but alternatively using a pull-wire, magnetic, or other catheter control system). While valve 1106 is held in position by the catheter structure proximal of the receptacle, sheath 1104 can be moved distally from over the receptacle by transmitting inflation fluid along deployment fluid path 1134, the inflation fluid preferably comprising a non-compressible fluid, typically a liquid such as water, saline, or other biocompatible hydraulic fluid. The inflation fluid axially expands deployment balloon 1116 from an uninflated configuration to a partially inflated configuration, with the deployment balloon preferably having an axial series of laterally opposed folds in the uninflated configuration. The fluid pressure in deployment balloon 1116 drives intermediate flange 1120 (and intermediate shaft 1130 on which the intermediate flange is mounted) distally, pushing distal end 1110 distally from the valve. As sheath 1104 is axially affixed to intermediate flange 1120 (in the exemplary embodiment, via a swage and/or adhesive bonding), this advances the sheath distally from over the prosthetic valve (the laterally stiff sheath advancing in an antegrade direction into the left ventricle, away from the bends of the catheter that maintain prosthetic valve alignment) and allows a proximal portion of the valve to radially expand into engagement with the surrounding native tissue of the mitral valve annulus. Sheath advancement forces can be significant (often being 1 lbf or more, generally being 3 or even 5 lbf or more, and in many cases being 10 or even 15 lbf or more) are generated by fluid pressures in deployment balloon 1116 and are applied locally between the sheath and the valve/receptacle without having to be transmitted around lateral bends of the catheter. Sheath 1104 may have a profile from 18 to 36 Fr, typically being 20 to 29 Fr, and inflation fluid pressures may be up to 10, 20, or even 30 atm or more.

Referring now to FIGS. 38B, 38C, 39B, 39C, and 40B, optional recapture balloon 1118 can be used to move sheath 1104 back over partially deployed valve 1106 by transmitting inflation fluid along recapture fluid path 1136 so as to inflate and axially elongate recapture balloon 1118. Inflation of recapture balloon initially again drives distal end 1110 distally away from the receptacle and valve 1106. A tension member, here in the form of 3 axial straps that limit separation of distal flange 1126 from proximal flange 1122 and are initially stowed in nosecone 1142, limit elongation of the deployment system distal of the valve as shown. As can be understood with reference to FIGS. 38C, 38D, 39C, and 39D, further inflation of recapture balloon 1118 thus drives intermediate flange 1120 (and sheath 1104) proximally (with the inflation fluid in deployment balloon 1116 typically being allowed to flow proximally via the deployment fluid path to facilitate sheath movement over valve 1106). Recapture sheath movement forces are again generated and applied locally, here via the tension members, as generally described above. Such recapture may be desired, for example, to allow removal of the valve if the system user determines that an alternative valve or other therapy may be better suited for the patient, or to allow the valve to be moved to a new position relative to the tissues of the heart. Note that some deployment systems may obviate recapture balloon 1118, for example, by including a simple tension member (such as a shaft, one or more filament such as a suture, or the like) extending between distal end 1110 and proximal end 1108 of the catheter system, allowing the user to manually pull sheath 1114 over valve 1106; or when the valve is released by proximal retraction of the sheath by providing an outer full-length sheath that can be pushed distally over the catheter body and retracted sheath from outside the body, or by simply eliminating the recapture capability.

Referring now to FIGS. 38D, 38E, 39D, 39E, and 40B, after recapture of valve 1106 under sheath 1104 is complete, recapture balloon 1118 may be in an elongate inflated state and may have axially compressed deployment balloon 1116 to a shortened deflated state. The distal portion of the catheter (including the receptacle and the valve supported therein) may be moved so as to reposition the valve and better align the valve with the heart tissue for deployment, movement of the valve often being induced using an articulation system of the catheter disposed proximally of the receptacle. Once the valve is in the target position, deployment balloon 1116 can be inflated, inflation optionally being initiated with the recapture balloon in a partially inflated state. Inflation fluid can be allowed to pass along the deflation flow path, so that the recapture balloon can be deflated. If partial inflation of the deployment balloon 1116 indicates alignment remains good (see FIGS. 38E, 39E), deployment balloon 1116 can be continued until sheath 1104 is moved axially sufficiently to fully release valve 1106 from the receptacle of the deployment system (see FIGS. 38F, 39F). Once the self-expanding annular frame structure of valve 1106 has fully expanded into fixed engagement with the surrounding heart tissue, deployment balloon 1116 can optionally be deflated (see FIGS. 38F, 38G, 39F, 39G) and the distal deployment and recapture balloons can be withdrawn proximally through the frame of expanded valve 1106 (see FIGS. 38G, 39G) and past the prosthetic valve leaflets (not shown).

A variety of different fluid control systems may be coupled to proximal end 1108 of deployment system 1100 to control inflation of the deployment and recapture balloons. Optionally, fluid at controlled pressures and/or volumes may be transmitted along the deployment and recapture flow paths from a computer-controlled manifold, with the fluid flows optionally being controlled using solenoid valves, the valves regulating flow pressurized using a gas/liquid canister as described above. When the deployment and/or recapture balloons are to be included in a deployment system having an articulated portion using selective inflation of a subset of balloons to control a bending state (as will often be the case), the deployment and recapture fluid flow paths may make use of the multi-channel substrates and extrusions described above, or may be formed using different catheter features. Referring again to FIGS. 38A-38G, 39A-39G, and 40D, an exemplary hydro-mechanical balloon drive system 1102 includes a deployment drive balloon 1150 and a recapture drive balloon 1152, with the exemplary drive balloons having structures and functionality that largely mirrors that of deployment balloon 1116 and recapture balloon 1118 described above, but inducing the fluid flow and corresponding axial movement of the intermediate and inner shafts. More specifically, deployment drive balloon 1150 and recapture drive balloon 1152 are separated by an intermediate drive flange 1154 affixed to intermediate shaft 1130. A proximal drive flange 1156 forms the proximal end of recapture drive balloon 1152, and is affixed to inner shaft 1132, and a distal drive flange 1158 affixed to catheter shaft 1124 (and hence to the valve receptacle). Deployment drive balloon is in fluid communication with the deployment fluid path 1136 (and hence with the distal deployment balloon 1116), and recapture drive balloon 1152 is in fluid communication with the annular recapture fluid path 1134 (and hence with the distal recapture balloon 1118). As shown schematically in FIG. 39B, a drive handle 1160 (or other mechanical or electromechanical actuating mechanism) is coupled to proximal balloon drive system 1102, with a support 1162 axially coupled to distal drive flange 1158 and first and second axially moveable arms 1164, 1166 coupled to the intermediate and proximal drive flanges 1154, 1156 so as to induce independent axial compression of the drive balloons. A wide variety of mechanisms may be included in drive handle 1160 to provide axial movement of the drive flanges, including levers, gears, or the like.

Referring once again to FIGS. 38A, 38B, 39A, 39B, and 40D, actuating proximal handle 1160 so as to move intermediate drive flange 1154 distally can axially compress drive deployment balloon 1150, sending inflation fluid through the deployment fluid path 1136 to deployment balloon 1116. The deployment balloon cross-sections can correspond so that the movement distances are similar (or they can differ so as to enhance mechanical advantage or limit handle stroke in some embodiments). The proximal end of intermediate shaft 1130 moves axially with intermediate drive flange 1154, limiting shaft friction loads associated with the distal balloon and flange movement, and fluid flow path can be sealed so that the volumetric flow and pressure of the inflation fluid corresponds at the proximal end to the deployment movement at the distal end, providing visual and haptic feedback to the user regarding sheath movement. Proximal flange 1156 optionally moves with the intermediate flange.

The other sheath deployment and recapture movements described above are similarly mirrored at the proximal balloon drive system 1102. For example, referring now to FIGS. 38B-38D, 39B-39D, and 40B, movement of proximal drive flange distally toward intermediate drive flange 1154 can pressurize fluid in recapture drive balloon 1152, driving fluid along the recapture fluid path to the distal recapture balloon and inducing movement of the sheath 1104 proximally back over a partially deployed valve 1106 (with the deployment drive balloon 1150 expanding to accommodate fluid from the axially compressed distal deployment balloon 1116 to complete recapture). As can be understood with reference to FIGS. 38E, 38F, 39E, 39F, and 40B, re-deployment (or complete deployment of) prosthetic valve 1104 can be induced by completing axial compression of the deployment balloon to a deflated state. Elongation of both drive balloons can optionally shorten the distal balloon system if that will facilitate proximal withdrawal of the deployment system from the deployed prosthetic valve and/or vasculature.

Referring now to FIGS. 41A-41D, an alternative distal fluid driven sheath actuation system 1170 includes many of the components of deployment system 1100, with the fluid driving the sheath deployment and retraction being radially contained between inner and outer balloons. More specifically, in fluid-driven deployment system 1170, an intermediate catheter shaft 1172 extends distally along a catheter axis to an intermediate flange 1174. Intermediate shaft 1172 has a deployment fluid lumen 1176 and a separate recapture fluid lumen 1178, with the lumens being in fluid communication with a deployment port 1180 and a recapture port 1182 in intermediate flange 1174, the intermediate flange and intermediate shaft again being axially coupled to sheath 1104 (and hence moving axially relative to the valve and receptacle during sheath deployment and recapture). Fluid flowing distally along deployment fluid path 1176 flows to a space that is at least in part disposed between an outer deployment balloon wall 1184 and an inner deployment balloon wall 1186, with both balloons being folded with laterally opposed indentations so as to facilitate axial expansion and contraction. Fluid from recapture fluid path 1178 flows to a space between an outer recapture balloon wall 1188 and an inner recapture balloon wall 1190.

Figure 42:
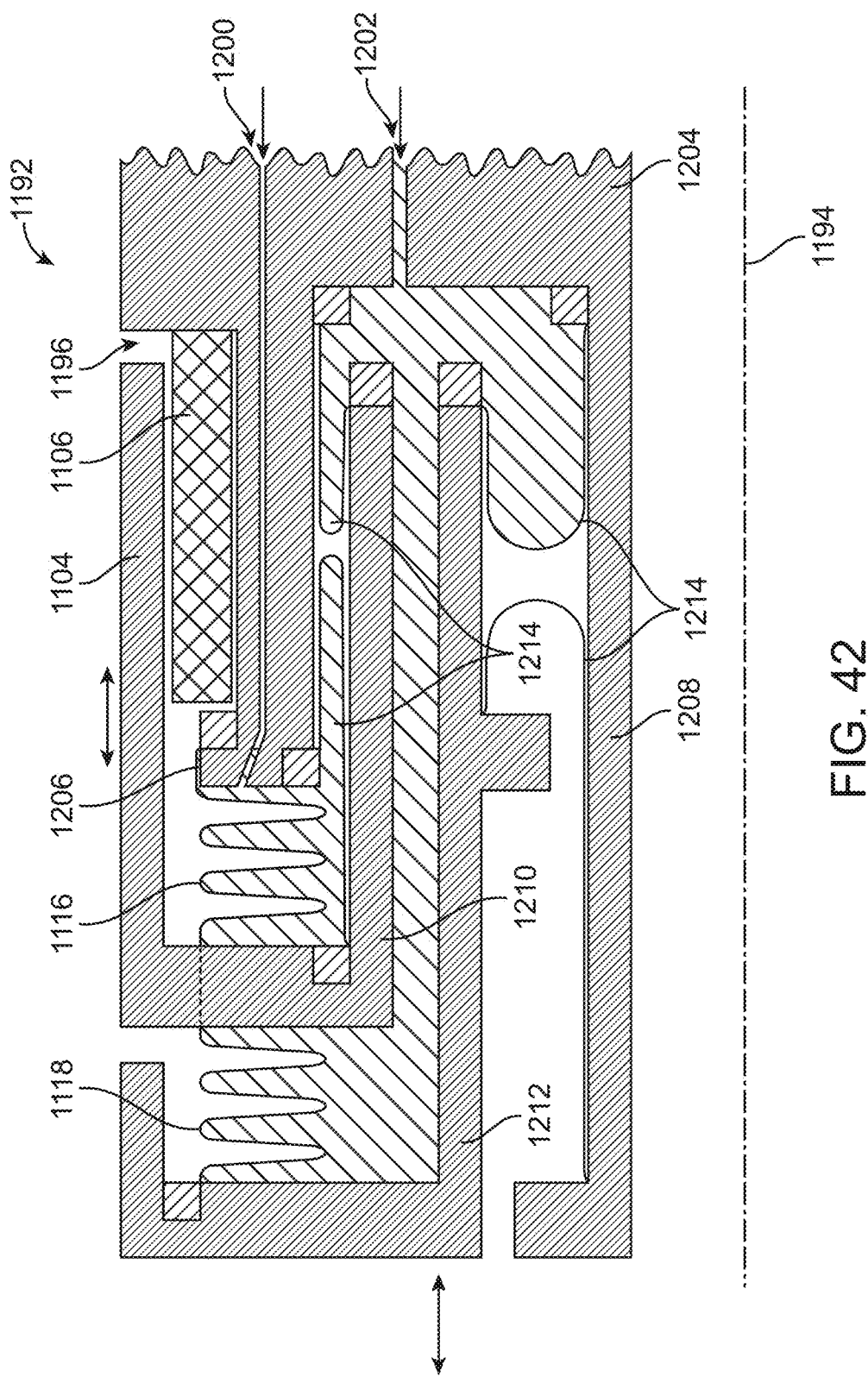
FIG. 42 is a schematic cross-section of another alternative valve delivery system having a fluid-driven sheath, wherein everting tubular membranes help seal the flowpath between distal shaft segments that move relative to, and distally of, an articulated catheter body.

Referring now to FIG. 42, a schematic illustration of yet another distal fluid driven sheath actuation system 1192 shows a cross section taken through one side of the distal catheter structure, with much of the remaining structure being symmetric about an axis 1194. This system avoids any need for axial movement of inner shafts along the body of the catheter significantly proximal of the valve receptacle 1196. Fluid flows to axially expand deployment balloon 1116 and recapture balloon 1118 through deployment fluid and recapture fluid lumens 1200 and 1202, respectively, in a catheter shaft 1204. Catheter shaft 1204 has an outer distal tubular extension 1206 (on which a portion of the receptacle and proximal flange are formed) and an inner tubular extension 1208, defining an annular space in which an intermediate shaft segment 1210 and an inner shaft segment 1212 can move axially. Engagement of stops on the inner extension 1208 of the catheter body and the inner shaft limit distal travel of the inner shaft, so the inner extension and inner shaft work together as tension members to limit distal movement of the distal end of the catheter during inflation of deployment and recapture balloons 1116, 1118. Inflation fluid between the deployment lumens 1200 and the deployment balloon 1116 is sealed by evertable tubular membranes 1214. The tubular membranes can extend axially in the annular spaces between the extensions of the catheter body and the axially movable shaft segments, with everted ends oriented so as that the inflation fluid loads the membranes in tension, and so that both the inner and outer surfaces of the membrane are supported by adjacent surfaces bordering the annular spaces, and so that rolling eversion of the membrane accommodates axial movement of the shaft segments without sliding of the membrane against the bordering surfaces. Suitable evertable membrane materials may comprise semi compliant or compliant balloon materials as generally described herein. The membranes can be affixed to the catheter shaft and shaft segments using rings that snap into position and are held by detents of the shaft structures, by adhesive bonding, or the like.

Figure 43A:
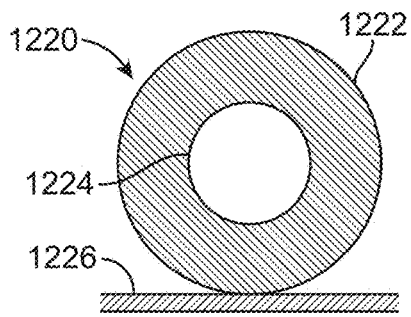
FIGS. 43A-43D schematically illustrate a relationship between balloon compression and balloon/frame engagement area.
Figure 43B:
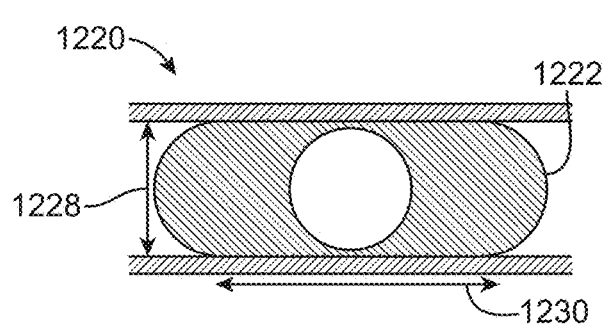

Referring now to FIGS. 43A-43D, the engagement forces transmitted between an inflated cylindrical balloon having a flexible balloon wall and an adjacent catheter structure surface vary with the area of balloon/structure interface, as those forces are largely defined by the pressure within the balloon pushing against the structure surface through the balloon wall. The examples of FIGS. 43A and 43B help to explain and bracket this relationship. In FIG. 43A, a cylindrical balloon 1220 has a thin flexible wall 1222 and a core shaft 1224 extending axially inside the wall. The balloon is inflated with fluid at a pressure P and engages a flat surface 1226 without deforming the round cross-section of the balloon wall, so that the balloon/surface engagement is defined by a line extending along the balloon axis. As the engagement has no area, no pressure within the balloon acts on the surface, and no engagement forces are present. In contrast, in FIG. 43B, balloon 1220 is confined in an offset 1228 between two opposed planar surfaces, with the offset being sufficiently small that the balloon is flattened with the core 1224 inside the balloon just barely touching the inner balloon wall surface. The unconstrained surfaces of the balloon wall extending between the offset surfaces will at least roughly form half-cylinders, with the minimum diameters of the half cylinders being equal to the core diameter. As the perimeter of a non-compliant (or even semi-compliant) balloon will remain largely constant, if the unconstrained balloon diameter is known and the core diameter is known, the width 1230 of the engagement area between the balloon and each surface can be calculated (½*π*(diameter of balloon-diameter of core)). If the length of the balloon is known (and preferably the variation in length with changes in radius), the engagement area between the balloon and each surface can be determined. Similarly, if the pressure in the balloon is known, the engagement force can also be estimated for any offset between the balloon diameter and the core diameter.

Figure 43C:
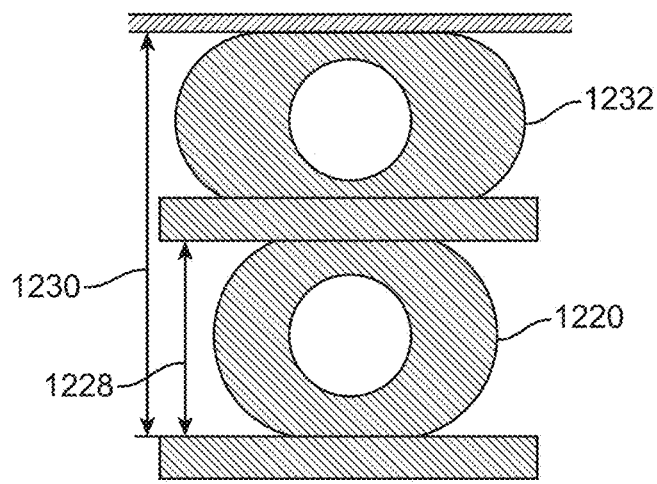
Figure 43D:
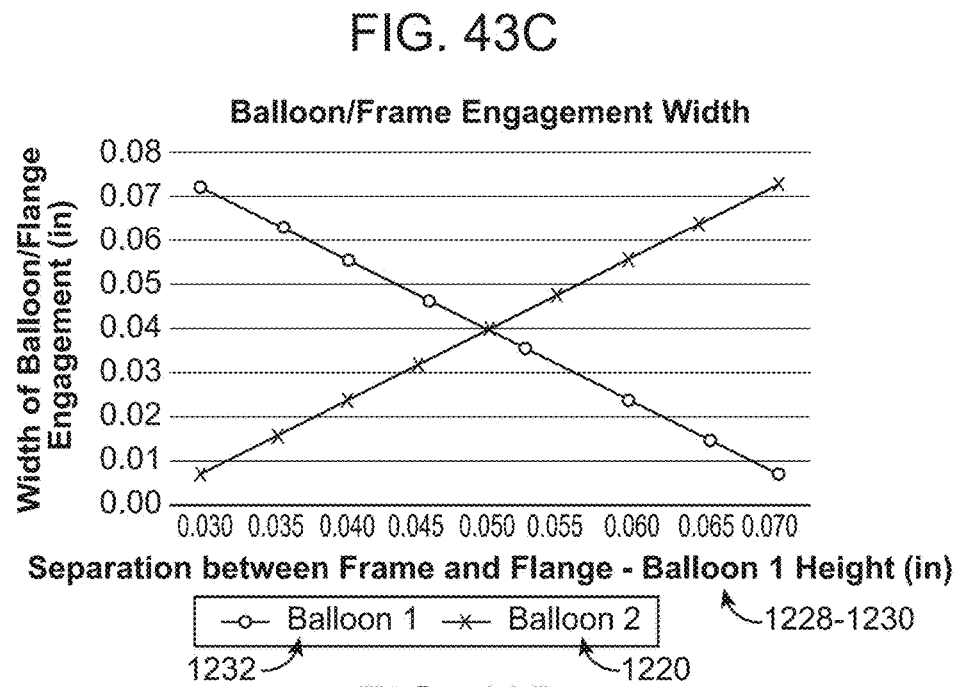

Referring now to FIGS. 43C and 43D, the articulating catheter systems described above often make use of opposed balloon balloons contained within a channel 1230 to push a flange (located between the balloons) to a desired location so as to effect a desired local bend, for example, of a ring frame or helical push-pull frame of a catheter. Other systems described herein use a balloon 1220 to push against a helical surface of a spring or the like, or even against an adjacent balloon. For many or all of these structures, relationship between engagement width and/or area and the distance between surfaces compressing each balloon can be determined from the relaxed balloon diameters and the balloon offset. As indicated in FIG. 43, the engagement area (and hence the engagement force at a given inflation pressure) varies substantially inversely with the offset, with engagement area increasing with decreasing offset.

Figure 44A:
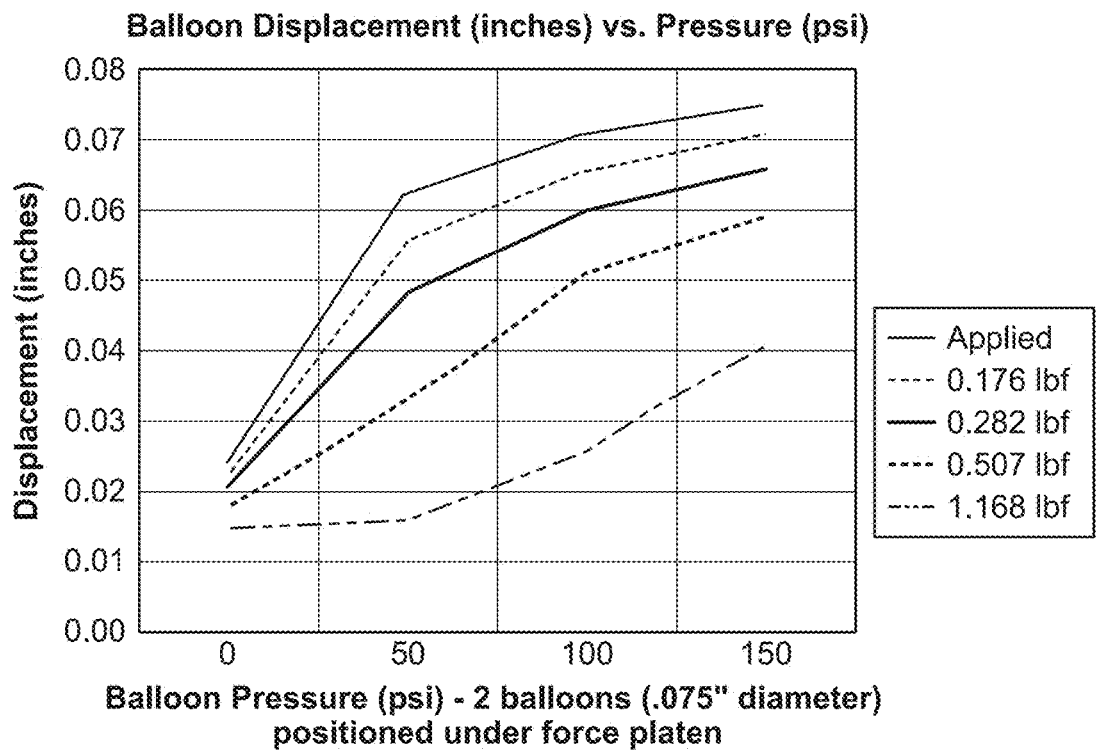
FIGS. 44A-44F illustrate relationships between balloon force, compression, and inflation fluid pressure.
Figure 44B:
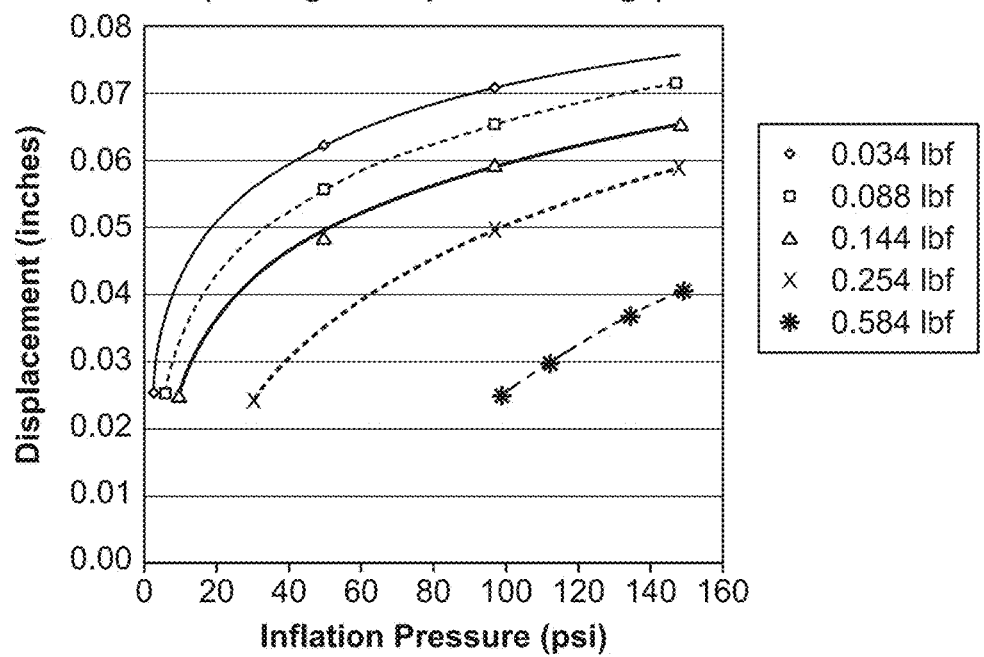

Referring now to FIGS. 44A and 44B, balloon compression force data was measured by positioning two balloons of a balloon string between parallel planar surfaces and inflating the balloons to different inflation pressures. The balloons had a diameter of about 0.075" and a length of about 0.080" and were blown from Pebax™ 63D thermoplastic tubing having an outer diameter of about 0.026" and an inner diameter of about 0.016," resulting in a semi-compliant balloon structure. Compressive loads of 0.067, 0.176, 0.287, 0.507, and 1.168 lbf, were applied to the balloons via the balloon/flat surface interfaces, and the resulting offset gaps (identified as "displacement" on the graphs) were measured, resulting in the graphical data shown in FIG. 44A. As offsets of less than 0.026" indicate the interface surfaces may have been engaging the tube between balloons, the pressures that would have provided this minimum offset were estimated (via linear interpolation where the adjacent data appeared consistent, otherwise via extrapolation). Additional intermediate datapoints were interpolated for the high-force measurements, and this operative range data is presented in FIG. 44B.

Figure 44C:
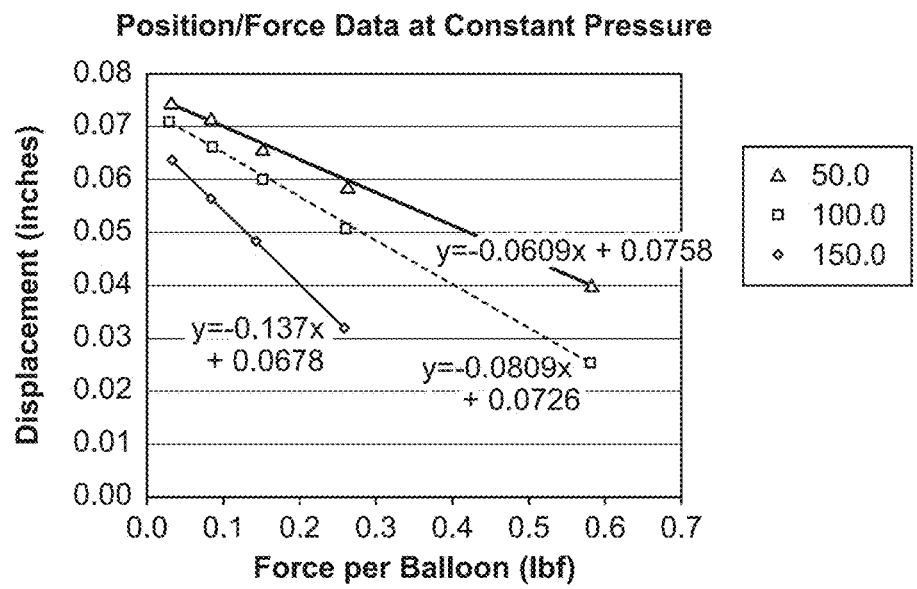
Figure 44D:
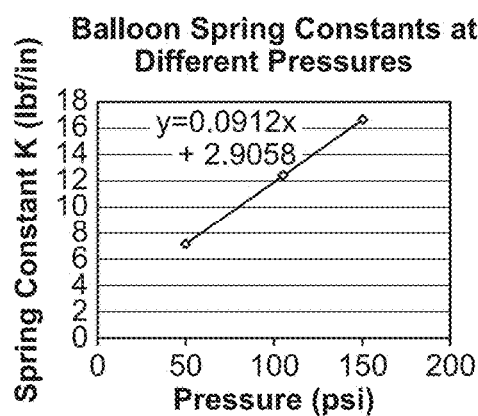

Referring now to FIGS. 44C-44D, a graph showing offsets verses the force per balloon from selected pressure data of FIG. 44B (specifically at 50, 100, and 150 psi) in FIG. 44C. For this subset of the operative range data, at any given pressure there is a linear relationship between i) compressive force applied to (and reacted by) the balloons, and ii) the compressive displacement or offset of those balloons. Note that the pressure was held constant in these tests, so that the increasing force of the balloons was not generated by increasing pressure inside the balloons. Instead, the increasing force was consistent with an increase in the balloon/surface engagement area, as described above regarding FIG. 43. Moreover, as can be understood with reference to the linear regression data presented in FIGS. 44C, 44D, and 44E, a linear relationship exists between the effective spring constant of the balloon system and the balloon inflation pressure, and between the initial spring force FO and the inflation pressure. It should be noted that many other hydraulic and/or pneumatic actuator structures (such as pistons or bellows) may have quite different behavior, such as providing a small initial compliance but, when sufficient force is applied to overcome the internal pressure, being displaced throughout most or all the range of travel. In contrast, the balloon systems described herein may, when included in an elongate flexible body, have effective lateral actuation spring constants which is at least a significant portion of the lateral bending spring constant of the body, which is at least a major portion of the body spring constant, which is at least as large as the body spring constant, which is larger than the spring constant, and/or which is at least two, three, five, or even ten times the body spring constant (with the larger balloon stiffnesses often being achieved when the balloons are inflated with a non-compressible liquid via a relatively rigid or non-conforming fluid control system). Regardless, as illustrated in FIG. 44F, operative range data from FIG. 44C can be used to calculate the effective balloon/surface force transmission area (by dividing the balloon/surface forces by the associated balloon inflation pressures), and plotted against the offset gap. As predicted above, the effective area and offset gaps have a linear relationship.

Figure 44E:
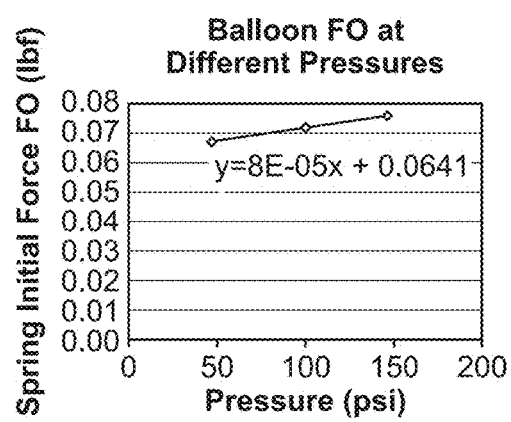
Figure 44F:
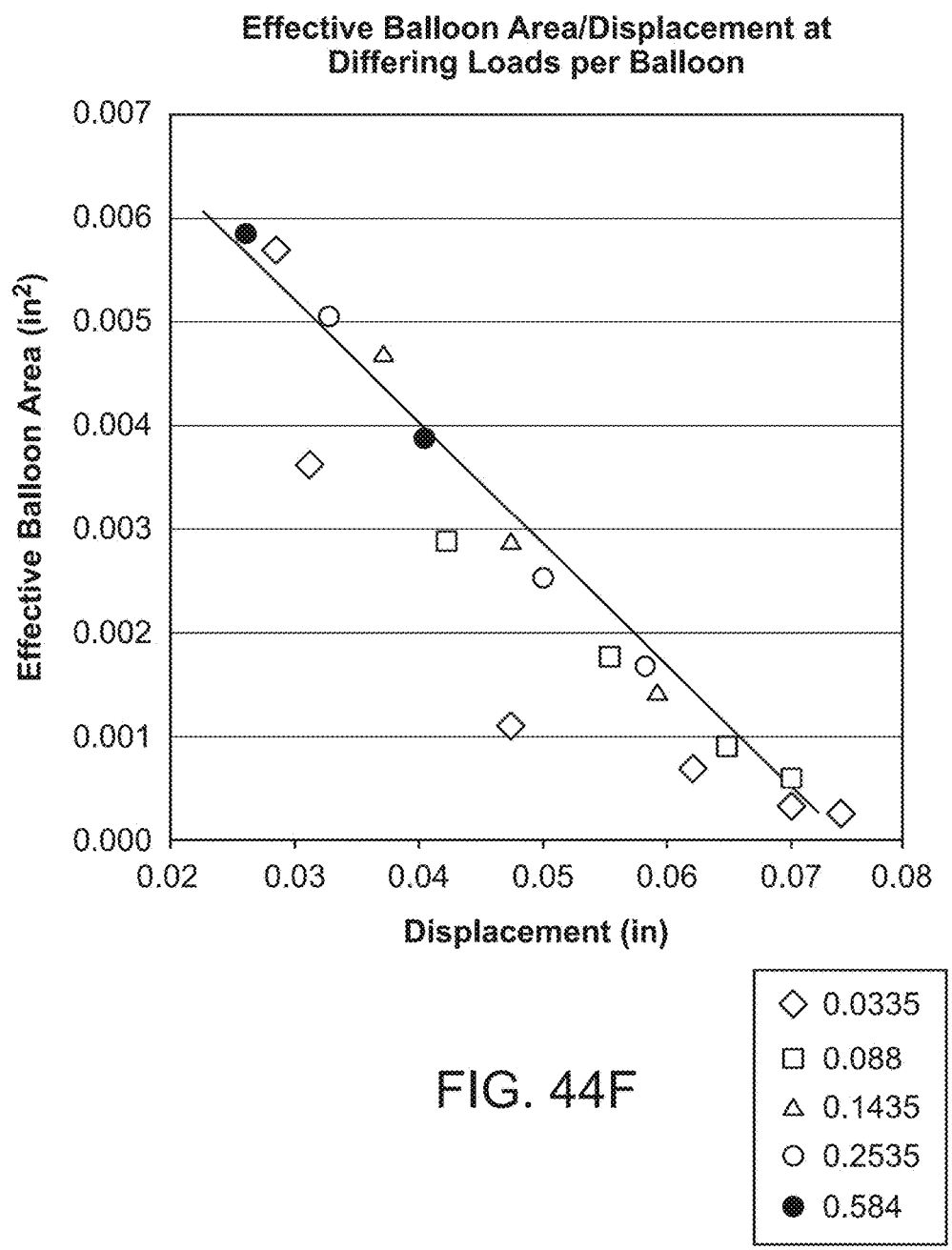

Referring now to FIGS. 36, 44E, and 44F, the variation in balloon-compression offset with local variations in curvature seen in variable area balloon system 1026 can be used to help more evenly distribute bending along an articulated segment. As there is an inverse relationship between offset and balloon force (see FIG. 44E), any balloons which are more compressed than other balloons on a common lumen aligned along one lateral bending axis of the segment (such as by an environmental force applied to the distal end of the segment), that compressed balloon will have an increase in effective balloon/surface engagement area, as well as an associated increase in the force transmitted between that balloon and the structure of the segment. In contrast, balloons along portions of the segment having less curvature will have smaller balloon/surface engagement areas and associated smaller balloon forces. This effective balloon spring constant can, in some bending states, be combined with the lateral bending spring constant of the catheter structure to limit a total curvature along the segment. In other states (such as when the articulation system is seeking to impose a bend rather than opposing the bend), the effective balloon stiffness may have to overcome the catheter structural stiffness, but the area-related variation in load by the balloons of a subset may still help to more evenly distribute the curvature along the segment and control the segment shape.

Referring now to FIGS. 45A-45E, an alternative articulated catheter 1250 has many balloon drive components similar to those of deployment catheter 1100 (see FIGS. 38A-39G), but with the distal drive balloons being mechanically coupled to a jaw 1252. Balloon drive system 1102 induces both flows of inflation fluid and axial movement of an intermediate shaft, here relative to both an inner shaft and to an outer catheter shaft 1254. First and second distal balloons have axially elongatable structures and ends coupled to the inner shaft (at the distal end the second balloon), to the intermediate shaft and sheath 1104 (at the proximal end of the second balloon and the distal end of the first balloon) and to the outer catheter shaft 1254 (at the proximal end of the first balloon), As a result, when proximal drive flange 1156 between drive balloons 1150 and 1152 moves proximally, the second (distal-most) of the distal balloons inflates and drives sheath 1104 proximally relative to distal shaft extension 1256. The jaw elements are pivotably mounted to distal shaft extension 1256 at pints 1258 while pins 1260 are axially coupled to sheath 1104 so that they slide proximally in slots in arms 1262 of the jaws when the sheath is driven proximally. This can result in significant grasping forces between jaws 1252 without having to transmit large forces along pull-wires or cables around any bends defined by the axis of catheter body 1254. These large jaw forces can be used to grasp, cut, seal (optionally using RF energy between the jaws), staple, or the like inside the patient. When incompressible fluids are used in the balloon system, the proximal drive system may give jaw state and haptic feedback regarding the jaw configuration and the pressure being applied by the jaws.

While the exemplary embodiment have been described in some detail for clarity of understanding and by way of example, a variety of modifications, changes, and adaptations of the structures and methods described herein will be obvious to those of skill in the art. Hence, the scope of the present invention is limited solely by the claims attached hereto.

What is claimed is:

1. A method for deploying a catheter-based tool, the method comprising:
   introducing an elongate flexible catheter body distally into a patient body, a distal portion of the catheter body supporting a tool, wherein the tool comprises a prosthetic heart valve and wherein the distal portion of the catheter body comprises an articulated segment disposed proximally of the tool;
   positioning or orienting the prosthetic valve by articulating the articulated segment, wherein the articulated segment comprises an articulation balloon array, and wherein the articulating of the articulated segment is performed by inflating the balloon array so as to position and orient the tool with at least 3 degrees of freedom;
   expanding the tool to a large profile configuration in the patient body, the tool biased to expand from a small profile configuration to the large profile configuration, wherein the tool is expanded by sliding a tubular sheath over the distal portion from a first position to a second position, the first position being over the tool, wherein the second position of the sheath is distal of the first position so that the sheath moves distally and away from the articulated segment when expanding the tool;
   transmitting fluid distally from outside the patient into a channel extending along the catheter body; and
   driving the sheath over the distal portion, toward the first position from the second position, with the transmitted fluid, wherein the sheath slides axially over the tool so as to recapture and radially constrain the tool in the small configuration.

2. The method of claim 1, wherein the expanding of the tool is performed by inflating a first balloon, the first balloon comprising a deployment balloon.

3. The method of claim 2, wherein the distal portion of the catheter body has a lumen slidably receiving a shaft, a distal end of the shaft being affixed to a distal end of the sheath, wherein a proximal end of the first balloon is affixed to the catheter body, wherein a distal end of the first balloon is affixed to the shaft, and wherein a seal is maintained between the shaft and the catheter body when the sheath moves between the first position and the second position.

4. The method of claim 2, further comprising an opposed balloon, inflation of the first balloon inducing deflation of the opposed balloon, inflation of the opposed balloon inducing deflation of the first balloon.

5. The method of claim 4, wherein alternating inflation of the first balloon and the opposed balloon incrementally drives the sheath axially.

6. The method of claim 2, wherein the driving of the sheath from the second position toward the first position is performed by inflating a second balloon with the transmitted fluid so as to radially compress the tool within the sheath, the second balloon comprising a recapture balloon.

7. A method for deploying a catheter-based tool, the method comprising:
  introducing an elongate flexible catheter body distally into a patient body, a distal portion of the catheter body supporting a tool;
  expanding the tool to a large profile configuration in the patient body, the tool biased to expand from a small profile configuration to the large profile configuration, wherein the tool is expanded by sliding a tubular sheath over the distal portion from a first position to a second position, the first position being over the tool, wherein the expanding of the tool is performed by inflating a first balloon, the first balloon comprising a deployment balloon;
  transmitting fluid distally from outside the patient into a channel extending along the catheter body; and
  driving the sheath over the distal portion, toward the first position from the second position, with the transmitted fluid, wherein the sheath slides axially over the tool so as to recapture and radially constrain the tool in the small configuration, wherein the driving of the sheath from the second position toward the first position is performed by inflating a second balloon with the transmitted fluid so as to radially compress the tool within the sheath, the second balloon comprising a recapture balloon,
  wherein inflating of the recapture balloon to compress the tool induces deflation of the deployment balloon; and
  limiting a combined length of the deployment and recapture balloons with a tension member so that inflation of the deployment balloon drives inflation fluid from the second balloon and the sheath toward the second position, and inflation of the second balloon drives inflation fluid from the first balloon and the sheath toward the first position.

8. The method of claim 7, wherein the inflating of the first balloon comprises expanding the first balloon from a first uninflated configuration toward a first inflated configuration, the first balloon in the first uninflated configuration having a first uninflated axial length, the first balloon in the first inflated configuration having a first inflated axial length greater than the first uninflated axial length, the inflating of the first balloon urging the sheath to move axially from over the tool so that the tool can expand radially, the first balloon being inflated via a first channel; and
  wherein the inflating of the second balloon comprises expanding the second balloon from a second uninflated configuration toward a second inflated configuration, the second balloon in the second uninflated configuration having a second uninflated axial length, the second balloon in the second inflated configuration having a second inflated axial length greater than the second uninflated axial length, the inflating of the second balloon urging the sheath to move axially back over the tool so that the tool is radially compressed, the channel through which the fluid is transmitted to the second balloon being a second channel.

9. The method of claim 7, wherein the inflating of the deployment balloon to expand the tool induces deflation of the recapture balloon.

10. The method of claim 7, wherein the inflating of the recapture balloon extends a distal end of an inner shaft distally relative to the catheter body.

11. The method of claim 7, wherein the first balloon is inflated by a first channel disposed between an outer tubular shaft and an intermediate tubular shaft, the outer shaft axially affixed to the tool, and wherein the channel comprises a second channel and is disposed between the inner shaft and the intermediate shaft, the tension member axially coupling the inner shaft to the outer shaft.

12. The method of claim 11, wherein the intermediate shaft and inner shaft extend proximally beyond the proximal end of the catheter body, and wherein a third balloon is in fluid communication with the second channel and a fourth balloon in fluid communication with the first channel, wherein the third balloon axially couples the intermediate shaft with the outer shaft, and wherein the fourth balloon axially couples the intermediate shaft with the inner shaft, the balloons having axially oriented ends coupled to the shafts, and further comprising distally driving a proximal portion of the inner shaft relative to the intermediate shaft so as to drive inflation fluid along the first channel to inflate the first balloon, and distally driving a proximal portion of the intermediate shaft relative to the outer shaft to drive inflation fluid along the second channel so as to inflate the second balloon.

13. The method of claim 7, wherein the catheter body defines an axis, and wherein the balloons have a first plurality of laterally opposed folds extending transverse to the axis and a second plurality of laterally opposed folds circumferentially offset from the first folds.

14. A catheter-based prosthetic heart valve deployment method comprising:
  inserting an elongate flexible catheter body into a patient body, the catheter body having a proximal end and a distal portion with an axis therebetween, the distal portion supporting a prosthetic heart valve and a deployment system distal end, a tubular sheath having a lumen slidably receiving the distal portion therein;
  transmitting inflation fluid into a first fluid channel extending axially along the catheter body; and
  driving the sheath axially between a first position and a second position relative to the catheter body in response to the transmitting of the fluid into the first channel with a first actuator so as to uncover the prosthetic heart valve and allow the valve to expand radially;
  inflating a recapture balloon distal of the valve so that the recapture balloon axially elongates and drives the distal end of the deployment system distally away from the valve;
  wherein the driving of the sheath induces deflation of the recapture balloon through a second channel extending axially along the catheter body, the recapture balloon axially coupling the prosthetic heart valve with the sheath, a tension member coupling the distal end of the deployment system to the distal portion so as to limit distal movement of the distal end of the deployment system from the driving of the sheath to uncover the valve.

* * * * *